United States Patent
Lippman et al.

(10) Patent No.: US 10,472,352 B2
(45) Date of Patent: Nov. 12, 2019

(54) RAC INHIBITORS

(71) Applicant: Geneyus LLC, Miami, FL (US)

(72) Inventors: Marc Lippman, Miami, FL (US); Erik Goka, Miami, FL (US); Shawn D. Johnstone, Miami, FL (US); Malken Bayrakdarian, Miami, FL (US); William Brown, Miami, FL (US); Jeffrey S. Albert, Miami, FL (US)

(73) Assignee: GENEYUS LLC, Miami, FL (US)

( * ) Notice: Subject to any disclaimer, the term of this patent is extended or adjusted under 35 U.S.C. 154(b) by 0 days.

(21) Appl. No.: 16/044,752

(22) Filed: Jul. 25, 2018

(65) Prior Publication Data
US 2019/0031647 A1  Jan. 31, 2019

Related U.S. Application Data

(60) Provisional application No. 62/536,681, filed on Jul. 25, 2017.

(51) Int. Cl.
| | |
|---|---|
| *C07D 413/14* | (2006.01) |
| *C07D 405/14* | (2006.01) |
| *C07D 215/36* | (2006.01) |
| *C07D 401/12* | (2006.01) |
| *C07D 497/04* | (2006.01) |
| *A61P 35/02* | (2006.01) |

(52) U.S. Cl.
CPC ......... *C07D 413/14* (2013.01); *C07D 215/36* (2013.01); *C07D 401/12* (2013.01); *C07D 405/14* (2013.01); *C07D 497/04* (2013.01); *A61P 35/02* (2018.01)

(58) Field of Classification Search
CPC .................................................. C07D 413/14
See application file for complete search history.

(56) References Cited

U.S. PATENT DOCUMENTS

| 7,514,432 B2 | 4/2009 | Leblond et al. |
| 8,884,006 B2 | 11/2014 | Hernandez et al. |

OTHER PUBLICATIONS

Marciniec et al., Med Chem Res (2017) 26:2432-2442.*
Abel et al., "Novel azolylalkyloxy compounds with antipicornaviral activity," Antivir. Chem. Chemoth., 6(4):245-254 (1995).
Berger et al., "Melanoma genome sequencing reveals frequent PREX2 mutations," Nature, 485(7399):502-506 (May 9, 2012).
Bid et al., "RAC1: An Emerging Therapeutic Option for Targeting Cancer Angiogenesis and Metastasis," Mol. Cancer Ther., 12(10):1925-1934 (Oct. 2013).
Bidaud-Meynard et al., "A novel small-molecule screening strategy identifies mitoxantrone as a RhoGTPase inhibitor," Biochem. J., 450(1):55-62 (Feb. 15, 2013).
Carrizzo et al., "Rac-1 as a New Therapeutic Target in Cerebro-and Cardio-Vascular Diseases," Curr. Drug Targets, 15(14):1-16 (2014).
Davis et al., " RAC1P29S is a spontaneously activating cancer-associated GTPase," Proc. Natl. Acad. Sci. USA, 110 (3):912-917 (Jan. 15, 2013).
Deribe et al., "Truncating PREX2 mutations activate its GEF activity and alter gene expression regulation in NRAS-mutant melanoma," Proc. Natl. Acad. Sci. USA,113(9):E1296-305 (Mar. 1, 2016).
Ferri et al., "Role of Small GTPase Protein Rac1 in Cardiovascular Diseases: Development of New Selective Pharmacological Inhibitors," J. Cardiovasc. Pharmacol., 62(5):425-435 (Nov. 2013).
Fisher et al., "Synthesis and Evaluation of Antimalarial Properties of Novel 4-Aminoquinoline Hybrid Compounds," Chem. Biol. Drug Des., 84:462-472 (2014).
Freitas et al., "Synthesis and antiproliferative activity of 8-hydroxyquinoline derivatives containing a 1,2,3-triazole moiety," Eur. J. Med. Chem., 84:595-604 (2014).
Goka et al., "Loss of the E3 ubiquitin ligase HACE1 results in enhanced Rac1 signaling contributing to breast cancer progression," Oncogene, 34(42):5395-5405 (Oct. 16, 2015).
Halaban, "RAC1 and Melanoma," Clin. Ther., 37(3): 682-685 (Nov. 22, 2014).
Hampsch et al., "Therapeutic targeting of Rac GTPases in ER+ and HER2+ breast cancer," San Antonio Breast Cancer Symposium, Abstract (2015).
Kadri et al., "The Potential of quinoline derivative for the treatment of Toxoplasma gondii infection," Exp. Parasitol., 145:135-144 (2014).
Kandi et al., "C5-curcuminoid-4-aminoquinoline based molecular hybrids: design, synthesis and mechanistic investigation of anticancer activity," New J. Chem., 39:224-234 (2015).
Katritzky et al., "Preparation and synthetic utility of 3-(benzotriazol-1-ylmethyl)areno-and-hetareno[b]thiophenes," J. Chem. Soc., Perkin Trans. 1, 19:2483-2486 (Sep. 7, 2001).
Kobarfard et al., Synthesis of aminoquinoline-based aminoalcohols and oxazolidinones and their antiplasmodial activity, Chem. Biol. Drug Des., 79(3):326-331 (Jan. 11, 2012).
Krauthammer et al., "Exome sequencing identifies recurrent somatic RAC1 mutations in melanoma," Nat. Genet., 44 (9)1006-1014 (Jul. 29, 2012).
Kushwaha et al., "Design and synthesis of novel 2H-chromen-2-one derivatives bearing 1,2,3-triazole moiety as lead antimicrobials," Bioorg. Med. Chem. Lett. 24(7):1795-1801 (Feb. 19, 2014).
Manohar et al., "Synthesis of 4-aminoquinoline-1,2,3-triazole and 4-aminoquinoline-1,2,3-triazole-1,3,5-triazine hybrids as potential antimalarial agents," Chem. Biol. Drug Des., 78(1):124-136 (Apr. 27, 2011).
Panda et al., "New trifluoromethyl quinolone derivatives: Synthesis and investigation of antimicrobial properties," Bioorg. Med. Chem. Lett., 23(11):3225-3229 (Apr. 3, 2013).
Raj et al., "Insights into activity enhancement of 4-aminoquinoline-based hybrids using atom-based and field-based QSAR studies," Med. Chem. Res., 24(3):1136-1154 (Aug. 6, 2014).

(Continued)

*Primary Examiner* — Rebecca L Anderson
(74) *Attorney, Agent, or Firm* — Pillsbury Winthrop Shaw Pittman, LLP

(57) ABSTRACT

The present invention relates to compounds that act as pan-Rac inhibitors, compositions including the compounds, and methods of using the compounds. In particular, the compounds are useful for treating certain cancers such as breast cancer.

18 Claims, 14 Drawing Sheets

(56) References Cited

OTHER PUBLICATIONS

Shibata et al., "Modification of mineralocorticoid receptor function by Rac1 GTPase: implication in proteinuric kidney disease," Nat. Med., 14:1370-1376 (Nov. 23, 2008).
Shtivelman et al., "Pathways and therapeutic targets in melanoma," Oncotarget, 5(7):1701-1752 (Apr. 15, 2014).
Shutes et al., "Specificity and mechanism of action of EHT 1864, a novel small molecule inhibitor of Rac family small GTPases," J. Biol. Chem., 282(49):35666-35678 (Oct. 11, 2007).
Sobhani et al., "A theory of mode of action of azolylalkylquinolines as DNA binding agents using automated flexible ligand docking," J. Mol. Graph. Model., 25(4):459-469 (Apr. 18, 2006).
Solomon et al., "Design and synthesis of chloroquine analogs with anti-breast cancer property," Eur. J. Med. Chem., 45(9):3916-3923 (May 31, 2010).
Taleli et al., "In vitro antiplasmodial activity of triazole-linked chloroquinoline derivatives synthesized from 7-chloro-N-(prop-2-yn-1-yl)quinolin-4-amine," Bioorg. Med. Chem., 23(15):4163-4171 (Jun. 27, 2015).
Vader et al., "Examining the role of Rac1 in tumor angiogenesis and growth: a clinically relevant RNAi-mediated approach," Angiogenesis,14(4):457-466 (Jul. 26, 2011).
Vashist et al., Synthesis of medicinally important quinazolines decorated with 1,4-disubstituted-1,2,3-triazoles using $CuSO_4$-$5H_2O$—$Et_3N$ catalytic system, RSC Adv. 4:23679-23684 (Apr. 29, 2014).
Wang et al., "Inhibition of prostate smooth muscle contraction and prostate stromal cell growth by the inhibitors of Rac, NSC23766 and EHT1864," Br. J. Pharmacol., 172(11):2905-2917 (May 5, 2015).
Watson et al., "The RAC1 P29S hotspot mutation in melanoma confers resistance to pharmacological inhibition of RAF," Cancer Res., 74(17):4845-4852 (Jul. 23, 2014).
Invitation to Pay Additional Fees and, Where Applicable, Protest Fee dated Sep. 21, 2018 in connection with PCT/US18/43631.
PubChem-CID-75377159, 2014.

\* cited by examiner

RAC INHIBITORS

CROSS-REFERENCE TO RELATED APPLICATIONS

This application claims priority to U.S. Provisional Patent Application No. 62/536,681 filed Jul. 25, 2017, the entirety of which is incorporated herein by reference.

FIELD OF INVENTION

The present invention relates to compounds which act as pan-Rac inhibitors, compositions including the compounds, and methods of using the compounds. In particular, the compounds are useful for treating certain cancers such as breast cancer.

BACKGROUND

Breast cancer (BrCa) is the most common malignancy in women; one-in-eight women will develop breast cancer during their lifetime. Mortality from breast cancer in the U.S. has been on the decline that is mostly attributed to effective systemic adjuvant therapies. However, there are still numerous deaths from breast cancer each year. Therefore, there is a significant unmet need to improve systemic therapies. Rac, a member of the Rho family GTPases, is commonly overexpressed in cancer and has been shown to play a pivotal role in initial transformation, disease progression, and metastatic dissemination of cancer. Additionally, previous studies have demonstrated elevated Rac signaling is capable of conferring resistance to both antiestrogen and HER2 targeted therapies, suggesting a common escape mechanism.

Rac is a member of the Rho GTPase family, which consists of Rho, Rac, and CDC42. As with other family members, Rac alternates between an inactive GDP-bound state and an active GTP-bound form that is capable of binding downstream effectors. Because the affinity for GDP is very strong and the intrinsic rate of GTP hydrolysis is very slow, Rac requires the aid of guanine nucleotide exchange factors (GEFs) that facilitate GDP dissociation allowing GTP replacement and of GTPase activation proteins (GAPs) that stimulate the intrinsic rate of GTP hydrolysis. External stimuli activate transmembrane receptor tyrosine kinases, G-protein coupled receptors, and integrins, activate Rac GEFs initiating Rac signal transduction. Rac activation canonically results in reorganization of the cytoskeleton resulting in increased phagocytosis, mesenchymal-like migration, axonal growth, adhesion and differentiation of various cell types. In addition to cytoskeletal rearrangements, Rac activation also results in enhanced gene expression, translation, cellular proliferation, and cell survival by activating numerous downstream effectors such as the p21-activated kinases (PAKs). The multitude of both upstream activators and downstream effectors highlight that Rac is a key signaling integrator whose activity controls numerous cellular phenotypes. Because Rac is a cytosolic molecular switch that becomes activated when bound to GTP, small molecules that prevent GTP binding to Rac and/or block the binding of Rac to downstream effectors will inhibit downstream signal propagation.

Rac is both overexpressed and hyperactive in a variety of different cancers (including breast cancer) driving malignant transformation by enhancing tumorigenesis, the angiogenic switch, invasion and metastatic dissemination. Under normal physiologic conditions, Rac activity is controlled both temporally and spatially by post-translational modifications. In breast cancer, overexpression/mutation of growth factor receptors such as EGFR and HER2 activate Rac GEFs resulting in Rac activation. Furthermore, numerous Rac GEFs such as Dock4, Tiam1, Trio, Vav3, PREX1 and PREX2 have been shown to be overexpressed in breast cancer. Oncogenic variants of Rac itself have also been identified. The recurring Rac1 P29S/L mutation observed in melanoma and Rac1 A159V mutation in head and neck cancer results in constitutive activation of Rac1. Less frequent mutations such as Rac1 C157Y and N92I have been reported in lung adenocarcinoma and the HT1080 fibrosarcoma cell line.

Therefore, efficacious pan-Rac inhibitors are desired for use as potentially valuable therapeutic agents for the treatment of cancer and other diseases that show a dependence on Rac protein signaling.

SUMMARY

Accordingly, one embodiment of the present invention is directed to a compound of formula I:

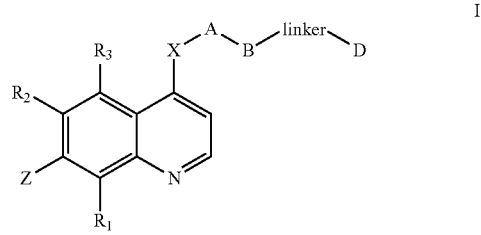

or a pharmaceutically acceptable salt thereof wherein

Z is selected from H, halogen, OH, $C_{1-4}$ alkoxy, and $C_{1-4}$ alkyl wherein said $C_{1-4}$ alkyl is optionally substituted with one or more halogen atoms;

$R_1$, $R_2$, and $R_3$ are independently selected from H and halogen;

X is selected from —O—, —S—, —S(O)—, —SO$_2$—, —CH$_2$—, and —N($R^a$)—;

A is $C_{1-7}$ alkylene wherein one or more of the methylene groups is optionally replaced with O, N($R^b$), S, C(O), or phenylene;

B is a 5- or 6-membered ring having at least one nitrogen atom;

Linker is selected from a bond, —C(O)—, —CH$_2$—N($R^c$)—, —CH$_2$—N($R^d$)—C(O)—, and $C_{1-2}$ alkylene wherein said $C_{1-2}$ alkylene is optionally substituted with OH;

D is selected from:

(i) a 4-7 membered ring optionally containing 1 or 2 heteroatoms independently selected from N and O; wherein said ring optionally contains a C=O; and wherein said ring is optionally substituted with one or more groups selected from halogen, OH, $C_{1-4}$ alkoxy, $C_{1-4}$ alkyl optionally substituted with one or more halogen atoms, C(O)—$R^e$, phenyl optionally substituted with $C_{1-4}$ alkoxy, and a 5 or 6 membered ring containing 1 or 2 heteroatoms independently selected from N and O;

(ii) —N($R^f$)($R^g$); and (iii) —C(O)—O—$C_{1-4}$ alkyl and —C(O)—OH;

$R^a$ is selected from H, $C_{1-4}$ alkyl, and C(O)—$C_{1-4}$ alkyl;

$R^b$ is selected from H and $C_{1-4}$ alkyl;

$R^c$ and $R^d$ are independently selected from H and $C_{1-4}$ alkyl, $R^e$ is selected from $C_{1-4}$ alkyl and a 5- or 6-membered ring optionally containing 1 or 2 heteroatoms independently selected from N and O;

$R^f$ is selected from H, $C_{1-4}$ alkyl, —C(O)—$C_{1-4}$ alkyl, —C(O)—O—$C_{1-4}$ alkyl, and —C(O)—OH; and $R^g$ is selected from $C_{1-4}$ alkyl, $C_{1-4}$ alkylene-O—$C_{1-4}$ alkyl.

In a preferred embodiment, the present invention is directed to a compound of formula I or a pharmaceutically acceptable salt thereof wherein Z is selected from H, halogen, and $C_{1-4}$ alkyl wherein said $C_{1-4}$ alkyl is optionally substituted with one or more halogen atoms;

A is $C_{2-7}$ alkylene wherein one or more of the methylene groups is optionally replaced with O, N($R^b$), C(O), or phenylene;

D is selected from:

(i) a 4-7 membered ring optionally containing 1 or 2 heteroatoms independently selected from N and O; wherein said ring optionally contains a C=O; and wherein said ring is optionally substituted with one or more groups selected from halogen, OH, $C_{1-4}$ alkoxy, $C_{1-4}$ alkyl optionally substituted with one or more halogen atoms, C(O)—$R^e$, phenyl optionally substituted with $C_{1-4}$ alkoxy, and a 5- or 6-membered ring containing 1 or 2 heteroatoms independently selected from N and O;

(ii) —N($R^f$)($R^g$); and (iii) —C(O)—O—$C_{1-4}$ alkyl; and $R^b$ is $C_{1-4}$ alkyl.

In a more preferred embodiment, the present invention is directed to a compound of formula I or a pharmaceutically acceptable salt thereof wherein Z is selected from H, Cl, F, $CH_3$, and $CF_3$;

$R_1$, $R_2$, and $R_3$ are independently selected from H and F;

X is selected from —O—, —S—, —S(O)—, —$CH_2$—, and —N($R^a$)—;

A is selected from —$(CH_2)_m$—, —$(CH_2)_3$—O—$(CH_2)_3$—, —$(CH_2)_3$—O—$(CH_2)_2$—, —O—$(CH_2)_5$—, —$(CH_2)_5$—O—, —$(CH_2)_3$—N($CH_3$)—$(CH_2)_2$—, —$(CH_2)_5$—C(O)—,

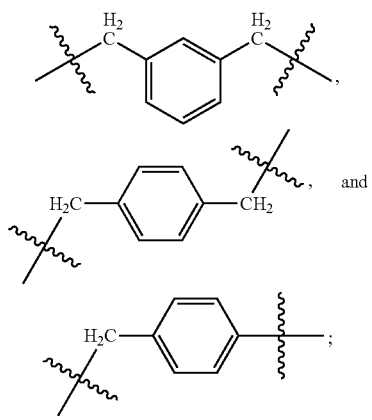

Linker is selected from a bond, —C(O)—, —$CH_2$—, —$(CH_2)_2$—, —CH($CH_3$)—, —CH(OH)—, —$CH_2$—NH—, —$CH_2$—N($CH_3$)—, —$CH_2$—N($CH_3$)—C(O)—, and —$CH_2$—NH—C(O)—;

D is selected from:

(i) a 4-7 membered ring optionally containing 1 or 2 heteroatoms independently selected from N and O; wherein said ring optionally contains a C=O; and wherein said ring is optionally substituted with one or more groups selected from $CH_3$, F, OH, $CF_3$, O—$CH_3$, C(O)—$R^e$, phenyl, 4-methoxyphenyl, and piperazine;

(ii) —N($R^f$)($R^g$); and (iii) —C(O)—O—C($CH_3$)$_3$;

$R^a$ is selected from H, $CH_3$, and C(O)—$CH_3$;

$R^e$ is selected from $CH_3$, CH($CH_3$)$_2$, and tetrahydropyran;

$R^f$ is selected from H, $CH_3$, $CH_2$—$CH_3$, C(O)—$CH_3$, and C(O)—O—C($CH_3$)$_3$;

$R^g$ is selected from $CH_2$—$CH_2$—O—$CH_3$, CH($CH_3$)—$CH_2$—O—$CH_3$, C($CH_3$)$_2$—$CH_2$—O—$CH_3$, $CH_2$—C($CH_3$)$_2$—O—$CH_3$, and $CH_2$—$CH_3$; and m is selected from 3, 4, 5, 6, and 7.

In an another preferred embodiment the present invention is directed to a compound of formula I or a pharmaceutically acceptable salt thereof, wherein Z is selected from halogen and $C_{1-4}$ alkyl wherein said $C_{1-4}$ alkyl is optionally substituted with one or more halogen atoms;

$R_1$, $R_2$, and $R_3$ are independently selected from H and halogen;

X is —S—;

A is $C_{1-7}$ alkylene wherein one or more of the methylene groups is optionally replaced with O, N($R^b$), S, C(O), or phenylene;

B is a 5- or 6-membered ring having at least one nitrogen atom;

Linker is selected from a bond, —C(O)—, —$CH_2$—N($R^c$)—, —$CH_2$—N($R^d$)—C(O)—, and $C_{1-2}$ alkylene wherein said $C_{1-2}$ alkylene is optionally substituted with OH;

D is selected from:

(i) a 4-7 membered ring optionally containing 1 or 2 heteroatoms independently selected from N and O; wherein said ring optionally contains a C=O; and wherein said ring is optionally substituted with one or more groups selected from halogen, OH, $C_{1-4}$ alkoxy, $C_{1-4}$ alkyl optionally substituted with one or more halogen atoms, C(O)—$R^e$, phenyl optionally substituted with $C_{1-4}$ alkoxy, and a 5 or 6 membered ring containing 1 or 2 heteroatoms independently selected from N and O;

(ii) —N($R^f$)($R^g$); and (iii) —C(O)—O—$C_{1-4}$ alkyl;

$R^b$ is selected from H and $C_{1-4}$ alkyl;

$R^c$ and $R^d$ are independently selected from H and $C_{1-4}$ alkyl, $R^e$ is selected from $C_{1-4}$ alkyl and a 5- or 6-membered ring optionally containing 1 or 2 heteroatoms independently selected from N and O;

$R^f$ is selected from H, $C_{1-4}$ alkyl, C(O)—$C_{1-4}$ alkyl, and C(O)—O—$C_{1-4}$ alkyl; and $R^g$ is selected from $C_{1-4}$ alkyl, $C_{1-4}$ alkylene-O—$C_{1-4}$ alkyl.

An additional embodiment of the present invention is directed to a compound of formula II:

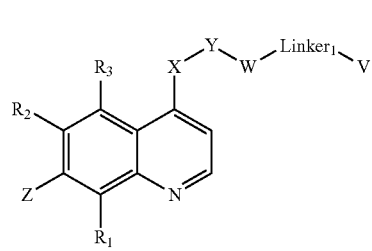

or a pharmaceutically acceptable salt thereof, wherein

Z is selected from H, halogen, OH, $C_{1-4}$ alkoxy, and $C_{1-4}$ alkyl wherein said $C_{1-4}$ alkyl is optionally substituted with one or more halogen atoms;

$R_1$, $R_2$, and $R_3$ are independently selected from H and halogen;

X is selected from —O—, —S—, —S(O)—, —SO$_2$—, —CH$_2$—, and —N($R^a$)—;

Y is $C_{1-7}$ alkylene wherein one or more of the methylene groups is optionally replaced with S, N($R^j$), NH—C(O), and C(O)—NH;

W is phenylene;

Linker$_1$ is selected from a bond, —CH$_2$— and —C(O)—;

V is a 5- or 6-membered ring optionally containing 1 or 2 heteroatoms independently selected from N and O; wherein said ring optionally contains a C=O; and wherein said ring is optionally substituted with $C_{1-4}$ alkyl, N($R^k$)($R^l$), or C(O)—$C_{1-4}$ alkyl;

$R^a$ is selected from H, $C_{1-4}$ alkyl, and C(O)—$C_{1-4}$ alkyl;

$R^j$ is selected from H, $C_{1-4}$ alkyl, and C(O)—$C_{1-4}$ alkyl; and $R^k$ and $R^l$ are independently selected from H and $C_{1-4}$ alkyl.

A preferred embodiment of the present invention is directed to a compound of formula II or pharmaceutically acceptable salt thereof wherein Z is selected from halogen and CF$_3$;

$R_1$ and $R_2$ are H;

X is —S—;

Y is $C_{1-7}$ alkylene wherein one or more of the methylene groups is optionally replaced with N($R^j$), NH—C(O), and C(O)—NH; and V is a 6 membered ring containing 1 or 2 heteroatoms independently selected from N and O; wherein said ring optionally contains a C=O; and wherein said ring is optionally substituted with N($R^k$)($R^l$).

In a more preferred embodiment, the present invention is directed to a compound of formula II or a pharmaceutically acceptable salt thereof wherein Z is selected from Cl, F, and CF$_3$;

$R_1$ and $R_2$ are H;

$R_3$ is selected from H and F;

X is —S—;

Y is selected from —(CH$_2$)$_p$—, —(CH$_2$)$_q$—NH—, —(CH$_2$)$_t$—NH—C(O)—, —(CH$_2$)$_v$—C(O)—HN—, —(CH$_2$)$_6$—N(C(O)—CH$_3$)—, and —(CH$_2$)$_4$—C(O)—NH—CH$_2$—;

V is a 6 membered ring containing 1 or 2 heteroatoms independently selected from N and O; wherein said ring optionally contains a C=O; and wherein said ring is optionally substituted with NH$_2$;

p is selected from 1 and 2;

q is selected from 4, 5, and 6;

t is selected from 5 and 6; and v is 5.

Another embodiment of the present invention is directed to a compound of formula III:

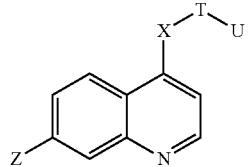

III or a pharmaceutically acceptable salt thereof wherein

Z is selected from H, halogen, OH, $C_{1-4}$ alkoxy, and $C_{1-4}$ alkyl wherein said $C_{1-4}$ alkyl is optionally substituted with one or more halogen atoms;

X is selected from —O—, —S—, —S(O)—, —SO$_2$—, —CH$_2$—, and —N($R^a$)—;

T is $C_{5-7}$ alkylene wherein one or more of the methylene groups is optionally replaced with O, N($R^b$), S, C(O), NH—C(O), and C(O)—NH;

U is selected from:

(i) a 4-9 membered monocyclic or bicyclic ring optionally containing 1, 2, or 3 heteroatoms independently selected from N and O; wherein said ring optionally contains 1 or 2 C=O, and wherein said ring is optionally substituted with a $C_{1-4}$ alkyl wherein said $C_{1-4}$ alkyl is optionally substituted with OH, or $C_{1-4}$ alkoxy; and (ii) —N($C_{1-4}$ alkyl)$_2$;

$R^a$ is selected from H, $C_{1-4}$ alkyl, and C(O)—$C_{1-4}$ alkyl; and $R^b$ is selected from H and $C_{1-4}$ alkyl.

In a preferred embodiment, the present invention is directed to a compound of formula III or a pharmaceutically acceptable salt thereof wherein Z is CF$_3$;

X is —S—;

T is selected from —(CH$_2$)$_w$—, —(CH$_2$)$_6$—NH—C(O)—, —(CH$_2$)$_5$—C(O)—NH—, —(CH$_2$)$_5$—C(O)—, —(CH$_2$)$_6$—NH—, and —(CH$_2$)$_5$—C(O)—NH—CH$_2$—; and U is a 4-9 membered monocyclic or bicyclic ring optionally containing 1, 2, or 3 heteroatoms independently selected from N and O; wherein said ring optionally includes 1 or 2 C=O, and wherein said ring is optionally substituted with CH$_3$, CH$_2$OH, and OCH$_3$; and w is selected from 5 and 6.

A further embodiment of the present invention is directed to a compound of formula IV:

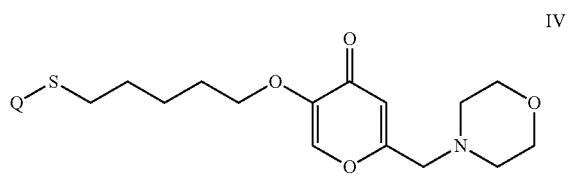

IV or a pharmaceutically acceptable salt thereof, wherein Q is selected from the group:

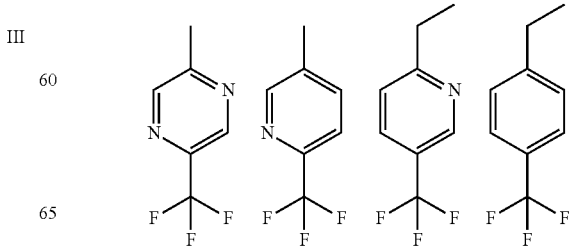

-continued

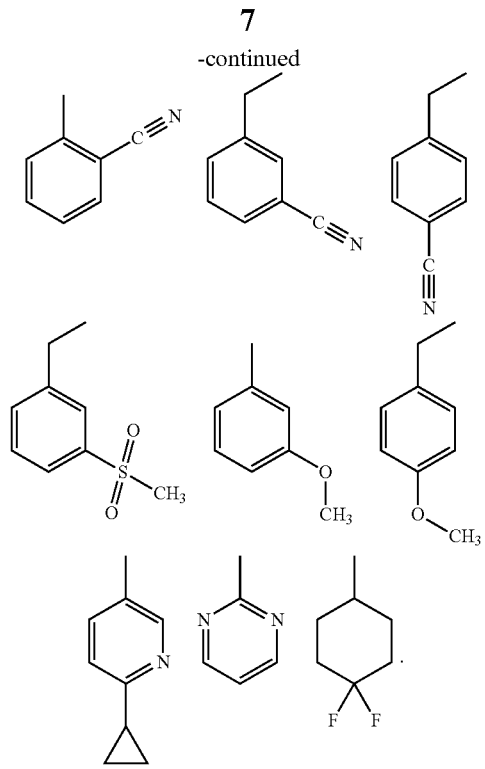

A further embodiment of the present invention is directed to a compound of formula V:

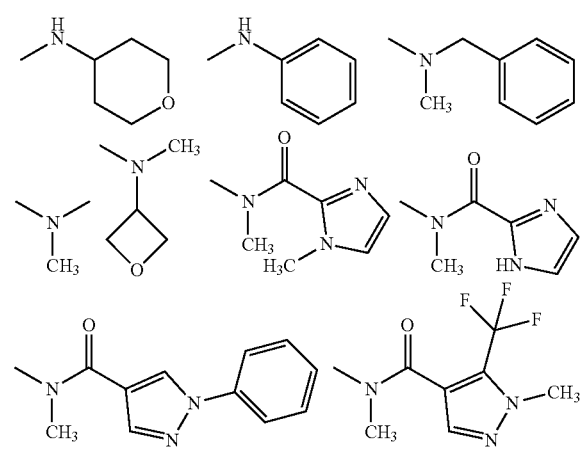

or a pharmaceutically acceptable salt thereof, wherein G is selected from the group:

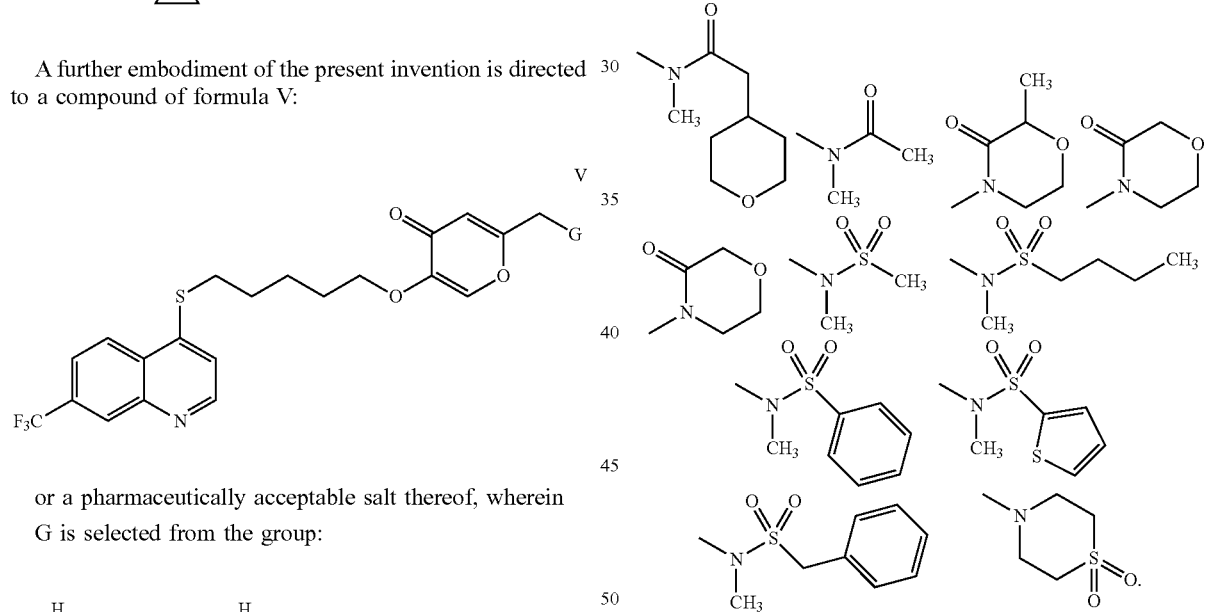

Another embodiment of the present invention is directed to a pharmaceutical composition comprising one or more compounds of the invention, and one or more pharmaceutically acceptable diluents, excipients, or carriers.

A further embodiment of the present invention is directed to a method of treating cancer comprising administering to a patient in need thereof a pharmaceutically effective amount of a compound or composition of the invention. In preferred embodiments the cancer is breast cancer or melanoma.

An additional embodiment of the present invention is directed to a method of treating kidney disease comprising administering to a patient in need thereof a pharmaceutically effective amount of a compound or composition of the invention.

A further embodiment of the present invention is directed to a method of treating heart disease comprising administering to a patient in need thereof a pharmaceutically effective amount of a compound or composition of the invention.

DETAILED DESCRIPTION OF THE INVENTION

Definitions

Figure 1:
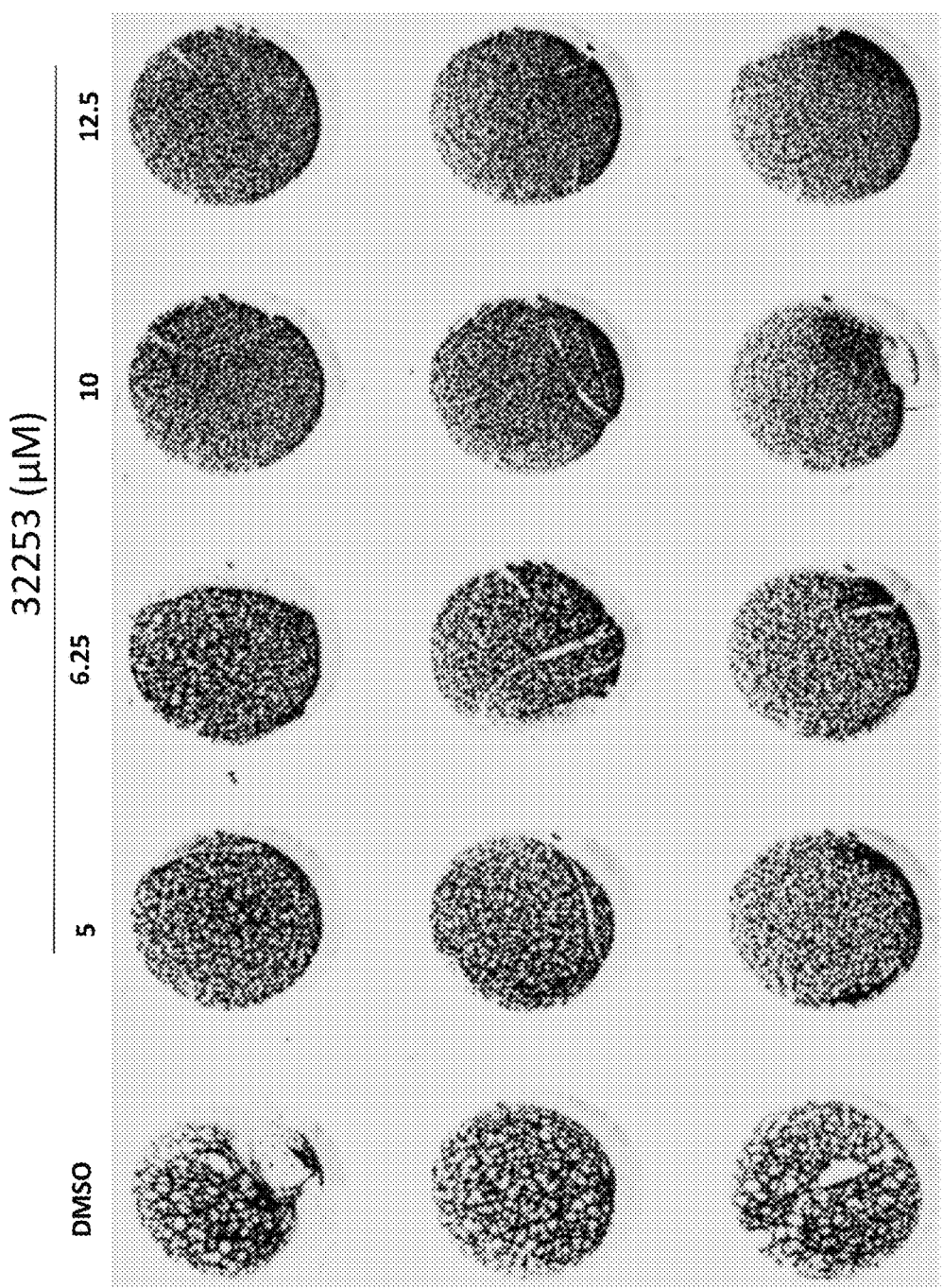
FIG. 1 shows the effect of different concentrations of the Rac1 inhibitor 0032253 on HUVEC tube formation.

The term "substituted," as used herein, means that any one or more hydrogens on the designated atom is replaced with a selection from the indicated group, provided that the designated atom's normal valency is not exceeded, and that the substitution results in a stable compound.

The term "alkyl," as used herein is intended to include both branched and straight-chain saturated aliphatic hydrocarbon groups having the specified number of carbon atoms. For example, $C_{1-4}$ alkyl, is intended to include a hydrocarbon chain that includes between 1 and 4 carbon atoms. Examples of alkyl groups include, but are not limited to, methyl, ethyl, n-propyl, i-propyl, n-butyl, s-butyl, and t-butyl.

The term "alkylene," as used herein, is intended to include both branched and straight-chain saturated aliphatic hydrocarbon diradicals containing the specified number of carbon atoms. For example, $C_{1-7}$ alkylene is intended to include a hydrocarbon chain that contains between 1 and 7 carbon atoms. Examples of alkylene groups include, but are not limited to methylene, ethylene, propylene, butylene, pentylene, hexylene, heptylene, and isopropylene.

The term "phenylene," as used herein, means a disubstituted benzene ring such as a 1,3-substituted benzene ring or a 1,4-substituted benzene ring.

The term "alkoxy," as used herein, represents an alkyl group as defined above with the indicated number of carbon atoms attached through an oxygen bridge. For example, $C_{1-4}$ alkoxy means that the alkoxy group includes between 1 and 4 carbon atoms. Examples of alkoxy include, but are not limited to, methoxy, ethoxy, n-propoxy, i-propoxy, n-butoxy, i-butoxy, s-butoxy, and t-butoxy.

The term "heteroatom," as used herein, means oxygen, sulfur, or nitrogen,

The term "halogen," as used herein, means chlorine, bromine, fluorine or iodine.

The term "ring," as used herein, includes both saturated, unsaturated, and partially unsaturated rings.

One embodiment of the present invention is directed to a compound of formula I:

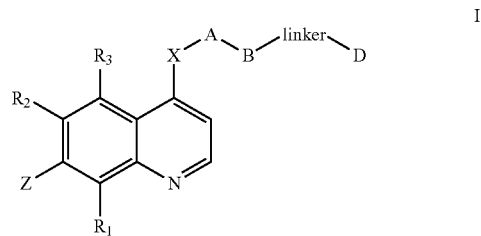

or a pharmaceutically acceptable salt thereof wherein

Z is selected from H, halogen, OH, $C_{1-4}$ alkoxy, and $C_{1-4}$ alkyl wherein said $C_{1-4}$ alkyl is optionally substituted with one or more halogen atoms;

$R_1$, $R_2$, and $R_3$ are independently selected from H and halogen;

X is selected from —O—, —S—, —S(O)—, —SO$_2$—, —CH$_2$—, and —N(R$^a$);

A is $C_{1-7}$ alkylene wherein one or more of the methylene groups is optionally replaced with O, N(R$^b$), S, C(O), or phenylene;

B is a 5- or 6-membered ring having at least one nitrogen atom;

Linker is selected from a bond, —C(O)—, —CH$_2$—NR$^c$—, —CH$_2$—N(R$^d$)—C(O)—, and $C_{1-2}$ alkylene wherein said $C_{1-2}$ alkylene is optionally substituted with OH;

D is selected from:

(i) a 4-7 membered ring optionally containing 1 or 2 heteroatoms independently selected from N and O; wherein said ring optionally includes a C=O; and wherein said ring is optionally substituted with one or more groups selected from halogen, OH, $C_{1-4}$ alkoxy, $C_{1-4}$ alkyl optionally substituted with one or more halogen atoms, C(O)—R$^e$, phenyl optionally substituted with $C_{1-4}$ alkoxy, and a 5- or 6-membered ring containing 1 or 2 heteroatoms independently selected from N and O;

(ii) —N(R$^f$)(R$^g$); and (iii) —C(O)—O—$C_{1-4}$ alkyl and —C(O)—OH;

R$^a$ is selected from H, $C_{1-4}$ alkyl, and C(O)—$C_{1-4}$ alkyl;

R$^b$ is selected from H and $C_{1-4}$ alkyl;

R$^c$ and R$^d$ are independently selected from H and $C_{1-4}$ alkyl, $R^e$ is selected from $C_{1-4}$ alkyl and a 5- or 6-membered ring optionally containing 1 or 2 heteroatoms independently selected from N and O;

$R^f$ is selected from H, $C_{1-4}$ alkyl, C(O)—$C_{1-4}$ alkyl, C(O)—O—$C_{1-4}$ alkyl, and C(O)—OH; and $R^g$ is selected from $C_{1-4}$ alkyl, $C_{1-4}$ alkylene-O—$C_{1-4}$ alkyl.

In a preferred embodiment, the present invention is directed to a compound of formula I or a pharmaceutically acceptable salt thereof wherein Z is selected from H, halogen, and $C_{1-4}$ alkyl wherein said $C_{1-4}$ alkyl is optionally substituted with one or more halogen atoms;

A is $C_{2-7}$ alkylene wherein one or more of the methylene groups is optionally replaced with O, $N(R^b)$, C(O), or phenylene;

D is selected from:

(i) a 4-7 membered ring optionally containing 1 or 2 heteroatoms independently selected from N and O; wherein said ring optionally contains a C=O; and wherein said ring is optionally substituted with one or more groups selected from halogen, OH, $C_{1-4}$ alkoxy, $C_{1-4}$ alkyl optionally substituted with one or more halogen atoms, C(O)—$R^e$, phenyl optionally substituted with $C_{1-4}$ alkoxy, and a 5- or 6-membered ring containing 1 or 2 heteroatoms independently selected from N and O;

(ii) —$N(R^f)(R^g)$; and (iii) —C(O)—O—$C_{1-4}$ alkyl; and $R^b$ is $C_{1-4}$ alkyl.

In a more preferred embodiment, the present invention is directed to a compound of formula I or a pharmaceutically acceptable salt thereof wherein Z is selected from H, Cl, F, $CH_3$, and $CF_3$;

$R_1$, $R_2$, and $R_3$ are independently selected from H and F;

X is selected from —O—, —S—, —S(O)—, —$CH_2$—, and —$N(R^a)$—;

A is selected from —$(CH_2)_m$—, —$(CH_2)_3$—O—$(CH_2)$—, —$(CH_2)_3$—O—$(CH_2)_2$—, —O—$(CH_2)_5$—, —$(CH_2)_5$—O—, —$(CH_2)_3$—$N(CH_3)$—$(CH_2)_2$—, —$(CH_2)_5$—C(O)—, Linker is selected from a bond, —C(O)—, —$CH_2$—, —$(CH_2)_2$—, —$CH(CH_3)$—, —CH(OH)—, —$CH_2$—NH—, —$CH_2$—$N(CH_3)$—, —$CH_2$—$N(CH_3)$—C(O)—, and —$CH_2$—NH—C(O)—;

D is selected from:

(i) a 4-7 membered ring optionally containing 1 or 2 heteroatoms independently selected from N and O; wherein said ring optionally contains a C=O; and wherein said ring is optionally substituted with one or more groups selected from $CH_3$, F, OH, $CF_3$, O—$CH_3$, C(O)—$R^e$, phenyl, 4-methoxyphenyl, and piperazine;

(ii) —$N(R^f)(R^g)$; and (iii) —C(O)—O—$C(CH_3)_3$;

$R^a$ is selected from H, $CH_3$, and C(O)—$CH_3$;

$R^e$ is selected from $CH_3$, $CH(CH_3)_2$, and tetrahydropyran;

$R^f$ is selected from H, $CH_3$, $CH_2$—$CH_3$, C(O)—$CH_3$, and C(O)—O—$C(CH_3)_3$;

$R^g$ is selected from $CH_2$—$CH_2$—O—$CH_3$, $CH(CH_3)$—$CH_2$—O—$CH_3$, $C(CH_3)_2$—$CH_2$—O—$CH_3$, $CH_2$—$C(CH_3)_2$—O—$CH_3$, and $CH_2$—$CH_3$; and m is selected from 3, 4, 5, 6, and 7.

In an another preferred embodiment the present invention is directed to a compound of formula I or a pharmaceutically acceptable salt thereof, wherein Z is selected from halogen and $C_{1-4}$ alkyl wherein said $C_{1-4}$ alkyl is optionally substituted with one or more halogen atoms;

$R_1$, $R_2$, and $R_3$ are independently selected from H and halogen;

X is —S—;

A is $C_{1-7}$ alkylene wherein one or more of the methylene groups is optionally replaced with O, $N(R^b)$, S, C(O), or phenylene;

B is a 5- or 6-membered ring having at least one nitrogen atom;

Linker is selected from a bond, —C(O)—, —$CH_2$—$N(R^c)$—, —$CH_2$—$N(R^d)$—C(O)—, and $C_{1-2}$ alkylene wherein said $C_{1-2}$ alkylene is optionally substituted with OH;

D is selected from:

(i) a 4-7 membered ring optionally containing 1 or 2 heteroatoms independently selected from N and O; wherein said ring optionally contains a C=O; and wherein said ring is optionally substituted with one or more groups selected from halogen, OH, $C_{1-4}$ alkoxy, $C_{1-4}$ alkyl optionally substituted with one or more halogen atoms, C(O)—$R^e$, phenyl optionally substituted with $C_{1-4}$ alkoxy, and a 5 or 6 membered ring containing 1 or 2 heteroatoms independently selected from N and O;

(ii) —$N(R^f)(R^g)$; and (iii) —C(O)—O—$C_{1-4}$ alkyl;

$R^b$ is selected from H and $C_{1-4}$ alkyl;

$R^c$ and $R^d$ are independently selected from H and $C_{1-4}$ alkyl, $R^e$ is selected from $C_{1-4}$ alkyl and a 5- or 6-membered ring optionally containing 1 or 2 heteroatoms independently selected from N and O;

$R^f$ is selected from H, $C_{1-4}$ alkyl, C(O)—$C_{1-4}$ alkyl, and C(O)—O—$C_{1-4}$ alkyl; and $R^g$ is selected from $C_{1-4}$ alkyl, $C_{1-4}$ alkylene-O—$C_{1-4}$ alkyl.

In a preferred embodiment, the present invention is directed to a compound of formula I wherein B is selected from the following:

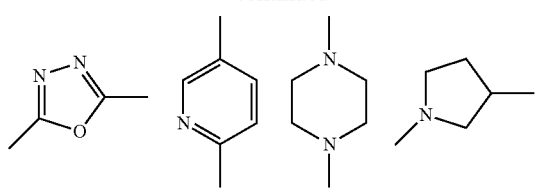

In a more preferred embodiment, the present invention is directed to a compound of formula I wherein B is selected from the following:

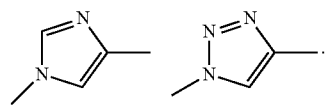

In a further embodiment, the present invention is directed to a compound of formula I wherein D is selected from the following:

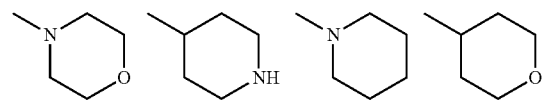

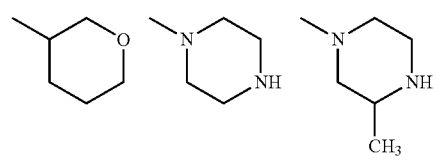

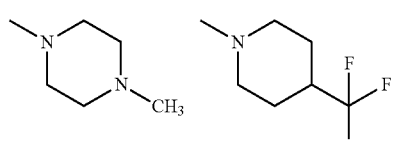

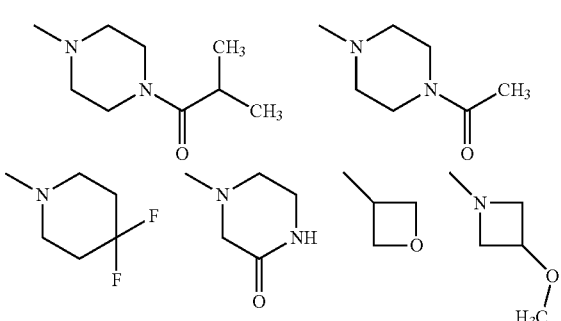

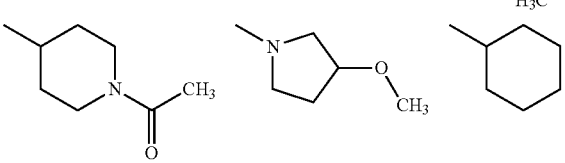

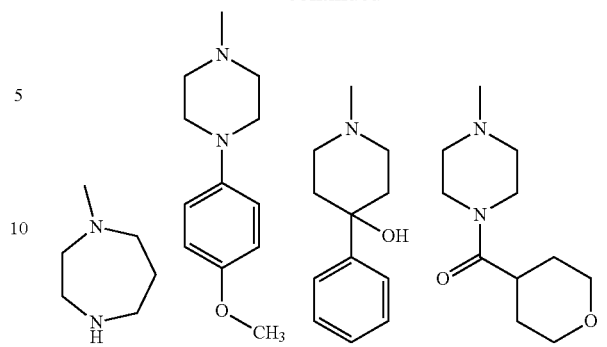

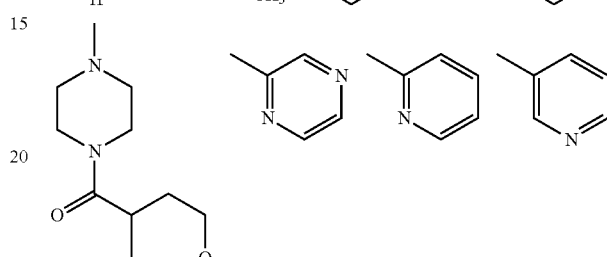

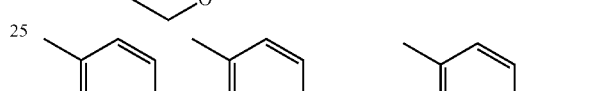

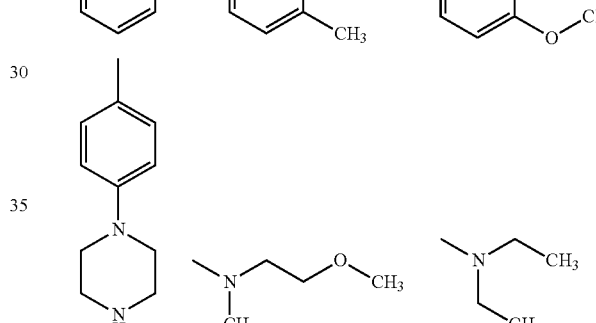

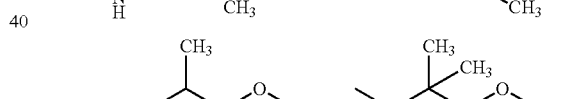

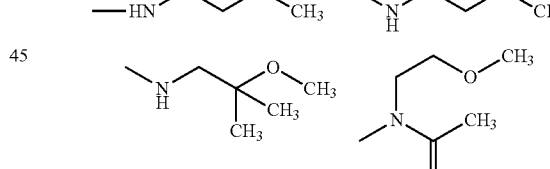

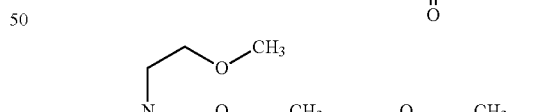

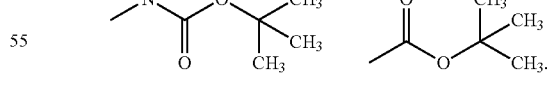

In another preferred embodiment, the present invention is directed to a compound of formula I wherein B is

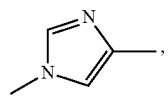

linker is —CH$_2$—, and D is

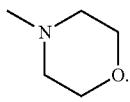

In a further preferred embodiment, the present invention is directed to a compound of formula I wherein B is

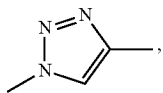

linker is —CH$_2$—, and D is

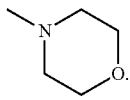

In another preferred embodiment, the present invention is directed to a compound of formula I selected from the following:

4-({(1-[4-({[7-(trifluoromethyl)quinolin-4-yl]sulfanyl}methyl)phenyl]-1H-imidazol-4-yl}methyl)piperazin-2-one;

4-[({4-[4-(piperazin-1-ylmethyl)-1H-imidazol-1-yl]phenyl}methyl)sulfanyl]-7-(trifluoromethyl)quinoline;

4-[({4-[4-(morpholin-4-ylmethyl)-1H-imidazol-1-yl]phenyl}methyl)sulfanyl]-7-(trifluoromethyl)quinoline;

4-{[1-(6-{[7-(trifluoromethyl)quinolin-4-yl]sulfanyl}hexyl)-1H-1,2,3-triazol-4-yl]methyl}morpholin-3-one;

4-({6-[3-(morpholine-4-carbonyl)pyrrolidin-1-yl]hexyl}sulfanyl)-7-(trifluoromethyl)quinoline;

4-({6-[4-(piperidine-4-carbonyl)piperazin-1-yl]hexyl}sulfanyl)-7-(trifluoromethyl)quinoline;

4-({6-[4-(oxane-4-carbonyl)piperazin-1-yl]hexyl}sulfanyl)-7-(trifluoromethyl)quinoline;

4-({6-[4-(morpholine-4-carbonyl)piperazin-1-yl]hexyl}sulfanyl)-7-(trifluoromethyl)quinoline;

tert-butyl 4-(6-{[7-(trifluoromethyl)quinolin-4-yl]sulfanyl}hexyl)piperazine-1-carboxylate;

1-[3-(morpholin-4-ylmethyl)pyrrolidin-1-yl]-6-{[7-(trifluoromethyl)quinolin-4-yl]sulfanyl}hexan-1-one;

4-({6-[4-(oxan-4-ylmethyl)-1H-1,2,3-triazol-1-yl]hexyl}sulfanyl)-7-(trifluoromethyl)quinoline;

4-[(6-{4-[(3-methylpiperazin-1-yl)methyl]-1H-1,2,3-triazol-1-yl}hexyl)sulfanyl]-7-(trifluoromethyl)quinoline;

4-methoxy-N-methyl-N-{[1-(6-{[7-(trifluoromethyl)quinolin-4-yl]sulfanyl}hexyl)-1H-imidazol-4-yl]methyl}aniline;

1-{4-[(1-{6-[(7-fluoroquinolin-4-yl)sulfanyl]hexyl}-1H-imidazol-4-yl)methyl]piperazin-1-yl}-2-methylpropan-1-one;

4-[(6-{4-[(4,4-difluoropiperidin-1-yl)methyl]-1H-imidazol-1-yl}hexyl)sulfanyl]-7-(trifluoromethyl)quinoline;

7-(trifluoromethyl)-4-{[6-(4-{[4-(trifluoromethyl)piperidin-1-yl]methyl}-1H-imidazol-1-yl)hexyl]sulfanyl}quinoline;

4-{[6-(4-phenyl-1H-imidazol-1-yl)hexyl]sulfanyl}-7-(trifluoromethyl)quinoline;

4-phenyl-1-{[1-(6-{[7-(trifluoromethyl)quinolin-4-yl]sulfanyl}hexyl)-1H-imidazol-4-yl]methyl}piperidin-4-ol;

4-(piperazin-1-yl)-N-{[1-(6-{[7-(trifluoromethyl)quinolin-4-yl]sulfanyl}hexyl)-1H-imidazol-4-yl]methyl}aniline;

7-fluoro-4-({6-[4-(morpholin-4-ylmethyl)-1H-imidazol-1-yl]hexyl}sulfanyl)quinoline;

4-[(6-{4-[1-(morpholin-4-yl)ethyl]-1H-imidazol-1-yl}hexyl)sulfanyl]-7-(trifluoromethyl)quinoline;

phenyl[1-(6-{[7-(trifluoromethyl)quinolin-4-yl]sulfanyl}hexyl)-1H-imidazol-4-yl]methanol;

N-[(1-{6-[(7-fluoroquinolin-4-yl)sulfanyl]hexyl}-1H-imidazol-4-yl)methyl]aniline;

4-[(1-{6-[(7-fluoroquinolin-4-yl)sulfanyl]hexyl}-1H-imidazol-4-yl)methyl]piperazin-2-one;

4-{6-[4-(morpholin-4-ylmethyl)-1H-imidazol-1-yl]hexanesulfinyl}-7-(trifluoromethyl)quinoline;

N-{[1-(6-{[7-(trifluoromethyl)quinolin-4-yl]sulfanyl}hexyl)-1H-1,2,3-triazol-4-yl]methyl}pyridin-3-amine;

4-({6-[4-(4-methoxyphenyl)piperazin-1-yl]hexyl}sulfanyl)-7-(trifluoromethyl)quinoline;

4-({6-[4-(piperidin-1-ylmethyl)-1H-imidazol-1-yl]hexyl}sulfanyl)-7-(trifluoromethyl)quinoline;

4-({6-[4-(piperidin-4-ylmethyl)-1H-1,2,3-triazol-1-yl]hexyl}sulfanyl)-7-(trifluoromethyl)quinoline;

4-({6-[6-(morpholin-4-ylmethyl)pyridin-3-yl]hexyl}sulfanyl)-7-(trifluoromethyl)quinoline;

8-fluoro-4-({6-[4-(morpholin-4-ylmethyl)-1H-1,2,3-triazol-1-yl]hexyl}sulfanyl)quinoline;

6-fluoro-4-({6-[4-(morpholin-4-ylmethyl)-1H-1,2,3-triazol-1-yl]hexyl}sulfanyl)quinoline;

N-{[1-(6-{[7-(trifluoromethyl)quinolin-4-yl]sulfanyl}hexyl)-1H-1,2,3-triazol-4-yl]methyl}pyridin-2-amine;

N-methyl-N-{[1-(6-{[7-(trifluoromethyl)quinolin-4-yl]sulfanyl}hexyl)-1H-1,2,3-triazol-4-yl]methyl}pyrazine-2-carboxamide;

N-{[1-(6-{[7-(trifluoromethyl)quinolin-4-yl]sulfanyl}hexyl)-1H-1,2,3-triazol-4-yl]methyl}oxetan-3-amine;

N-{[1-(6-{[7-(trifluoromethyl)quinolin-4-yl]sulfanyl}hexyl)-1H-1,2,3-triazol-4-yl]methyl}oxan-3-amine;

(1-methoxypropan-2-yl)({[1-(6-{[7-(trifluoromethyl)quinolin-4-yl]sulfanyl}hexyl)-1H-1,2,3-triazol-4-yl]methyl})amine;

(1-methoxy-2-methylpropan-2-yl)({[1-(6-{[7-(trifluoromethyl)quinolin-4-yl]sulfanyl}hexyl)-1H-1,2,3-triazol-4-yl]methyl})amine;

4-[(6-{4-[(3-methoxyazetidin-1-yl)methyl]-1H-1,2,3-triazol-1-yl}hexyl)sulfanyl]-7-(trifluoromethyl)quinoline;

(2-methoxy-2-methylpropyl)({[1-(6-{[7-(trifluoromethyl)quinolin-4-yl]sulfanyl}hexyl)-1H-1,2,3-triazol-4-yl]methyl})amine;

4-{[6-(4-{[4-(4-methoxyphenyl)piperazin-1-yl]methyl}-1H-1,2,3-triazol-1-yl)hexyl]sulfanyl}-7-(trifluoromethyl)quinoline;

N-{[1-(6-{[7-(trifluoromethyl)quinolin-4-yl]sulfanyl}hexyl)-1H-1,2,3-triazol-4-yl]methyl}pyrazine-2-carboxamide;

4-[(6-{4-[(3-methoxypyrrolidin-1-yl)methyl]-1H-1,2,3-triazol-1-yl}hexyl)sulfanyl]-7-(trifluoromethyl)quinoline;

7,8-difluoro-4-({6-[4-(morpholin-4-ylmethyl)-1H-1,2,3-triazol-1-yl]hexyl}sulfanyl)quinoline;

5,7-difluoro-4-({6-[4-(morpholin-4-ylmethyl)-1H-1,2,3-triazol-1-yl]hexyl}sulfanyl)quinoline;

1-(4-{[1-(6-{[7-(trifluoromethyl)quinolin-4-yl]
sulfanyl}hexyl)-1H-1,2,3-triazol-4-yl]methyl}piperidin-
1-yl)ethan-1-one;
4-{[6-(4-{[4-(oxane-4-carbonyl)piperazin-1-yl]methyl}-
1H-1,2,3-triazol-1-yl)hexyl]sulfanyl}-7-(trifluoromethyl)
quinoline;
2-methyl-1-(4-{[1-(6-{[7-(trifluoromethyl)quinolin-4-yl]
sulfanyl}hexyl)-1H-1,2,3-triazol-4-yl]methyl}piperazin-
1-yl)propan-1-one;
1-(4-{[1-(6-{[7-(trifluoromethyl)quinolin-4-yl]
sulfanyl}hexyl)-1H-1,2,3-triazol-4-yl]methyl}piperazin-
1-yl)ethan-1-one;
N-{[1-(6-{[7-(trifluoromethyl)quinolin-4-yl]
sulfanyl}hexyl)-1H-1,2,3-triazol-4-yl]methyl}pyridine-
2-carboxamide;
4-({6-[4-(cyclohexylmethyl)-1H-1,2,3-triazol-1-yl]
hexyl}sulfanyl)-7-(trifluoromethyl)quinoline;
N-{[1-(6-{[7-(trifluoromethyl)quinolin-4-yl]
sulfanyl}hexyl)-1H-1,2,3-triazol-4-yl]methyl}oxane-4-
carboxamide;
4-[(6-{4-[2-(morpholin-4-yl)ethyl]-1H-1,2,3-triazol-1-
yl}hexyl)sulfanyl]-7-(trifluoromethyl)quinoline;
4-({6-[5-(morpholin-4-ylmethyl)-1H-pyrazol-1-yl]
hexyl}sulfanyl)-7-(trifluoromethyl)quinoline;
4-({6-[3-(morpholin-4-ylmethyl)-1H-pyrazol-1-yl]
hexyl}sulfanyl)-7-(trifluoromethyl)quinoline;
N-{[1-(6-{[7-(trifluoromethyl)quinolin-4-yl]
sulfanyl}hexyl)-1H-1,2,3-triazol-4-yl]
methyl}cyclohexanecarboxamide;
N-{[1-(6-{[7-(trifluoromethyl)quinolin-4-yl]
sulfanyl}hexyl)-1H-1,2,3-triazol-4-yl]
methyl}benzamide;
N-methyl-N-{[1-(6-{[7-(trifluoromethyl)quinolin-4-yl]
sulfanyl}hexyl)-1H-imidazol-4-yl]methyl}aniline;
N-{[1-(6-{[7-(trifluoromethyl)quinolin-4-yl]
sulfanyl}hexyl)-1H-imidazol-4-yl]methyl}aniline;
4-methoxy-N-{[1-(6-{[7-(trifluoromethyl)quinolin-4-yl]
sulfanyl}hexyl)-1H-imidazol-4-yl]methyl}aniline;
4-methyl-N-{[1-(6-{[7-(trifluoromethyl)quinolin-4-yl]
sulfanyl}hexyl)-1H-imidazol-4-yl]methyl}aniline;
(2-methoxyethyl)(methyl){[1-(6-{[7-(trifluoromethyl)qui-
nolin-4-yl]sulfanyl}hexyl)-1H-imidazol-4-yl]
methyl}amine;
4-({6-[4-(1,4-diazepan-1-ylmethyl)-1H-1,2,3-triazol-1-yl]
hexyl}sulfanyl)-7-(trifluoromethyl)quinoline;
4-[({5-[4-(morpholin-4-ylmethyl)-1H-1,2,3-triazol-1-yl]
pentyl}oxy)methyl]-7-(trifluoromethyl)quinoline;
4-({6-[4-(piperidin-1-ylmethyl)-1H-1,2,3-triazol-1-yl]
hexyl}sulfanyl)-7-(trifluoromethyl)quinoline;
4-{[1-(6-{[7-(trifluoromethyl)quinolin-4-yl]
sulfanyl}hexyl)-1H-1,2,3-triazol-4-yl]methyl}piperazin-
2-one;
4-({6-[4-(morpholin-4-ylmethyl)-1H-pyrazol-1-yl]
hexyl}sulfanyl)-7-(trifluoromethyl)quinoline;
diethyl({[1-(6-{[7-(trifluoromethyl)quinolin-4-yl]
sulfanyl}hexyl)-1H-1,2,3-triazol-4-yl]methyl})amine;
4-({6-[3-(morpholin-4-ylmethyl)-1,2,4-oxadiazol-5-yl]
hexyl}sulfanyl)-7-(trifluoromethyl)quinoline;
7-chloro-4-({6-[4-(morpholin-4-ylmethyl)-1H-1,2,3-tri-
azol-1-yl]hexyl}sulfanyl)quinoline;
7-fluoro-4-({6-[4-(morpholin-4-ylmethyl)-1H-1,2,3-triazol-
1-yl]hexyl}sulfanyl)quinoline;
4-({6-[4-(piperazin-1-ylmethyl)-1H-imidazol-1-yl]
hexyl}sulfanyl)-7-(trifluoromethyl)quinoline;
(2-methoxyethyl)({[1-(6-{[7-(trifluoromethyl)quinolin-4-
yl]sulfanyl}hexyl)-1H-imidazol-4-yl]methyl})amine;
4-({6-[5-(morpholin-4-ylmethyl)-1,3,4-oxadiazol-2-yl]
hexyl}sulfanyl)-7-(trifluoromethyl)quinoline;
7-methyl-4-({6-[4-(morpholin-4-ylmethyl)-1H-1,2,3-tri-
azol-1-yl]hexyl}sulfanyl)quinoline;
N-(2-methoxyethyl)-N-{[1-(6-{[7-(trifluoromethyl)quino-
lin-4-yl]sulfanyl}hexyl)-1H-1,2,3-triazol-4-yl]
methyl}acetamide;
N-{6-[4-(morpholin-4-ylmethyl)-1H-1,2,3-triazol-1-yl]
hexyl}-N-[7-(trifluoromethyl)quinolin-4-yl]acetamide;
4-({6-[4-(morpholin-4-ylmethyl)-1H-1,2,3-triazol-1-yl]
hexyl}sulfanyl)quinoline;
(2-methoxyethyl)(methyl){[1-(6-{[7-(trifluoromethyl)qui-
nolin-4-yl]sulfanyl}hexyl)-1H-1,2,3-triazol-4-yl]
methyl})amine;
N-methyl-N-{6-[4-(morpholin-4-ylmethyl)-1H-1,2,3-tri-
azol-1-yl]hexyl}-7-(trifluoromethyl)quinolin-4-amine;
4-[(6-{4-[(4-methylpiperazin-1-yl)methyl]-1H-1,2,3-tri-
azol-1-yl}hexyl)sulfanyl]-7-(trifluoromethyl)quinoline;
4-({6-[4-(piperazin-1-ylmethyl)-1H-1,2,3-triazol-1-yl]
hexyl}sulfanyl)-7-(trifluoromethyl)quinoline;
4-{[(3-{[4-(morpholin-4-ylmethyl)-1H-1,2,3-triazol-1-yl]
methyl}phenyl)methyl]sulfanyl}-7-(trifluoromethyl)qui-
noline;
4-{7-[4-(morpholin-4-ylmethyl)-1H-1,2,3-triazol-1-yl]hep-
tyl}-7-(trifluoromethyl)quinoline;
4-methyl-N-{[1-(6-{[7-(trifluoromethyl)quinolin-4-yl]
sulfanyl}hexyl)-1H-1,2,3-triazol-4-yl]methyl}aniline;
4-methoxy-N-{[1-(6-{[7-(trifluoromethyl)quinolin-4-yl]
sulfanyl}hexyl)-1H-1,2,3-triazol-4-yl]methyl}aniline;
4-({7-[4-(morpholin-4-ylmethyl)-1H-1,2,3-triazol-1-yl]
heptyl}oxy)-7-(trifluoromethyl)quinoline;
N-{[1-(6-{[7-(trifluoromethyl)quinolin-4-yl]
sulfanyl}hexyl)-1H-1,2,3-triazol-4-yl]methyl}aniline;
4-({6-[5-(morpholin-4-ylmethyl)-1H-imidazol-1-yl]
hexyl}sulfanyl)-7-(trifluoromethyl)quinoline;
4-({6-[4-(morpholin-4-ylmethyl)-1H-imidazol-1-yl]
hexyl}sulfanyl)-7-(trifluoromethyl)quinoline;
N-{6-[4-(morpholin-4-ylmethyl)-1H-1,2,3-triazol-1-yl]
hexyl}-7-(trifluoromethyl)quinolin-4-amine;
4-({6-[4-(morpholin-4-ylmethyl)-1H-1,2,3-triazol-1-yl]
hexyl}oxy)-7-(trifluoromethyl)quinoline;
(2-methoxyethyl)({[1-(6-{[7-(trifluoromethyl)quinolin-4-
yl]sulfanyl}hexyl)-1H-1,2,3-triazol-4-yl]methyl})amine;
tert-butyl N-(2-methoxyethyl)-N-{[1-(6-{[7-(trifluorom-
ethyl)quinolin-4-yl]sulfanyl}hexyl)-1H-1,2,3-triazol-4-
yl]methyl}carbamate;
methyl({2-[4-(morpholin-4-ylmethyl)-1H-1,2,3-triazol-1-
yl]ethyl})(3-{[7-(trifluoromethyl)quinolin-4-yl]
sulfanyl}propyl)amine;
4-[(3-{3-[4-(morpholin-4-ylmethyl)-1H-1,2,3-triazol-1-yl]
propoxy}propyl)sulfanyl]-7-(trifluoromethyl)quinoline;
4-[(3-{2-[4-(morpholin-4-ylmethyl)-1H-1,2,3-triazol-1-yl]
ethoxy}propyl)sulfanyl]-7-(trifluoromethyl)quinoline;
4-({7-[4-(morpholin-4-ylmethyl)-1H-1,2,3-triazol-1-yl]
heptyl}sulfanyl)-7-(trifluoromethyl)quinoline;
4-({6-[4-(morpholin-4-ylmethyl)-1H-1,2,3-triazol-1-yl]
hexyl}sulfanyl)-7-(trifluoromethyl)quinoline;
4-({3-[4-(morpholin-4-ylmethyl)-1H-1,2,3-triazol-1-yl]
propyl}sulfanyl)-7-(trifluoromethyl)quinoline;
4-({4-[4-(morpholin-4-ylmethyl)-1H-1,2,3-triazol-1-yl]
butyl}sulfanyl)-7-(trifluoromethyl)quinoline;
4-({5-[4-(morpholin-4-ylmethyl)-1H-1,2,3-triazol-1-yl]
pentyl}sulfanyl)-7-(trifluoromethyl)quinoline;
4-[(5-{[6-(morpholin-4-ylmethyl)pyridin-3-yl]oxy}pentyl)
sulfanyl]-7-(trifluoromethyl)quinoline;
diethyl((5-[(5-{[7-(trifluoromethyl)quinolin-4-yl]
sulfanyl}pentyl)oxy]pyridin-2-yl)methyl)amine; and 4-[[1-[[4-[[7-(trifluoromethyl)-4-quinolyl]sulfanylmethyl]phenyl]methyl]imidazol-4-yl]methyl]morpholine.

In a more preferred embodiment the compound of formula I is:

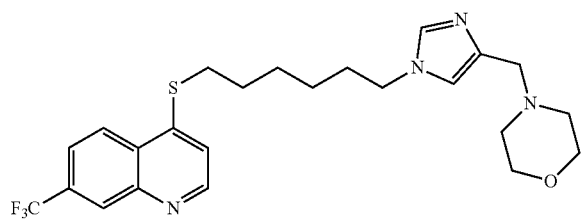 [SMILES: FC(F)(F)c1ccc2c(SCCCCCCn3cc(CN4CCOCC4)nn3)ccnc2c1]

Additionally, in another more preferred embodiment the compound of formula I is:

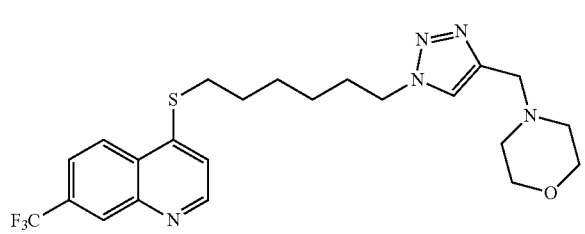

In another more preferred embodiment the compound of formula I is:

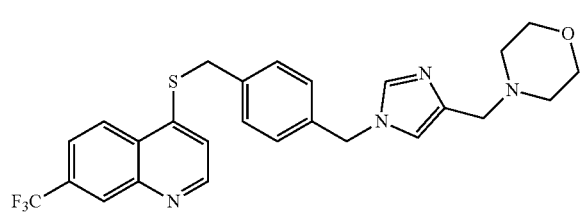 [SMILES: FC(F)(F)c1ccc2c(SCc3ccc(Cn4cnc(CN5CCOCC5)c4)cc3)ccnc2c1]

In a further more preferred embodiment the compound of formula I is:

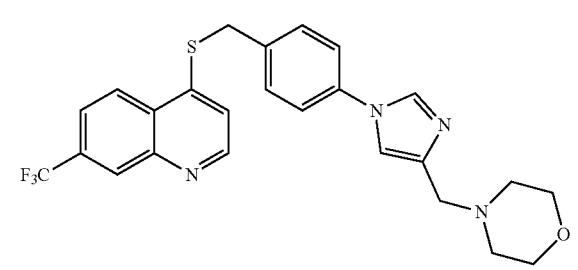 [SMILES: FC(F)(F)c1ccc2c(SCc3ccc(-n4cnc(CN5CCOCC5)c4)cc3)ccnc2c1]

An additional embodiment of the present invention is directed to a compound of formula II:

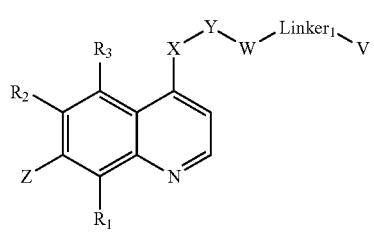

or a pharmaceutically acceptable salt thereof, wherein

Z is selected from H, halogen, OH, $C_{1-4}$ alkoxy, and $C_{1-4}$ alkyl wherein said $C_{1-4}$ alkyl is optionally substituted with one or more halogen atoms;

$R_1$, $R_2$, and $R_3$ are independently selected from H and halogen;

X is selected from —O—, —S—, —S(O)—, —SO$_2$—, —CH$_2$—, and —N(R$^a$)—;

Y is $C_{1-7}$ alkylene wherein one or more of the methylene groups is optionally replaced with S, N(R$^j$), NH—C(O), and C(O)—NH;

W is phenylene;

Linker$_1$ is selected from a bond, —CH$_2$— and —C(O)—;

V is a 5- or 6-membered ring optionally containing 1 or 2 heteroatoms independently selected from N and O; wherein said ring optionally contains a C═O; and wherein said ring is optionally substituted with $C_{1-4}$ alkyl, N(R$^k$)(R$^l$), or C(O)—$C_{1-4}$ alkyl;

R$^a$ is selected from H, $C_{1-4}$ alkyl, and C(O)—$C_{1-4}$ alkyl;

R$^j$ is selected from H, $C_{1-4}$ alkyl, and C(O)—$C_{1-4}$ alkyl; and

R$^k$ and R$^l$ are independently selected from H and $C_{1-4}$ alkyl.

A further embodiment of the present invention is directed to a compound of formula II or pharmaceutically acceptable salt thereof wherein Z is selected from halogen and CF$_3$;

$R_1$ and $R_2$ are H;

X is —S—;

Y is $C_{1-7}$ alkylene wherein one or more of the methylene groups is optionally replaced with N(R$^j$), NH—C(O), and C(O)—NH; and V is a 6 membered ring containing 1 or 2 heteroatoms independently selected from N and O; wherein said ring optionally contains a C═O; and wherein said ring is optionally substituted with N(R$^k$)(R$^l$).

In another embodiment, the present invention is directed to a compound of formula II or a pharmaceutically acceptable salt thereof wherein Z is selected from Cl, F, and CF$_3$;

$R_1$ and $R_2$ are H;

$R_3$ is selected from H and F;

X is —S—;

Y is selected from —(CH$_2$)$_p$—, —(CH$_2$)$_q$—NH—, —(CH$_2$)$_t$—NH—C(O)—, —(CH$_2$)$_v$—C(O)—HN—, —(CH$_2$)$_6$—N(C(O)—CH$_3$)—, and —(CH$_2$)$_4$—C(O)—NH—CH$_2$—;

V is a 6 membered ring containing 1 or 2 heteroatoms independently selected from N and O; wherein said ring is optionally substituted with C═O; and wherein said ring is optionally substituted with NH$_2$;

p is selected from 1 and 2;

q is selected from 4, 5, and 6;

t is selected from 5 and 6; and v is 5.

In a preferred embodiment, the present invention is directed to a compound of formula II wherein V is selected from the following:

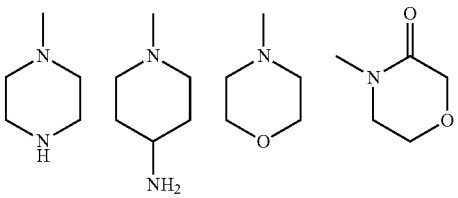

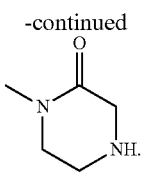

In a more preferred embodiment, the present invention is directed to a compound of formula II wherein Y is —(CH$_2$)$_q$NH— and V is selected from the following:

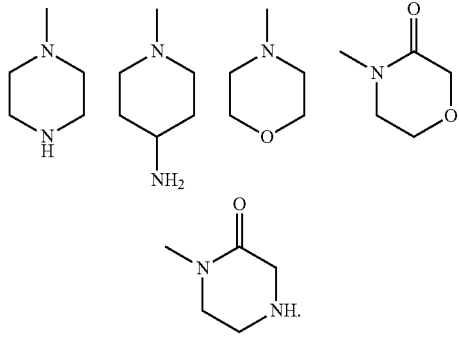

In another preferred embodiment, the present invention is directed to a compound of formula II selected from the following:

4-(piperazine-1-carbonyl)-N-(6-{[7-(trifluoromethyl)quinolin-4-yl]sulfanyl}hexyl)aniline;
4-{[4-({[7-(trifluoromethyl)quinolin-4-yl]sulfanyl}methyl)phenyl]methyl}morpholin-3-one;
4-({2-[3-(morpholine-4-carbonyl)phenyl]ethyl}sulfanyl)-7-(trifluoromethyl)quinoline;
4-{[3-({[7-(trifluoromethyl)quinolin-4-yl]sulfanyl}methyl)phenyl]methyl}morpholin-3-one;
4-{3-[(6-{[7-(trifluoromethyl)quinolin-4-yl]sulfanyl}hexyl)amino]phenyl}morpholin-3-one;
3-(morpholin-4-yl)-N-(6-{[7-(trifluoromethyl)quinolin-4-yl]sulfanyl}hexyl)aniline;
1-{4-[(6-{[7-(trifluoromethyl)quinolin-4-yl]sulfanyl}hexyl)amino]phenyl}piperazin-2-one;
4-(piperazin-1-yl)-N-(6-{[7-(trifluoromethyl)quinolin-4-yl]sulfanyl}hexyl)benzamide;
1-{4-[(6-{[7-(trifluoromethyl)quinolin-4-yl]sulfanyl}hexyl)amino]phenyl}piperidin-4-amine;
4-(piperazin-1-yl)-N-(5-{[7-(trifluoromethyl)quinolin-4-yl]sulfanyl}pentyl)benzamide;
N-{6-[(5,7-difluoroquinolin-4-yl)sulfanyl]hexyl}-4-(piperazin-1-yl)aniline;
N-{6-[(7-chloroquinolin-4-yl)sulfanyl]hexyl}-4-(piperazin-1-yl)aniline;
N-{6-[(7-fluoroquinolin-4-yl)sulfanyl]hexyl}-4-(piperazin-1-yl)aniline;
4-(piperazin-1-yl)-N-(5-{[7-(trifluoromethyl)quinolin-4-yl]sulfanyl}pentyl)aniline;
3-(piperazin-1-yl)-N-(6-{[7-(trifluoromethyl)quinolin-4-yl]sulfanyl}hexyl)aniline;
N-[4-(piperazin-1-yl)phenyl]-N-(6-{[7-(trifluoromethyl)quinolin-4-yl]sulfanyl}hexyl)acetamide;
4-(piperazin-1-yl)-N-(4-{[7-(trifluoromethyl)quinolin-4-yl]sulfanyl}butyl)aniline;
4-(morpholin-4-yl)-N-(6-{[7-(trifluoromethyl)quinolin-4-yl]sulfanyl}hexyl)aniline;
N-{[4-(piperazin-1-yl)phenyl]methyl}-5-{[7-(trifluoromethyl)quinolin-4-yl]sulfanyl}pentanamide;
N-[4-(piperazin-1-yl)phenyl]-6-{[7-(trifluoromethyl)quinolin-4-yl]sulfanyl}hexanamide; and
4-(piperazin-1-yl)-N-(6-{[7-(trifluoromethyl)quinolin-4-yl]sulfanyl}hexyl)aniline.

In a more preferred embodiment, the compound of formula II is:

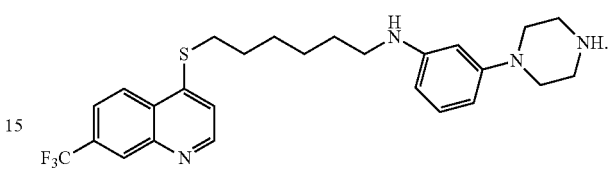

Another embodiment of the present invention is directed to a compound of formula

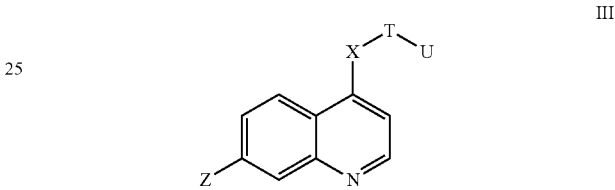

or a pharmaceutically acceptable salt thereof wherein
Z is selected from H, halogen, OH, C$_{1-4}$ alkoxy, and C$_{1-4}$ alkyl wherein said C$_{1-4}$ alkyl is optionally substituted with one or more halogen atoms;
X is selected from —O—, —S—, —S(O)—, —SO-$_2$, —CH$_2$—, and —N(R$^a$)—;
T is a C$_{5-7}$ alkylene wherein one or more of the methylene groups is optionally replaced with O, N(R$^b$), S, C(O), NH—C(O), and C(O)—NH;
U is selected from:
(i) a 4-9 membered monocyclic or bicyclic ring optionally containing 1, 2, or 3 heteroatoms independently selected from N and O; wherein said ring optionally contains 1 or 2 C=O, and wherein said ring is optionally substituted with a C$_{1-4}$ alkyl wherein said C$_{1-4}$ alkyl is optionally substituted with OH, or C$_{1-4}$ alkoxy; and
(ii) —N(C$_{1-4}$ alkyl)$_2$;
R$^a$ is selected from H, C$_{1-4}$ alkyl, and C(O)—C$_{1-4}$ alkyl; and
R$^b$ is selected from H and C$_{1-4}$ alkyl.

In a preferred embodiment, the present invention provides a compound of formula III wherein
Z is CF$_3$;
X is —S—;
T is selected from —(CH$_2$)$_w$—, —(CH$_2$)$_6$—NH—C(O)—, —(CH$_2$)$_5$—C(O)—NH—, —(CH$_2$)$_5$—C(O)—, —(CH$_2$)$_6$—NH—, and —(CH$_2$)$_5$—C(O)—NH—CH$_2$—;
U is a 4-9 membered monocyclic or bicyclic ring optionally containing 1, 2, or 3 heteroatoms independently selected from N and O; wherein said ring optionally contains 1 or 2 C=O, and wherein said ring is optionally substituted with CH$_3$, CH$_2$OH, or OCH$_3$; and
w is selected from 5 and 6.

In another preferred embodiment, the present invention is directed to a compound of formula III where U is selected from:

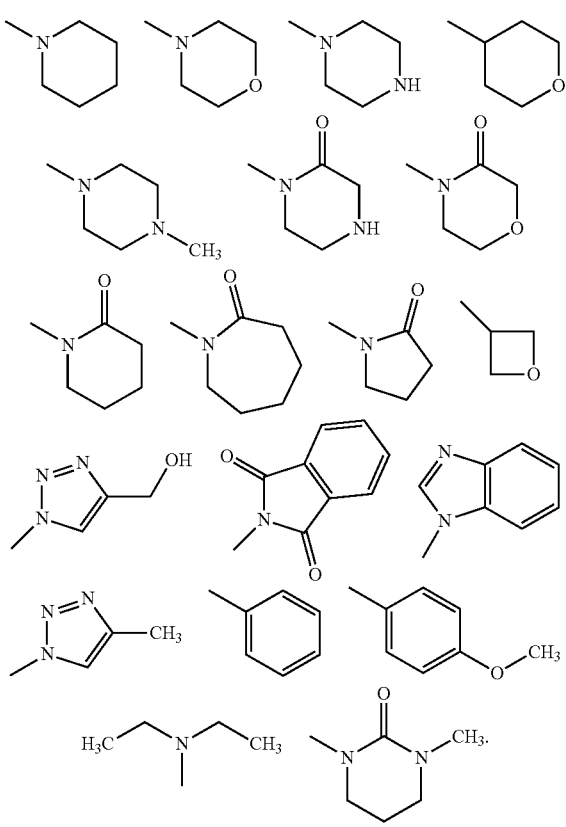

In a more preferred embodiment, the present invention is directed to a compound of formula III selected from the following:
1-methyl-3-(6-{[7-(trifluoromethyl)quinolin-4-yl]sulfanyl}hexyl)-1,3-diazinan-2-one
N-(6-{[7-(trifluoromethyl)quinolin-4-yl]sulfanyl}hexyl)piperazine-1-carboxamide;
N-(6-{[7-(trifluoromethyl)quinolin-4-yl]sulfanyl}hexyl)piperidine-1-carboxamide;
1-(6-{[7-(trifluoromethyl)quinolin-4-yl]sulfanyl}hexyl)piperazin-2-one;
3,3-diethyl-1-(6-{[7-(trifluoromethyl)quinolin-4-yl]sulfanyl}hexyl)urea;
N-(6-{[7-(trifluoromethyl)quinolin-4-yl]sulfanyl}hexyl)morpholine-4-carboxamide;
4-{[6-(piperazin-1-yl)hexyl]sulfanyl}-7-(trifluoromethyl)quinoline;
1-(piperazin-1-yl)-6-{[7-(trifluoromethyl)quinolin-4-yl]sulfanyl}hexan-1-one;
1-(4-methylpiperazin-1-yl)-6-{[7-(trifluoromethyl)quinolin-4-yl]sulfanyl}hexan-1-one;
2-(6-{[7-(trifluoromethyl)quinolin-4-yl]sulfanyl}hexyl)-2,3-dihydro-1H-isoindole-1,3-dione;
1-(6-{[7-(trifluoromethyl)quinolin-4-yl]sulfanyl}hexyl)azepan-2-one;
1-(6-{[7-(trifluoromethyl)quinolin-4-yl]sulfanyl}hexyl)pyrrolidin-2-one;
N-(oxan-4-yl)-6-{[7-(trifluoromethyl)quinolin-4-yl]sulfanyl}hexanamide;
1-(piperidin-1-yl)-6-{[7-(trifluoromethyl)quinolin-4-yl]sulfanyl}hexan-1-one;
N-(oxetan-3-yl)-6-{[7-(trifluoromethyl)quinolin-4-yl]sulfanyl}hexanamide;
4-(6-{[7-(trifluoromethyl)quinolin-4-yl]sulfanyl}hexyl)morpholin-3-one;
N-(4-methoxyphenyl)-6-{[7-(trifluoromethyl)quinolin-4-yl]sulfanyl}hexanamide;
N-[(4-methoxyphenyl)methyl]-6-{[7-(trifluoromethyl)quinolin-4-yl]sulfanyl}hexanamide;
N-phenyl-6-{[7-(trifluoromethyl)quinolin-4-yl]sulfanyl}hexanamide;
4-{[6-(1H-1,3-benzodiazol-1-yl)hexyl]sulfanyl}-7-(trifluoromethyl)quinoline;
1-(6-{[7-(trifluoromethyl)quinolin-4-yl]sulfanyl}hexyl)piperidin-2-one;
4-methoxy-N-(6-{[7-(trifluoromethyl)quinolin-4-yl]sulfanyl}hexyl)aniline;
1-(morpholin-4-yl)-6-{[7-(trifluoromethyl)quinolin-4-yl]sulfanyl}hexan-1-one;
4-{[6-(piperidin-1-yl)hexyl]sulfanyl}-7-(trifluoromethyl)quinoline;
4-{[6-(morpholin-4-yl)hexyl]sulfanyl}-7-(trifluoromethyl)quinoline;
4-{[6-(4-methyl-1H-1,2,3-triazol-1-yl)hexyl]sulfanyl}-7-(trifluoromethyl)quinoline; and
[1-(5-{[7-(trifluoromethyl)quinolin-4-yl]sulfanyl}pentyl)-1H-1,2,3-triazol-4-yl]methanol.

A further embodiment of the present invention is directed to a compound of formula IV:

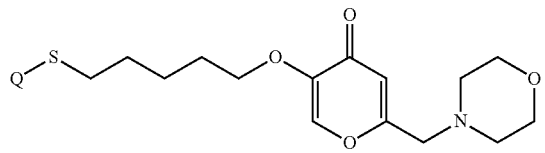

or a pharmaceutically acceptable salt thereof, wherein Q is selected from the group:

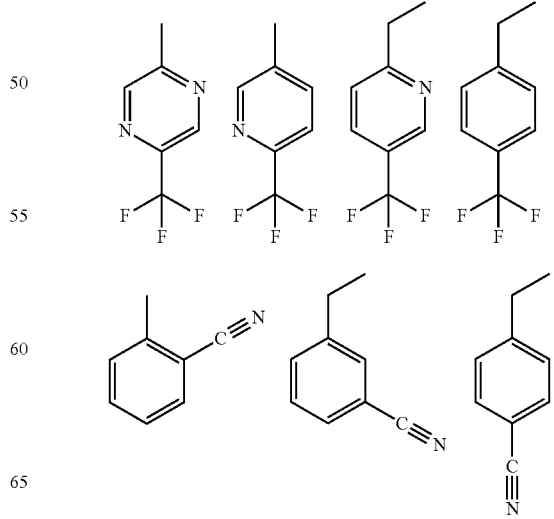

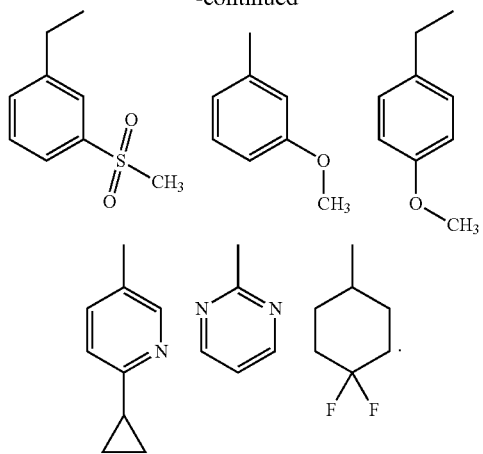

Preferred compounds of formula IV include:
2-[(5-{[6-(morpholin-4-ylmethyl)-4-oxo-4H-pyran-3-yl]oxy}pentyl)sulfanyl]benzonitrile;
4-{[(5-{[6-(morpholin-4-ylmethyl)-4-oxo-4H-pyran-3-yl]oxy}pentyl)sulfanyl]methyl}benzonitrile;
5-[(5-{[(4-methoxyphenyl)methyl]sulfanyl}pentyl)oxy]-2-(morpholin-4-ylmethyl)-4H-pyran-4-one;
5-({5-[(6-cyclopropylpyridin-3-yl)sulfanyl]pentyl}oxy)-2-(morpholin-4-ylmethyl)-4H-pyran-4-one;
2-(morpholin-4-ylmethyl)-5-{[5-(pyrimidin-2-ylsulfanyl)pentyl]oxy}-4H-pyran-4-one;
5-[(5-{[(3-methoxyphenyl)methyl]sulfanyl}pentyl)oxy]-2-(morpholin-4-ylmethyl)-4H-pyran-4-one;
3-{[(5-{[6-(morpholin-4-ylmethyl)-4-oxo-4H-pyran-3-yl]oxy}pentyl)sulfanyl]methyl}benzonitrile;
5-({5-[(4,4-difluorocyclohexyl)sulfanyl]pentyl}oxy)-2-(morpholin-4-ylmethyl)-4H-pyran-4-one;
5-[(5-{[(3-methanesulfonylphenyl)methyl]sulfanyl}pentyl)oxy]-2-(morpholin-4-ylmethyl)-4H-pyran-4-one;
2-(morpholin-4-ylmethyl)-5-[(5-{[5-(trifluoromethyl)pyrazin-2-yl]sulfanyl}pentyl)oxy]-4H-pyran-4-one;
2-(morpholin-4-ylmethyl)-5-[(5-{[2-(trifluoromethyl)pyridin-4-yl]sulfanyl}pentyl)oxy]-4H-pyran-4-one;
2-(morpholin-4-ylmethyl)-5-{[5-({[5-(trifluoromethyl)pyridin-2-yl]methyl}sulfanyl)pentyl]oxy}-4H-pyran-4-one; and
2-(morpholin-4-ylmethyl)-5-{[5-({[4-(trifluoromethyl)phenyl]methyl}sulfanyl)pentyl]oxy}-4H-pyran-4-one.

A further embodiment of the present invention is directed to a compound of formula V:

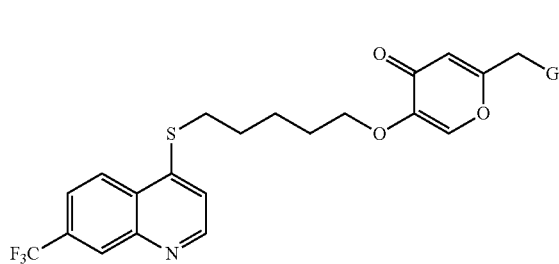

V or a pharmaceutically acceptable salt thereof wherein
G is selected from the group:

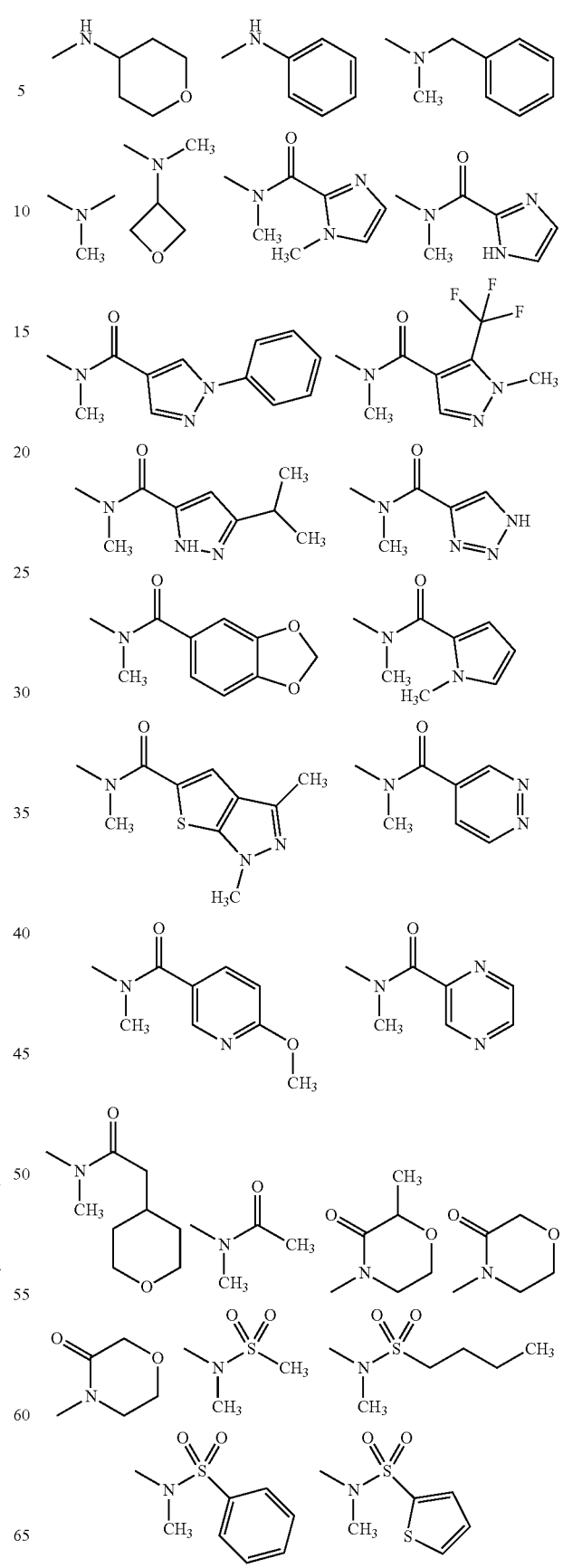

-continued

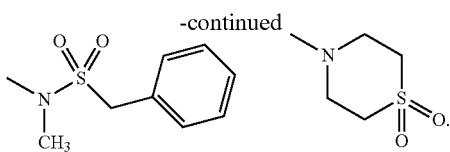

Preferred compounds of formula V include:

2-{[benzyl(methyl)amino]methyl}-5-[(5-{[7-(trifluoromethyl)quinolin-4-yl]sulfanyl}pentyl)oxy]-4H-pyran-4-one;

2-[(phenylamino)methyl]-5-[(5-{[7-(trifluoromethyl)quinolin-4-yl]sulfanyl}pentyl)oxy]-4H-pyran-4-one;

N-methyl-N-({4-oxo-5-[(5-{[7-(trifluoromethyl)quinolin-4-yl]sulfanyl}pentyl)oxy]-4H-pyran-2-yl}methyl)-3-(propan-2-yl)-1H-pyrazole-5 carboxamide;

N,1-dimethyl-N-({4-oxo-5-[(5-{[7-(trifluoromethyl)quinolin-4-yl]sulfanyl}pentyl)oxy]-4H-pyran-2-yl}methyl)-1H-imidazole-2-carboxamide;

N-methyl-N-({4-oxo-5-[(5-{[7-(trifluoromethyl)quinolin-4-yl]sulfanyl}pentyl)oxy]-4H-pyran-2-yl}methyl)-1H-pyrrole-2-carboxamide;

N,1-dimethyl-N-({4-oxo-5-[(5-{[7-(trifluoromethyl)quinolin-4-yl]sulfanyl}pentyl)oxy]-4H-pyran-2-yl}methyl)-5-(trifluoromethyl)-1H-pyrazole-4-carboxamide;

N-methyl-N-({4-oxo-5-[(5-{[7-(trifluoromethyl)quinolin-4-yl]sulfanyl}pentyl)oxy]-4H-pyran-2-yl}methyl)-1-phenyl-1H-pyrazole-4-carboxamide;

N-methyl-N-({4-oxo-5-[(5-{[7-(trifluoromethyl)quinolin-4-yl]sulfanyl}pentyl)oxy]-4H-pyran-2-yl}methyl)-2H-1,3-benzodioxole-5-carboxamide;

N-methyl-N-({4-oxo-5-[(5-{[7-(trifluoromethyl)quinolin-4-yl]sulfanyl}pentyl)oxy]-4H-pyran-2-yl}methyl)-1H-1,2,3-triazole-4-carboxamide;

N-methyl-N-({4-oxo-5-[(5-{[7-(trifluoromethyl)quinolin-4-yl]sulfanyl}pentyl)oxy]-4H-pyran-2-yl}methyl)butane-1-sulfonamide;

N-methyl-N-({4-oxo-5-[(5-{[7-(trifluoromethyl)quinolin-4-yl]sulfanyl}pentyl)oxy]-4H-pyran-2-yl}methyl)thiophene-2-sulfonamide;

N-methyl-N-({4-oxo-5-[(5-{[7-(trifluoromethyl)quinolin-4-yl]sulfanyl}pentyl)oxy]-4H-pyran-2-yl}methyl)-1-phenylmethanesulfonamide;

N-methyl-N-({4-oxo-5-[(5-{[7-(trifluoromethyl)quinolin-4-yl]sulfanyl}pentyl)oxy]-4H-pyran-2-yl}methyl)benzenesulfonamide;

N,1,3-trimethyl-N-({4-oxo-5-[(5-{[7-(trifluoromethyl)quinolin-4-yl]sulfanyl}pentyl)oxy]-4H-pyran-2-yl}methyl)-1H-thieno[2,3-c]pyrazole-5-carboxamide;

N-methyl-N-({4-oxo-5-[(5-{[7-(trifluoromethyl)quinolin-4-yl]sulfanyl}pentyl)oxy]-4H-pyran-2-yl}methyl)pyridazine-4-carboxamide;

N-methyl-2-(oxan-4-yl)-N-({4-oxo-5-[(5-{[7-(trifluoromethyl)quinolin-4-yl]sulfanyl}pentyl)oxy]-4H-pyran-2-yl}methyl)acetamide;

N-methyl-N-({4-oxo-5-[(5-{[7-(trifluoromethyl)quinolin-4-yl]sulfanyl}pentyl)oxy]-4H-pyran-2-yl}methyl)acetamide;

2-[(dimethylamino)methyl]-5-[(5-{[7-(trifluoromethyl)quinolin-4-yl]sulfanyl}pentyl)oxy]-4H-pyran-4-one;

2-methyl-4-({4-oxo-5-[(5-{[7-(trifluoromethyl)quinolin-4-yl]sulfanyl}pentyl)oxy]-4H-pyran-2-yl}methyl)morpholin-3-one;

N, 1-dimethyl-N-({4-oxo-5-[(5-{[7-(trifluoromethyl)quinolin-4-yl]sulfanyl}pentyl)oxy]-4H-pyran-2-yl}methyl)-1H-pyrrole-2-carboxamide;

2-{[methyl(oxetan-3-yl)amino]methyl}-5-[(5-{[7-(trifluoromethyl)quinolin-4-yl]sulfanyl}pentyl)oxy]-4H-pyran-4-one;

6-methoxy-N-methyl-N-({4-oxo-5-[(5-{[7-(trifluoromethyl)quinolin-4-yl]sulfanyl}pentyl)oxy]-4H-pyran-2-yl}methyl)pyridine-3-carboxamide;

N-methyl-N-({4-oxo-5-[(5-{[7-(trifluoromethyl)quinolin-4-yl]sulfanyl}pentyl)oxy]-4H-pyran-2-yl}methyl)pyrazine-2-carboxamide;

N-methyl-N-({4-oxo-5-[(5-{[7-(trifluoromethyl)quinolin-4-yl]sulfanyl}pentyl)oxy]-4H-pyran-2-yl}methyl)methanesulfonamide;

2-((1,1-dioxidothiomorpholino)methyl)-5-((5-((7-(trifluoromethyl)quinolin-4-yl)thio)pentyl)oxy)-4H-pyran-4-one 2-{[(oxan-4-yl)amino]methyl}-5-[(5-{[7-(trifluoromethyl)quinolin-4-yl]sulfanyl}pentyl)oxy]-4H-pyran-4-one;

5-methyl-4-({4-oxo-5-[(5-{[7-(trifluoromethyl)quinolin-4-yl]sulfanyl}pentyl)oxy]-4H-pyran-2-yl}methyl)morpholin-3-one; and 4-({4-oxo-5-[(5-{[7-(trifluoromethyl)quinolin-4-yl]sulfanyl}pentyl)oxy]-4H-pyran-2-yl}methyl)morpholin-3-one.

When the compounds according to the invention are in the form of a salt, they are preferably pharmaceutically acceptable salts. Such salts include pharmaceutically acceptable acid addition salts, pharmaceutically acceptable base addition salts, pharmaceutically acceptable metal salts, and ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in Berge et al., Pharmaceutical Salts, J. Pharm. Sci., 66(1):1-19 (1977), which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compounds of the invention with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. A mixture of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. A mixture of solvents may also be used.

The compounds of the present invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In some embodiments, compounds of the invention are R enantiomers. In some embodiments, compounds of the invention are S enantiomers. In some embodiments, compounds of the invention are varying mixtures of enantiomers.

The compounds of the present invention can be prepared in a number of ways known to one skilled in the art of organic synthesis. The compounds of the invention can be synthesized using the methods described below, together with synthetic methods known in the art of synthetic organic chemistry, or by variations thereon as appreciated by those skilled in the art. Preferred methods include, but are not limited to, those described below. In some instances, the compounds of the invention can be prepared in a manner described in U.S. Pat. No. 7,514,432. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1991). All references cited herein are hereby incorporated in their entirety by reference.

The compounds of the invention may be prepared using the route shown in Scheme 1.

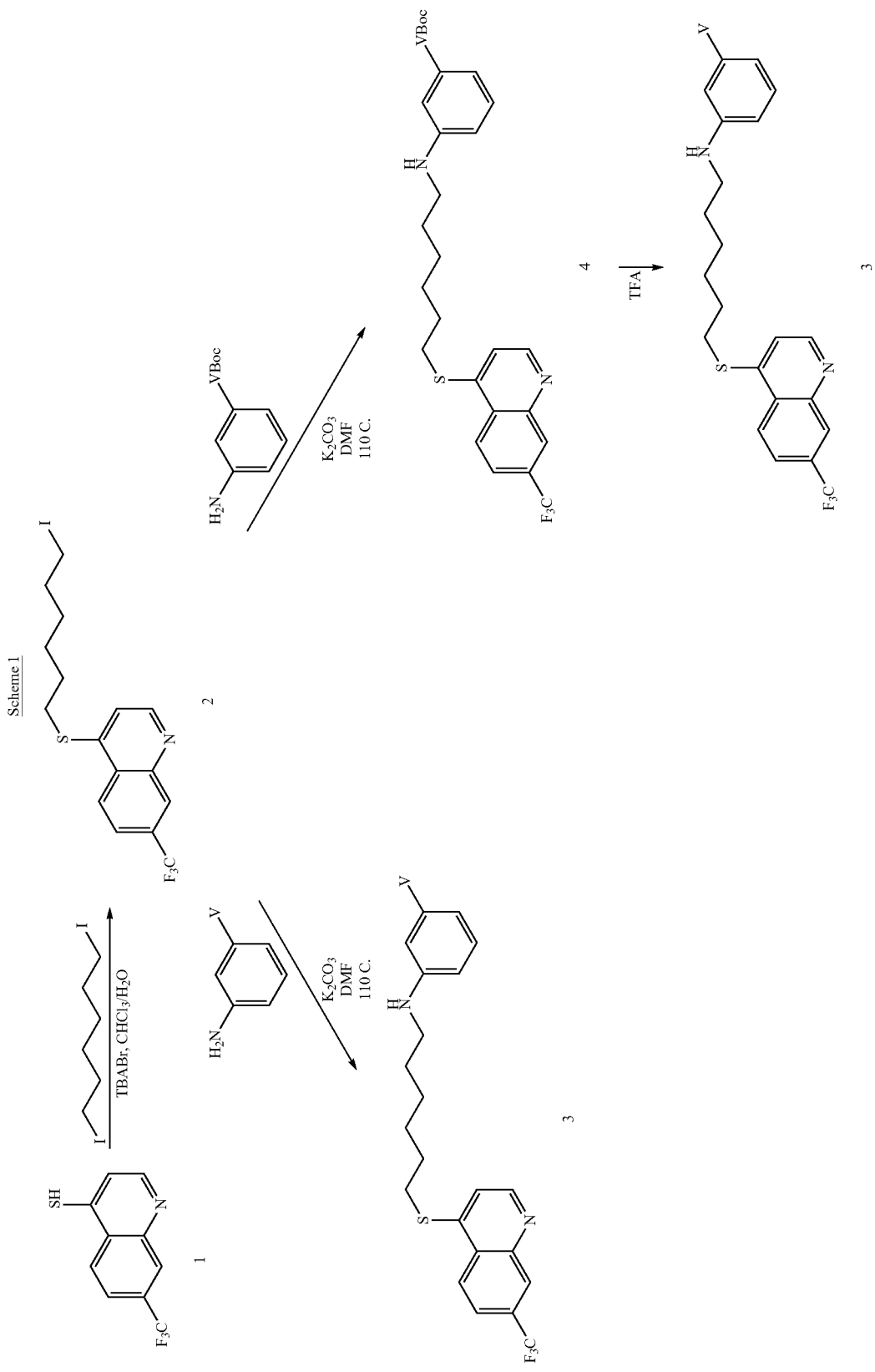
Scheme 1

Compound 1 can be treated with an alkyl dihalide in a solvent, such as CHCl₃, at room temperature followed by the addition of a phase transfer catalyst, such as TBABr, and water to yield compound 2.

The resulting compound 2 can then be reacted with a phenyl amine nucleophile that may be unprotected or protected to yield a compound of formula 3 or 4 respectively. Specifically, the reaction involves treating the phenyl amine nucleophile with a base, such as potassium carbonate, in a solvent such as DMF, at room temperature followed by the addition of compound 2. The reaction is heated at 110° C. to yield a compound of formula 3 or 4. If a protected phenyl amine nucleophile is used resulting in compound 4, compound 4 can be treated with, for example, TFA at 0° C. to yield compound 3.

The compounds of the invention may also be prepared using the route shown in Scheme 2.

Compound 1 can be treated with an alkyl dihalide in a solvent, such as CHCl₃, at room temperature followed by the addition of water and a phase transfer catalyst, such as TBABr, to yield compound 5.

Compound 5 can then be reacted with a nucleophile that is pretreated with a base, such as potassium carbonate, to yield compound 6. Compound 6 can then be reacted with an amine using a catalytic amount of acetic acid in a solvent such as dichloromethane followed by the addition of a reducing agent, such as sodium triacetoxyborohydride, to yield compound 7.

The compounds of the invention may also be prepared using the route shown in Scheme 3.

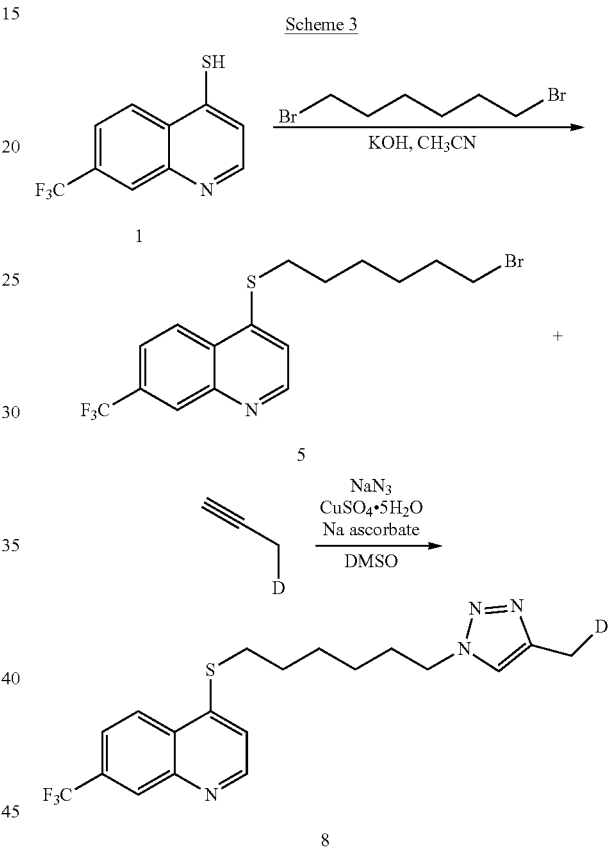

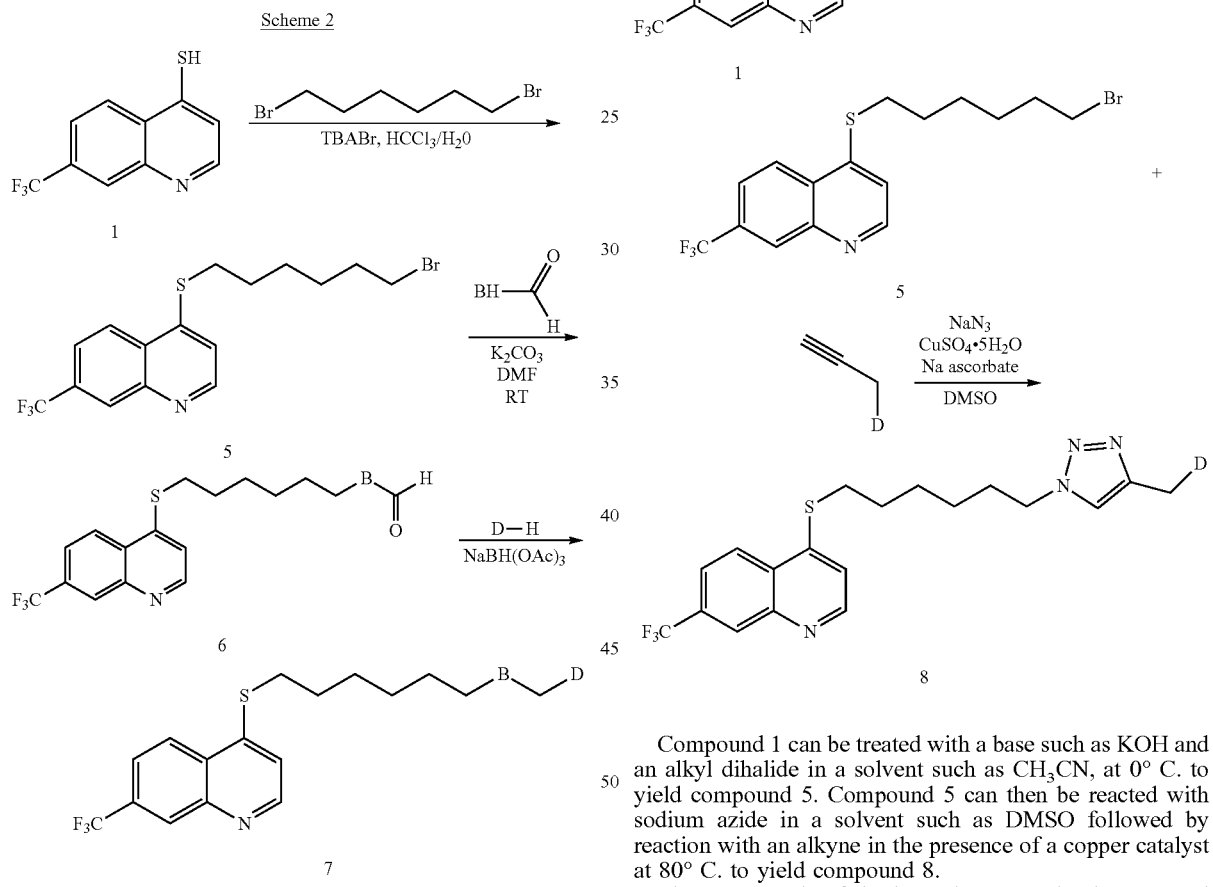

Compound 1 can be treated with a base such as KOH and an alkyl dihalide in a solvent such as CH₃CN, at 0° C. to yield compound 5. Compound 5 can then be reacted with sodium azide in a solvent such as DMSO followed by reaction with an alkyne in the presence of a copper catalyst at 80° C. to yield compound 8.

The compounds of the invention may also be prepared using the route shown in Scheme 4.

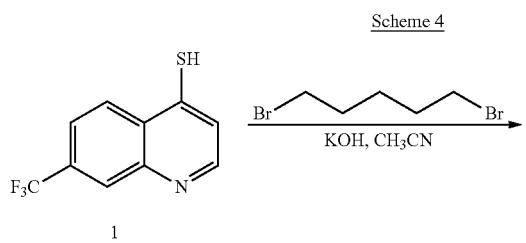

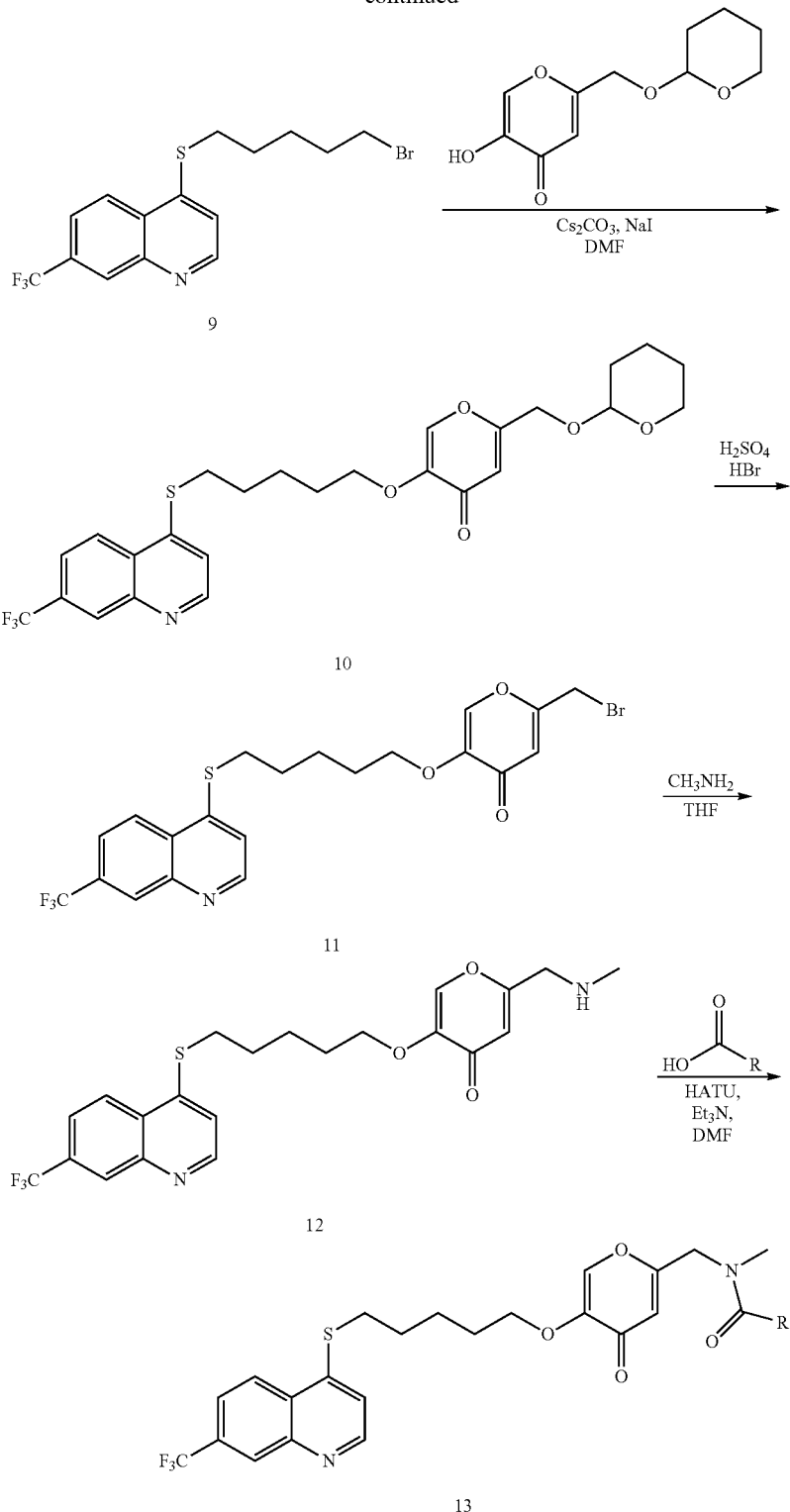

Compound 1 can be treated with a base such as KOH and an alkyl dihalide in a solvent, such as CH₃CN, to yield compound 9. A protected 4-pyrone can be treated with cesium carbonate in a solvent such as DMF followed by the addition of compound 9 and NaI to yield compound 10. Compound 10 can be treated with H₂SO₄ and HBr to yield compound 11, and compound 11 can then be reacted with a primary amine to yield compound 12. A carboxylic acid can then be coupled to compound 12 using, for example HATU as the coupling reagent, to yield compound 13.

The compounds of the invention act as pan-Rac inhibitors. Thus, the compounds of the invention are intended to treat cancers that show a dependence on Rac protein signaling for their growth and survival. Specific examples include breast cancer, melanoma, head cancer, neck cancer, prostate cancer, colorectal cancer, pancreatic cancer, liver cancer, bladder cancer, non-Hodgkin's lymphoma, and leukemia (acute lymphoblastic leukemia, chronic myeloid leukemia, acute myeloid leukemia). Additionally, the compounds of the invention can be used to treat kidney disease and heart disease.

The compounds of the invention are also intended to treat diseases associated with unregulated angiogenesis including growth and metastasis of solid tumors. Specific examples include metastatic colorectal cancer, non-squamous non-small cell lung cancer, glioblastoma, metastatic renal cell carcinoma, metastatic cervical cancer, platinum-resistant recurrent epithelial ovarian cancer, ocular diseases, and retinopathies (e.g., diabetic retinopathies, retinal degenerative diseases, Age-Related Macular Degeneration (ARMD)), and arthritis.

As indicated above, a further embodiment of the invention relates to a pharmaceutical composition comprising at least one compound of the invention and a pharmaceutically acceptable diluent, excipient, or carrier.

The compounds of the invention are typically administered with suitable pharmaceutical diluents, excipients, or carriers (collectively referred to herein as pharmaceutically acceptable carriers). Suitable pharmaceutical diluents, excipients, and carriers include, but are not limited to, lubricants, solvents, binders, and stabilizers that are suitably selected with respect to the intended form of administration including solid and liquid forms, such as capsules, tablets, gels, solutions, syrups, suspensions, powders, aerosols, ointments, etc.

Diluents that may be used in the compositions of the invention include but are not limited to dicalcium phosphate, calcium sulfate, lactose, cellulose, kaolin, mannitol, sodium chloride, dry starch, powdered sugar and hydroxy propyl methyl cellulose (HPMC). The binders that may be used in the compositions of the invention include but are not limited to starch and gelatin. Additionally, fillers such as sucrose, glucose, dextrose and lactose may also be used.

Natural and synthetic gums that may be used in the compositions of the invention include but are not limited to sodium alginate, ghatti gum, carboxymethyl cellulose, methyl cellulose, polyvinyl pyrrolidone and veegum. Excipients that may be used in the compositions of the invention include but are not limited to microcrystalline cellulose, calcium sulfate, dicalcium phosphate, starch, magnesium stearate, lactose, and sucrose. Stabilizers that may be used in the compositions of the invention include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that may be used in the composition of the invention include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds of the invention are administered will vary according to the dosage form, mode of administration, the condition being treated and particulars of the patient being treated. Accordingly, optimal therapeutic concentrations will be best determined at the time and place through routine experimentation.

The compounds according to the invention can also be used enterally. Orally, the compounds according to the invention are suitably administered at the rate of 10 µg to 300 mg per day per kg of body weight. The required dose can be administered in one or more portions. For oral administration, suitable forms are, for example, capsules, tablets, gels, aerosols, pills, dragees, syrups, suspensions, emulsions, solutions, powders and granules. A preferred method of administration consists of using a suitable form containing from 0.01 mg to about 500 mg of active substance.

The compounds according to the invention can also be administered parenterally in the form of solutions or suspensions for intravenous, subcutaneous or intramuscular perfusions or injections. In that case, the compounds according to the invention are generally administered at the rate of about 10 µg to 10 mg per day per kg of body weight. A preferred method of administration consists of using solutions or suspensions containing approximately from 0.01 mg to 1 mg of active substance per ml.

The compounds may be administered according to various routes, typically by oral route or by injection, such as local or systemic injection(s). Intratumoral injections are preferred for treating existing cancers. However, other administration routes may be used as well, such as intramuscular, intravenous, intradermic, subcutaneous, etc. Furthermore, repeated injections may be performed, if needed, although it is believed that a limited number of injections will be needed in view of the efficacy of the compounds.

The compounds of the invention can be used in a substantially similar manner to other known anti-tumor agents for treating (both chemopreventively and therapeutically) various tumors. For the compounds of this invention, the dose to be administered, whether a single dose, multiple dose, or a daily dose, will of course vary with the particular compound employed because of the varying potency of the compound, the chosen route of administration, the size of the recipient, the type of disease, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment or a doctor skilled in the art in treating kidney or heart disease will be able to ascertain, without undue experimentation, appropriate protocols for the effective administration of the compounds of this present invention.

The compounds of the invention may also be administered in combination with other known therapies. For example, the compounds of the invention can be administered in combination with other known chemotherapy drugs such as the tyrosine kinase inhibitors lapatinib and gefitinib or the estrogen receptor positive metastatic breast cancer drug fulvestrant (Faslodex®). When co-administered with one or more other therapies, the compounds of the invention can be administered either simultaneously with the other treatment(s), or sequentially. If administered sequentially, the attending physician will decide on the appropriate sequence of administering the compounds of the invention in combination with the other therapy.

EXAMPLES

Compound Examples

| Compound Structure | Compound Designation | Compound Name |
|---|---|---|
| 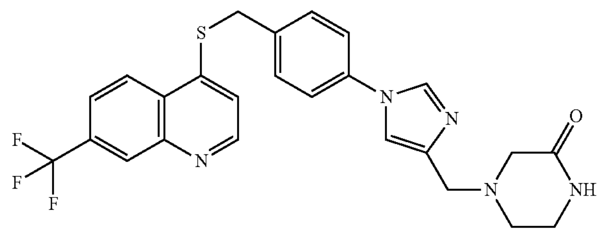 [SMILES: O=C1CN(Cc2cn(-c3ccc(CSc4ccnc5cc(C(F)(F)F)ccc45)cc3)cn2)CCN1] | 0033386 | 4-({1-[4-({[7-(trifluoromethyl)quinolin-4-yl]sulfanyl}methyl)phenyl]-1H-imidazol-4-yl}methyl)piperazin-2-one |
| 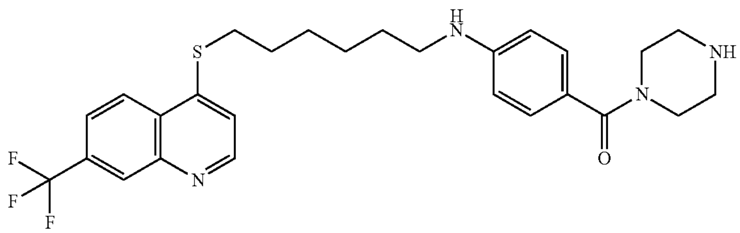 [SMILES: O=C(c1ccc(NCCCCCCSc2ccnc3cc(C(F)(F)F)ccc23)cc1)N1CCNCC1] | 0033354 | 4-(piperazine-1-carbonyl)-N-(6-{[7-(trifluoromethyl)quinolin-4-yl]sulfanyl}hexyl)aniline |
| 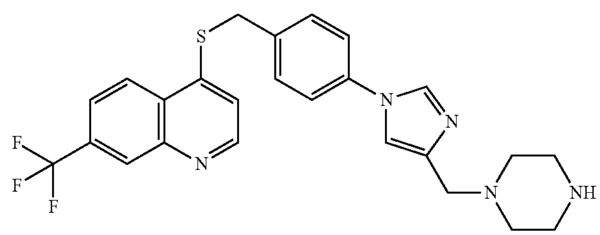 [SMILES: FC(F)(F)c1ccc2c(SCc3ccc(-n4cnc(CN5CCNCC5)c4)cc3)ccnc2c1] | 0033350 | 4-[({4-[4-(piperazin-1-ylmethyl)-1H-imidazol-1-yl]phenyl}methyl)sulfanyl]-7-(trifluoromethyl)quinoline |
| 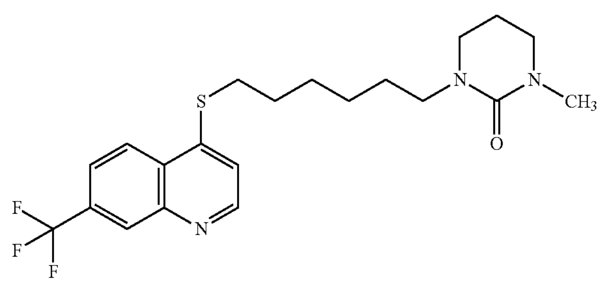 [SMILES: CN1CCCN(CCCCCCSc2ccnc3cc(C(F)(F)F)ccc23)C1=O] | 0033334 | 1-methyl-3-(6-{[7-(trifluoromethyl)quinolin-4-yl]sulfanyl}hexyl)-1,3-diazinan-2-one |
| 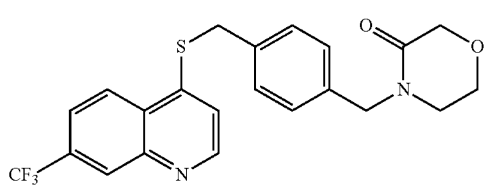 [SMILES: O=C1COCCN1Cc1ccc(CSc2ccnc3cc(C(F)(F)F)ccc23)cc1] | 0033333 | 4-({4-({[7-(trifluoromethyl)quinolin-4-yl]sulfanyl}methyl)phenyl}methyl)morpholin-3-one |
| 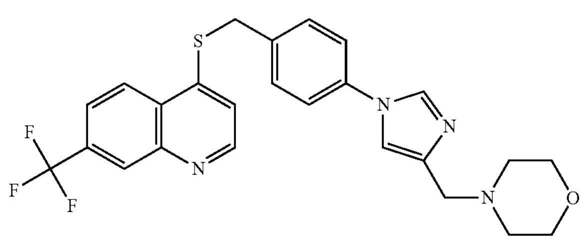 [SMILES: FC(F)(F)c1ccc2c(SCc3ccc(-n4cnc(CN5CCOCC5)c4)cc3)ccnc2c1] | 0033331 | 4-[{(4-[4-(morpholin-4-ylmethyl)-1H-imidazol-1-yl]phenyl}methyl)sulfanyl]-7-(trifluoromethyl)quinoline |

-continued

| Compound Structure | Compound Designation | Compound Name |
|---|---|---|
| 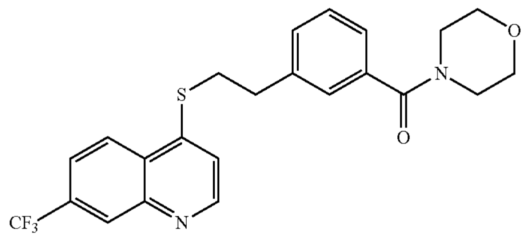 [SMILES: O=C(c1cccc(CCSc2ccnc3cc(C(F)(F)F)ccc23)c1)N1CCOCC1] | 0033317 | 4-({2-[3-(morpholine-4-carbonyl)phenyl]ethyl}sulfanyl)-7-(trifluoromethyl)quinoline |
| 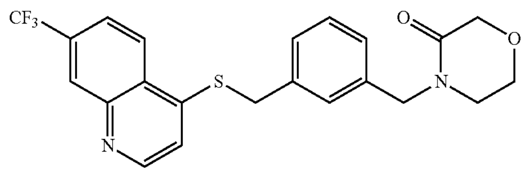 [SMILES: O=C1COCCN1Cc1cccc(CSc2ccnc3cc(C(F)(F)F)ccc23)c1] | 0033307 | 4-({3-({[7-(trifluoromethyl)quinolin-4-yl]sulfanyl}methyl)phenyl]methyl}morpholin-3-one |
| 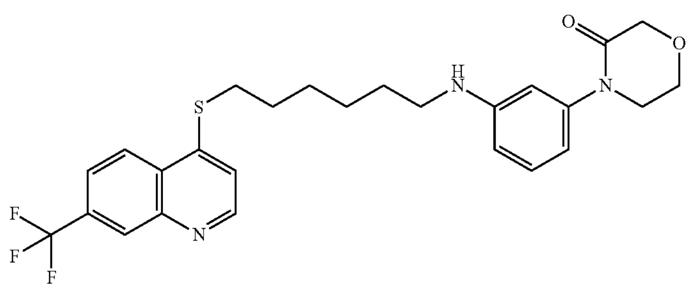 [SMILES: O=C1COCCN1c1cccc(NCCCCCCSc2ccnc3cc(C(F)(F)F)ccc23)c1] | 0033306 | 4-(3-{(6-{[7-(trifluoromethyl)quinolin-4-yl]sulfanyl)hexyl}amino]phenyl}morpholin-3-one |
| 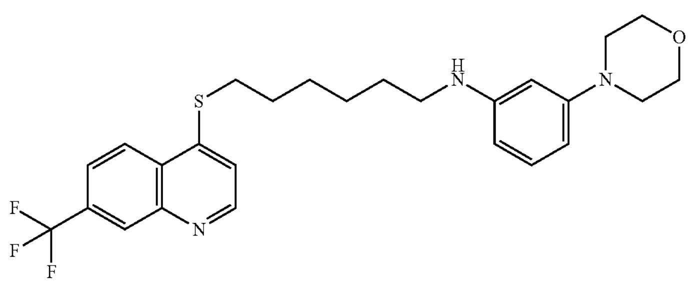 [SMILES: FC(F)(F)c1ccc2c(SCCCCCCNc3cccc(N4CCOCC4)c3)ccnc2c1] | 0033286 | 3-(morpholin-4-yl)-N-(6-{[7-(trifluoromethyl)quinolin-4-yl]sulfanyl}hexyl)aniline |
| 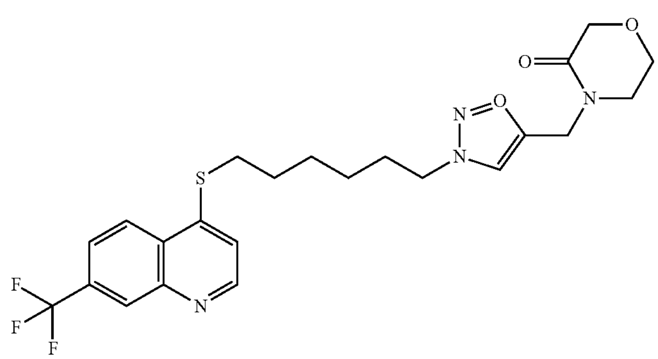 | 0033284 | 4-{{1-(6-{[7-(trifluoromethyl)quinolin-4-yl]sulfanyl}hexyl)-1H-1,2,3-triazol-4-yl}methyl}morpholin-3-one |

-continued

| Compound Structure | Compound Designation | Compound Name |
|---|---|---|
| 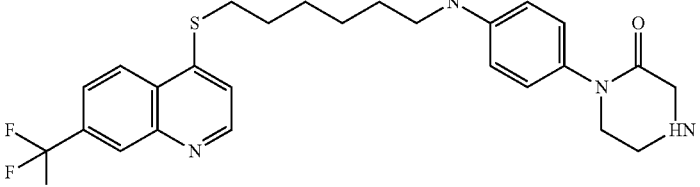 | 0033283 | 1-{4-[(6-{[7-(trifluoromethyl)quinolin-4-yl]sulfanyl}hexyl)amino]phenyl}piperazin-2-one |
| 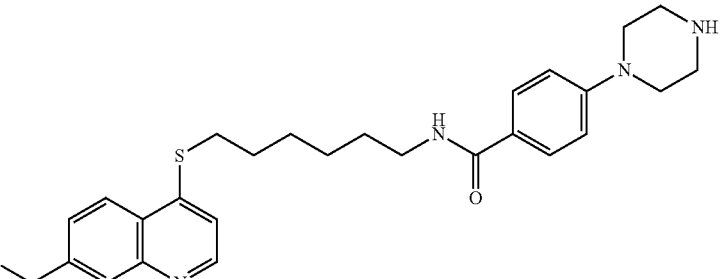 | 0033279 | 4-(piperazin-1-yl)-N-(6-{[7-(trifluoromethyl)quinolin-4-yl]sulfanyl}hexyl)benzamide |
| 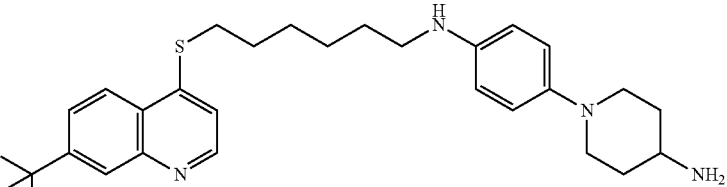 | 0033278 | 1-{4-[(6-{[7-(trifluoromethyl)quinolin-4-yl]sulfanyl}hexyl)amino]phenyl}piperidin-4-amine |
| 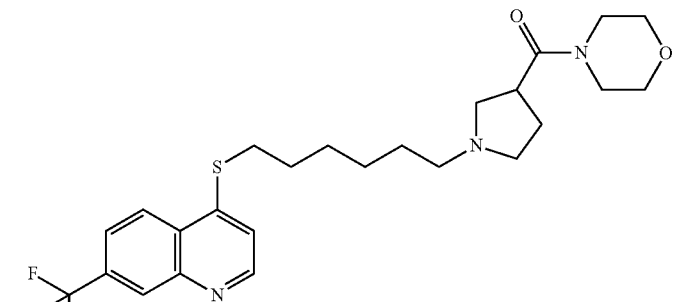 | 0033276 | 4-{(6-[3-(morpholine-4-carbonyl)pyrrolidin-1-yl]hexyl}sulfanyl)-7-(trifluoromethyl)quinoline |
| 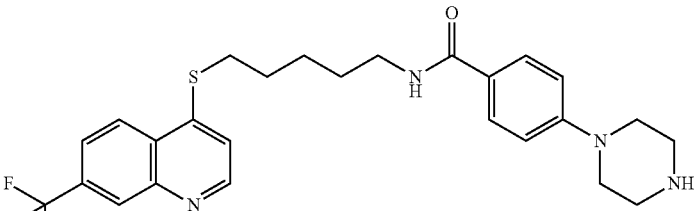 | 0033275 | 4-(piperidin-1-yl)-N-(5-{[7-(trifluoromethyl)quinolin-4-yl]sulfanyl}pentyl)benzamide |

| Compound Structure | Compound Designation | Compound Name |
|---|---|---|
| 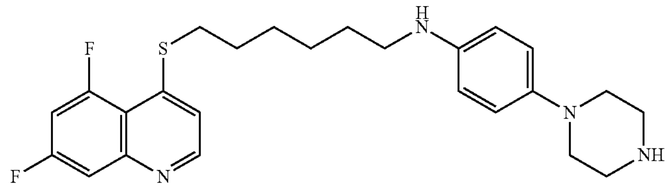 [SMILES: Fc1cc(F)c2c(SCCCCCCNc3ccc(N4CCNCC4)cc3)ccnc2c1] | 0033268 | N-(6-[(5,7-difluoroquinolin-4-yl)sulfanyl]hexyl}-4-(piperazin-1-yl)aniline |
| 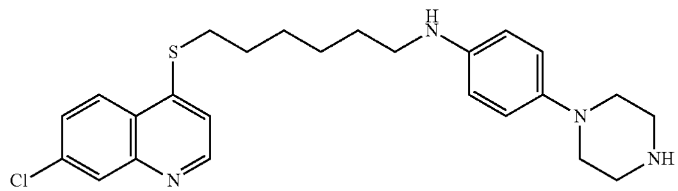 [SMILES: Clc1ccc2c(SCCCCCCNc3ccc(N4CCNCC4)cc3)ccnc2c1] | 0033266 | N-{6-[(7-chloroquinolin-4-yl)sulfanyl]hexyl}-4-(piperazin-1-yl)aniline |
| 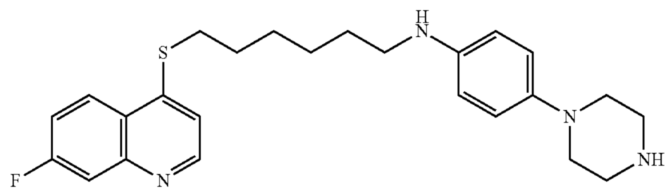 [SMILES: Fc1ccc2c(SCCCCCCNc3ccc(N4CCNCC4)cc3)ccnc2c1] | 0033265 | N-{6-[(7-fluoroquinolin-4-yl)sulfanyl]hexyl}-4-(piperazin-1-yl)aniline |
| 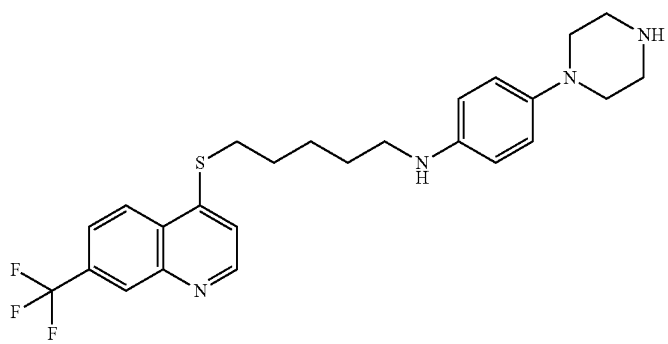 [SMILES: FC(F)(F)c1ccc2c(SCCCCCNc3ccc(N4CCNCC4)cc3)ccnc2c1] | 0033240 | 4-(piperazin-1-yl)-N-(5-{[7-(trifluoromethyl)quinolin-4-yl]sulfanyl}pentyl)aniline |
| 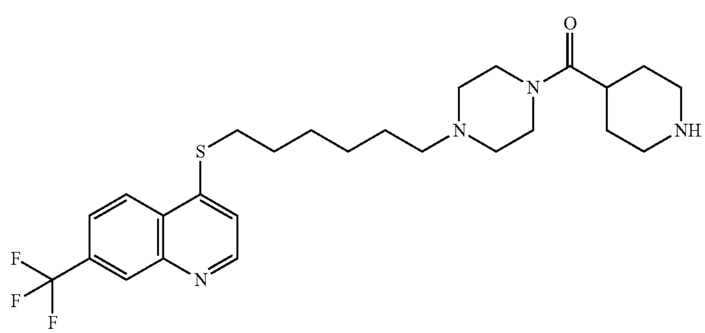 [SMILES: O=C(C1CCNCC1)N1CCN(CCCCCCSc2ccnc3cc(C(F)(F)F)ccc23)CC1] | 0033238 | 4-({6-[4-(piperidine-4-carbonyl)piperazin-1-yl]hexyl}sulfanyl)-7-(trifluoromethyl)quinoline |
| 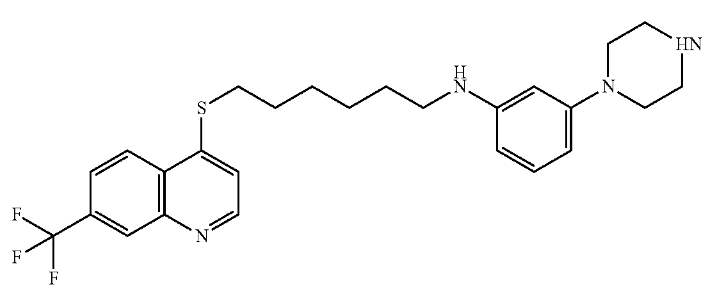 [SMILES: FC(F)(F)c1ccc2c(SCCCCCCNc3cccc(N4CCNCC4)c3)ccnc2c1] | 0033235 | 3-(piperazin-1-yl)-N-(6-{[7-(trifluoromethyl)quinolin-4-yl]sulfanyl}hexyl)aniline |

-continued

| Compound Structure | Compound Designation | Compound Name |
|---|---|---|
| 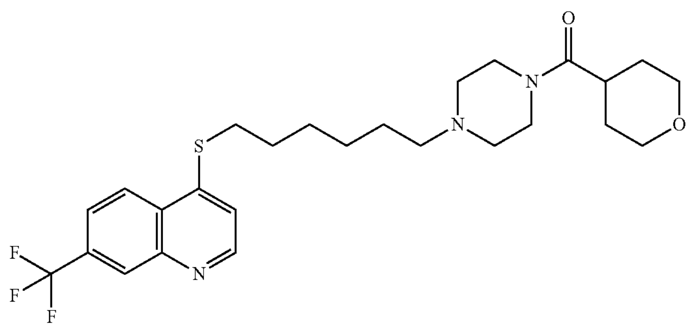 [SMILES: O=C(C1CCOCC1)N1CCN(CCCCCCSc2ccnc3cc(C(F)(F)F)ccc23)CC1] | 0033234 | 4-({6-[4-(oxane-4-carbonyl)piperazin-1-yl]hexyl}sulfanyl)-7-(trifluoromethyl)quinoline |
| 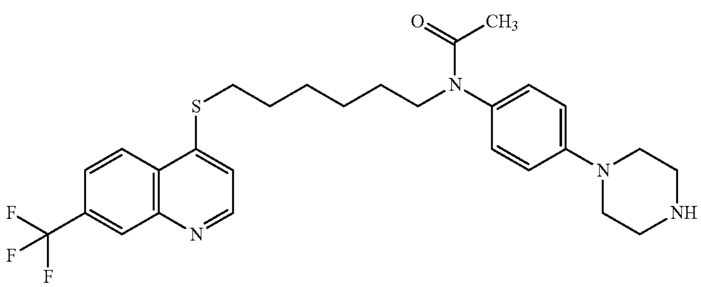 [SMILES: CC(=O)N(CCCCCCSc1ccnc2cc(C(F)(F)F)ccc12)c1ccc(N2CCNCC2)cc1] | 0033222 | N-[4-(piperazin-1-yl)phenyl]-N-(6-{[7-(trifluoromethyl)quinolin-4-yl]sulfanyl}hexyl)acetamide |
| 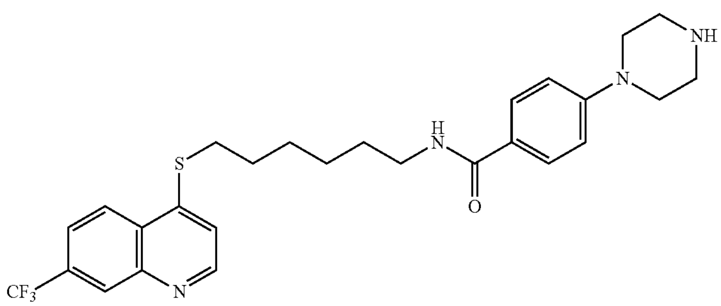 [SMILES: O=C(NCCCCCCSc1ccnc2cc(C(F)(F)F)ccc12)c1ccc(N2CCNCC2)cc1] | 0033221 | N-(6-[{7-(trifluoromethyl)quinolin-4-yl}sulfanyl]hexyl)piperazine-1-carboxamide |
| 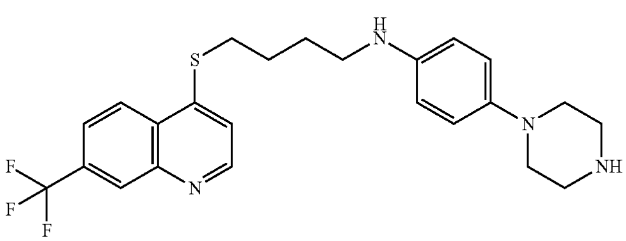 [SMILES: FC(F)(F)c1ccc2c(SCCCCNc3ccc(N4CCNCC4)cc3)ccnc2c1] | 0033220 | 4-(piperazin-1-yl)-N-(4-{[7-(trifluoromethyl)quinolin-4-yl]sulfanyl}butyl)aniline |
| 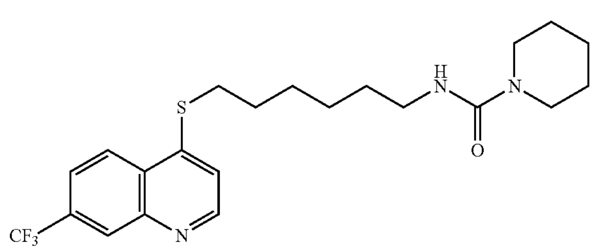 [SMILES: O=C(NCCCCCCSc1ccnc2cc(C(F)(F)F)ccc12)N1CCCCC1] | 0033218 | N-(6-{[7-(trifluoromethyl)quinolin-4-yl]sulfanyl}hexyl)piperidine-1-carboxamide |

-continued

| Compound Structure | Compound Designation | Compound Name |
|---|---|---|
| 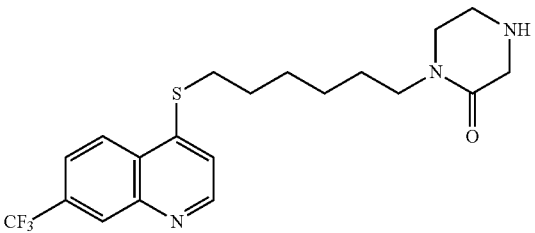 [SMILES: O=C1CNCCN1CCCCCCSc1ccnc2cc(C(F)(F)F)ccc12] | 0033217 | 1-(6-{[7-(trifluoromethyl)quinolin-4-yl]sulfanyl}hexyl)piperazin-2-one |
| 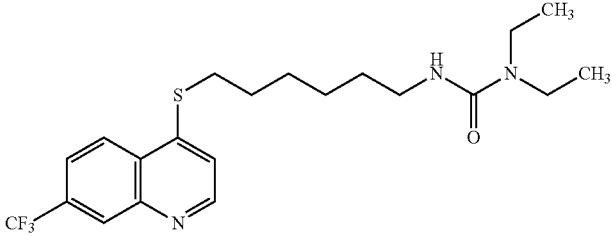 [SMILES: CCN(CC)C(=O)NCCCCCCSc1ccnc2cc(C(F)(F)F)ccc12] | 0033209 | 3,3-diethyl-1-(6-{[7-(trifluoromethyl)quinolin-4-yl]sulfanyl}hexyl)urea |
| 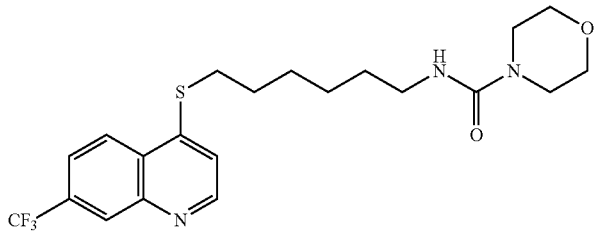 [SMILES: O=C(NCCCCCCSc1ccnc2cc(C(F)(F)F)ccc12)N1CCOCC1] | 0033208 | N-(6-{[7-(trifluoromethyl)quinolin-4-yl]sulfanyl}hexyl)morpholine-4-carboxamide |
| 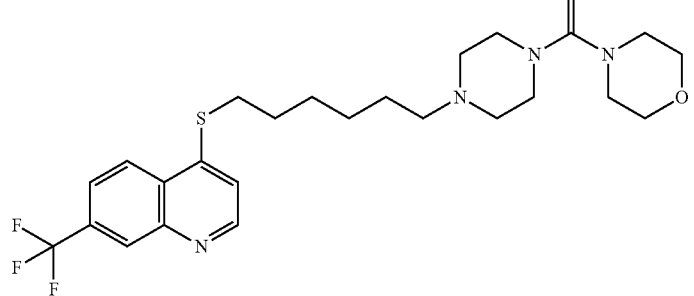 | 0033207 | 4-({6-[4-(morpholine-4-carbonyl)piperazin-1-yl]hexyl}sulfanyl)-7-(trifluoromethyl)quinoline |
| 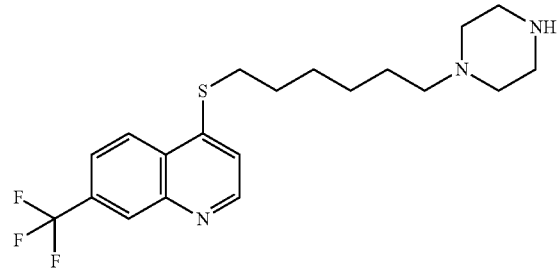 [SMILES: FC(F)(F)c1ccc2c(SCCCCCCN3CCNCC3)ccnc2c1] | 0033201 | 4-({6-(piperazin-1-yl)hexyl]sulfanyl}-7-(trifluoromethyl)quinoline |

-continued

| Compound Structure | Compound Designation | Compound Name |
|---|---|---|
| 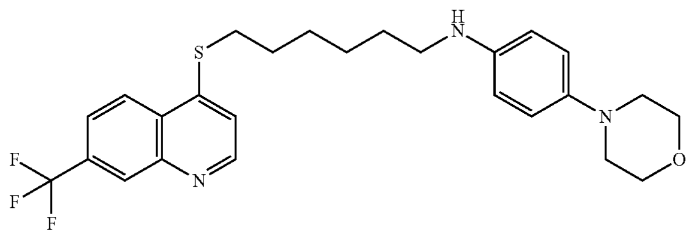 [SMILES: FC(F)(F)c1ccc2c(SCCCCCCNc3ccc(N4CCOCC4)cc3)ccnc2c1] | 0033200 | 4-(morpholin-4-yl)-N-(6-{[7-(trifluoromethyl)quinolin-4-yl]sulfanyl}hexyl)aniline |
| 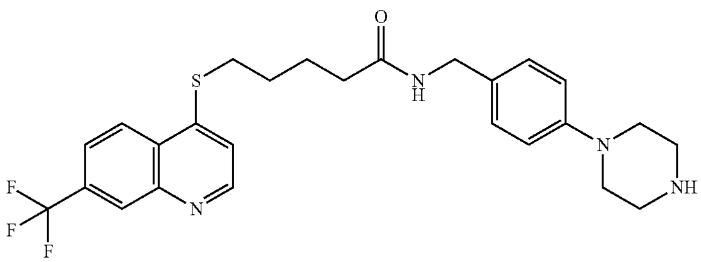 [SMILES: O=C(CCCCSc1ccnc2cc(C(F)(F)F)ccc12)NCc1ccc(N2CCNCC2)cc1] | 0033199 | N-{[4-(piperazin-1-yl)phenyl]methyl}-5-{[7-(trifluoromethyl)quinolin-4-yl]sulfanyl}pentanamide |
| 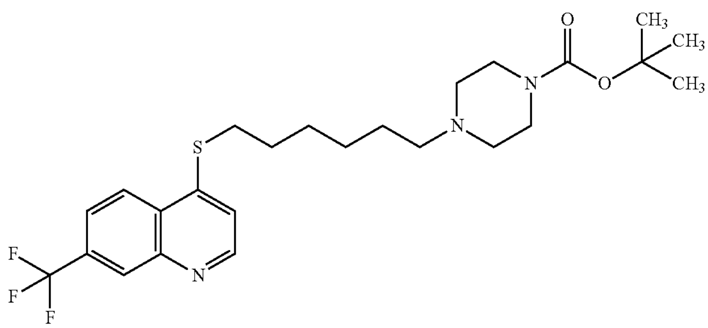 [SMILES: CC(C)(C)OC(=O)N1CCN(CCCCCCSc2ccnc3cc(C(F)(F)F)ccc23)CC1] | 0033188 | tert-butyl 4-(6-{[7-(trifluoromethyl)quinolin-4-yl]sulfanyl}hexyl)piperazine-1-carboxylate |
| 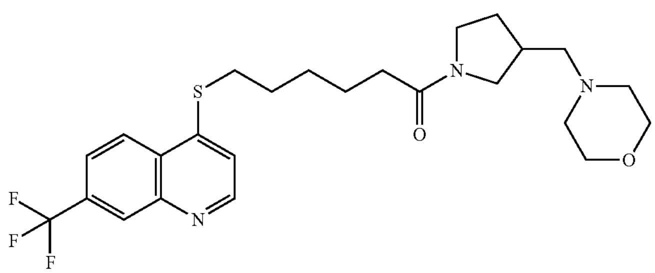 [SMILES: O=C(CCCCCSc1ccnc2cc(C(F)(F)F)ccc12)N1CCC(CN2CCOCC2)C1] | 0033187 | 1-[3-(morpholin-4-ylmethyl)pyrrolidin-1-yl]-6-{[7-(trifluoromethyl)quinolin-4-yl]sulfanyl}hexan-1-one |
| 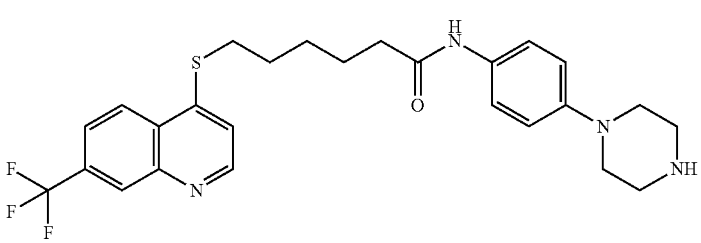 [SMILES: O=C(CCCCCSc1ccnc2cc(C(F)(F)F)ccc12)Nc1ccc(N2CCNCC2)cc1] | 0033186 | N-[4-(piperazin-1-yl)phenyl]-6-{[7-(trifluoromethyl)quinolin-4-yl]sulfanyl}hexanamide |

-continued

| Compound Structure | Compound Designation | Compound Name |
|---|---|---|
| 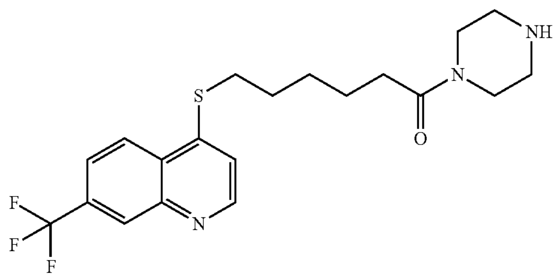 [SMILES: O=C(CCCCCSc1ccnc2cc(C(F)(F)F)ccc12)N1CCNCC1] | 0033185 | 1-(piperazin-1-yl)-6-{[7-(trifluoromethyl)quinolin-4-yl]sulfanyl}hexan-1-one |
| 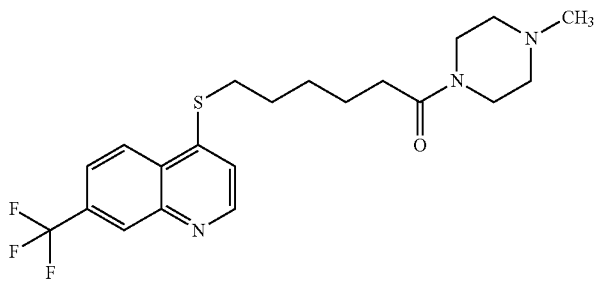 [SMILES: CN1CCN(C(=O)CCCCCSc2ccnc3cc(C(F)(F)F)ccc23)CC1] | 0033184 | 1-(4-methylpiperazin-1-yl)-6-[{7-(trifluoromethyl)quinolin-4-yl]sulfanyl}hexan-1-one |
| 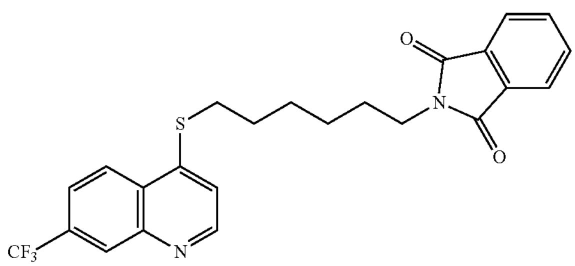 [SMILES: O=C1c2ccccc2C(=O)N1CCCCCCSc1ccnc2cc(C(F)(F)F)ccc12] | 0033183 | 2-(6-[{7-(trifluoromethyl)quinolin-4-yl]sulfanyl}hexyl)-2,3-dihydro-1H-isoindole-1,3-dione |
| 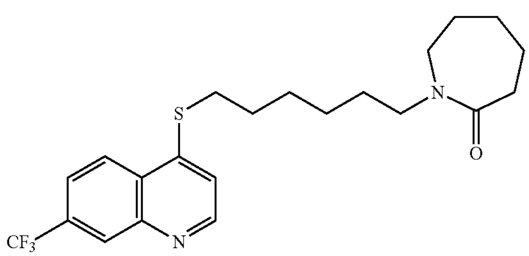 [SMILES: O=C1CCCCCN1CCCCCCSc1ccnc2cc(C(F)(F)F)ccc12] | 0033182 | 1-(6-[{7-(trifluoromethyl)quinolin-4-yl]sulfanyl}hexyl)azepan-2-one |
| 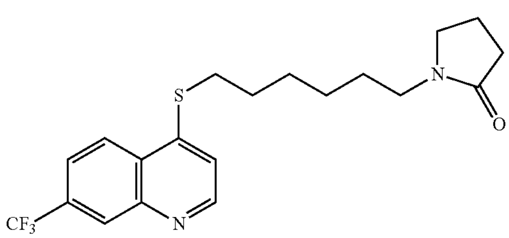 [SMILES: O=C1CCCN1CCCCCCSc1ccnc2cc(C(F)(F)F)ccc12] | 0033181 | 1-(6-{[7-(trifluoromethyl)quinolin-4-yl]sulfanyl}hexyl)pyrrolidin-2-one |

-continued

| Compound Structure | Compound Designation | Compound Name |
|---|---|---|
| 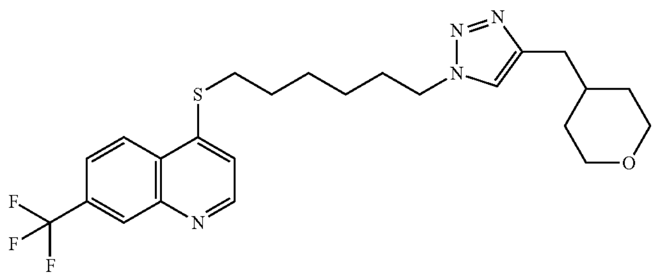 [SMILES: FC(F)(F)c1ccc2c(SCCCCCCn3cc(CC4CCOCC4)nn3)ccnc2c1] | 0033146 | 4-{(6-[4-(oxan-4-ylmethyl)-1H-1,2,3-triazol-1-yl]hexyl}sulfanyl)-7-(trifluoromethyl)quinoline |
| 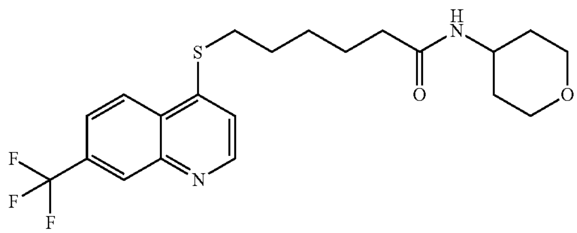 [SMILES: O=C(CCCCCSc1ccnc2cc(C(F)(F)F)ccc12)NC1CCOCC1] | 0033138 | N-(oxan-4-yl)-6-{[7-(trifluoromethyl)quinolin-4-yl]sulfanyl}hexanamide |
| 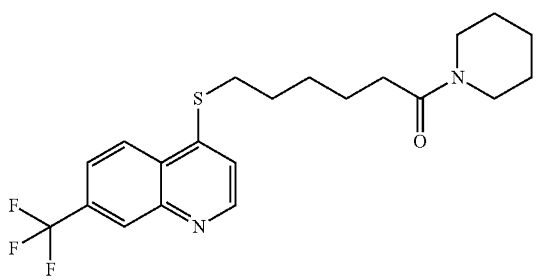 [SMILES: O=C(CCCCCSc1ccnc2cc(C(F)(F)F)ccc12)N1CCCCC1] | 0033137 | 1-(piperidin-1-yl)-6-{[7-(trifluoromethyl)quinolin-4-yl]sulfanyl}hexan-1-one |
| 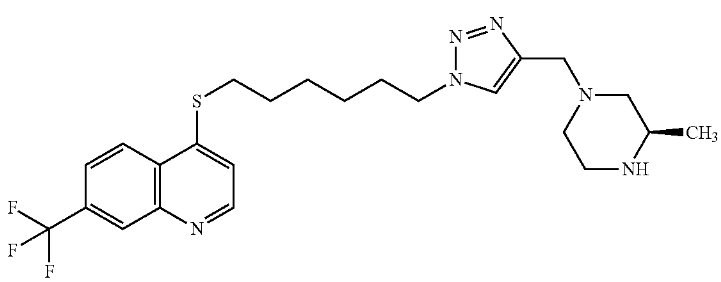 [SMILES: C[C@@H]1CN(Cc2cn(CCCCCCSc3ccnc4cc(C(F)(F)F)ccc34)nn2)CCN1] | 0033136 | 4-[(6-{4-[(3-methylpiperazin-1-yl)methyl]-1H-1,2,3-triazol-1-yl}hexyl)sulfanyl]-7-(trifluoromethyl)quinoline |
| 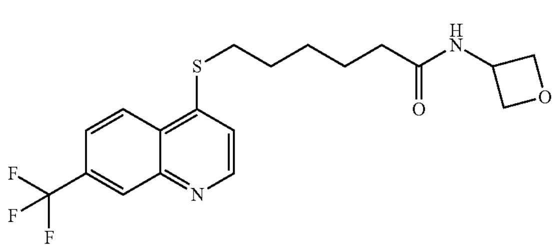 [SMILES: O=C(CCCCCSc1ccnc2cc(C(F)(F)F)ccc12)NC1COC1] | 0033133 | N-(oxetan-3-yl)-6-{[7-(trifluoromethyl)quinolin-4-yl]sulfanyl}hexanamide |

| Compound Structure | Compound Designation | Compound Name |
|---|---|---|
| 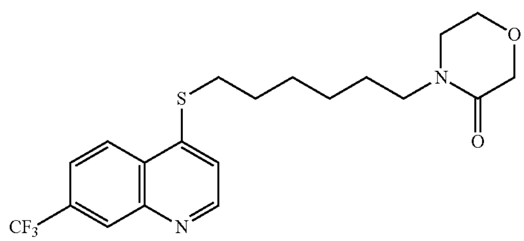 [SMILES: O=C1COCCN1CCCCCCSc1ccnc2cc(C(F)(F)F)ccc12] | 0033132 | 4-(6-{[7-(trifluoromethyl)quinolin-4-yl]sulfanyl}hexyl)morpholin-3-one |
| 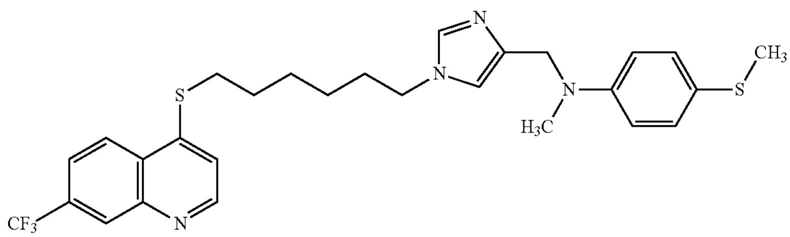 [SMILES: CSc1ccc(N(C)Cc2cn(CCCCCCSc3ccnc4cc(C(F)(F)F)ccc34)cn2)cc1] | 0033131 | 4-methoxy-N-methyl-N-{[1-(6-{[7-(trifluoromethyl)quinolin-4-yl]sulfanyl}hexyl)-1H-imidazol-4-yl]methyl}aniline |
| 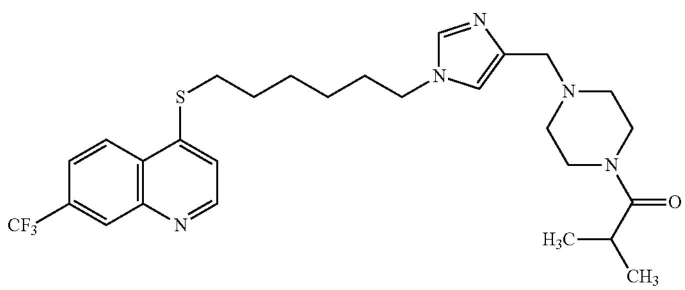 [SMILES: CC(C)C(=O)N1CCN(Cc2cn(CCCCCCSc3ccnc4cc(C(F)(F)F)ccc34)cn2)CC1] | 0033130 | 1-{4-[(1-{6-[(7-fluoroquinolin-4-yl)sulfanyl]hexyl}-1H-imidazol-4-yl)methyl]piperazin-1-yl}-2-methylpropan-1-one |
| 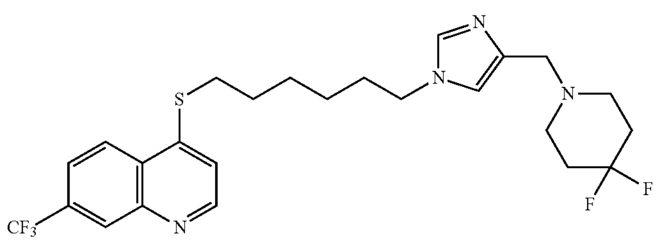 [SMILES: FC1(F)CCN(Cc2cn(CCCCCCSc3ccnc4cc(C(F)(F)F)ccc34)cn2)CC1] | 0033129 | 4-[(6-{4-[(4,4-difluoropiperidin-1-yl)methyl]-1H-imidazol-1-yl}hexyl)sulfanyl]-7-(trifluoromethyl)quinoline |
| 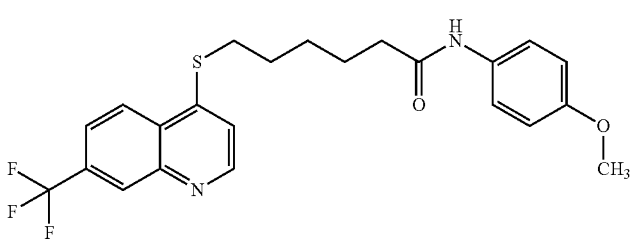 [SMILES: COc1ccc(NC(=O)CCCCCSc2ccnc3cc(C(F)(F)F)ccc23)cc1] | 0033122 | N-(4-methoxyphenyl)-6-{[7-(trifluoromethyl)quinolin-4-yl]sulfanyl}hexanamide |

-continued

| Compound Structure | Compound Designation | Compound Name |
|---|---|---|
| 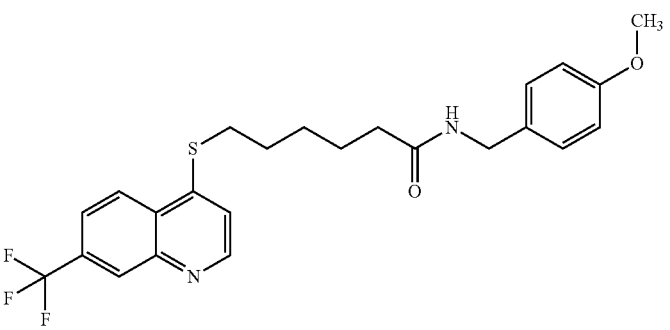 [SMILES: COc1ccc(CNC(=O)CCCCCSc2ccnc3cc(C(F)(F)F)ccc23)cc1] | 0033121 | N-[(4-methoxyphenyl) methyl]-6-{[7-(trifluoromethyl) quinolin-4-yl]sulfanyl} hexanamide |
| 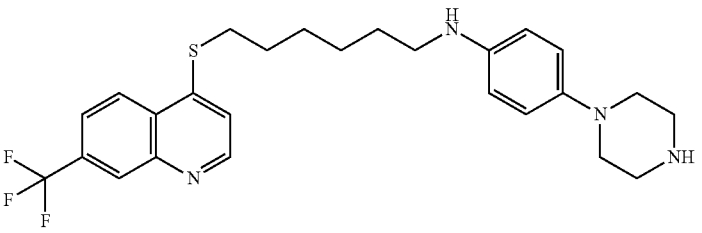 [SMILES: FC(F)(F)c1ccc2c(SCCCCCCNc3ccc(N4CCNCC4)cc3)ccnc2c1] | 0033102 | 4-(piperazin-1-yl)-N-(6-{[7-(trifluoromethyl) quinolin-4-yl] sulfanyl}hexyl)aniline |
| 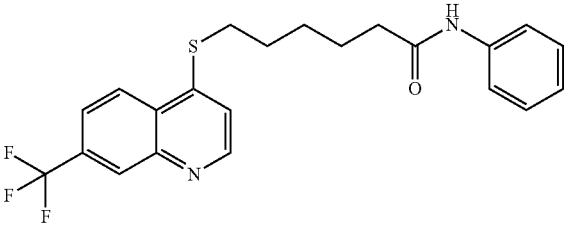 [SMILES: O=C(CCCCCSc1ccnc2cc(C(F)(F)F)ccc12)Nc1ccccc1] | 0033101 | N-phenyl-6-{[7-(trifluoromethyl) quinolin-4-yl] sulfanyl}hexanamide |
| 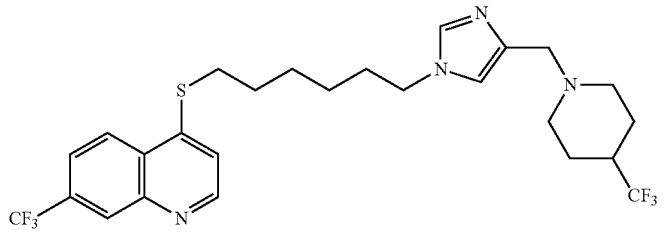 [SMILES: FC(F)(F)c1ccc2c(SCCCCCCn3cnc(CN4CCC(C(F)(F)F)CC4)c3)ccnc2c1] | 0033099 | 7-(trifluoromethyl)-4-[{6-(4-[{4-(trifluoromethyl) piperidin-1-yl]methyl}-1H-imidazol-3-yl) hexyl}sulfanyl)quinoline |
| 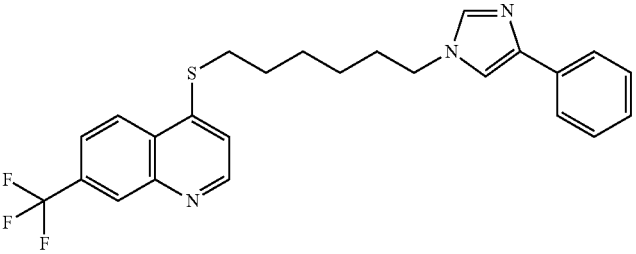 [SMILES: FC(F)(F)c1ccc2c(SCCCCCCn3cnc(-c4ccccc4)c3)ccnc2c1] | 0033097 | 4-[{6-(4-phenyl-1H-imidazol-1-yl)hexyl}sulfanyl)-7-(trifluoromethyl) quinoline |

-continued

| Compound Structure | Compound Designation | Compound Name |
|---|---|---|
| 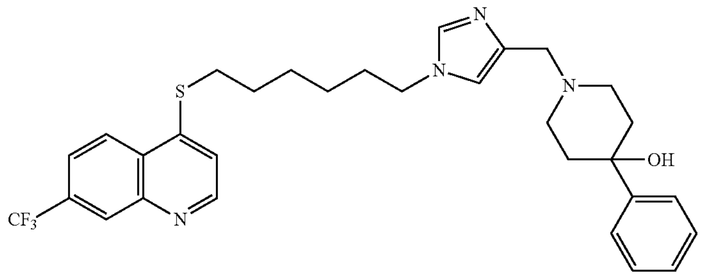 [SMILES: OC1(c2ccccc2)CCN(Cc2cn(CCCCCCSc3ccnc4cc(C(F)(F)F)ccc34)cn2)CC1] | 0033094 | 4-phenyl-1-{[1-(6-{[7-(trifluoromethyl)quinolin-4-yl]sulfanyl}hexyl)-1H-imidazol-4-yl]methyl)piperidin-4-ol |
| 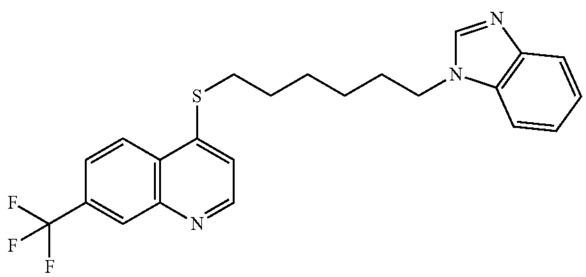 [SMILES: FC(F)(F)c1ccc2c(SCCCCCCn3cnc4ccccc43)ccnc2c1] | 0033093 | 4-[{6-(1H-1,3-benzodiazol-1-yl)hexyl]sulfanyl}-7-(trifluoromethyl)quinoline |
| 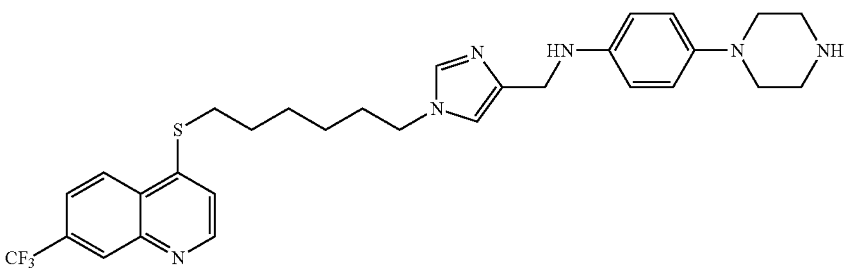 [SMILES: FC(F)(F)c1ccc2c(SCCCCCCn3cnc(CNc4ccc(N5CCNCC5)cc4)c3)ccnc2c1] | 0033087 | 4-(piperazin-1-yl)-N-{[1-(6-{[7-(trifluoromethyl)quinolin-4-yl]sulfanyl}hexyl)-1H-imidazol-4-yl]methyl}aniline |
| 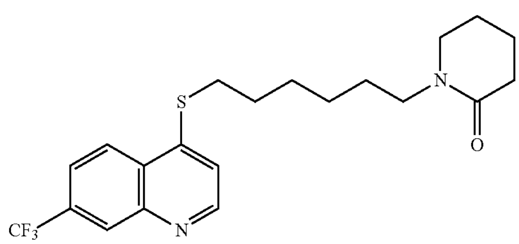 [SMILES: O=C1CCCCN1CCCCCCSc1ccnc2cc(C(F)(F)F)ccc12] | 0033086 | 1-(6-{[7-(trifluoromethyl)quinolin-4-yl]sulfanyl}hexyl)piperidin-2-one |
| 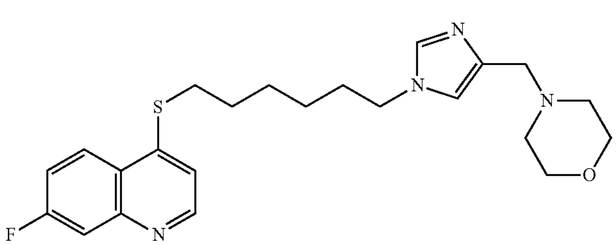 [SMILES: Fc1ccc2c(SCCCCCCn3cnc(CN4CCOCC4)c3)ccnc2c1] | 0033055 | 7-fluoro-4-({6-[4-(morpholin-4-ylmethyl)-1H-imidazol-1-yl]hexyl}sulfanyl)quinoline |

-continued

| Compound Structure | Compound Designation | Compound Name |
|---|---|---|
| 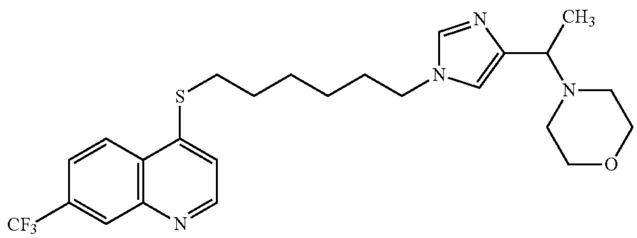 [SMILES: CC(c1cn(CCCCCCSc2ccnc3cc(C(F)(F)F)ccc23)cn1)N1CCOCC1] | 0033044 | 4-[{6-(4-[1-(morpholin-4-yl)ethyl}-1H-imidazol-1-yl}hexyl)sulfanyl]-7-(trifluoromethyl)quinoline |
| 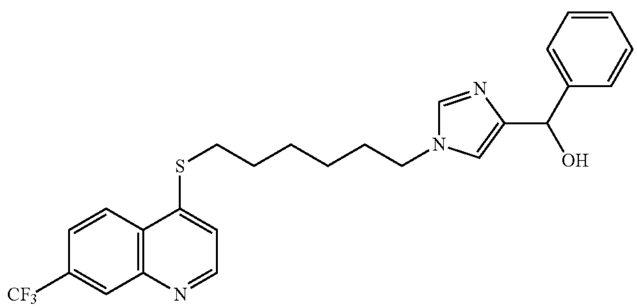 [SMILES: OC(c1ccccc1)c1cn(CCCCCCSc2ccnc3cc(C(F)(F)F)ccc23)cn1] | 0033043 | phenyl[1-(6-{[7-(trifluoromethyl)quinolin-4-yl]sulfanyl}hexyl)-1H-imidazol-4-yl]methanol |
| 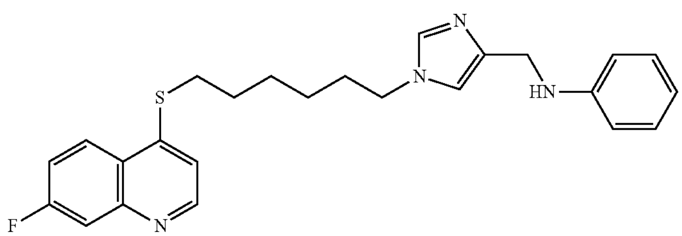 [SMILES: Fc1ccc2c(SCCCCCCn3cnc(CNc4ccccc4)c3)ccnc2c1] | 0033042 | N-{(1-(6-[(7-fluoroquinolin-4-yl)sulfanyl]hexyl}-1H-imidazol-4-yl}methyl]aniline |
| 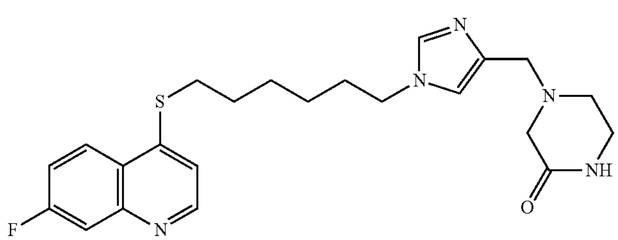 [SMILES: O=C1CN(Cc2cn(CCCCCCSc3ccnc4cc(F)ccc34)cn2)CCN1] | 0033041 | 4-[(1-(6-[(7-fluoroquinolin-4-yl)sulfanyl]hexyl}-1H-imidazol-4-yl)methyl]piperazin-2-one |
| 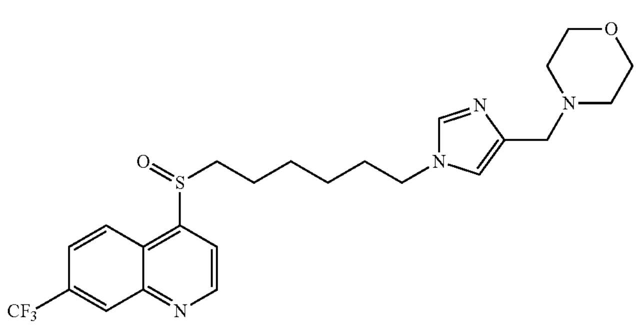 [SMILES: O=S(CCCCCCn1cnc(CN2CCOCC2)c1)c1ccnc2cc(C(F)(F)F)ccc12] | 0033024 | 4-{6-[4-(morpholin-4-ylmethyl)-1H-imidazol-1-yl]hexanesulfinyl}-7-(trifluoromethyl)quinoline |

-continued

| Compound Structure | Compound Designation | Compound Name |
|---|---|---|
| 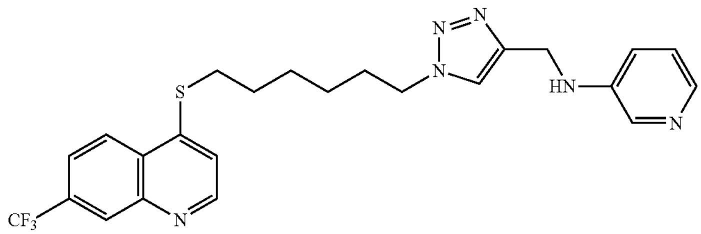 [SMILES: FC(F)(F)c1ccc2c(SCCCCCCn3cc(CNc4cccnc4)nn3)ccnc2c1] | 0033023 | N-{[1-(6-{[7-(trifluoromethyl)quinolin-4-yl]sulfanyl}hexyl)-1H-1,2,3-triazol-4-yl]methyl)pyridin-3-amine |
| 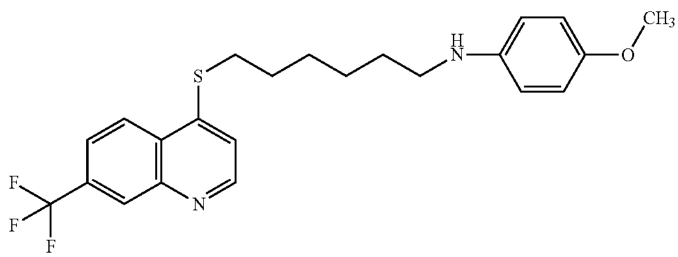 [SMILES: COc1ccc(NCCCCCCSc2ccnc3cc(C(F)(F)F)ccc23)cc1] | 0033019 | 4-methoxy-N-(6-{[7-(trifluoromethyl)quinolin-4-yl]sulfanyl}hexyl)aniline |
| 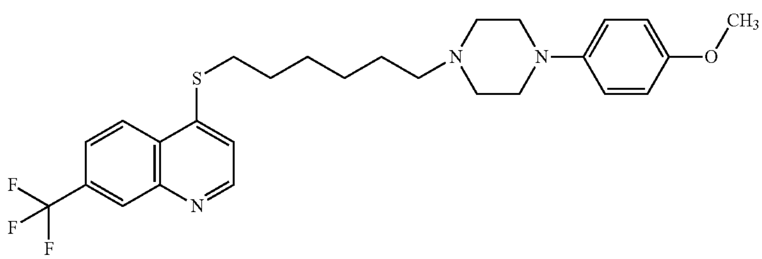 [SMILES: COc1ccc(N2CCN(CCCCCCSc3ccnc4cc(C(F)(F)F)ccc34)CC2)cc1] | 0033016 | 4-{(6-[4-(4-methoxyphenyl)piperazin-1-yl]hexyl)sulfanyl}-7-(trifluoromethyl)quinoline |
| 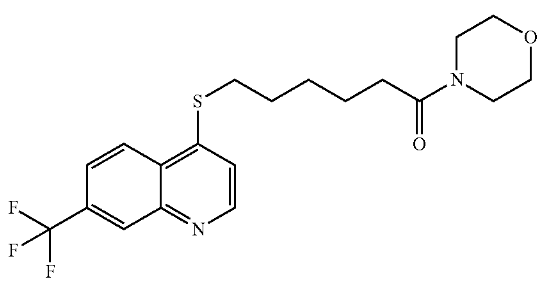 [SMILES: O=C(CCCCCSc1ccnc2cc(C(F)(F)F)ccc12)N1CCOCC1] | 0033015 | 1-(morpholin-4-yl)-6-{[7-(trifluoromethyl)quinolin-4-yl]sulfanyl}hexan-1-one |
| 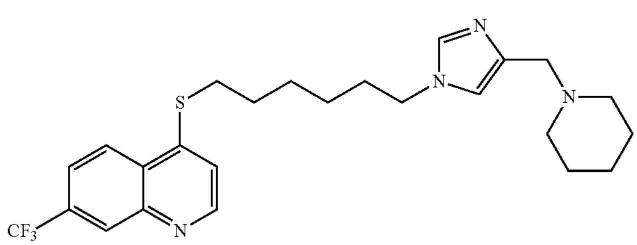 [SMILES: FC(F)(F)c1ccc2c(SCCCCCCn3cnc(CN4CCCCC4)c3)ccnc2c1] | 0033010 | 4-({6-[4-(piperidin-1-ylmethyl)-1H-imidazol-1-yl]hexyl}sulfanyl)-7-(trifluoromethyl)quinoline |

-continued

| Compound Structure | Compound Designation | Compound Name |
|---|---|---|
| 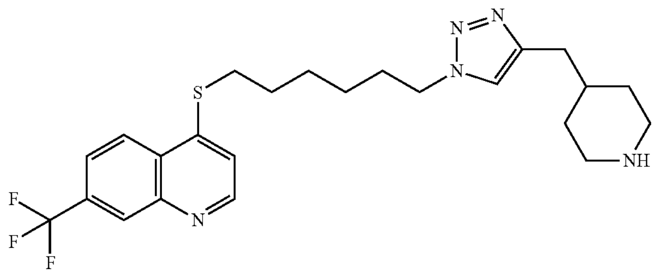 [SMILES: FC(F)(F)c1ccc2c(SCCCCCCn3cc(CC4CCNCC4)nn3)ccnc2c1] | 0033002 | 4-({6-[4-(piperidin-4-ylmethyl)-1H-1,2,3-triazol-1-yl]hexyl}sulfanyl)-7-(trifluoromethyl)quinoline |
| 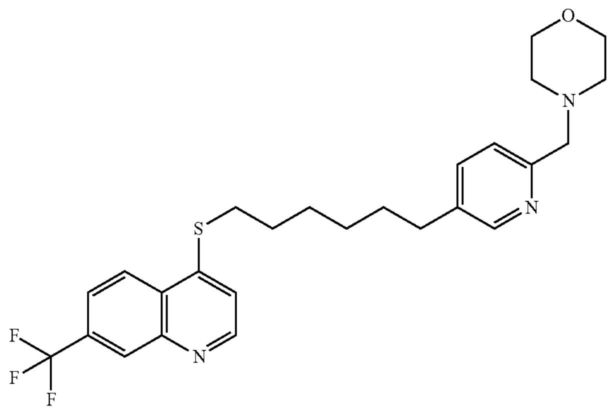 [SMILES: FC(F)(F)c1ccc2c(SCCCCCCc3ccc(CN4CCOCC4)nc3)ccnc2c1] | 0033001 | 4-{(6-[6-(morpholin-4-ylmethyl)pyridin-3-yl]hexyl}sulfanyl)-7-(trifluoromethyl)quinoline |
| 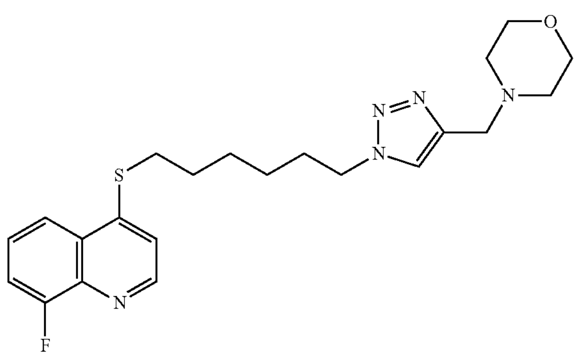 [SMILES: Fc1cccc2c(SCCCCCCn3cc(CN4CCOCC4)nn3)ccnc12] | 0032982 | 8-fluoro-4-({6-[4-(morpholin-4-ylmethyl)-1H-1,2,3-triazol-1-yl]hexyl}sulfanyl)quinoline |
| 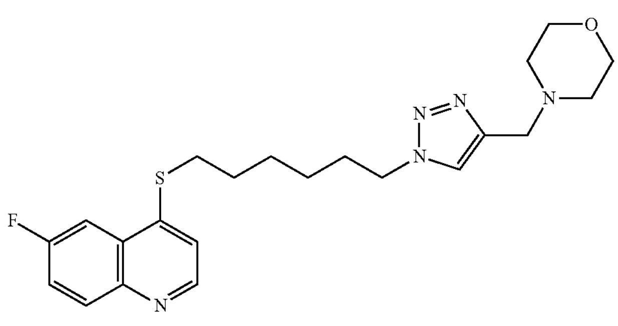 [SMILES: Fc1ccc2nccc(SCCCCCCn3cc(CN4CCOCC4)nn3)c2c1] | 0032981 | 6-fluoro-4-([6-{4-(morpholin-4-ylmethyl)-1H-1,2,3-triazol-1-yl]hexyl}sulfanyl)quinoline |

-continued

| Compound Structure | Compound Designation | Compound Name |
|---|---|---|
| 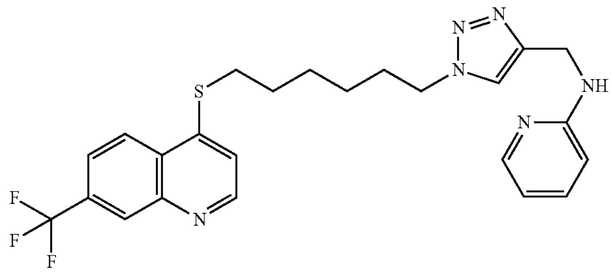 [SMILES: FC(F)(F)c1ccc2c(SCCCCCCn3cc(CNc4ccccn4)nn3)ccnc2c1] | 0032980 | N-{[1-(6-{[7-(trifluoromethyl)quinolin-4-yl]sulfanyl}hexyl)-1H-1,2,3-triazol-4-yl]methyl}pyridin-2-amine |
| 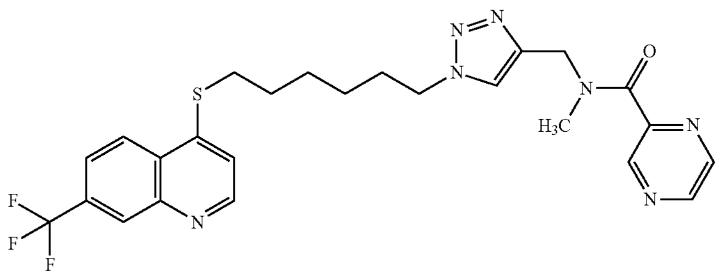 [SMILES: CN(Cc1cn(CCCCCCSc2ccnc3cc(C(F)(F)F)ccc23)nn1)C(=O)c1cnccn1] | 0032979 | N-methyl-N-{[1-(6-{[7-(trifluoromethyl)quinolin-4-yl]sulfanyl)hexyl]-1H-1,2,3-triazol-4-yl]methyl}pyrazine-2-carboxamide |
| 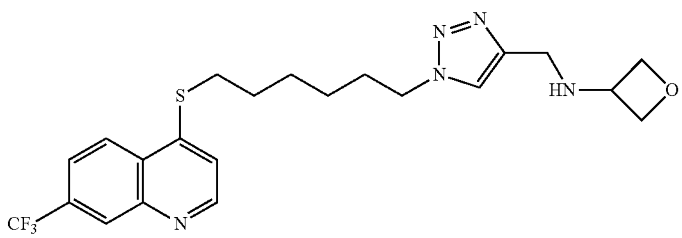 [SMILES: FC(F)(F)c1ccc2c(SCCCCCCn3cc(CNC4COC4)nn3)ccnc2c1] | 0032978 | N-{[1-(6-{[7-(trifluoromethyl)quinolin-4-yl]sulfanyl}hexyl)-1H-1,2,3-triazol-4-yl}methyl)-oxetan-3-amine |
| 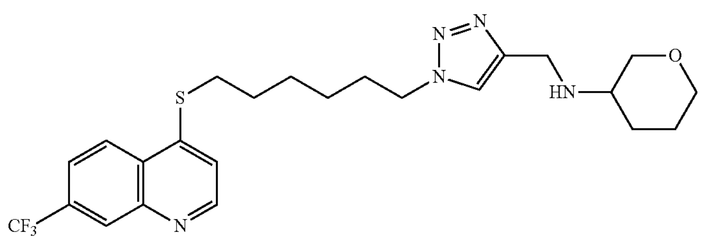 [SMILES: FC(F)(F)c1ccc2c(SCCCCCCn3cc(CNC4CCCOC4)nn3)ccnc2c1] | 0032977 | N-{[1-(6-{[7-(trifluoromethyl)quinolin-4-yl]sulfanyl}hexyl)-1H-1,2,3-triazol-4-yl}methyl)-oxan-3-amine |
| 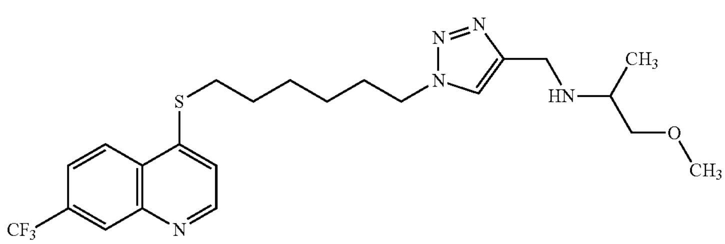 [SMILES: COCC(C)NCc1cn(CCCCCCSc2ccnc3cc(C(F)(F)F)ccc23)nn1] | 0032976 | (1-methoxypropan-2-yl)({[1-(6-{[7-(trifluoromethyl)quinolin-4-yl]sulfanyl}hexyl)-1H-1,2,3-triazol-4-yl]methyl})amine |
| 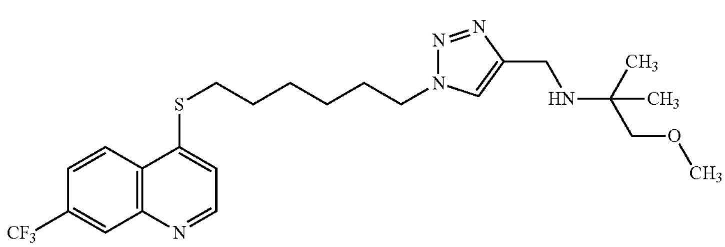 [SMILES: COCC(C)(C)NCc1cn(CCCCCCSc2ccnc3cc(C(F)(F)F)ccc23)nn1] | 0032975 | (1-methoxy-2-methylpropan-2-yl)({[1-(6-{[7-(trifluoromethyl)quinolin-4-yl]sulfanyl}hexyl)-1H-1,2,3-triazol-4-yl]methyl})amine |

-continued

| Compound Structure | Compound Designation | Compound Name |
|---|---|---|
| 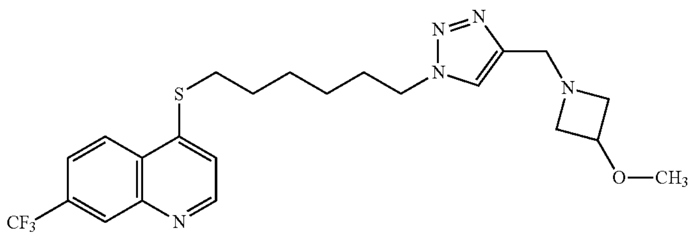 [SMILES: COC1CN(Cc2cn(CCCCCCSc3ccnc4cc(C(F)(F)F)ccc34)nn2)C1] | 0032959 | 4-{(6-{4-[(3-methoxyazetidin-1-yl)methyl]-1H-1,2,3-triazol-1-yl}hexyl)sulfanyl]-7-(trifluoromethyl)quinoline |
| 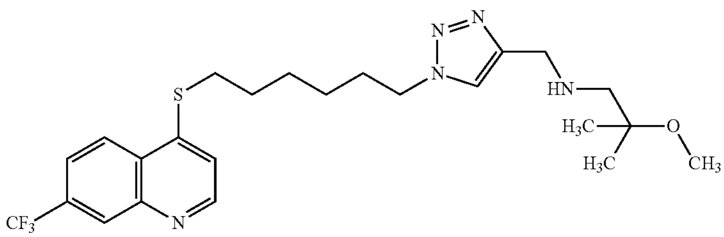 [SMILES: COC(C)(C)CNCc1cn(CCCCCCSc2ccnc3cc(C(F)(F)F)ccc23)nn1] | 0032958 | (2-methoxy-2-methylpropyl)({[1-(6-{[7-(trifluoromethyl)quinolin-4-yl]sulfanyl}hexyl)-1H-1,2,3-triazol-4-yl]methyl})amine |
| 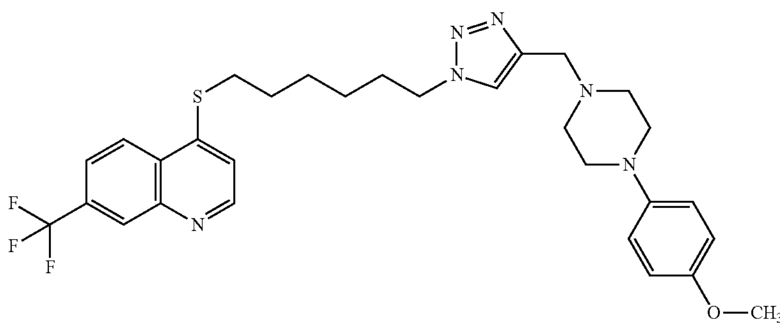 [SMILES: COc1ccc(N2CCN(Cc3cn(CCCCCCSc4ccnc5cc(C(F)(F)F)ccc45)nn3)CC2)cc1] | 0032956 | 4-{[6-(4-{[4-(4-methoxyphenyl)piperazin-1-yl]methyl}-1H-1,2,3-triazol-1-yl)hexyl]sulfanyl}-7-(trifluoromethyl)quinoline |
| 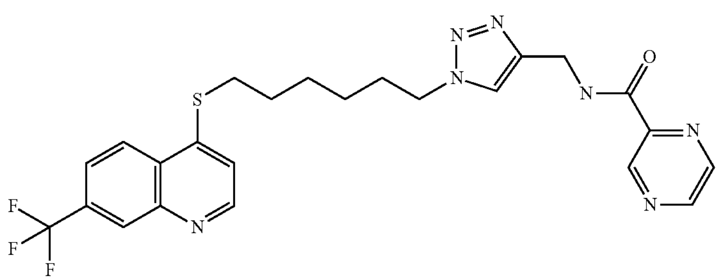 [SMILES: O=C(NCc1cn(CCCCCCSc2ccnc3cc(C(F)(F)F)ccc23)nn1)c1cnccn1] | 0032955 | N-{[1-(6-{[7-(trifluoromethyl)quinolin-4-yl]sulfanyl}hexyl)-1H-1,2,3-triazol-4-yl]methyl}pyrazine-2-carboxamide |
| 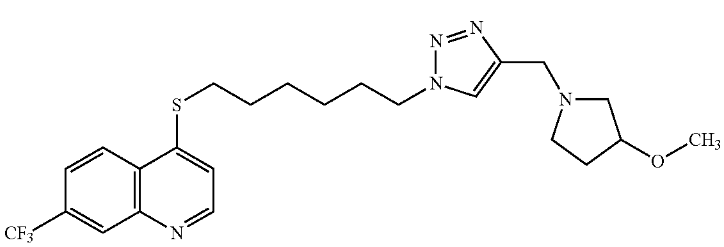 [SMILES: COC1CCN(Cc2cn(CCCCCCSc3ccnc4cc(C(F)(F)F)ccc34)nn2)C1] | 0032953 | 4-[(6-[4-{[3-methoxypyrrolidin-1-yl)methyl]-1H-1,2,3-triazol-1-yl}hexyl)sulfanyl]-7-(trifluoromethyl)quinoline |

-continued

| Compound Structure | Compound Designation | Compound Name |
|---|---|---|
| 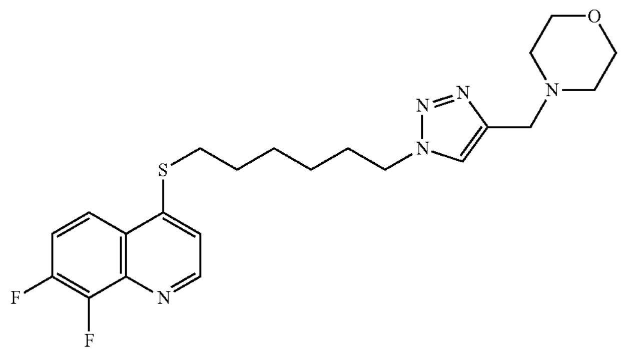 [SMILES: Fc1ccc2c(SCCCCCCn3cc(CN4CCOCC4)nn3)ccnc2c1F] | 0032952 | 7,8-difluoro-4-{(6-[4-(morpholin-4-ylmethyl)-1H-1,2,3-triazol-1-yl]hexyl}sulfanyl)quinoline |
| 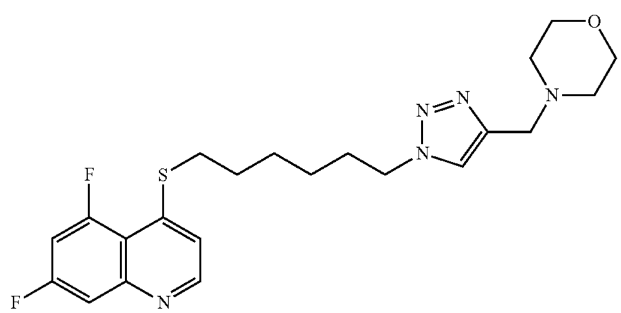 [SMILES: Fc1cc(F)c2c(SCCCCCCn3cc(CN4CCOCC4)nn3)ccnc2c1] | 0032951 | 5,7-difluoro-4-{(6-[4-(morpholin-4-ylmethyl)-1H-1,2,3-triazol-1-yl]hexyl}sufanyl)quinoline |
| 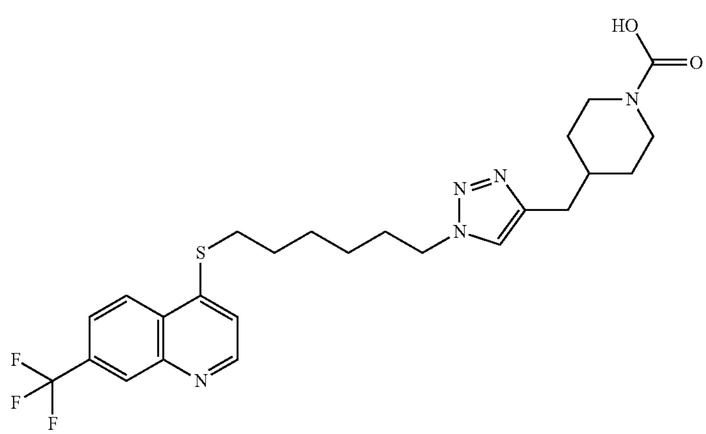 [SMILES: O=C(O)N1CCC(Cc2cn(CCCCCCSc3ccnc4cc(C(F)(F)F)ccc34)nn2)CC1] | 0032939 | 1-(4-{[1-(6-{[7-(trifluoromethyl)quinolin-4-yl]sulfanyl}hexyl)-1H-1,2,3-triazol-4-yl]methyl}piperidin-1-yl)ethan-1-one |

-continued

| Compound Structure | Compound Designation | Compound Name |
|---|---|---|
| 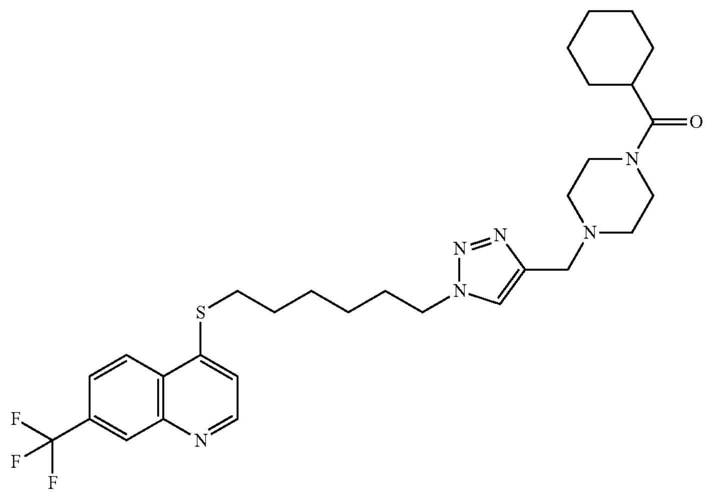 [SMILES: O=C(C1CCCCC1)N1CCN(Cc2cn(CCCCCCSc3ccnc4cc(C(F)(F)F)ccc34)nn2)CC1] | 0032938 | 4-{[6-(4-{[4-(oxane-4-carbonyl)piperazin-1-yl]methyl]-1H-1,2,3-triazol-1-yl)hexyl]sulfanyl}-7-(trifluoromethyl)quinoline |
| 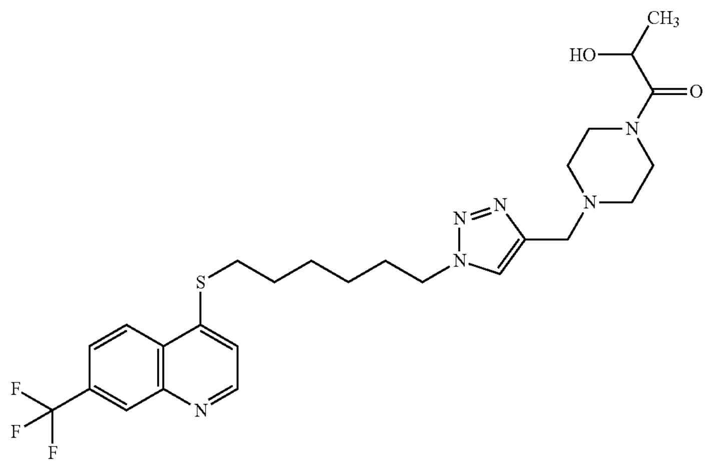 [SMILES: CC(O)C(=O)N1CCN(Cc2cn(CCCCCCSc3ccnc4cc(C(F)(F)F)ccc34)nn2)CC1] | 0032937 | 2-methyl-1-(4-[{1-(6-{[7-(trifluoromethyl)quinolin-4-yl]sulfanyl}hexyl)-1H-1,2,3-triazol-4-yl]methyl}piperazin-1-yl)propan-1-one |
| 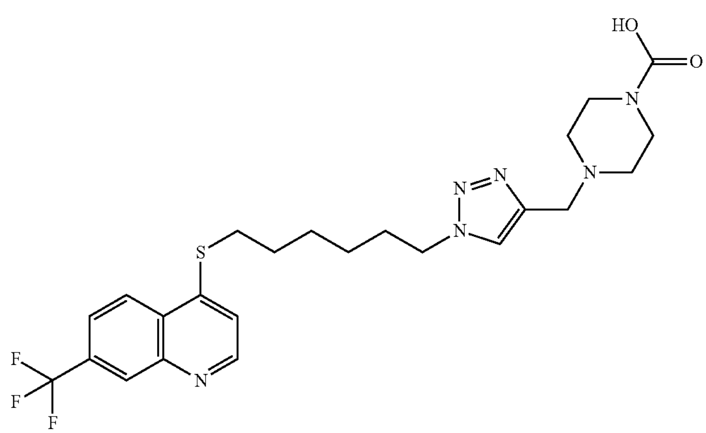 [SMILES: O=C(O)N1CCN(Cc2cn(CCCCCCSc3ccnc4cc(C(F)(F)F)ccc34)nn2)CC1] | 0032936 | 1-(4-{[1-(6-{[7-(trifluoromethyl)quinolin-4-yl]sulfanyl}hexyl)-1H-1,2,3-triazol-4-yl]methyl}piperazin-1-yl)ethan-1-one |

-continued

| Compound Structure | Compound Designation | Compound Name |
|---|---|---|
| 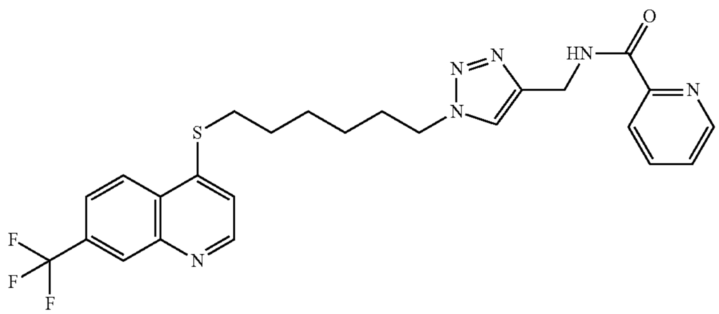 [SMILES: O=C(NCc1cn(CCCCCCSc2ccnc3cc(C(F)(F)F)ccc23)nn1)c1ccccn1] | 0032935 | N-{[1-(6-{[7-(trifluoromethyl)quinolin-4-yl]sulfanyl}hexyl)-1H-1,2,3-triazol-4-yl]methyl}pyridine-2-carboxamide |
| 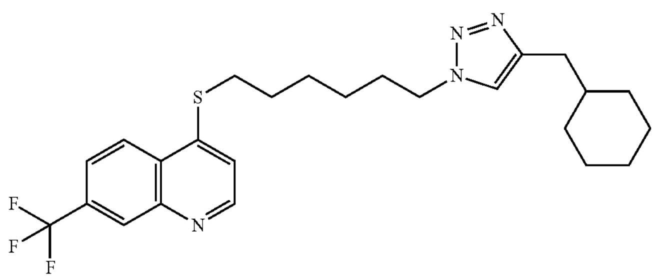 | 0032918 | 4-({6-[4-(cyclohexylmethyl)-1H-1,2,3-triazol-1-yl]hexyl}sulfanyl)-7-(trifluoromethyl)quinoline |
| 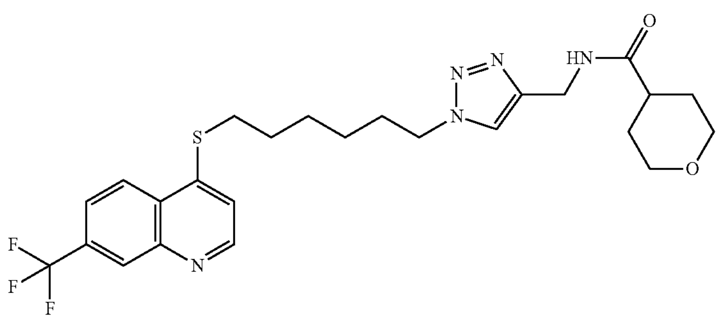 [SMILES: O=C(NCc1cn(CCCCCCSc2ccnc3cc(C(F)(F)F)ccc23)nn1)C1CCOCC1] | 0032917 | N-{[1-(6-{[7-(trifluoromethyl)quinolin-4-yl]sulfanyl}hexyl)-1H-1,2,3-triazol-4-yl]methyl}oxane-2-carboxamide |
| 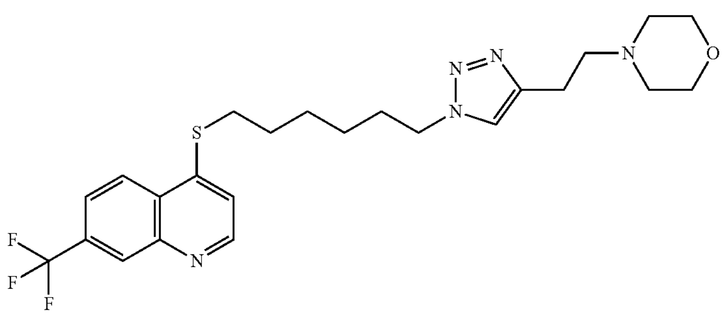 [SMILES: FC(F)(F)c1ccc2c(SCCCCCCn3cc(CCN4CCOCC4)nn3)ccnc2c1] | 0032912 | 4-[(6-{4-[2-(morpholin-4-yl)ethyl]-1H-1,2,3-triazol-1-yl}hexyl)sulfanyl]-7-(trifluoromethyl)quinoline |
| 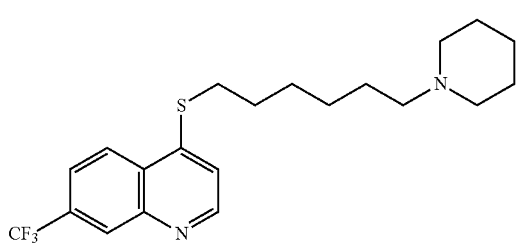 [SMILES: FC(F)(F)c1ccc2c(SCCCCCCN3CCCCC3)ccnc2c1] | 0032906 | 4-{[6-(piperidin-1-yl)hexyl]sulfanyl}-7-(trifluoromethyl)quinoline |

-continued

| Compound Structure | Compound Designation | Compound Name |
|---|---|---|
| 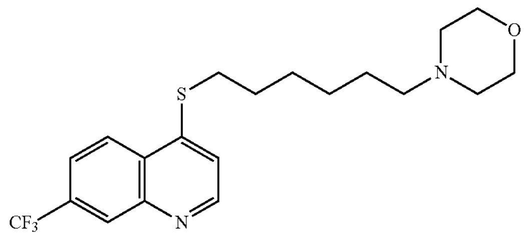 [SMILES: FC(F)(F)c1ccc2c(SCCCCCCN3CCOCC3)ccnc2c1] | 0032905 | 4-{[6-(morpholin-4-yl)hexyl]sulfanyl}-7-(trifluoromethyl)quinoline |
| 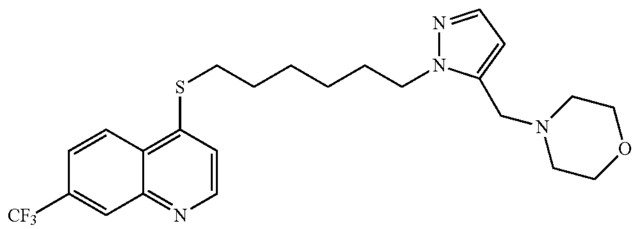 [SMILES: FC(F)(F)c1ccc2c(SCCCCCCn3nccc3CN3CCOCC3)ccnc2c1] | 0032903 | 4-({6-[5-(morpholin-4-ylmethyl)-1H-pyrazol-1-yl]hexyl}sulfanyl)-7-(trifluoromethyl)quinoline |
| 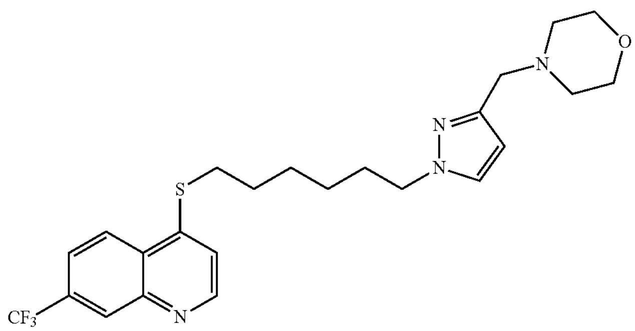 [SMILES: FC(F)(F)c1ccc2c(SCCCCCCn3ccc(CN4CCOCC4)n3)ccnc2c1] | 0032897 | 4-({6-[3-(morpholin-4-ylmethyl)-1H-pyrazol-1-yl]hexyl}sulfanyl)-7-(trifluoromethyl)quinoline |
| 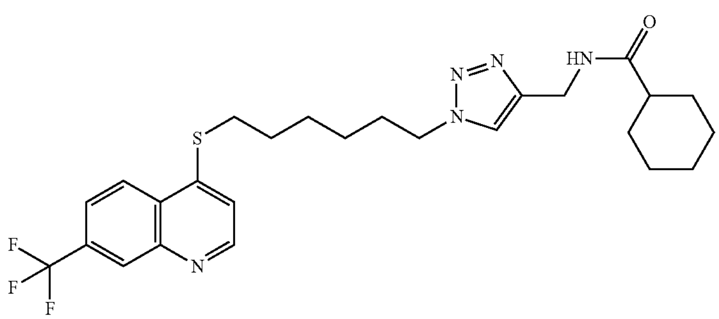 [SMILES: O=C(NCc1cn(CCCCCCSc2ccnc3cc(C(F)(F)F)ccc23)nn1)C1CCCCC1] | 0032896 | N-{[1-(6-{[7-(trifluoromethyl)quinolin-4-yl]sulfanyl}hexyl)-1H-1,2,3-triazol-4-yl]methyl}cyclohexanecarboxamide |
| 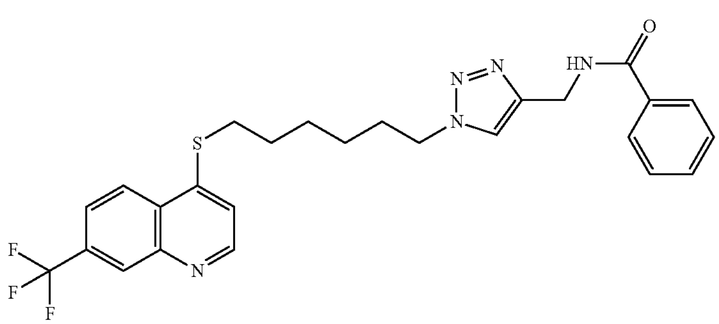 [SMILES: O=C(NCc1cn(CCCCCCSc2ccnc3cc(C(F)(F)F)ccc23)nn1)c1ccccc1] | 0032895 | N-{[1-(6-{[7-(trifluoromethyl)quinolin-4-yl]sulfanyl}hexyl)-1H-1,2,3-triazol-4-yl]methyl}benzamide |

-continued

| Compound Structure | Compound Designation | Compound Name |
|---|---|---|
| 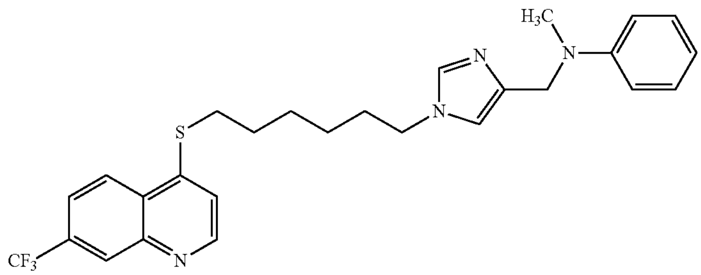 [SMILES: CN(Cc1cn(CCCCCCSc2ccnc3cc(C(F)(F)F)ccc23)cn1)c1ccccc1] | 0032887 | N-methyl-N-{[1-(6-{[7-(trifluoromethyl)quinolin-4-yl]sulfanyl}hexyl}-1H-imidazol-4-yl]methyl}aniline |
| 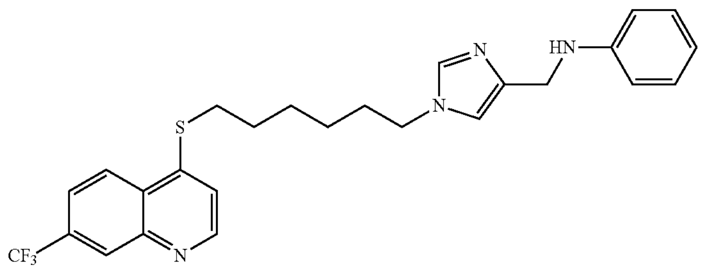 [SMILES: FC(F)(F)c1ccc2c(SCCCCCCn3cnc(CNc4ccccc4)c3)ccnc2c1] | 0032886 | N-{[1-(6-{[7-(trifluoromethyl)quinolin-4-yl]sulfanyl}hexyl}-1H-imidazol-4-yl]methyl}aniline |
| 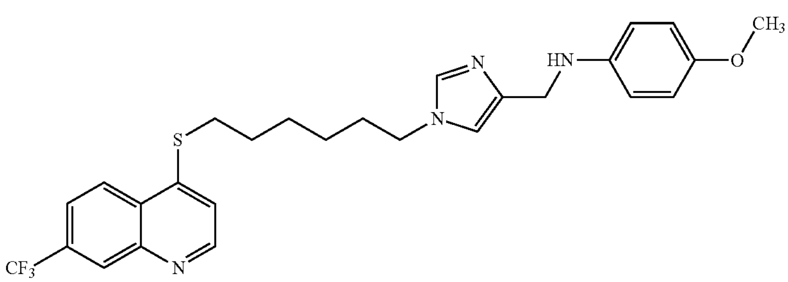 [SMILES: COc1ccc(NCc2cn(CCCCCCSc3ccnc4cc(C(F)(F)F)ccc34)cn2)cc1] | 0032881 | 4-methoxy-N-{[1-(6-{[7-(trifluoromethyl)quinolin-4-yl]sulfanyl}hexyl)-1H-imidazol-4-yl]methyl}aniline |
| 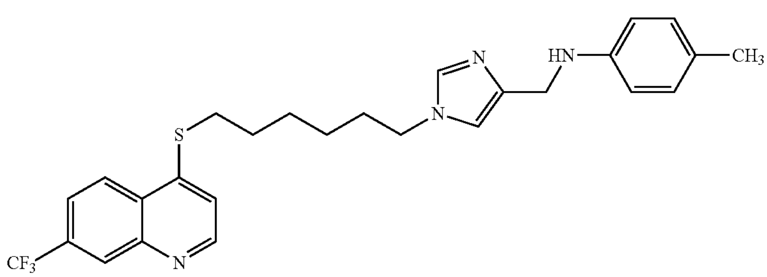 [SMILES: Cc1ccc(NCc2cn(CCCCCCSc3ccnc4cc(C(F)(F)F)ccc34)cn2)cc1] | 0032880 | 4-methyl-N-{[1-(6-{[7-(trifluoromethyl)quinolin-4-yl]sulfanyl}hexyl}-1H-imidazol-4-yl]methyl)aniline |
| 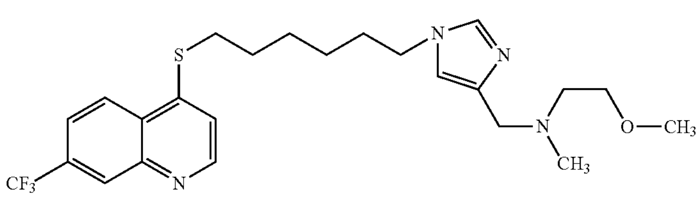 [SMILES: COCCN(C)Cc1cn(CCCCCCSc2ccnc3cc(C(F)(F)F)ccc23)cn1] | 0032879 | (2-methoxyethyl)(methyl){[1-(6-{[7-(trifluoromethyl)quinolin-4-yl]sulfanyl}hexyl)-1H-imidzol-4-yl]methyl}amine |

-continued

| Compound Structure | Compound Designation | Compound Name |
|---|---|---|
| 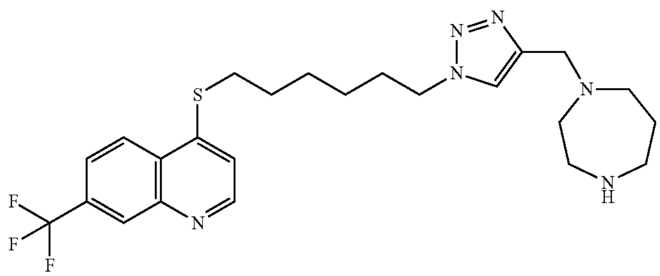 [SMILES: FC(F)(F)c1ccc2c(SCCCCCCn3cc(CN4CCCNCC4)nn3)ccnc2c1] | 0032868 | 4-({6-[4-(1,4-diazepan-1-ylmethyl)-1H-1,2,3-triazol-1-yl]hexyl}sulfanyl)-7-(trifluoromethyl)quinoline |
| 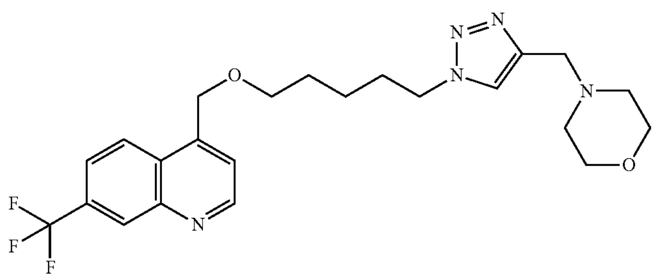 [SMILES: FC(F)(F)c1ccc2c(COCCCCCn3cc(CN4CCOCC4)nn3)ccnc2c1] | 0032867 | 4-[{(5-{4-(morpholin-4-ylmethyl)-1H-1,2,3-triazol-1-yl]pentyl}oxy)methyl]-7-(trifluoromethyl)quinoline |
| 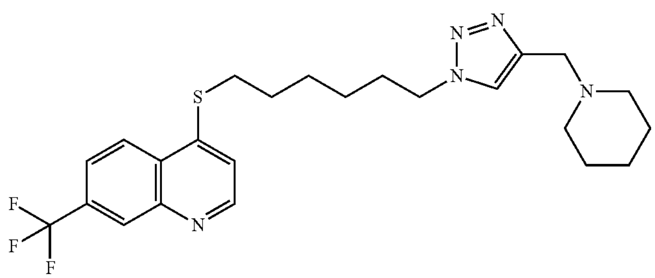 | 0032855 | 4-{(6-[4-(piperidin-1-ylmethyl)-1H-1,2,3-triazol-1-yl]hexyl}sulfanyl)-7-(trifluoromethyl)quinoline |
| 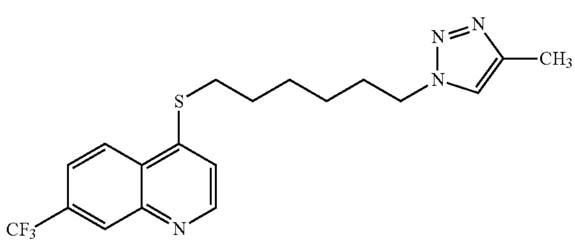 [SMILES: Cc1cn(CCCCCCSc2ccnc3cc(C(F)(F)F)ccc23)nn1] | 0032853 | 4-{[6-(4-methyl-1H-1,2,3-triazol-1-yl)hexyl]sulfanyl}-7-(trifluoromethyl)quinoline |
| 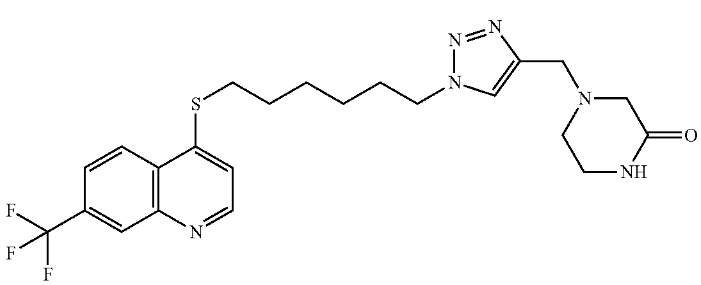 [SMILES: O=C1CN(Cc2cn(CCCCCCSc3ccnc4cc(C(F)(F)F)ccc34)nn2)CCN1] | 0032851 | 4-{[1-(6-{[7-(trifluoromethyl)quinolin-4-yl]sulfanyl}hexyl)-1H-1,2,3-triazol-4-yl]methyl}piperazin-2-one |

| Compound Structure | Compound Designation | Compound Name |
|---|---|---|
| 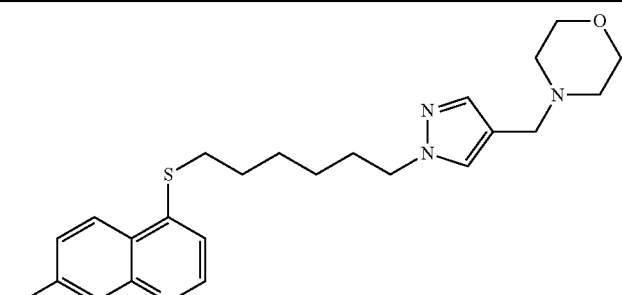 | 0032850 | 4-({6-[4-(morpholin-4-ylmethyl)-1H-pyrazol-1-yl]hexyl}sulfanyl)-7-(trifluoromethyl)quinoline |
| 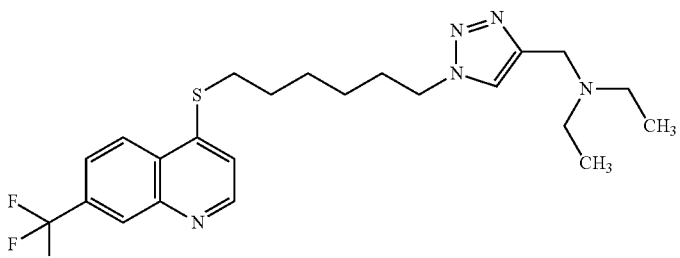 | 0032843 | diethyl({[1-(6-{[7-(trifluoromethyl)quinolin-4-yl]sulfanyl}hexyl)-1H-1,2,3-triazol-4-yl]methyl})amine |
| 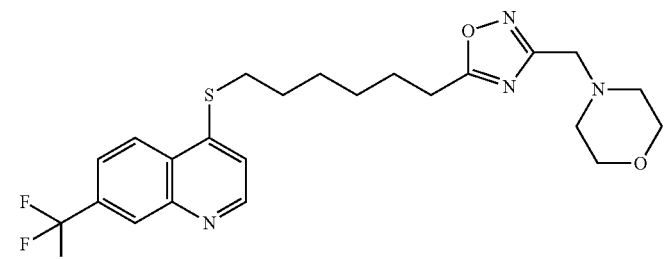 | 0032835 | 4-({6-[3-(morpholin-4-ylmethyl)-1,2,4-oxadiazol-5-yl]hexyl}sulfanyl)-7-(trifluoromethyl)quinoline |
| 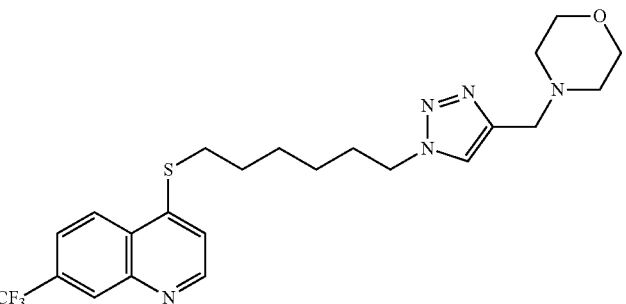 | 0032834 | 7-chloro-4-{(6-[4-(morpholin-4-ylmethyl)-1H-1,2,3-triazol-1-yl]hexyl}sulfanyl)quinoline |
| 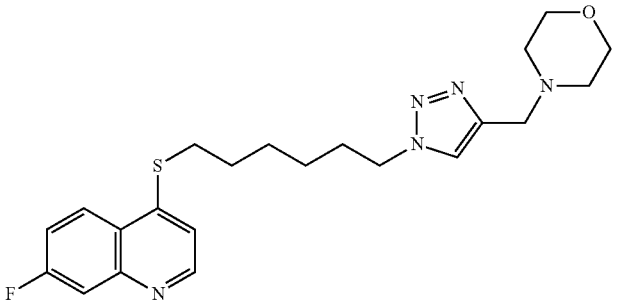 [SMILES: Fc1ccc2c(SCCCCCCn3cc(CN4CCOCC4)nn3)ccnc2c1] | 0032833 | 7-fluoro-4-{(6-[4-(morpholin-4-ylmethyl)-1H-1,2,3-triazol-1-yl]hexyl}sulfanyl)quinoline |

| Compound Structure | Compound Designation | Compound Name |
|---|---|---|
| 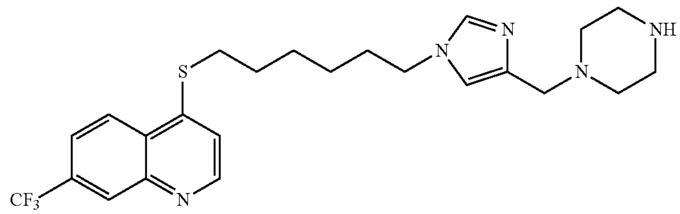 [SMILES: FC(F)(F)c1ccc2c(SCCCCCCn3cnc(CN4CCNCC4)c3)ccnc2c1] | 0032822 | 4-({6-[4-(piperidin-1-ylmethyl)-1H-imidazol-1-yl]hexyl}sulfanyl)-7-(trifluoromethyl)quinoline |
| 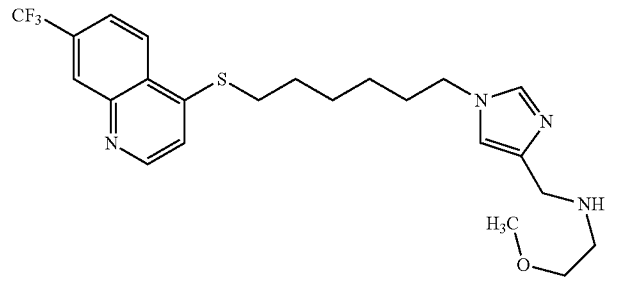 [SMILES: COCCNCc1cn(CCCCCCSc2ccnc3cc(C(F)(F)F)ccc23)cn1] | 0032796 | (2-methoxyethyl)({[1-(6-{[7-(trifluoromethyl)quinolin-4-yl]sulfanyl}hexyl)-1H-imidazol-4-yl]methyl})amine |
| 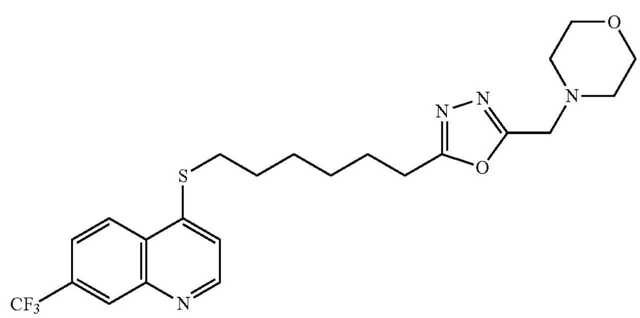 [SMILES: FC(F)(F)c1ccc2c(SCCCCCCc3nnc(CN4CCOCC4)o3)ccnc2c1] | 0032794 | 4-({6-[5-(morpholin-4-ylmethyl)-1,3,4-oxadiazol-2-yl]hexyl}sulfanyl)-7-(trifluoromethyl)quinoline |
| 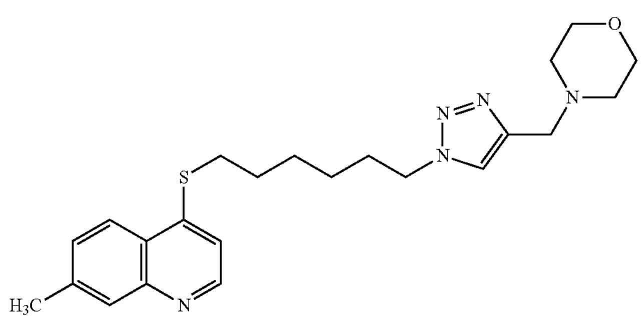 [SMILES: Cc1ccc2c(SCCCCCCn3cc(CN4CCOCC4)nn3)ccnc2c1] | 0032793 | 7-methyl-4-({6-[4-(morpholin-4-ylmethyl)-1H-1,2,3-triazol-1-yl]hexyl}sulfanyl)quinoline |
| 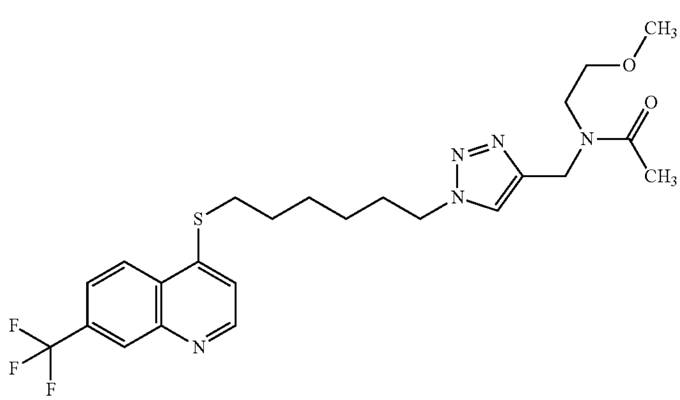 [SMILES: COCCN(Cc1cn(CCCCCCSc2ccnc3cc(C(F)(F)F)ccc23)nn1)C(C)=O] | 0032789 | N-(2-methoxyethyl)-N-{[1-(6-{[7-(trifluoromethyl)quinolin-4-yl]sulfanyl}hexyl)-1H-1,2,3-triazol-4-yl]methyl)acetamide |

-continued

| Compound Structure | Compound Designation | Compound Name |
|---|---|---|
| 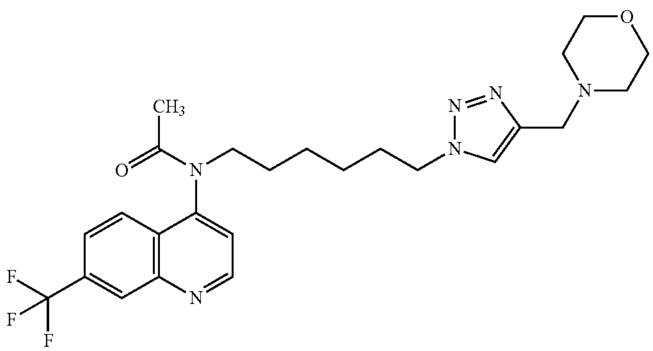 [SMILES: CC(=O)N(CCCCCCn1cc(CN2CCOCC2)nn1)c1ccnc2cc(C(F)(F)F)ccc12] | 0032767 | N-(6-[4-(morpholin-4-ylmethyl)-1H-1,2,3-triazol-1-yl]hexyl)-N-[7-(trifluoromethyl)quinolin-4-yl]acetamide |
| 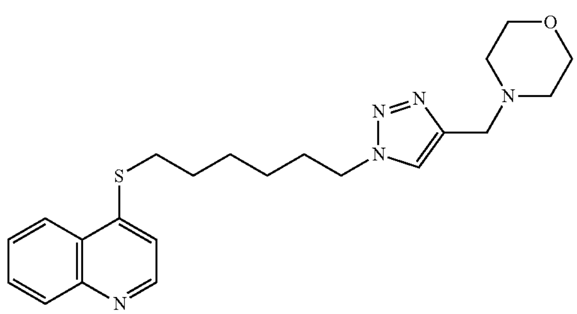 [SMILES: c1ccc2c(SCCCCCCn3cc(CN4CCOCC4)nn3)ccnc2c1] | 0032766 | 4-({6-[4-(morpholin-4-ylmethyl)-1H-1,2,3-triazol-1-yl]hexyl]sulfanyl}quinoline |
| 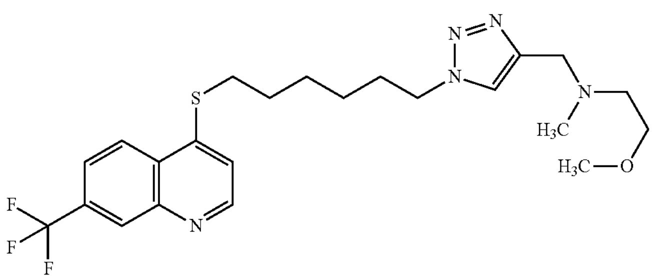 [SMILES: COCCN(C)Cc1cn(CCCCCCSc2ccnc3cc(C(F)(F)F)ccc23)nn1] | 0032761 | (2-methoxyethyl)(methyl){1-(6-{[7-(trifluoromethyl)quinolin-4-yl]sulfanyl]hexyl}-1H-1,2,3-triazol-4-yl]methyl}amine |
| 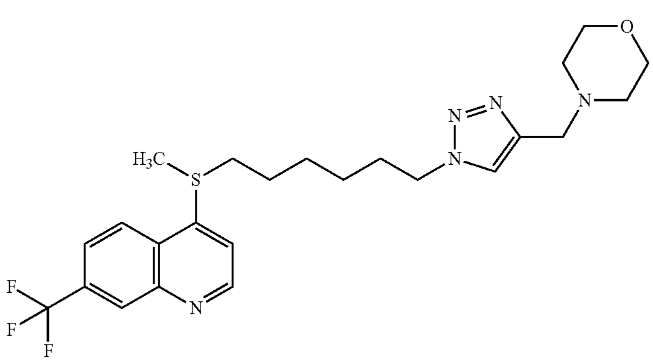 | 0032734 | N-methyl-N-{6-[4-(morpholin-4-ylmethyl)-1H-1,2,3-triazol-1-yl]hexyl}-7-(trifluoromethyl)quinolin-4-amine |

| Compound Structure | Compound Designation | Compound Name |
|---|---|---|
| 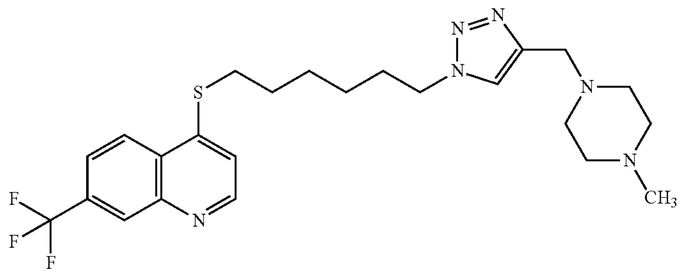 [SMILES: CN1CCN(Cc2cn(CCCCCCSc3ccnc4cc(C(F)(F)F)ccc34)nn2)CC1] | 0032733 | 4-[(6-[4-[(4-methylpiperazin-1-yl)methyl]-1H-1,2,3-triazol-1-yl}hexyl)sulfanyl]-7-(trifluoromethyl)quinoline |
| 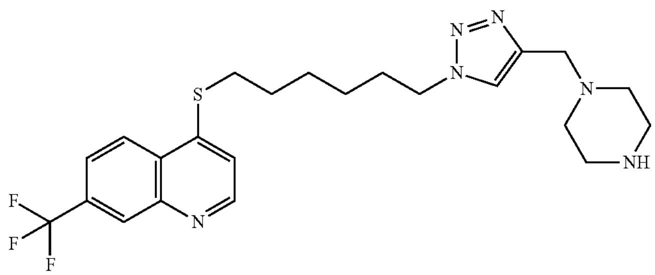 | 0032732 | 4-({6-[4-(piperazin-1-ylmethyl)-1H-1,2,3-triazol-1-yl]hexyl}sulfanyl)-7-(trifluoromethyl)quinoline |
| 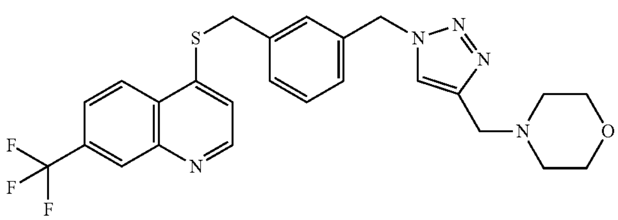 [SMILES: FC(F)(F)c1ccc2c(SCc3cccc(Cn4cc(CN5CCOCC5)nn4)c3)ccnc2c1] | 0032731 | 4-[{(3-{[4-(morpholin-4-ylmethyl)-1H-1,2,3-triazol-1-yl]methyl}phenyl)methyl]sulfanyl)-7-(trifluoromethyl)quinoline |
| 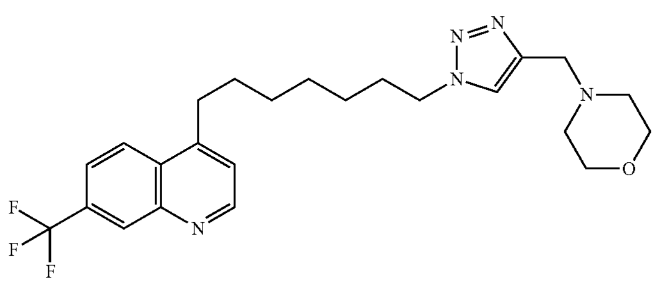 [SMILES: FC(F)(F)c1ccc2c(CCCCCCCn3cc(CN4CCOCC4)nn3)ccnc2c1] | 0032694 | 4-(7-{4-(morpholin-4-ylmethyl)-1H-1,2,3-triazol-1-yl]heptyl}-7-(trifluoromethyl)quinoline |
| 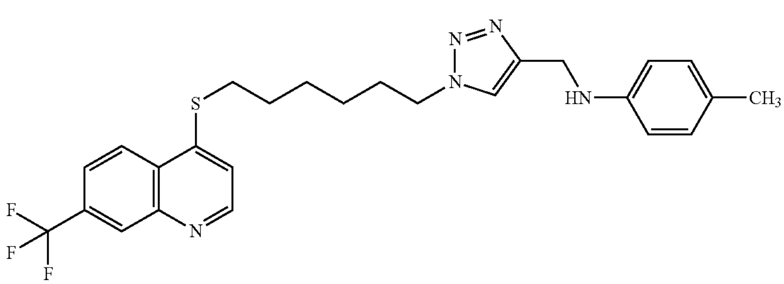 [SMILES: Cc1ccc(NCc2cn(CCCCCCSc3ccnc4cc(C(F)(F)F)ccc34)nn2)cc1] | 0032693 | 4-methyl-N-{[1-(6-{[7-(trifluoromethyl)quinolin-4-yl]sulfanyl}hexyl)-1H-1,2,3-triazol-4-yl]methyl}aniline |

-continued

| Compound Structure | Compound Designation | Compound Name |
|---|---|---|
| 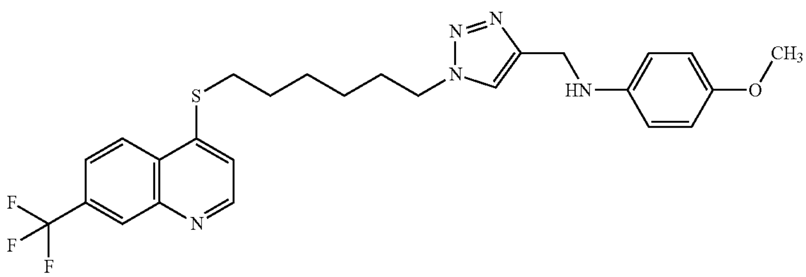 [SMILES: COc1ccc(NCc2cn(CCCCCCSc3ccnc4cc(C(F)(F)F)ccc34)nn2)cc1] | 0032692 | 4-methoxy-N-{[1-(6-{[7-(trifluoromethyl)quinolin-4-yl]sulfanyl}hexyl)-1H-1,2,3-triazol-4-yl]methyl}aniline |
| 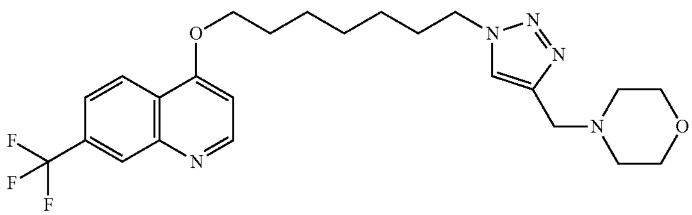 [SMILES: FC(F)(F)c1ccc2c(OCCCCCCCn3cc(CN4CCOCC4)nn3)ccnc2c1] | 0032689 | 4-({7-[4-(morpholin-4-ylmethyl)-1H-1,2,3-triazol-1-yl]heptyl}oxy)-7-(trifluoromethyl)quinoline |
| 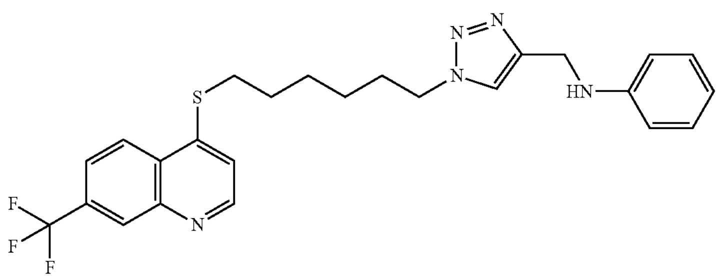 [SMILES: FC(F)(F)c1ccc2c(SCCCCCCn3cc(CNc4ccccc4)nn3)ccnc2c1] | 0032682 | N-{[1-(6-{[7-(trifluoromethyl)quinolin-4-yl]sulfanyl}hexyl)-1H-1,2,3-triazol-4-yl]methyl}aniline |
| 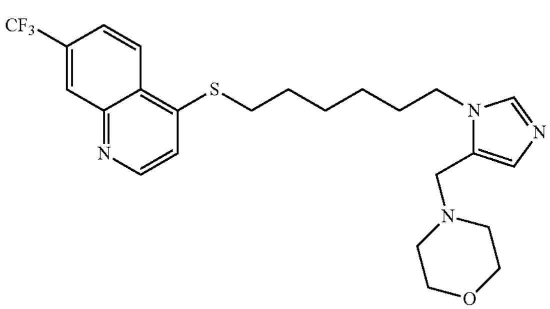 [SMILES: FC(F)(F)c1ccc2c(SCCCCCCn3cncc3CN3CCOCC3)ccnc2c1] | 0032662 | 4-({6-[5-(morpholin-4-ylmethyl)-1H-imidazol-1-yl]hexyl}sulfanyl)-7-(trifluoromethyl)quinoline |
| 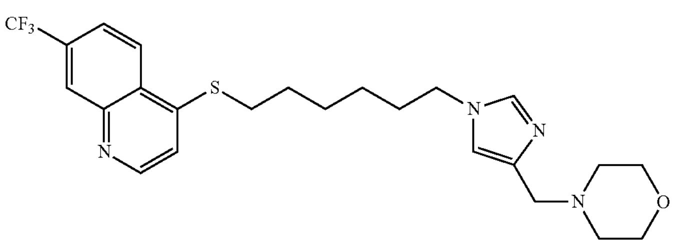 [SMILES: FC(F)(F)c1ccc2c(SCCCCCCn3cnc(CN4CCOCC4)c3)ccnc2c1] | 0032661 | 4-({6-[4-(morpholin-4-ylmethyl)-1H-imidazol-1-yl]hexyl}sulfanyl)-7-(trifluoromethyl)quinoline |

-continued

| Compound Structure | Compound Designation | Compound Name |
|---|---|---|
| 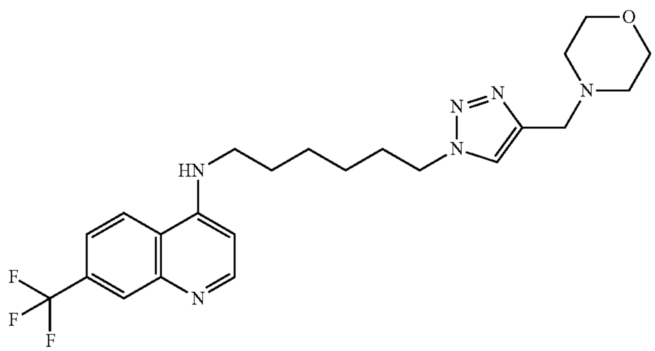 [SMILES: FC(F)(F)c1ccc2c(NCCCCCCn3cc(CN4CCOCC4)nn3)ccnc2c1] | 0032650 | N-[6-{4-(morpholin-4-ylmethyl)-1H-1,2,3-triazol-1-yl}hexyl]-7-(trifluoromethyl)quinolin-4-amine |
| 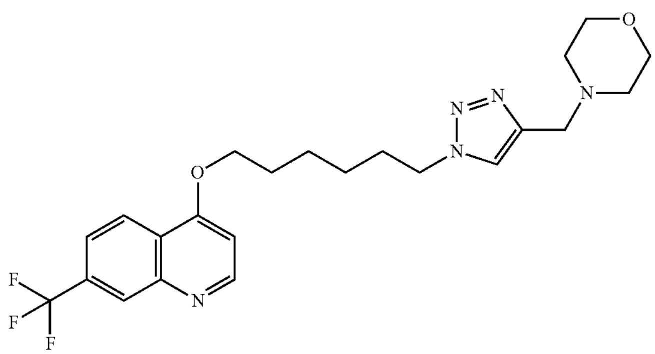 [SMILES: FC(F)(F)c1ccc2c(OCCCCCCn3cc(CN4CCOCC4)nn3)ccnc2c1] | 0032630 | 4-({6-[4-(morpholin-4-ylmethyl)-1H-1,2,3-triazol-1-yl]hexyl}oxy)-7-(trifluoromethyl)quinoline |
| 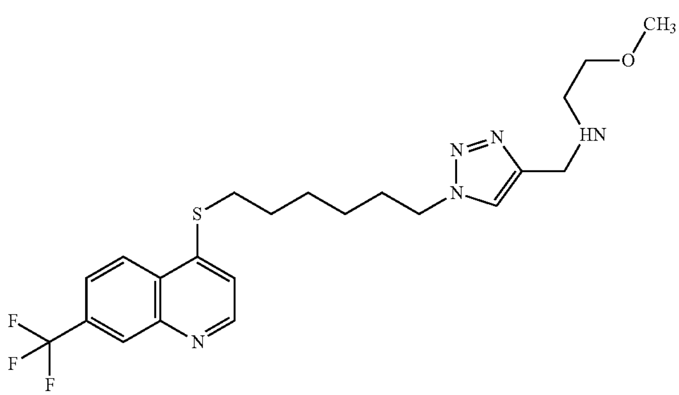 [SMILES: COCCNCc1cn(CCCCCCSc2ccnc3cc(C(F)(F)F)ccc23)nn1] | 0032622 | (2-methoxyethyl)({[1-(6-{[7-(trifluoromethyl)quinolin-4-yl]sulfanyl}hexyl)-1H-1,2,3-triazol-4-yl]methyl})amine |
| 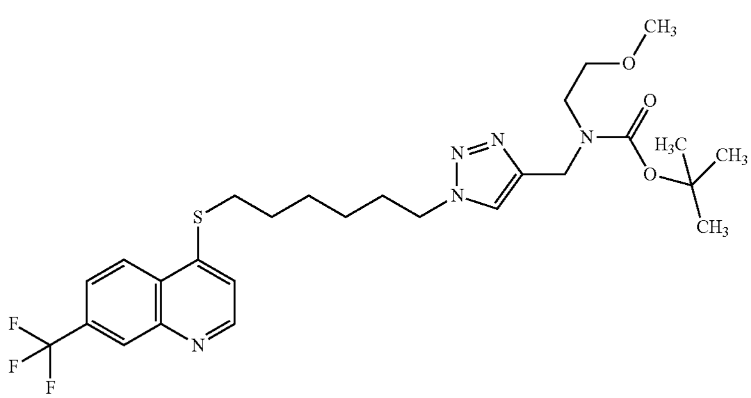 [SMILES: COCCN(Cc1cn(CCCCCCSc2ccnc3cc(C(F)(F)F)ccc23)nn1)C(=O)OC(C)(C)C] | 0032621 | tert-butyl N-(2-methoxyethyl)-N-{[1-(6-{[7-(trifluoromethyl)quinolin-4-yl]sulfanyl}hexyl)-1H-1,2,3-triazol-4-yl]methyl}carbamate |

-continued

| Compound Structure | Compound Designation | Compound Name |
|---|---|---|
| 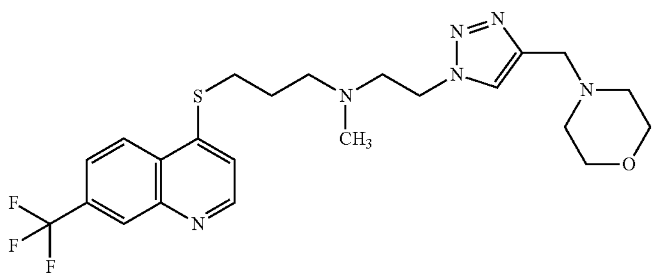 [SMILES: CN(CCCSc1ccnc2cc(C(F)(F)F)ccc12)CCn1cc(CN2CCOCC2)nn1] | 0032514 | methyl({2-[4-(morpholin-4-ylmethyl)-1H-1,2,3-triazol-1-yl]ethyl]}(3-{[7-(trifluoromethyl)quinolin-4-yl]sulfanyl}propyl)amine |
| 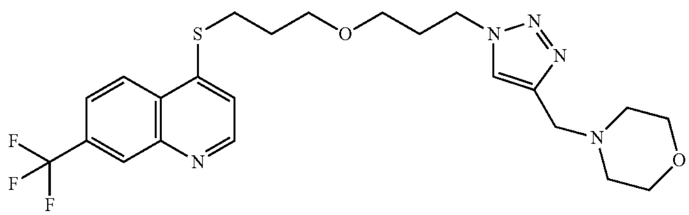 | 0032469 | 4-[(3-{3-[4-(morpholin-4-ylmethyl)-1H-1,2,3-triazol-1-yl]propoxy}propyl)sulfanyl]-7-(trifluoromethyl)quinoline |
| 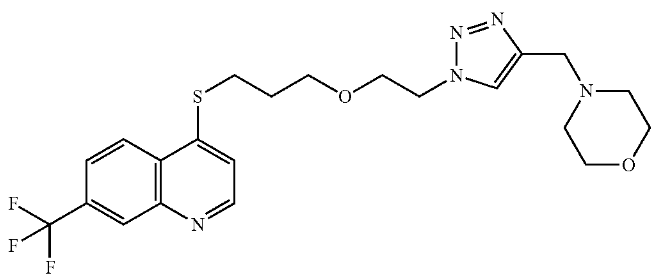 [SMILES: FC(F)(F)c1ccc2c(SCCCOCCn3cc(CN4CCOCC4)nn3)ccnc2c1] | 0032435 | 4-[(3-{2-[4-(morpholin-4-ylmethyl)-1H-1,2,3-triazol-1-yl]ethoxy}propyl)sulfanyl]-7-(trifluoromethyl)quinoline |
| 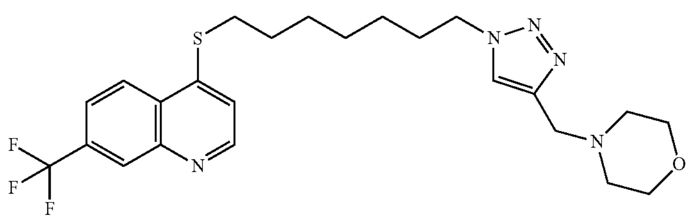 [SMILES: FC(F)(F)c1ccc2c(SCCCCCCCn3cc(CN4CCOCC4)nn3)ccnc2c1] | 0032371 | 4-({7-[4-(morpholin-4-ylmethyl)-1H-1,2,3-triazol-1-yl]heptyl}sulfanyl)-7-(trifluoromethyl)quinoline |
| 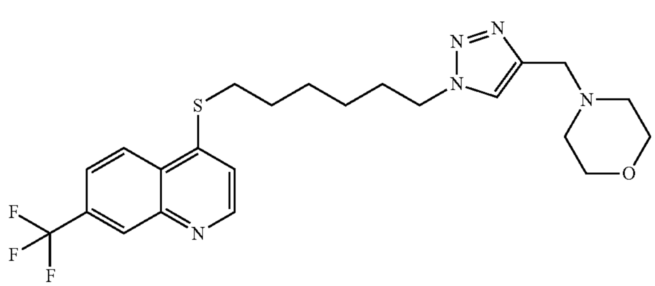 [SMILES: FC(F)(F)c1ccc2c(SCCCCCCn3cc(CN4CCOCC4)nn3)ccnc2c1] | 0032253 | 4-({6-[4-(morpholin-4-ylmethyl)-1H-1,2,3-triazol-1-yl]heptyl}sulfanyl)-7-(trifluoromethyl)quinoline |
| 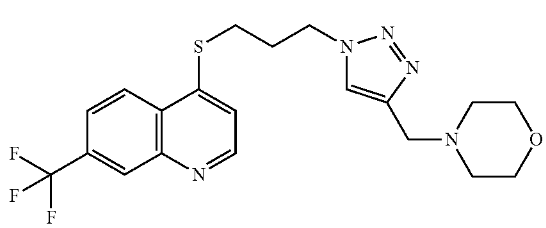 [SMILES: FC(F)(F)c1ccc2c(SCCCn3cc(CN4CCOCC4)nn3)ccnc2c1] | 0032252 | 4-({3-[4-(morpholin-4-ylmethyl)-1H-1,2,3-triazol-1-yl]propyl}sulfanyl)-7-(trifluoromethyl)quinoline |

-continued

| Compound Structure | Compound Designation | Compound Name |
|---|---|---|
| 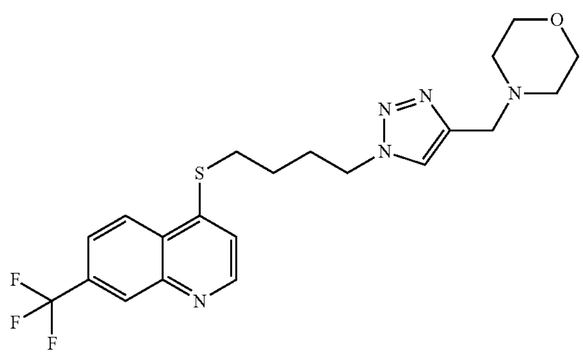 [SMILES: FC(F)(F)c1ccc2c(SCCCCn3cc(CN4CCOCC4)nn3)ccnc2c1] | 0032250 | 4-({4-[4-(morpholin-4-ylmethyl)-1H-1,2,3-triazol-1-yl]butyl}sulfanyl)-7-(trifluoromethyl)quinoline |
| 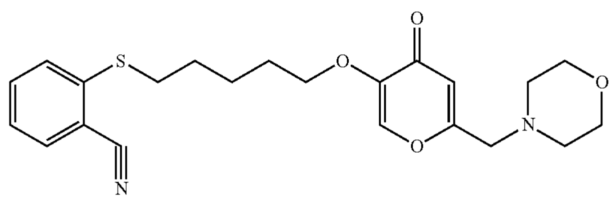 [SMILES: N#Cc1ccccc1SCCCCCOc1coc(CN2CCOCC2)cc1=O] | 0031884 | 2-[(5-{[6-(morpholin-4-ylmethyl)-4-oxo-4H-pyran-3-yl]oxy}pentyl)sulfanyl]benzonitrile |
| 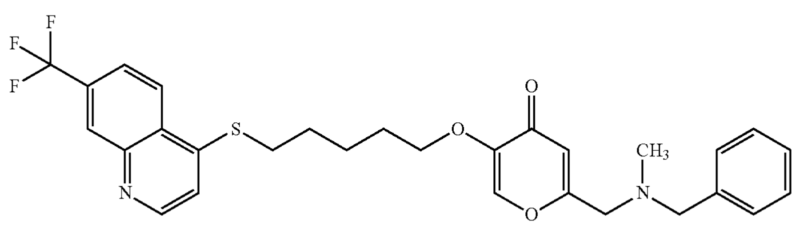 [SMILES: CN(Cc1ccccc1)Cc1cc(=O)c(OCCCCCSc2ccnc3cc(C(F)(F)F)ccc23)co1] | 0031875 | 2-[{benzyl(methyl)amino]methyl}-5-{(5-({7-(trifluoromethyl)quinolin-4-yl]sulfanyl}pentyl)oxy}-4H-pyran-4-one |
| 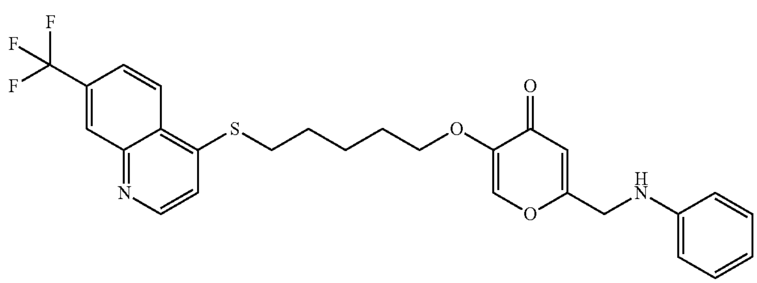 [SMILES: O=c1cc(CNc2ccccc2)occ1OCCCCCSc1ccnc2cc(C(F)(F)F)ccc12] | 0031871 | 2-{(phenylamino)methyl}-5-[{5-{[7-(trifluoromethyl)quinolin-4-yl]sulfanyl}pentyl)oxy}-4H-pyran-4-one |
| 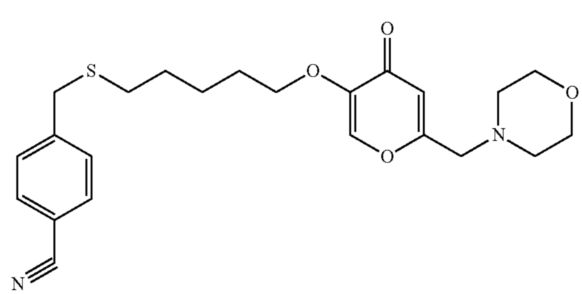 [SMILES: N#Cc1ccc(CSCCCCCOc2coc(CN3CCOCC3)cc2=O)cc1] | 0031870 | 4-{[(5-{[6-(morpholin-4-ylmethyl)-4-oxo-4H-pyran-3-yl]oxy}pentyl)sulfanyl]methyl}benzonitrile |

| Compound Structure | Compound Designation | Compound Name |
|---|---|---|
| 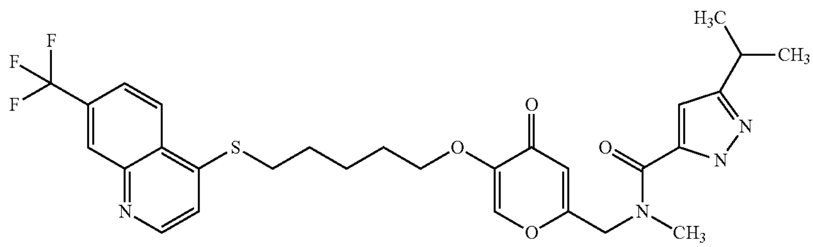 [SMILES: CC(C)c1cc(C(=O)N(C)Cc2cc(=O)c(OCCCCCSc3ccnc4cc(C(F)(F)F)ccc34)co2)[nH]n1] | 0031869 | N-methyl-N-([4-oxo-5-{(5-{[7-(trifluoromethyl)quinolin-4-yl]sulfanyl]pentyl)oxy}-4H-pyran-2-yl]methyl)-3-(propan-2-yl)-1H-pyrazole-5-carboxamide |
| 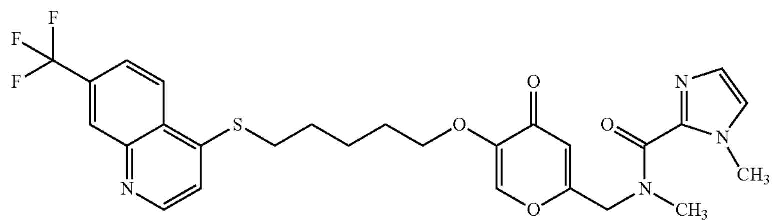 | 0031868 | N,1-dimethyl-N-({4-oxo-5-[(5-{[7-(trifluoromethyl)quinolin-4-yl]sulfanyl)pentyl)oxy]-4H-pyran-2-yl}methyl)-1H-imidazole-2-carboxamide |
| 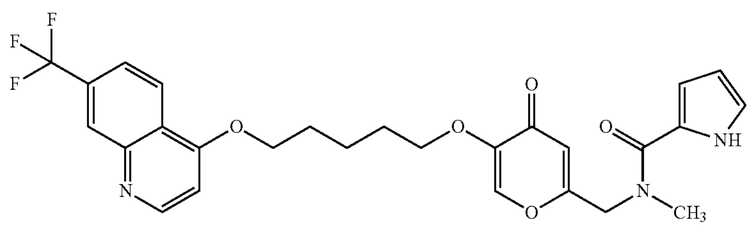 [SMILES: CN(Cc1cc(=O)c(OCCCCCOc2ccnc3cc(C(F)(F)F)ccc23)co1)C(=O)c1ccc[nH]1] | 0031867 | N-methyl-N-({4-oxo-5-{(5-{[7-(trifluoromethyl)quinolin-4-yl]sulfanyl]pentyl)oxy}-4H-pyran-2-yl]methyl)-1H-pyrrole-2-carboxamide |
| 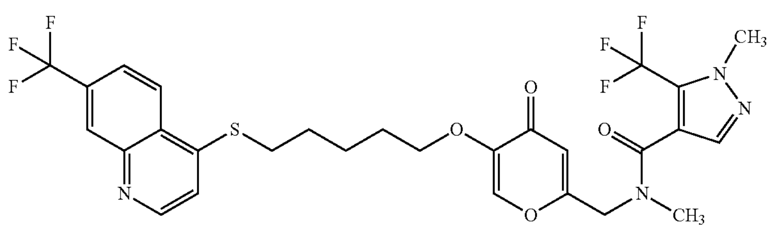 [SMILES: CN(Cc1cc(=O)c(OCCCCCSc2ccnc3cc(C(F)(F)F)ccc23)co1)C(=O)c1cnn(C)c1C(F)(F)F] | 0031866 | N,1-dimethyl-N-({4-oxo-5-[(5-{[7-(trifluoromethyl)quinolin-4-yl]sulfanyl)pentyl)oxy]-4H-pyran-2-yl}methyl)-5-(trifluoromethyl)-1H-pyrazole-2-carboxamide |
| 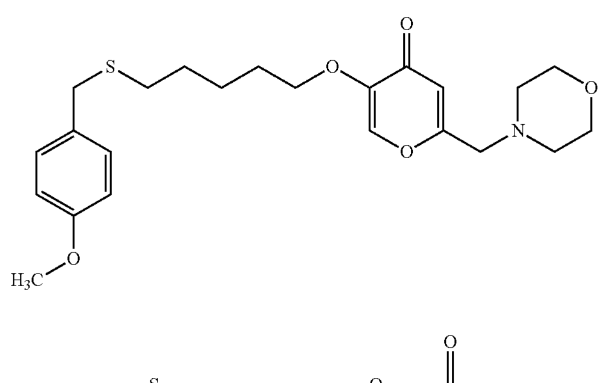 | 0031860 | 5-{(5-({[(4-methoxyphenyl)methyl]sulfanyl}pentyl)oxy]-2-(morpholin-4-ylmethyl)-4H-pyran-4-one |
| 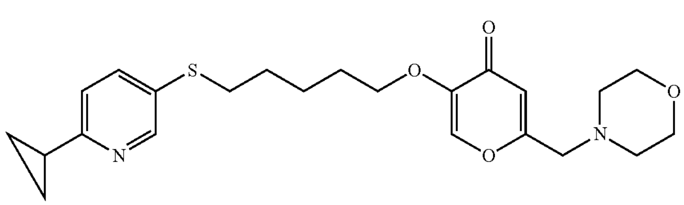 [SMILES: O=c1cc(CN2CCOCC2)occ1OCCCCCSc1ccc(C2CC2)nc1] | 0031859 | 5-{(5-[(6-cyclopropylpyridin-3-yl)sulfanyl]pentyl}oxy)-2-(morpholin-4-ylmethyl)-4H-pyran-4-one |

-continued

| Compound Structure | Compound Designation | Compound Name |
|---|---|---|
| 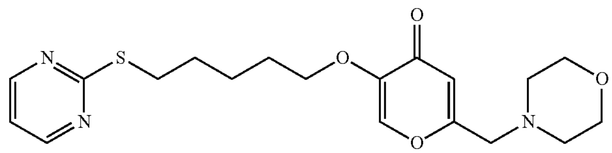 [SMILES: O=c1cc(CN2CCOCC2)occ1OCCCCCSc1ncccn1] | 0031858 | 2-(morpholin-4-ylmethyl)-5-{[5-(pyrimidin-2-ylsulfanyl)pentyl]oxy}-4H-pyran-4-one |
| 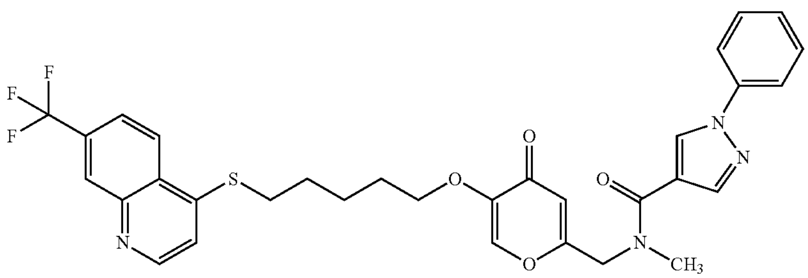 [SMILES: CN(Cc1cc(=O)c(OCCCCCSc2ccnc3cc(C(F)(F)F)ccc23)co1)C(=O)c1cnn(-c2ccccc2)c1] | 0031846 | N-methyl-N-({4-oxo-5-[(5-{[7-(trifluoromethyl)quinolin-4-yl]sulfanyl}pentyl)oxy]-4H-pyran-2-yl]methyl)-1-phenyl-1H-pyrazole-4-carboxamide |
| 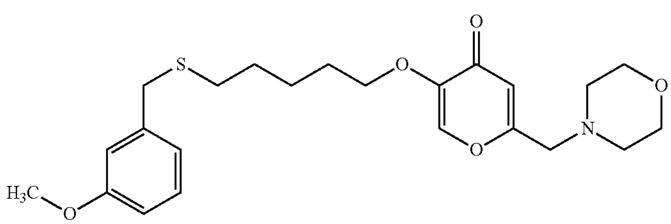 [SMILES: COc1cccc(CSCCCCCOc2coc(CN3CCOCC3)cc2=O)c1] | 0031839 | 5-[(5-[{(3-methoxyphenyl)methyl]sulfanyl}pentyl)oxy}-2-(morpholin-4-ylmethyl)-4H-pyran-4-one |
| 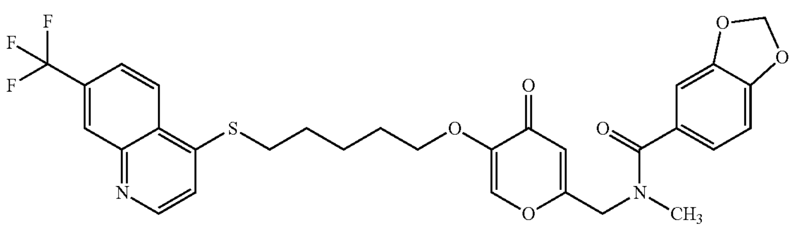 [SMILES: CN(Cc1cc(=O)c(OCCCCCSc2ccnc3cc(C(F)(F)F)ccc23)co1)C(=O)c1ccc2c(c1)OCO2] | 0031838 | N-methyl-N-({4-oxo-5-[(5-{[7-(trifluoromethyl)quinolin-4-yl]sulfanyl}pentyl)oxy]-4H-pyran-2-yl]methyl)-2H-1,3-benzodioxale-4-carboxamide |
| 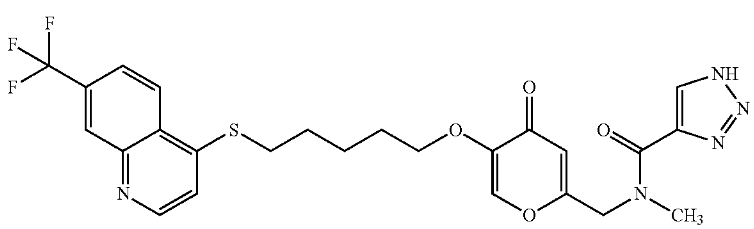 [SMILES: CN(Cc1cc(=O)c(OCCCCCSc2ccnc3cc(C(F)(F)F)ccc23)co1)C(=O)c1c[nH]nn1] | 0031837 | N-methyl-N-({4-oxo-5-[(5-{[7-(trifluoromethyl)quinolin-4-yl]sulfanyl}pentyl)oxy]-4H-pyran-2-yl]methyl)-1H-1,2,3-triazole-4-carboxamide |
| 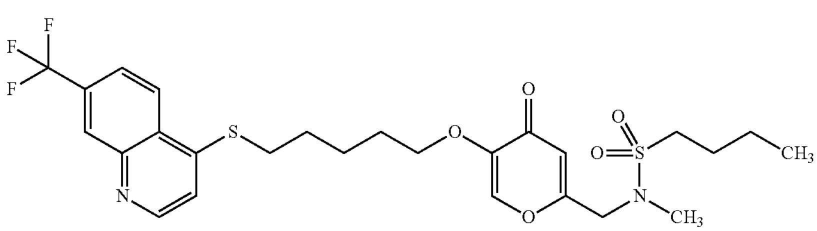 [SMILES: CCCCS(=O)(=O)N(C)Cc1cc(=O)c(OCCCCCSc2ccnc3cc(C(F)(F)F)ccc23)co1] | 0031836 | N-methyl-N-({4-oxo-5-[(5-{[7-(trifluoromethyl)quinolin-4-yl]sulfanyl}pentyl)oxy]-4H-pyran-2-yl]methyl)butane-1-sulfonamide |

-continued

| Compound Structure | Compound Designation | Compound Name |
|---|---|---|
| 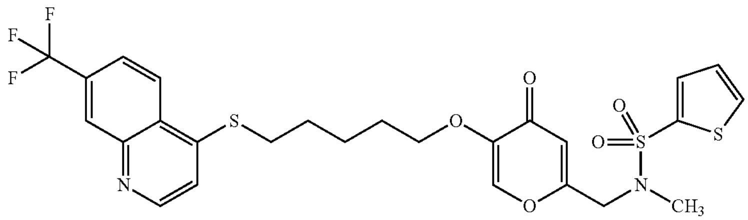 [SMILES: CN(Cc1cc(=O)c(OCCCCCSc2ccnc3cc(C(F)(F)F)ccc23)co1)S(=O)(=O)c1cccs1] | 0031835 | N-methyl-N-({4-oxo-5-[(5-{[7-(trifluoromethyl)quinolin-4-yl]sulfanyl}pentyl)oxy]-4H-pyran-2-yl]methyl)thiophene-2-sulfonamide |
| 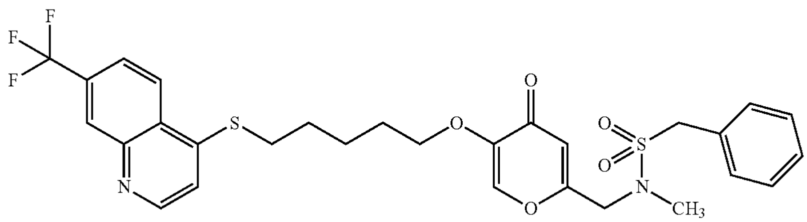 [SMILES: CN(Cc1cc(=O)c(OCCCCCSc2ccnc3cc(C(F)(F)F)ccc23)co1)S(=O)(=O)Cc1ccccc1] | 0031834 | N-methyl-N-({4-oxo-5-[(5-{[7-(trifluoromethyl)quinolin-4-yl]sulfanyl}pentyl)oxy]-4H-pyran-2-yl]methyl)-1-phenylmethane-sulfonamide |
| 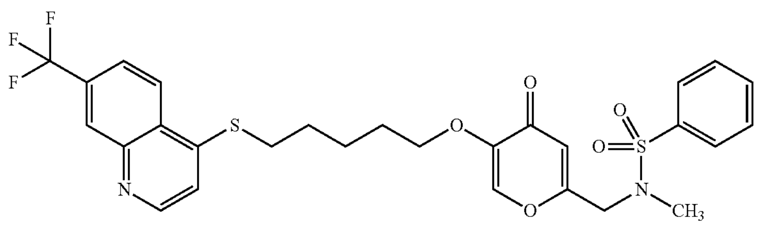 [SMILES: CN(Cc1cc(=O)c(OCCCCCSc2ccnc3cc(C(F)(F)F)ccc23)co1)S(=O)(=O)c1ccccc1] | 0031833 | N-methyl-N-({4-oxo-5-[(5-{[7-(trifluoromethyl)quinolin-4-yl]sulfanyl}pentyl)oxy]-4H-pyran-2-yl]methyl)benzenesulfonamide |
| 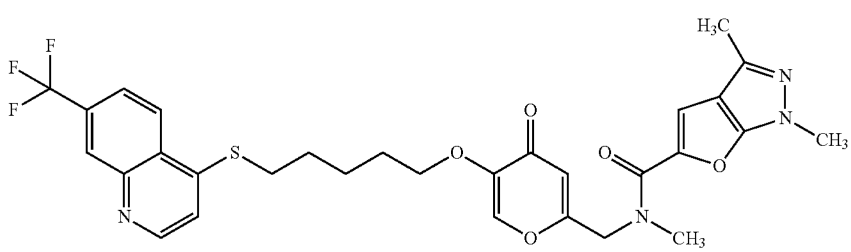 [SMILES: Cc1nn(C)c2oc(C(=O)N(C)Cc3cc(=O)c(OCCCCCSc4ccnc5cc(C(F)(F)F)ccc45)co3)cc12] | 0031832 | N,1,3-trimethyl-N-({4-oxo-5-{[7-(trifluoromethyl)quinolin-4-yl]sulfanyl}pentyl)oxy]-4H-pyran-2-yl]methyl)-1H-thieno[2,3-c]pyrazole-5-carboxamide |
| 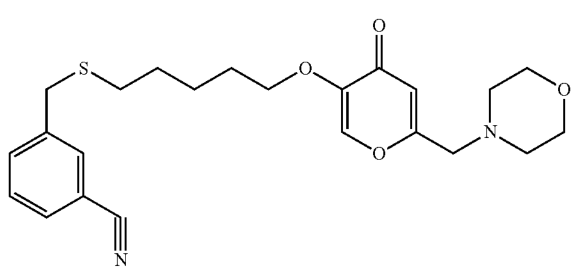 [SMILES: N#Cc1cccc(CSCCCCCOc2coc(CN3CCOCC3)cc2=O)c1] | 0031830 | 3-[{(5-{[6-(morpholin-4-ylmethyl)-4-oxo-4H-pyran-3-yl]oxy}pentyl)sulfanyl}methyl]benzonitrile |
| 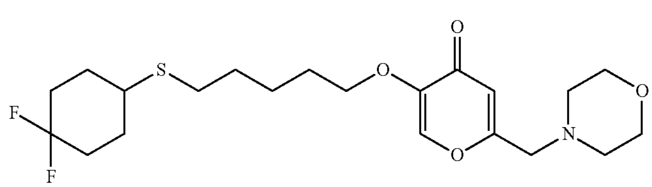 [SMILES: O=c1cc(CN2CCOCC2)occ1OCCCCCSC1CCC(F)(F)CC1] | 0031829 | 5-[{5-[{4,4-difluorocyclohexyl)sulfanyl]pentyl}oxy)-2-(morpholin-4-ylmethyl)-4H-pyran-4-one |

-continued

| Compound Structure | Compound Designation | Compound Name |
|---|---|---|
| 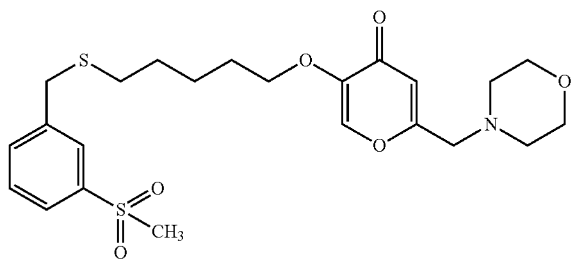 [SMILES: CS(=O)(=O)c1cccc(CSCCCCCOc2coc(CN3CCOCC3)cc2=O)c1] | 0031824 | 5-[{5-{[(3-methanesulfonyl-phenyl)methyl]sulfanyl}pentyl)oxy]-2-(morpholin-4-ylmethyl)-4H-pyran-4-one |
| 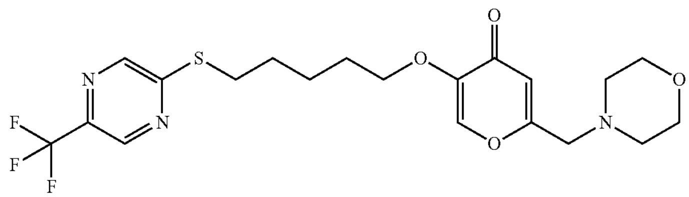 [SMILES: O=c1cc(CN2CCOCC2)occ1OCCCCCSc1cnc(C(F)(F)F)cn1] | 0031823 | 2-(morpholin-4-ylmethyl)-5-[{5-{[5-(trifluoromethyl)pyrazin-2-yl]sulfanyl}pentyl)oxy}-4H-pyran-4-one |
| 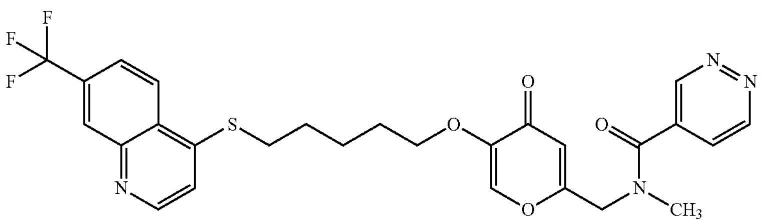 [SMILES: CN(Cc1cc(=O)c(OCCCCCSc2ccnc3cc(C(F)(F)F)ccc23)co1)C(=O)c1ccnnc1] | 0031816 | N-methyl-N-{(4-oxo-5-[(5-{[7-(trifluoromethyl)quinolin-4-yl]sulfanyl)pentyl]oxy}-4H-pyran-2-yl}methyl)pyridazine-4-carboxamide |
| 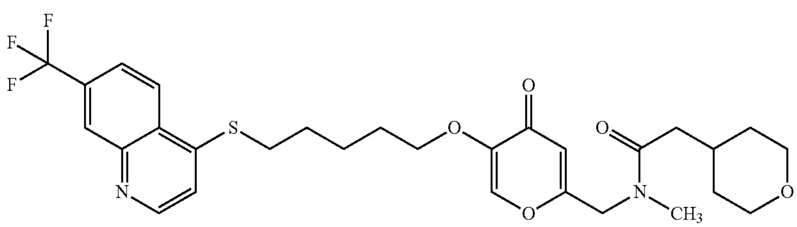 [SMILES: CN(Cc1cc(=O)c(OCCCCCSc2ccnc3cc(C(F)(F)F)ccc23)co1)C(=O)CC1CCOCC1] | 0031815 | N-methyl-2-(oxan-4-yl)-N-({4-oxo-5-[(5-{[7-(trifluoromethyl)quinolin-4-yl]sulfanyl}pentyl)oxy}-4H-pyran-2-yl}methyl)acetamide |
| 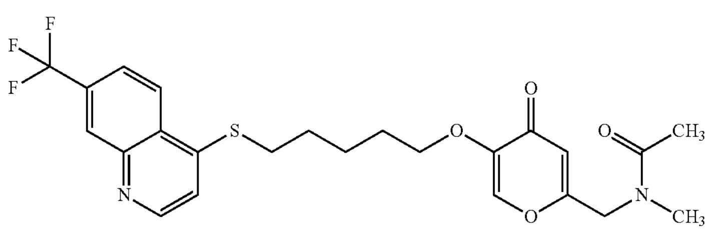 [SMILES: CC(=O)N(C)Cc1cc(=O)c(OCCCCCSc2ccnc3cc(C(F)(F)F)ccc23)co1] | 0031812 | N-methyl-N-({4-oxo-5-[{5-{[7-(trifluoromethyl)quinolin-4-yl]sulfanyl]pentyl}oxy}-4H-pyran-2-yl]methyl}acetamide |
| 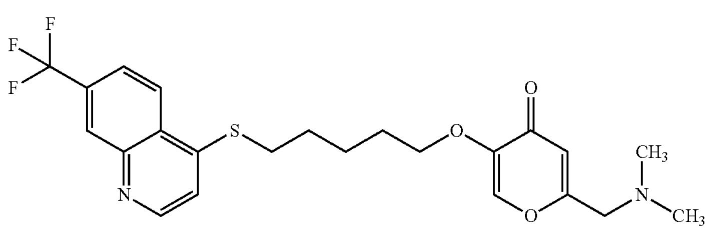 [SMILES: CN(C)Cc1cc(=O)c(OCCCCCSc2ccnc3cc(C(F)(F)F)ccc23)co1] | 0031811 | 2-[(dimethylamino)methyl]-5-[(5-{[7-(trifluoromethyl)quinolin-4-yl]sulfanyl)pentyl}oxy]-4H-pyran-4-one |

-continued

| Compound Structure | Compound Designation | Compound Name |
|---|---|---|
| 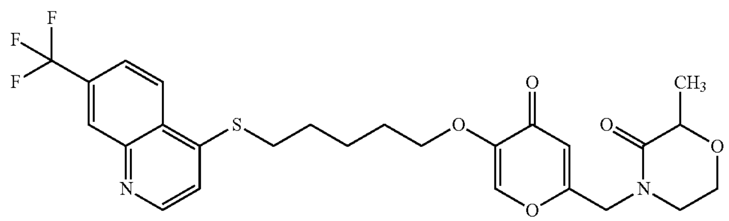 [SMILES: CC1OCCN(Cc2cc(=O)c(OCCCCCSc3ccnc4cc(C(F)(F)F)ccc34)co2)C1=O] | 0031810 | 2-methyl-4-({4-oxo-5-[{5-{[7-(trifluoromethyl)quinolin-4-yl]sulfanyl}pentyl)oxy]-4H-pyran-2-yl]methyl)morpholin-3-one |
| 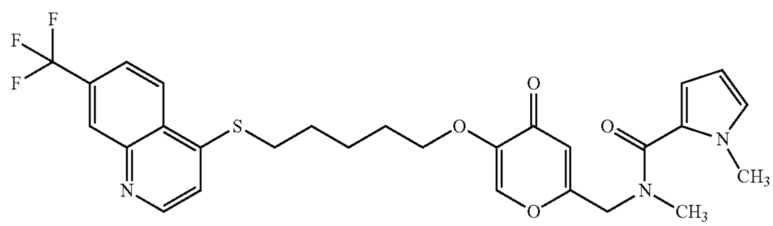 [SMILES: CN(Cc1cc(=O)c(OCCCCCSc2ccnc3cc(C(F)(F)F)ccc23)co1)C(=O)c1cccn1C] | 0031809 | N,1-dimethyl-N-{[4-oxo-5-[(5-{[7-(trifluoromethyl)quinolin-4-yl]sulfanyl}pentyl)oxy]-4H-pyran-2-yl]methyl)-1H-pyrrole-2-carboxamide |
| 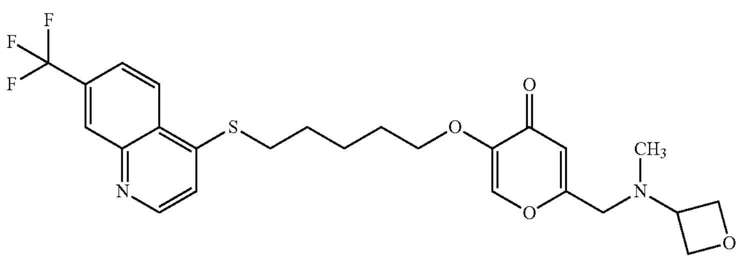 [SMILES: CN(Cc1cc(=O)c(OCCCCCSc2ccnc3cc(C(F)(F)F)ccc23)co1)C1COC1] | 0031808 | 2-{[methyl(oxetan-3-yl)amino]methyl}-5-[(5-[{7-(trifluoromethyl)quinolin-4-yl]sulfanyl}pentyl)oxy]-4H-pyran-4-one |
| 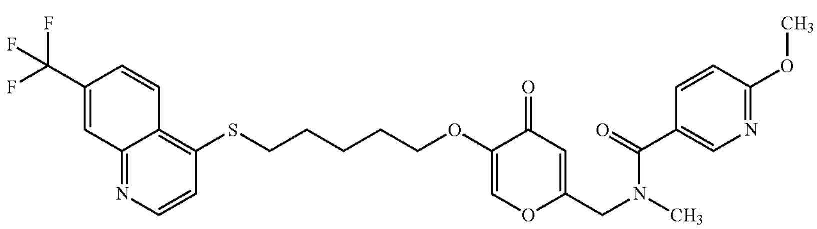 [SMILES: COc1ccc(C(=O)N(C)Cc2cc(=O)c(OCCCCCSc3ccnc4cc(C(F)(F)F)ccc34)co2)cn1] | 0031807 | 6-methoxy-N-methyl-N-({4-oxo-5-[{5-[{7-(trifluoromethyl)quinolin-4-yl]sulfanyl}pentyl)oxy]-4H-pyran-2-yl]methyl)pyridine-3-carboxamide |
| 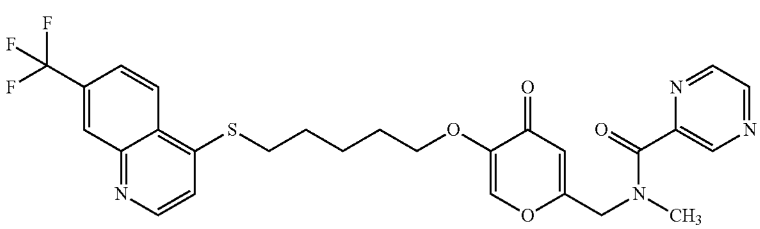 [SMILES: CN(Cc1cc(=O)c(OCCCCCSc2ccnc3cc(C(F)(F)F)ccc23)co1)C(=O)c1cnccn1] | 0031806 | N-methyl-N-({4-oxo-5-[(5-{[7-(trifluoromethyl)quinolin-4-yl]sulfanyl}pentyl)oxy]-4H-pyran-2-yl]methyl)pyrazine-2-carboxamide |
| 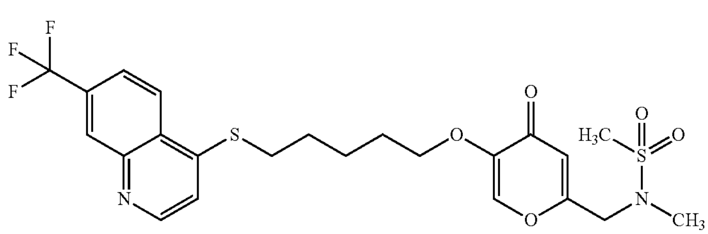 [SMILES: CN(Cc1cc(=O)c(OCCCCCSc2ccnc3cc(C(F)(F)F)ccc23)co1)S(C)(=O)=O] | 0031805 | N-methyl-N-({4-oxo-5-[(5-{[7-(trifluoromethyl)quinolin-4-yl]sulfanyl}pentyl)oxy]-4H-pyran-2-yl]methyl)methanesulfonamide |

-continued

| Compound Structure | Compound Designation | Compound Name |
|---|---|---|
| 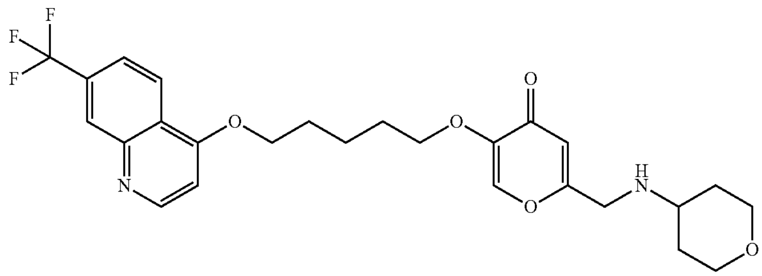 [SMILES: O=c1cc(CNC2CCOCC2)occ1OCCCCCOc1ccnc2cc(C(F)(F)F)ccc12] | 0031801 | 2-[{(oxan-4-yl)amino]methyl}-5-[(5-{[7-(trifluoromethyl)quinolin-4-yl]sulfanyl]pentyl)oxy}-4H-pyran-4-one |
| 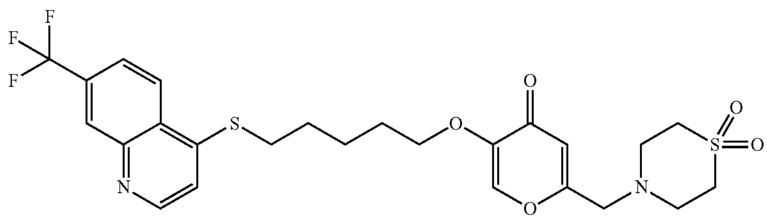 [SMILES: O=c1cc(CN2CCS(=O)(=O)CC2)occ1OCCCCCSc1ccnc2cc(C(F)(F)F)ccc12] | 0031804 | 2-((1,1-dioxidothiomorpholino)methyl)-5-((5-((7-(trifluoromethyl)quinolin-4-yl)thio)pentyl)oxy)-4H-pyran-4-one |
| 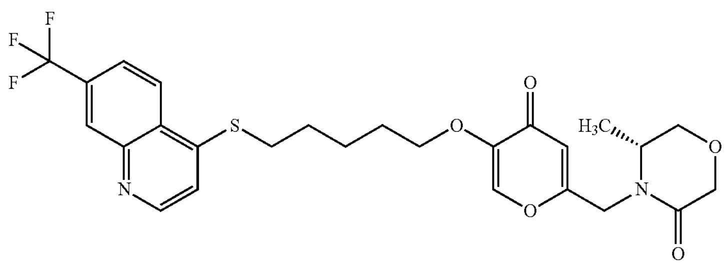 [SMILES: C[C@@H]1COCC(=O)N1Cc1cc(=O)c(OCCCCCSc2ccnc3cc(C(F)(F)F)ccc23)co1] | 0031800 | 5-methyl-4-{(4-oxo-5-[(5-{[7-(trifluoromethyl)quinolin-4-yl]sulfanyl}pentyl)oxy]-4H-pyran-2-yl]methyl}morpholin-3-one |
| 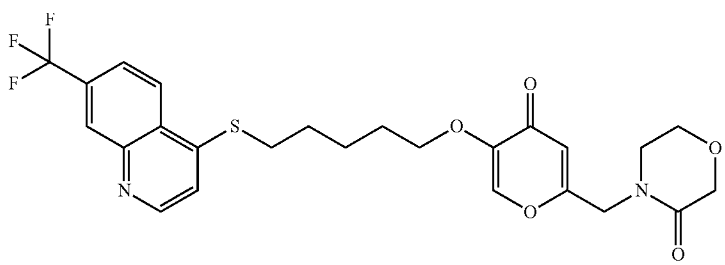 [SMILES: O=C1COCCN1Cc1cc(=O)c(OCCCCCSc2ccnc3cc(C(F)(F)F)ccc23)co1] | 0031799 | 4-({4-oxo-5-{(5-{[7-(trifluoromethyl)quinolin-4-yl]sulfanyl}pentyl)oxy]-4H-pyran-2-yl]methyl}morpholin-3-one |
| 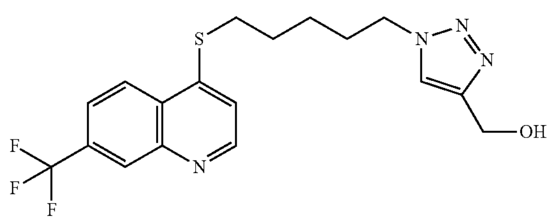 [SMILES: OCc1cn(CCCCCSc2ccnc3cc(C(F)(F)F)ccc23)nn1] | 0031780 | [1-(5-{[7-(trifluoromethyl)quinolin-4-yl]sulfanyl}pentyl)-1H-1,2,3-triazol-4-yl]methanol |
| 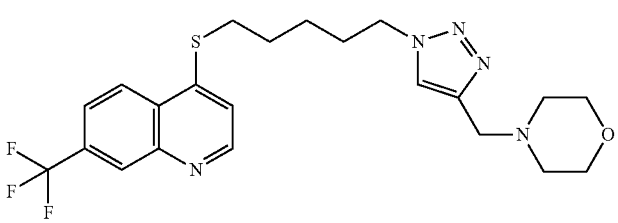 [SMILES: FC(F)(F)c1ccc2c(SCCCCCn3cc(CN4CCOCC4)nn3)ccnc2c1] | 0031779 | 4-({5-[4-(morpholin-4-ylmethyl)-1H-1,2,3-triazol-1-yl]pentyl)sulfanyl]-7-(trifluoromethyl)quinoline |

-continued

| Compound Structure | Compound Designation | Compound Name |
|---|---|---|
| 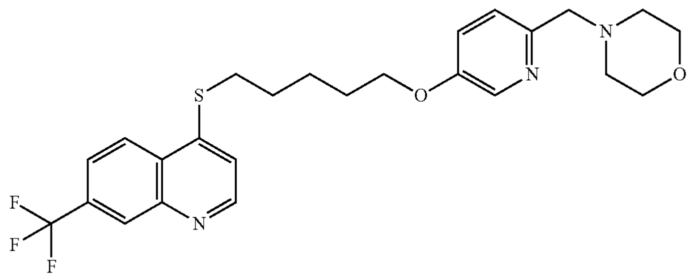 [SMILES: FC(F)(F)c1ccc2c(SCCCCCOc3ccc(CN4CCOCC4)nc3)ccnc2c1] | 0031778 | 4-({5-{[6-(morpholin-4-ylmethyl)pyridin-3-yl]oxy}pentyl)sulfanyl]-7-(trifluoromethyl)quinoline |
| 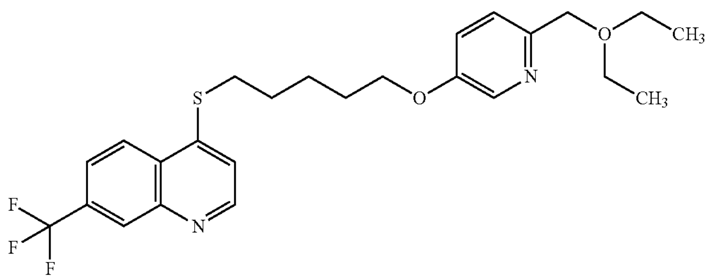 | 0031777 | diethyl({5-[(5-{[(7-(trifluoromethyl)quinolin-4-yl]sulfanyl}pentyl)oxy}pyridin-2-yl]methyl)amine |
| 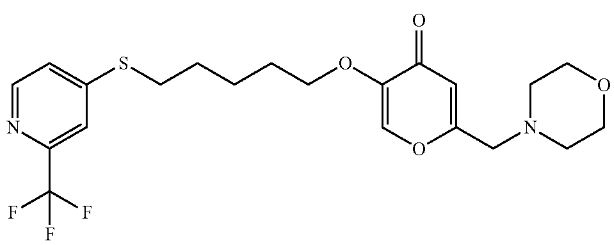 [SMILES: O=c1cc(CN2CCOCC2)occ1OCCCCCSc1ccnc(C(F)(F)F)c1] | 0031733 | 2-(morpholin-4-ylmethyl)-5-[{5-{[2-(trifluoromethyl)pyridin-4-yl]sulfanyl}pentyl)oxy}-4H-pyran-4-one |
| 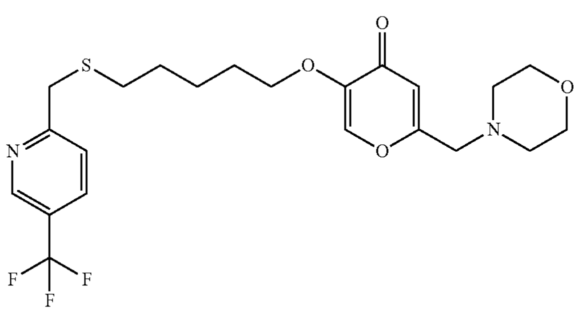 [SMILES: O=c1cc(CN2CCOCC2)occ1OCCCCCSCc1ccc(C(F)(F)F)cn1] | 0031732 | 2-(morpholin-4-ylmethyl)-5-[{5-({[5-(trifluoromethyl)pyridin-2-yl]methyl}sulfanyl}pentyl]oxy}-4H-pyran-4-one |
| 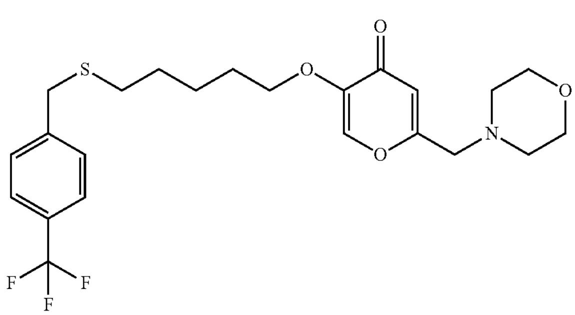 [SMILES: O=c1cc(CN2CCOCC2)occ1OCCCCCSCc1ccc(C(F)(F)F)cc1] | 0031731 | 2-(morpholin-4-ylmethyl)-5-[{5-({[4-(trifluoromethyl)phenyl]methyl}sulfanyl)pentyl]oxy}-4H-pyran-4-one |

| Compound Structure | Compound Designation | Compound Name |
|---|---|---|
| 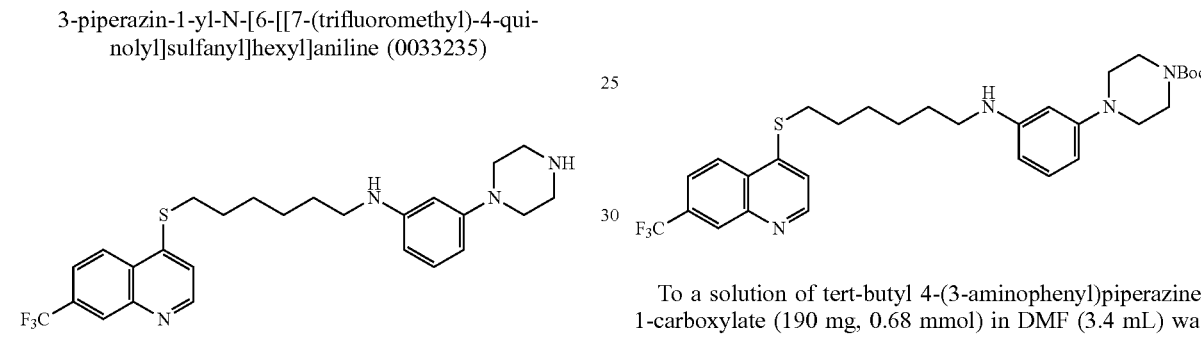 | 0033418 | 1,4-[[1-[[4-[[7-(trifluoromethyl)-4-quinolyl]sulfanylmethyl]phenyl]methyl]imidazol-4-yl]methyl]morpholine |

Synthetic Examples

Example 1

3-piperazin-1-yl-N-[6-[[7-(trifluoromethyl)-4-quinolyl]sulfanyl]hexyl]aniline (0033235)

Step 1: 4-(6-iodohexylsulfanyl)-7-(trifluoromethyl) quinoline

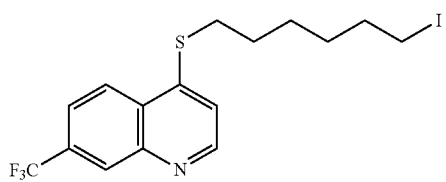 [SMILES: FC(F)(F)c1ccc2c(SCCCCCCI)ccnc2c1]

To a solution of 7-(trifluoromethyl)quinoline-4-thiol (4.00 g, 17.45 mmol) in CHCl$_3$ (52.0 mL) was added 1,6-diiodohexane (8.60 mL, 52.35 mmol) at rt followed by TBAB (569 mg, 1.74 mmol) and water (32.0 mL) and the reaction mixture was stirred at rt for 48 h. The layers were separated, and the organic layer was washed with brine (40.0 mL), dried (Na$_2$SO$_4$), filtered and concentrated under reduced pressure. The material was purified by column chromatography on silica gel (120 g) using a gradient of 0-100% EtOAc in hexane as eluent to provide title compound (3.7 g, 48%) as a solid.

$^1$H NMR (500 MHz, CDCl$_3$) δ 8.79 (d, J=4.8 Hz, 1H), 8.36 (s, 1H), 8.24 (d, J=8.8 Hz, 1H), 7.71 (dd, J=8.8, 1.8 Hz, 1H), 7.26 (d, J=4.2 Hz, 1H), 3.20 (t, J=6.9 Hz, 2H), 3.13 (t, J=7.3 Hz, 2H), 1.91-1.77 (m, 4H), 1.61-1.53 (m, 2H), 1.53-1.45 (m, 2H).

MS (ESI) [M+H]$^+$ 440.2.

Step 2: tert-butyl 4-[3-[6-[[7-(trifluoromethyl)-4-quinolyl]sulfanyl]hexylamino]phenyl]piperazine-1-carboxylate

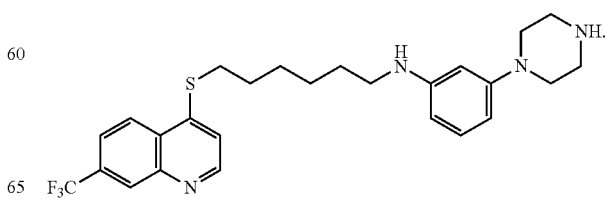

To a solution of tert-butyl 4-(3-aminophenyl)piperazine-1-carboxylate (190 mg, 0.68 mmol) in DMF (3.4 mL) was added K$_2$CO$_3$ (189 mg, 1.37 mmol) and the mixture was stirred at rt for 15 min and then 4-(6-iodohexylsulfanyl)-7-(trifluoromethyl)quinoline (300 mg, 0.68 mmol) was added and the reaction mixture was stirred at 110° C. for 18 h. The mixture was cooled to rt, and then diluted with water (30.0 mL) and the aqueous layer extracted with DCM (3×30.0 mL). The combined organic layers were washed with brine (40.0 mL), dried (Na$_2$SO$_4$), filtered, and concentrated under reduced pressure. The material was purified by column chromatography on silica gel (12 g) using a gradient of 0-3% MeOH in DCM as eluent to provide title compound (360 mg, 89%) as an oil.

$^1$H NMR (500 MHz, CDCl$_3$) δ 8.78 (t, J=4.7 Hz, 1H), 8.36 (s, 1H), 8.23 (dd, J=8.7, 5.9 Hz, 1H), 7.76-7.62 (m, 1H), 7.26-7.21 (m, 1H), 7.13-6.95 (m, 1H), 6.41-6.05 (m, 3H), 3.71-3.47 (m, 5H), 3.21-2.99 (m, 1H), 1.92-1.78 (m, 2H), 1.71-1.61 (m, 2H), 1.62-1.53 (m, 2H), 1.53-1.44 (m, 11H).

MS (ESI) [M+H]$^+$ 589.6.

Step 3: 3-piperazin-1-yl-N-[6-[[7-(trifluoromethyl)-4-quinolyl]sulfanyl]hexyl]aniline A solution of tert-butyl 4-[3-[6-[[7-(trifluoromethyl)-4-quinolyl]sulfanyl]hexylamino]phenyl]-piperazine-1-carboxylate (270 mg, 0.46 mmol) in TFA (3.0 mL) was stirred at 0° C. for 30 min. The volatiles were evaporated under reduced pressure and the material was dissolved in saturated NaHCO₃ (30.0 mL) and the mixture was stirred at rt for 30 min. The aqueous layer was extracted with DCM (3×30.0 mL), and the combined organic layers were washed with brine (40.0 mL), dried (Na₂SO₄), filtered and concentrated under reduced pressure. The material was purified by preparative HPLC (Gemini NX, 150×30, 5 micron, C18 column, eluting with a gradient of 50-100% ACN in water (ammonium bicarbonate; pH 10) to provide title compound (80 mg, 35%) as a solid.

$^1$H NMR (500 MHz, CDCl₃) δ 8.78 (d, J=4.7 Hz, 1H), 8.36 (s, 1H), 8.24 (d, J=8.7 Hz, 1H), 7.71 (dd, J=8.9, 1.8 Hz, 1H), 7.25 (d, J=4.9 Hz, 1H), 7.06 (t, J=8.0 Hz, 1H), 6.37-6.25 (m, 1H), 6.19-6.10 (m, 2H), 3.51 (s, 1H), 3.20-3.04 (m, 8H), 3.06-2.82 (m, 4H), 1.93-1.75 (m, 2H), 1.69-1.60 (m, 2H), 1.62-1.53 (m, 2H), 1.54-1.39 (m, 2H).

MS (ESI) [M+H]⁺ 489.5.

Example 2

4-[[1-[6-[[7-(trifluoromethyl)-4-quinolyl]sulfanyl]hexyl]imidazol-4-yl]methyl]morpholine (0032661)

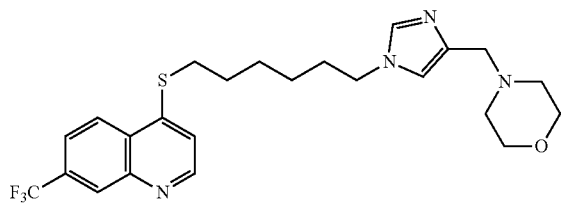 [SMILES: FC(F)(F)c1ccc2c(SCCCCCCn3cnc(CN4CCOCC4)c3)ccnc2c1]

Step 1: 4-(6-bromohexylsulfanyl)-7-(trifluoromethyl)quinoline

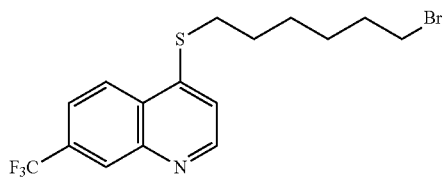

To a solution of 7-(trifluoromethyl)quinoline-4-thiol (4.00 g, 17.45 mmol) in CHCl₃ (52.0 mL) was added 1,6-dibromohexane (12.1 mL, 78.53 mmol) at rt followed by TBAB (1.12 g, 3.49 mmol) and water (32 mL) and the reaction mixture was stirred at rt for 48 h. The layers were separated, and the organic layer was washed with brine, dried (Na₂SO₄), filtered and concentrated under reduced pressure. The material was purified by column chromatography on silica gel (120 g) using a gradient of 0-60% EtOAc in hexane as eluent to provide title compound (4.25 g, 62%) as a solid.

$^1$H NMR (500 MHz, CDCl₃) δ 8.79 (d, J=4.8 Hz, 1H), 8.36 (s, 1H), 8.24 (d, J=8.8 Hz, 1H), 7.71 (dd, J=8.8, 1.8 Hz, 1H), 7.25 (d, J=4.8 Hz, 1H), 3.42 (t, J=6.7 Hz, 2H), 3.13 (t, J=7.3 Hz, 2H), 1.95-1.77 (m, 4H), 1.64-1.42 (m, 4H).

MS (ESI) [M+H]⁺ 392.8.

Step 2: 1-[6-[[7-(trifluoromethyl)-4-quinolyl]sulfanyl]hexyl]imidazole-4-carbaldehyde

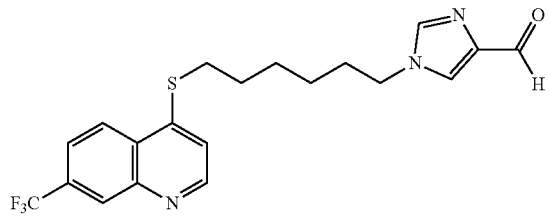 [SMILES: O=Cc1cn(CCCCCCSc2ccnc3cc(C(F)(F)F)ccc23)cn1]

To a solution of 1H-imidazole-4-carbaldehyde (1.17 g, 12.24 mmol) in DMF (30.0 mL) was added K₂CO₃ (1.55 g, 11.22 mmol) and the mixture was stirred for 30 min at rt and then 4-(6-bromohexylsulfanyl)-7-(trifluoromethyl)quinoline (4.0 g, 10.20 mmol) was added and the reaction mixture was stirred at rt for 6 h. The mixture was filtered, and the filtrate was diluted with water (50.0 mL). The aqueous layer was extracted with DCM (3×50.0 mL). The combined organic layers were washed with brine (50.0 mL), dried (Na₂SO₄), filtered and concentrated under reduced pressure. The material was purified by column chromatography on silica gel (40 g) using a gradient of 0-5% of MeOH (contains 1% Et₃N) in DCM as eluent to afford title compound (1.1 g, 26%) as a solid.

$^1$H NMR (500 MHz, CDCl₃) δ 9.87 (s, 1H), 8.78 (d, J=4.8 Hz, 1H), 8.36 (s, 1H), 8.23 (d, J=8.8 Hz, 1H), 7.71 (d, J=8.8, 1.9 Hz, 1H), 7.62 (d, J=1.2 Hz, 1H), 7.54 (d, J=1.2 Hz, 1H), 7.23 (d, J=4.8 Hz, 1H), 4.01 (t, J=7.1 Hz, 2H), 3.11 (t, J=7.2 Hz, 2H), 1.91-1.75 (m, 4H), 1.64-1.45 (m, 2H), 1.47-1.27 (m, 2H).

MS (ESI) [M+H]⁺ 408.3.

Step 3: 4-[[1-[6-[[7-(trifluoromethyl)-4-quinolyl]sulfanyl]hexyl]imidazol-4-yl]methyl]morpholine

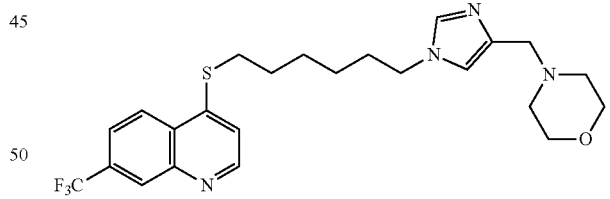

To a solution of 1-[6-[[7-(trifluoromethyl)-4-quinolyl]sulfanyl]hexyl]imidazole-4-carbaldehyde (1.0 g, 2.45 mmol) in DCE (12.0 mL), were added morpholine (423 μL, 4.91 mmol), AcOH (catalytic) and NaBH(OAc)₃ (1.0 g, 4.91 mmol) at rt and the resulting mixture was stirred for 2 h. The volatiles were evaporated under reduced pressure and the mixture was diluted with a saturated NaHCO₃ (40.0 mL). The aqueous layer was extracted with DCM (3×40.0 mL) and the combined organic layers were washed with brine (40.0 mL), dried (Na₂SO₄), filtered and concentrated under reduced pressure. The material was purified by column chromatography on silica gel using a gradient of 0-10% of MeOH (contains 1% NH₄OH) in DCM to provide title compound (920 mg, 78%) as an oil.

¹H NMR (500 MHz, CDCl₃) δ 8.77 (d, J=4.8 Hz, 1H), 8.35 (s, 1H), 8.22 (d, J=8.8 Hz, 1H), 7.70 (dd, J=8.8, 1.8 Hz, 1H), 7.38 (d, J=1.3 Hz, 1H), 7.22 (d, J=4.8 Hz, 1H), 6.85-6.74 (m, 1H), 3.88 (t, J=7.1 Hz, 2H), 3.74-3.65 (m, 4H), 3.46 (s, 2H), 3.09 (t, J=7.2 Hz, 2H), 2.51 (s, 4H), 1.92-1.67 (m, 4H), 1.62-1.47 (m, 2H), 1.44-1.28 (m, 2H).

MS (ESI) [M+H]⁺ 479.5.

Example 3

4-({6-[4-(morpholin-4-ylmethyl)-1H-1,2,3-triazol-1-yl]hexyl}sulfanyl)-7-(trifluoromethyl)quinoline (0032253)

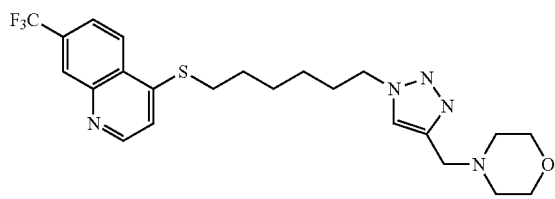 [SMILES: FC(F)(F)c1ccc2c(SCCCCCCN3C=C(CN4CCOCC4)NN3)ccnc2c1]

Step 1: 4-(6-bromohexylsulfanyl)-7-(trifluoromethyl)quinoline

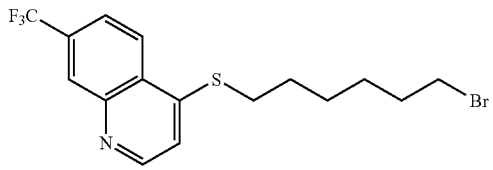 [SMILES: FC(F)(F)c1ccc2c(SCCCCCCBr)ccnc2c1]

Step 1: 4-(6-bromohexylsulfanyl)-7-(trifluoromethyl)quinoline

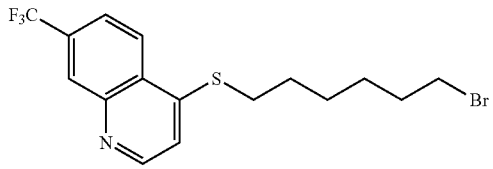 [SMILES: FC(F)(F)c1ccc2c(SCCCCCCBr)ccnc2c1]

To a solution of KOH (1.82 g, 32.5 mmol) in CH₃CN (600 mL) at 0° C. was added 1,6-dibromohexane (15.0 mL, 97.5 mmol) followed by a slow addition of 7-(trifluoromethyl)quinoline-4-thiol (7.45 g, 32.5 mmol). The reaction mixture was warmed to rt and stirred for 18 h. The volatiles were evaporated under reduced pressure and the residue was dissolved in DCM (100 mL). The organic layer was washed with water (50.0 mL) and brine (50.0 mL), then was dried (MgSO₄), filtered and concentrated under reduced pressure. The material was purified by column chromatography on silica gel (330 g) using a gradient of 10-50% EtOAc in hexane as eluent to afford title compound (8.03 g, 63%) as a solid.

¹H NMR (500 MHz, CDCl₃) δ 8.80 (d, J=4.8 Hz, 1H), 8.37 (s, 1H), 8.25 (d, J=8.8 Hz, 1H), 7.72 (dd, J=8.8, 1.8 Hz, 1H), 7.27 (s, 1H), 3.44 (t, J=6.7 Hz, 2H), 3.14 (t, J=7.3 Hz, 2H), 1.94-1.82 (m, 4H), 1.61-1.49 (m, 4H).

MS (ESI) [M+H]⁺ 392.3.

Step 2: 4-({6-[4-(morpholin-4-ylmethyl)-1H-1,2,3-triazol-1-yl]hexyl}sulfanyl)-7-(trifluoromethyl)quinoline (0032253)

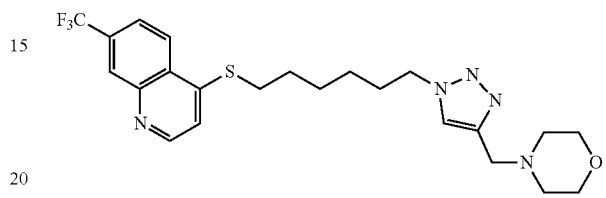

To a solution of 4-(6-bromohexylsulfanyl)-7-(trifluoromethyl)quinoline (1.6 g, 4.08 mmol) in DMSO (25.0 mL) was added NaN₃ (265 mg, 4.08 mmol). The mixture was stirred at rt until complete disappearance of the starting material (~4 h). 4-prop-2-ynylmorpholine (664 mg, 5.30 mmol) was then added followed by sodium ascorbate (121 mg, 0.61 mmol) and CuSO₄.5H₂O (51 mg, 0.20 mmol) and the reaction mixture was stirred at 80° C. for 3 days. The mixture was cooled to rt, and then was poured into water (100.0 mL). The aqueous layer was extracted with DCM (3×50.0 mL) and the combined organic layers were washed with brine (100.0 mL), dried (Na₂SO₄), filtered, and concentrated under reduced pressure. The material was purified by column chromatography on silica gel (120 g) using a gradient of 0-10% MeOH in DCM as eluent followed by reverse phase chromatography (C18, 120 g) to afford title compound (1.85 g, 94%) as a solid.

¹H NMR (500 MHz, CDCl₃) δ 8.79 (d, J=4.8 Hz, 1H), 8.36 (s, 1H), 8.23 (d, J=8.7 Hz, 1H), 7.71 (dd, J=8.8, 1.7 Hz, 1H), 7.46 (s, 1H), 7.24 (d, J=4.8 Hz, 1H), 4.36 (t, J=7.1 Hz, 2H), 3.74-3.68 (m, 4H), 3.67 (s, 2H), 3.11 (t, J=7.2 Hz, 2H), 2.52 (s, 4H), 2.02-1.84 (m, 2H), 1.88-1.75 (m, 2H), 1.63-1.49 (m, 2H), 1.46-1.31 (m, 2H).

MS (ESI) [M+H]⁺ 480.5.

Example 4

Diethyl({5-[(5-{[7-(trifluoromethyl)quinolin-4-yl]sulfanyl}pentyl)oxy]pyridin-2-yl}methyl)amine (0031777)

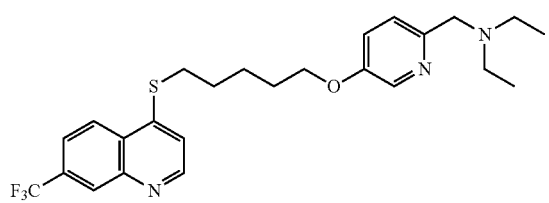 [SMILES: CCN(CC)Cc1ccc(OCCCCCSc2ccnc3cc(C(F)(F)F)ccc23)cn1]

121

Step 1: 4-(5-bromopentylsulfanyl)-7-(trifluoromethyl)quinoline

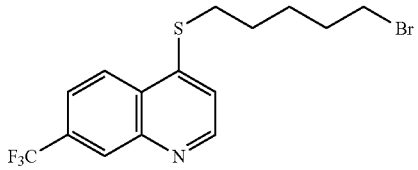 [SMILES: FC(F)(F)c1ccc2c(SCCCCCBr)ccnc2c1]

To a stirred solution of KOH (656 mg, 10.5 mmol) in acetonitrile (100 mL) at 0° C. was added 1,5-dibromopentane (3.4 mL, 30.3 mmol) followed by 7-(trifluoromethyl)quinoline-4-thiol (1.93 g, 2.18 mmol) and the reaction mixture was warmed to rt and stirred for 12 h. The volatiles were evaporated under reduced pressure and the residue was diluted with EtOAc (50.0 mL). The organic layer was washed with water (10.0 mL) and brine (10.0 mL) then dried ($Na_2SO_4$), filtered and concentrated under reduced pressure. The material was purified by column chromatography on silica gel (80 g) using a gradient of 0-100% EtOAc in hexane as eluent to afford title compound (2.43 g, 76%) as a solid.

$^1$H NMR (500 MHz, $CDCl_3$) δ 8.71 (d, J=4.8 Hz, 1H), 8.29 (s, 1H), 8.16 (d, J=8.7 Hz, 1H), 7.64 (dd, J=8.8, 1.9 Hz, 1H), 7.18 (d, J=4.8 Hz, 1H), 3.36 (t, J=6.6 Hz, 2H), 3.06 (t, J=7.3 Hz, 2H), 1.82-1.91 (m, 2H), 1.74-1.83 (m, 2H), 1.57-1.68 (m, 2H).

MS (ESI) [M+H]$^+$ 379.9.

Step 2: 5-[5-[[7-(trifluoromethyl)-4-quinolyl]sulfanyl]pentoxy]pyridine-2-carbaldehyde

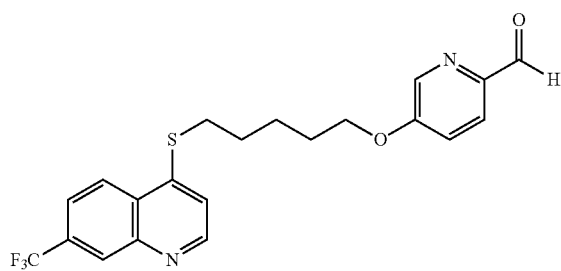

To a solution of 5-hydroxypyridine-2-carbaldehyde (77 mg, 0.625 mmol) in DMF (4.0 mL) was added $K_2CO_3$ (86.4 mg, 0.625 mmol) at 0° C., followed by 4-(5-bromopentylsulfanyl)-7-(trifluoromethyl)quinoline (197 mg, 0.521 mmol) and the reaction mixture was stirred at 110° C. for 2 h. The mixture was poured into $H_2O$ (6.0 mL) and the aqueous layer was extracted with DCM (3×25 mL). The combined organic layers were washed with brine (2×25 mL), dried ($MgSO_4$), filtered, and concentrated under reduced pressure. The material was purified by column chromatography on silica gel (12 g) using a gradient of 0-10% MeOH in DCM as eluent to afford title compound (175 mg, 80%) as a solid.

$^1$H NMR (500 MHz, $CDCl_3$) δ 9.99 (d, J=0.8 Hz, 1H), 8.80 (d, J=4.8 Hz, 1H), 8.43 (d, J=2.3 Hz, 1H), 8.37 (s, 1H), 8.25 (d, J=8.8 Hz, 1H), 7.96 (dd, J=8.6, 0.5 Hz, 1H), 7.72 (dd, J=8.7, 1.9 Hz, 1H), 7.28 (dd, J=8.9, 3.7 Hz, 2H), 4.14 (t, J=6.2 Hz, 2H), 3.18 (t, J=7.2 Hz, 2H), 1.97-1.89 (m, 4H), 1.77 (dd, J=15.4, 8.1 Hz, 2H).

MS (ESI) [M+H]$^+$ 421.4.

122

Step 3: N-ethyl-N-[[5-[5-[[7-(trifluoromethyl)-4-quinolyl]sulfanyl]pentoxy]-2-pyridyl]methyl]ethanamine (0031777)

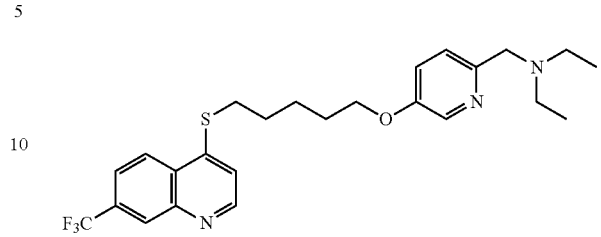

To a solution of 5-[5-[[7-(trifluoromethyl)-4-quinolyl]sulfanyl]pentoxy]pyridine-2-carbaldehyde (154.0 mg, 0.366 mmol) in DCM (7.9 mL) was added diethylamine (0.057 mL, 0.549 mmol) and 4 Å MS in DCM (7.9 mL). The suspension was stirred at rt for 30 min and then $NaBH(OAc)_3$ (155.0 mg, 0.733 mmol) was added and the reaction mixture was stirred at rt for 12 h. The mixture was filtered through a pad of Celite and washed with DCM (50.0 mL). A saturated $NaHCO_3$ (50.0 mL) was added to the filtrate and the layers were separated. The aqueous layer was extracted with DCM (3×50.0 mL) and the combined organic layers were washed with brine (100 mL), dried ($MgSO_4$), filtered and concentrated under reduced pressure. The material was purified by column chromatography on silica gel (12 g) using a gradient of 0-15% MeOH in $CH_2Cl_2$ as eluent to provide title compound (119 mg, 68%) as a solid.

$^1$H NMR (500 MHz, $CDCl_3$) δ 8.70 (d, J=4.8 Hz, 1H), 8.28 (s, 1H), 8.15 (dd, J=10.0, 5.8 Hz, 2H), 7.63 (dd, J=8.8, 1.8 Hz, 1H), 7.27 (d, J=8.6 Hz, 1H), 7.22-7.14 (m, 1H), 7.07 (dd, J=8.6, 2.9 Hz, 1H), 3.95 (t, J=6.2 Hz, 2H), 3.58 (s, 2H), 3.08 (t, J=7.3 Hz, 2H), 2.48 (q, J=7.1 Hz, 4H), 1.93-1.74 (m, 4H), 1.73-1.60 (m, 2H), 0.97 (t, J=7.1 Hz, 6H).

MS (ESI [M+H]$^+$ 478.3.

Example 5

4-[(5-{[6-(morpholin-4-ylmethyl)pyridin-3-yl]oxy}pentyl)sulfanyl]-7-(trifluoromethyl)quinoline (0031778)

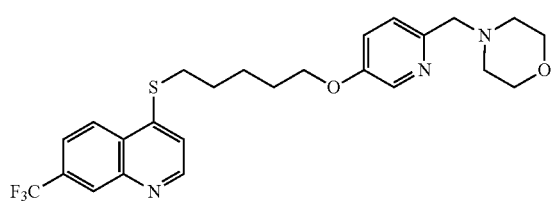 [SMILES: FC(F)(F)c1ccc2c(SCCCCCOc3ccc(CN4CCOCC4)nc3)ccnc2c1]

Step 1: 4-(5-bromopentylsulfanyl)-7-(trifluoromethyl)quinoline

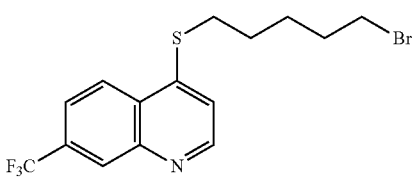 [SMILES: FC(F)(F)c1ccc2c(SCCCCCBr)ccnc2c1]

To a solution of KOH (656.0 mg, 10.5 mmol) in acetonitrile (100.0 mL) at 0° C., was added 1,5-dibromopentane (3.4 mL, 30.3 mmol) followed by 7-(trifluoromethyl)quinoline-4-thiol (1.93 g, 2.18 mmol). After the addition was completed, the reaction was warmed to rt and stirred for 12 h. The volatiles were evaporated under reduced pressure. EtOAc (50.0 mL) and water (10.0 mL) were added, and the layers were separated. The organic layer was washed with brine (10.0 mL), dried (Na$_2$SO$_4$), filtered and concentrated under reduced pressure. The material was purified by column chromatography on silica gel (80 g) using a gradient of 0-100% EtOAc in hexane as eluent to provide title compound (2.43 g, 76%) as a solid.

$^1$H NMR (500 MHz, CHCl$_3$) δ 8.71 (d, J=4.8 Hz, 1H), 8.29 (s, 1H), 8.16 (d, J=8.7 Hz, 1H), 7.64 (dd, J=8.8, 1.9 Hz, 1H), 7.18 (d, J=4.8 Hz, 1H), 3.36 (t, J=6.6 Hz, 2H), 3.06 (t, J=7.3 Hz, 2H), 1.82-1.91 (m, 2H), 1.74-1.83 (m, 2H), 1.57-1.68 (m, 2H).

MS (ESI) [M+H]$^+$ 379.9.

Step 2: 5-[5-[[7-(trifluoromethyl)-4-quinolyl]sulfanyl]pentoxy]pyridine-2-carbaldehyde

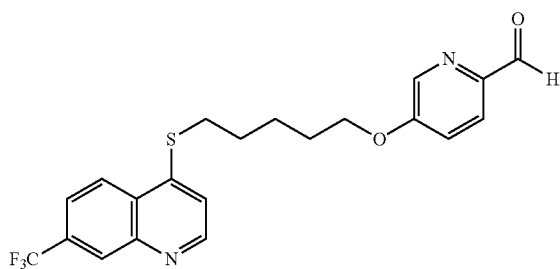 [SMILES: O=Cc1ccc(OCCCCCSc2ccnc3cc(C(F)(F)F)ccc23)cn1]

To a solution of 5-hydroxypyridine-2-carbaldehyde (77.0 mg, 0.625 mmol) in DMF (4.00 mL) at 0° C., was added K$_2$CO$_3$ (86.4 mg, 0.625 mmol) followed by 4-(5-bromopentylsulfanyl)-7-(trifluoromethyl)quinoline (197.0 mg, 0.521 mmol) and the reaction was stirred at 110° C. for 2 h and then cooled to rt. The mixture was poured into H$_2$O (6.0 mL) and the aqueous layer was extracted with DCM (3×25.0 mL). The combined organic layers were washed with brine (2×25.0 mL), dried (MgSO$_4$), filtered, and concentrated under reduced pressure. The material was purified by column chromatography on silica gel (12 g) using a gradient of 0-10% MeOH in DCM as eluent to provide title compound (175 mg, 80%) as a solid.

$^1$H NMR (500 MHz, CDCl$_3$) δ 9.99 (d, J=0.8 Hz, 1H), 8.80 (d, J=4.8 Hz, 1H), 8.43 (d, J=2.3 Hz, 1H), 8.37 (s, 1H), 8.25 (d, J=8.8 Hz, 1H), 7.96 (dd, J=8.6, 0.5 Hz, 1H), 7.72 (dd, J=8.7, 1.9 Hz, 1H), 7.28 (dd, J=8.9, 3.7 Hz, 2H), 4.14 (t, J=6.2 Hz, 2H), 3.18 (t, J=7.2 Hz, 2H), 1.97-1.89 (m, 4H), 1.77 (dd, J=15.4, 8.1 Hz, 2H).

MS (ESI) [M+H]$^+$ 421.4.

Step 3: 4-[(5-{[6-(morpholin-4-ylmethyl)pyridin-3-yl]oxy}pentyl)sulfanyl]-7-(trifluoromethyl)quinoline (0031778)

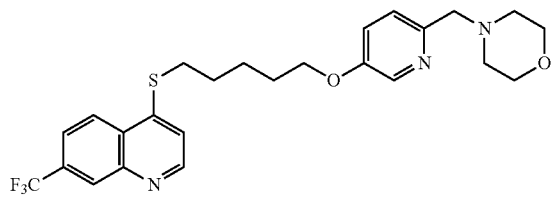 [SMILES: FC(F)(F)c1ccc2c(SCCCCCOc3ccc(CN4CCOCC4)nc3)ccnc2c1]

To a solution of 5-[5-[[7-(trifluoromethyl)-4-quinolyl]sulfanyl]pentoxy]pyridine-2-carbaldehyde (53.0 mg, 0.126 mmol) in DCM (2.62 mL), was added morpholine (17.0 mg, 0.189 mmol) and 4 Å MS and the resulting suspension was stirred at rt for 30 min. NaBH(OAc)$_3$ (54.0 mg, 0.252 mmol) was then added, and the reaction mixture was stirred at rt for 12 h. The mixture was filtered through a pad of Celite and washed with DCM (3×25.0 mL). A saturated NaHCO$_3$ (50.0 mL) was added to the filtrate and the layers were separated. The aqueous layer was extracted with DCM (3×50.0 mL) and the combined organic layers were washed with brine (100.0 mL), dried (MgSO$_4$), filtered, and concentrated under reduced pressure. The material was purified by column chromatography on silica gel (4 g) using a gradient of 0-10% MeOH in DCM as eluent to provide title compound (45.0 mg, 73%) as a solid.

$^1$H NMR (500 MHz, CDCl$_3$) δ 8.79 (d, J=4.8 Hz, 1H), 8.37 (s, 1H), 8.33-8.20 (m, 2H), 7.72 (dd, J=8.8, 1.8 Hz, 1H), 7.36-7.22 (m, 2H), 7.16 (dd, J=8.5, 3.0 Hz, 1H), 4.04 (t, J=6.2 Hz, 2H), 3.81-3.70 (m, 4H), 3.60 (s, 2H), 3.18 (t, J=7.3 Hz, 2H), 2.61-2.37 (m, 4H), 1.99-1.82 (m, 4H), 1.76 (ddd, J=12.3, 7.2, 2.2 Hz, 2H).

MS (ESI) [M+H]$^+$ 492.2.

Example 6

N,1-dimethyl-N-({4-oxo-5-[(5-{[7-(trifluoromethyl)quinolin-4-yl]sulfanyl}pentyl)oxy]-4H-pyran-2-yl}methyl)-1H-pyrrole-2-carboxamide (0031809)

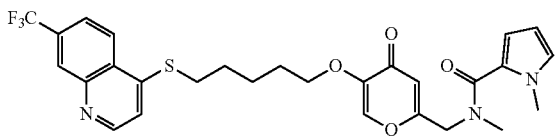 [SMILES: CN(Cc1cc(=O)c(OCCCCCSc2ccnc3cc(C(F)(F)F)ccc23)co1)C(=O)c1cccn1C]

Step 1: 4-(5-bromopentylsulfanyl)-7-(trifluoromethyl)quinoline

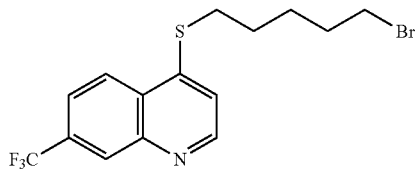 [SMILES: FC(F)(F)c1ccc2c(SCCCCCBr)ccnc2c1]

To a solution of KOH (656.0 mg, 10.5 mmol) in acetonitrile (100.0 mL) at 0° C., was added 1,5-dibromopentane (3.4 mL, 30.3 mmol) followed by 7-(trifluoromethyl)quinoline-4-thiol (1.93 g, 2.18 mmol). After the addition was completed, the reaction was warmed to rt and stirred for 12 h. The volatiles were evaporated under reduced pressure, EtOAc (50.0 mL) and water (10.0 mL) were added. The layers were separated, and the organic layer was washed with brine (10.0 mL), dried (Na$_2$SO$_4$), filtered and concentrated under reduced pressure. The material was purified by column chromatography on silica gel (80 g) using a gradient of 0-100% EtOAc in hexane as eluent to provide title compound (2.43 g, 76%) as a solid.

$^1$H NMR (500 MHz, CDCl$_3$) δ 8.71 (d, J=4.8 Hz, 1H), 8.29 (s, 1H), 8.16 (d, J=8.7 Hz, 1H), 7.64 (dd, J=8.8, 1.9 Hz, 1H), 7.18 (d, J=4.8 Hz, 1H), 3.36 (t, J=6.6 Hz, 2H), 3.06 (t, J=7.3 Hz, 2H), 1.82-1.91 (m, 2H), 1.74-1.83 (m, 2H), 1.57-1.68 (m, 2H).

MS (ESI) [M+H]$^+$ 379.9.

Step 2: 2-(tetrahydropyran-2-yloxymethyl)-5-[5-[[7-(trifluoromethyl)-4-quinolyl]sulfanyl]pentoxy]pyran-4-one

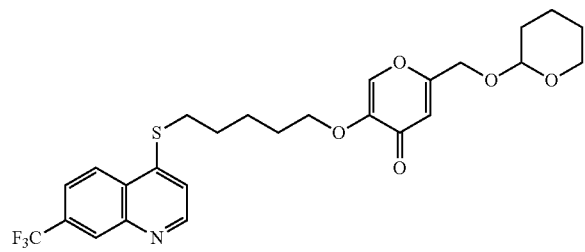 [SMILES: O=c1cc(COC2CCCCO2)occ1OCCCCCSc1ccnc2cc(C(F)(F)F)ccc12]

To a solution of 5-hydroxy-2-(tetrahydropyran-2-yloxymethyl)pyran-4-one (224.0 mg, 0.99 mmol) in DMF (2.7 mL) was added cesium carbonate (323.0 mg, 0.99 mmol) under nitrogen atmosphere. After the addition was completed, the mixture was heated at 50° C. for 30 min and then a solution of 4-(5-bromopentylsulfanyl)-7-(trifluoromethyl)-quinoline (312.0 mg, 0.83 mmol) in DMF (1.3 mL) and NaI (16.0 mg, 0.11 mmol) were sequentially added. The reaction mixture was stirred at 85° C. for 3 h. The mixture was cooled to rt and the volatiles were evaporated under reduced pressure. Water (25.0 mL) and EtOAc (25.0 mL) were added, and the layers were separated. The aqueous layer was extracted with EtOAc (2×25.0 mL), the combined organic layers were dried (MgSO$_4$), filtered and concentrated under reduced pressure. The material was purified by column chromatography on silica gel (40 g) using a gradient of 0-5% MeOH in DCM as eluent to provide title compound (400 mg, 93%) as a solid.

$^1$H NMR (500 MHz, CDCl$_3$) δ 8.66 (s, 1H), 8.23 (s, 1H), 8.10 (d, J=8.6 Hz, 1H), 7.69-7.54 (m, 1H), 7.50 (d, J=1.9 Hz, 1H), 7.23-7.08 (m, 1H), 6.40 (d, J=2.4 Hz, 1H), 4.61 (d, J=2.9 Hz, 1H), 4.41 (dd, J=14.4, 2.1 Hz, 1H), 4.22 (dd, J=14.4, 2.2 Hz, 1H), 3.88-3.64 (m, 3H), 3.55-3.35 (m, 1H), 3.02 (t, J=7.1 Hz, 2H), 2.85-2.75 (m, 1H), 1.88-1.31 (m, 11H).

MS (ESI) [M+H]$^+$ 524.2.

Step 3: 2-(bromomethyl)-5-[5-[[7-(trifluoromethyl)-4-quinolyl]sulfanyl]pentoxy]pyran-4-one

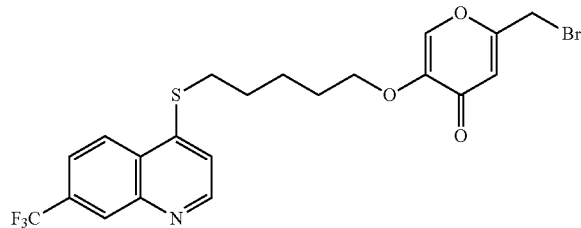 [SMILES: O=c1cc(CBr)occ1OCCCCCSc1ccnc2cc(C(F)(F)F)ccc12]

To a solution of 2-(tetrahydropyran-2-yloxymethyl)-5-[5-[[7-(trifluoromethyl)-4-quinolyl]sulfanyl]pentoxy]-pyran-4-one (248.0 mg, 0.474 mmol) in sulfuric acid (1.0 mL) was added HBr (48% in water, 0.8 mL) dropwise at 0° C. The reaction mixture was heated at 70° C. for 18 h, and then cooled to rt. The mixture was diluted with water (10.0 mL) and the pH was adjusted to ~8-9 with a 2 M solution of NaOH. The aqueous layer was extracted with CH$_2$Cl$_2$ (3×25.0 mL). The combined organic layers were washed with brine, dried (MgSO$_4$), filtered and concentrated under reduced pressure. The material was purified by column chromatography on silica gel (12 g) using a gradient of 0-5% MeOH in CH$_2$Cl$_2$ as eluent to provide title compound (154.0 mg, 64%) as a solid.

$^1$H NMR (500 MHz, CDCl$_3$) δ 8.81 (d, J=4.8 Hz, 1H), 8.38 (s, 1H), 8.26 (d, J=8.7 Hz, 1H), 7.73 (d, J=8.8, 1.8 Hz, 1H), 7.61 (s, 1H), 7.29 (s, 1H), 6.47 (s, 1H), 4.19 (s, 2H), 3.93 (t, J=6.3 Hz, 2H), 3.17 (t, J=7.3 Hz, 2H), 1.99-1.86 (m, 4H), 1.80-1.67 (m, 2H).

MS (ESI) [M+H]$^+$ 502.0.

Step 4: 2-(methylaminomethyl)-5-[5-[[7-(trifluoromethyl)-4-quinolyl]sulfanyl]pentoxy]pyran-4-one

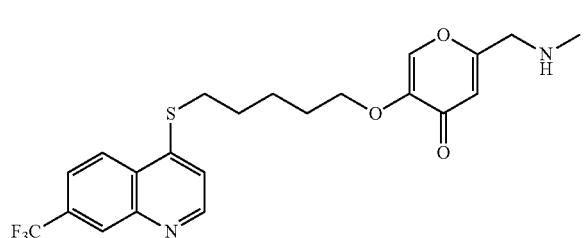

To a solution of 2-(bromomethyl)-5-[5-[[7-(trifluoromethyl)-4-quinolyl]sulfanyl]pentoxy]pyran-4-one (37.0 mg, 0.074 mmol) in THF (0.5 mL) was added dropwise methylamine (2M in THF, 0.184 mL, 0.368 mmol) and the reaction mixture was stirred at rt for 1 h. The volatiles were evaporated under reduced pressure, and the residue was diluted with DCM (50.0 mL) and saturated NaHCO$_3$ (25.0 mL). The layers were separated, and the organic layer was washed with brine, dried (MgSO$_4$), filtered and concentrated under reduced pressure to provide title compound (27.0 mg, 81%) as an oil, which was used in the next step without further purification.

$^1$H NMR (500 MHz, CDCl$_3$) δ 8.71 (d, J=4.8 Hz, 1H), 8.28 (s, 1H), 8.16 (d, J=8.8 Hz, 1H), 7.63 (dd, J=8.8, 1.8 Hz, 1H), 7.49 (s, 1H), 7.25-7.13 (m, 1H), 6.32 (s, 1H), 3.83 (t,

J=6.3 Hz, 2H), 3.53 (s, 2H), 3.07 (t, J=7.3 Hz, 2H), 2.38 (s, 3H), 1.85-1.75 (m, 4H), 1.70-1.60 (m, 2H).

MS (ESI) [M+H]⁺ 453.1.

Step 5: N,1-dimethyl-N-[[4-oxo-5-[5-[[7-(trifluoromethyl)-4-quinolyl]sulfanyl]pentoxy]pyran-2-yl]methyl]pyrrole-2-carboxamide (0031809)

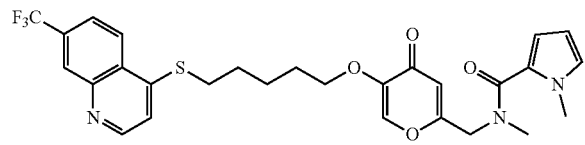 [SMILES: CN(Cc1cc(=O)c(OCCCCCSc2ccnc3cc(C(F)(F)F)ccc23)co1)C(=O)c1cccn1C]

To a solution of 1-methyl-2-pyrrolecarboxylic acid (15.6 mg, 0.125 mmol) in DMF (1.4 mL), were sequentially added HATU (47.39 mg, 0.125 mmol), Et₃N (29.0 µL, 0.208 mmol) and a solution of 2-(methylaminomethyl)-5-[5-[[7-(trifluoromethyl)-4-quinolyl]sulfanyl]pentoxy]pyran-4-one (47 mg, 0.104 mmol) in DMF (1.4 mL) at 0° C. The reaction mixture was stirred at rt for 2 h and then the volatiles were evaporated under reduced pressure. Water (25.0 mL) and DCM (25.0 mL) were added, and the layers were separated. The aqueous layer was extracted with CH₂Cl₂ (2×25.0 mL), and the combined organic layers were dried (MgSO₄), filtered and concentrated under reduced pressure. The material was purified by column chromatography on silica gel (4 g) using a gradient of 0-10% MeOH in DCM as eluent to provide title compound (35.0 mg, 60%) as a solid.

¹H NMR (500 MHz, CDCl₃) δ 8.81 (d, J=4.8 Hz, 1H), 8.37 (s, 1H), 8.26 (d, J=8.8 Hz, 1H), 7.73 (dd, J=8.8, 1.8 Hz, 1H), 7.59 (s, 1H), 7.28 (t, J=2.4 Hz, 1H), 6.75 (dd, J=2.3, 1.8 Hz, 1H), 6.47 (d, J=2.5 Hz, 1H), 6.36 (s, 1H), 6.11 (dd, J=3.9, 2.6 Hz, 1H), 4.58 (s, 2H), 3.92 (t, J=6.3 Hz, 2H), 3.82 (s, 3H), 3.23 (s, 3H), 3.17 (t, J=7.3 Hz, 2H), 1.98-1.85 (m, 4H), 1.79-1.71 (m, 2H).

MS (ESI) [M+H]⁺ 560.3.

Example 7

4-[[1-[[4-[[7-(trifluoromethyl)-4-quinolyl]sulfanylmethyl]phenyl]methyl]imidazol-4-yl]methyl]morpholine (0033418)

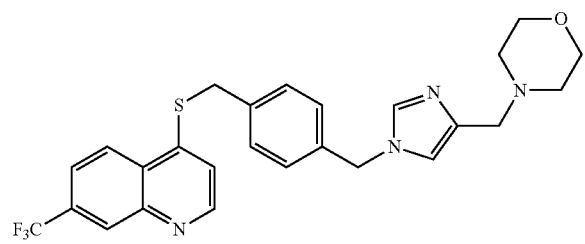 [SMILES: FC(F)(F)c1ccc2c(SCc3ccc(Cn4cnc(CN5CCOCC5)c4)cc3)ccnc2c1]

Step 1: tert-butyl-[[4-(chloromethyl)phenyl]methoxy]-dimethyl-silane

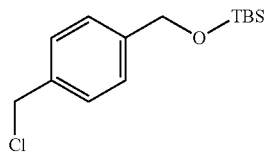

To a solution of 4-(chloromethyl)phenyl]methanol (1.35 g, 8.62 mmol) in DCM (8.60 mL) cooled to 0° C. were sequentially added imidazole (763.0 mg, 11.21 mmol), TBDMSCl (1.43 g, 9.50 mmol) portionwise and the reaction mixture was then stirred at 0° C. for 1 h. Water (30.0 mL) and a 1.0 M aqueous solution of KHSO₄ (30.0 mL) were added, and the mixture was stirred for 30 min. The separated organic layer was washed with brine, dried (Na₂SO₄), filtered and concentrated under reduced pressure to provide title compound (2.36 g, 100%) as an oil, which was used in the next step without further purification. ¹H NMR (500 MHz, CDCl₃) δ 7.43-7.27 (m, 4H), 4.74 (s, 2H), 4.59 (s, 2H), 0.95 (s, 9H), 0.10 (s, 6H).

Step 2: 1-[[4-[[tert-butyl(dimethyl)silyl]oxymethyl]phenyl]methyl]imidazole-4-carbaldehyde and 3-[[4-[[tert-butyl(dimethyl)silyl]oxymethyl]phenyl]methyl]imidazole-4-carbaldehyde

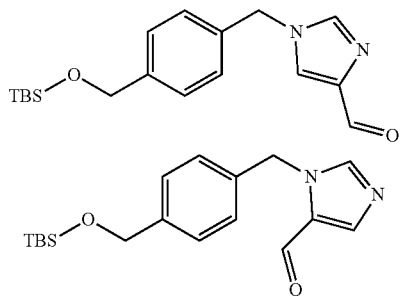

To a suspension of NaH (60% dispersion in mineral oil, 221.0 mg, 5.52 mmol) in DMF (14.0 mL) was added 1H-imidazole-4-carbaldehyde (531.0 mg, 5.52 mmol) at room temperature and after stirring for 30 min, the mixture was cooled to 0° C. A solution of tert-butyl-[[4-(chloromethyl)phenyl]methoxy]-dimethyl-silane (1.36 g, 5.02 mmol) in DMF (3.0 mL) was added dropwise and the reaction mixture was then stirred at rt for 4 h. The volatiles were evaporated under reduced pressure, and then a saturated aqueous solution of ammonium chloride (40.0 mL) and DCM (40.0 mL) were added. The layers were separated, and the aqueous phase was extracted with DCM (2×40.0 mL). The combined organic extracts were washed with brine (40.0 mL), dried (Na₂SO₄), filtered and concentrated under reduced pressure. The material was purified by silica gel chromatography using a gradient of 0-3% MeOH in DCM as eluent to provide title compounds (1.09 g, 66%) as an inseparable mixture.

Step 3: tert-butyl-dimethyl-[[4-[[4-(morpholinomethyl)imidazol-1-yl]methyl]phenyl]methoxy]silane

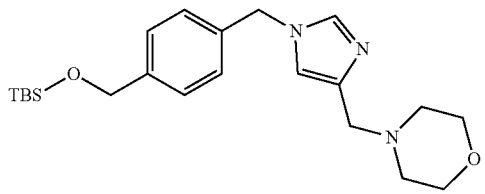

To a solution of 1-[[4-[[tert-butyl(dimethyl)silyl]oxymethyl]phenyl]methyl]imidazole-4-carbaldehyde and 3-[[4-[[tert-butyl(dimethyl)silyl]oxymethyl]phenyl]methyl]imidazole-4-carbaldehyde (1.9 g, 5.75 mmol) in DCE (11.5 mL) were sequentially added morpholine (1.0 mL, 11.50 mmol), NaBH(OAc)$_3$ (2.43 g, 11.50 mmol) and the reaction mixture was then stirred at rt for 2 h. The volatiles were evaporated under reduced pressure, and then a saturated aqueous solution of NaHCO$_3$ (40.0 mL) and DCM (40.0 mL) were added. The layers were separated, and the aqueous phase was extracted with DCM (2×40.0 mL). The combined organic layers were dried (Na$_2$SO$_4$), filtered and concentrated under reduced pressure. The material was purified by silica gel chromatography using a gradient of 0-10% MeOH in DCM as eluent to provide title compound (1.2 g, 52%) as a solid. $^1$H NMR (500 MHz, CDCl$_3$) δ 7.48 (d, J=1.2 Hz, 1H), 7.30 (d, J=8.2 Hz, 2H), 7.12 (d, J=8.1 Hz, 2H), 6.80 (s, 1H), 5.03 (s, 2H), 4.71 (s, 2H), 3.76-3.66 (m, 4H), 3.49 (s, 2H), 2.55-2.51 (m, 4H), 0.92 (s, 9H), 0.08 (s, 6H).

Step 4: [4-[[4-(morpholinomethyl)imidazol-1-yl]methyl]phenyl]methanol

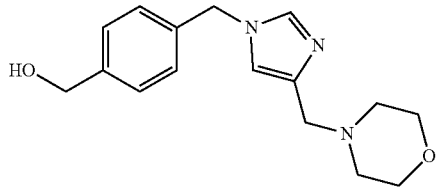 [SMILES: OCc1ccc(Cn2cnc(CN3CCOCC3)c2)cc1]

To a solution of tert-butyl-dimethyl-[[4-[[4-(morpholinomethyl)imidazol-1-yl]methyl]phenyl]methoxy]silane (1.2 g, 3.00 mmol) in THF (25.0 mL) cooled to 0° C. was added a 1.0 M solution of TBAF in THF (3.0 mL, 3.0 mmol) dropwise. After the addition was completed, the reaction was stirred at rt overnight. A saturated aqueous solution of ammonium chloride (30.0 mL) and ethyl acetate (40.0 mL) were added, and the layers were separated. The aqueous phase was extracted with ethyl acetate (2×40.0 mL), and the combined organic extracts were washed with brine (50.0 mL), dried (Na$_2$SO$_4$), filtered and concentrated under reduced pressure. The material was purified by silica gel chromatography using a gradient of 0-10% MeOH in DCM as eluent to provide title compound (210.0 mg, 21%) as a solid. MS (ESI) [M+H]$^+$ 288.4.

Step 5: 4-[[1-[[4-(chloromethyl)phenyl]methyl]imidazol-4-yl]methyl]morpholine

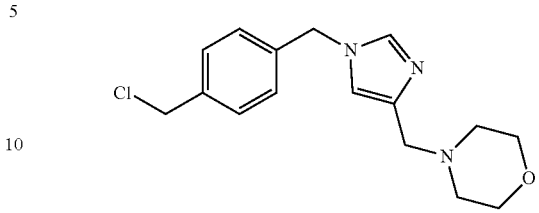

To a solution [4-[[4-(morpholinomethyl)imidazol-1-yl]methyl]phenyl]methanol (205.0 mg, 0.71 mmol) in chloroform (3.50 mL) was added thionyl chloride (259.0 μL, 3.57 mmol) dropwise at rt and the reaction mixture was stirred at rt for 30 min. The volatiles were evaporated under reduced pressure, and then a saturated aqueous solution of NaHCO$_3$ (30.0 mL) and DCM (30.0 mL) were added. The layers were separated, and the aqueous phase was extracted with DCM (2×30.0 mL). The combined organic extracts were washed with brine (40.0 mL), dried (Na$_2$SO$_4$), filtered and concentrated under reduced pressure to provide title compound (200 mg, 92%) as a solid, which was used in the next step without further purification. $^1$H NMR (500 MHz, CDCl$_3$) δ 7.48 (d, J=1.2 Hz, 1H), 7.40-7.36 (m, 2H), 7.14 (d, J=8.3 Hz, 2H), 6.79 (s, 1H), 5.06 (s, 2H), 4.57 (s, 2H), 3.77-3.67 (m, 4H), 3.48 (s, 2H), 2.53-2.48 (m, 4H). MS (ESI) [M+H]$^+$ 306.4.

Step 6: 4-[[1-[[4-[[7-(trifluoromethyl)-4-quinolyl]sulfanylmethyl]phenyl]methyl]imidazol-4-yl]methyl]morpholine

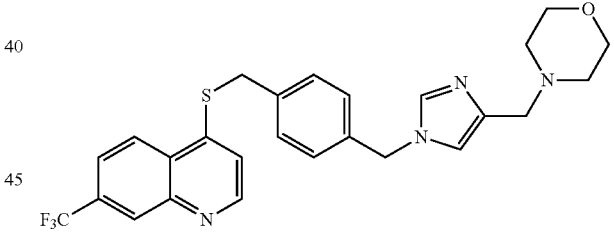

To a solution of 7-(trifluoromethyl)quinoline-4-thiol (150.0 mg, 0.65 mmol) in acetonitrile (3.0 mL) was added KOH (44.9 mg, 0.72 mmol) and after stirring for 15 min the mixture was cooled to 0° C. A solution of 4-[[1-[[4-(chloromethyl)phenyl]methyl]imidazol-4-yl]methyl]morpholine (200.0 mg, 0.65 mmol) in acetonitrile (1.0 mL) was added dropwise and the reaction mixture was then stirred at rt for 4 h. The volatiles were evaporated under reduced pressure, and then water (30.0 mL) and DCM (30.0 mL) were added. The layers were separated, and the aqueous phase was extracted with DCM (2×30.0 mL). The combined organic extracts were washed with brine (50.0 mL), dried (Na$_2$SO$_4$), filtered and concentrated under reduced pressure. The material was purified by silica gel chromatography using a gradient of 0-10% MeOH in DCM as eluent to provide title compound (63.0 mg, 19%) as a solid. $^1$H NMR (500 MHz, CDCl$_3$) δ 8.77 (d, J=4.8 Hz, 1H), 8.37 (s, 1H), 8.49-8.20 (m, 1H), 8.24 (d, J=8.8 Hz, 1H), 7.72 (dd, J=8.8, 1.8 Hz, 1H), 7.45 (d, J=8.2 Hz, 2H), 7.28 (d, J=4.8 Hz, 1H), 7.16 (d, J=8.1

Hz, 2H), 7.05 (s, 1H), 5.09 (s, 2H), 4.35 (s, 2H), 3.90-3.86 (m, 6H), 2.90-2.86 (m, 4H). MS (ESI) [M+H]+ 499.6.

Example 8

4-[[1-[4-[[7-(trifluoromethyl)-4-quinolyl]sulfanylmethyl]phenyl]imidazol-4-yl]methyl]morpholine (0033331)

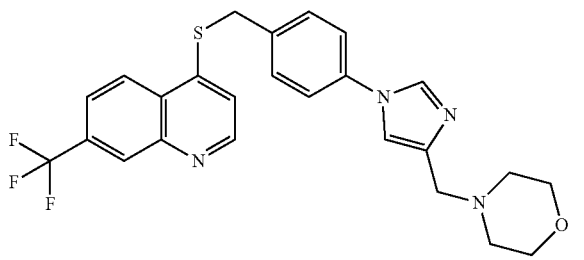 [SMILES: FC(F)(F)c1ccc2c(SCc3ccc(-n4cnc(CN5CCOCC5)c4)cc3)ccnc2c1]

Step 1: methyl 4-(4-formylimidazol-1-yl)benzoate

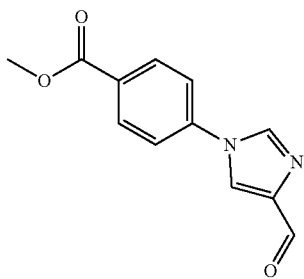 [SMILES: COC(=O)c1ccc(-n2cnc(C=O)c2)cc1]

A degassed mixture of 1H-imidazole-4-carbaldehyde (500.0 mg, 5.2 mmol), methyl 4-iodobenzoate (1.5 g, 5.72 mmol), $Cs_2CO_3$ (3.4 g, 10.4 mmol), CuI (99.0 mg, 0.52 mmol) and trans-N1,N2-dimethylcyclohexane-1,2-diamine (164.0 µL, 1.04 mmol) in DMF (10.0 mL) was heated at 110° C. for 12 h. The mixture was cooled to rt and the insoluble material was removed by filtration. The volatiles were evaporated under reduced pressure and the material was purified by silica gel chromatography using a gradient of 0-100% ethyl acetate in hexane as eluent to provide title compound (350.0 mg, 29%) as a solid. $^1$H NMR (500 MHz, $CDCl_3$) δ 9.91 (s, 1H), 8.10-8.24 (m, 2H), 7.94 (dd, J=9.9, 1.3 Hz, 2H), 7.37-7.55 (m, 2H), 7.19 (s, 1H), 3.90 (s, 3H). MS (ESI) [M+H]+ 231.0.

Step 2: methyl 4-[4-(morpholinomethyl)imidazol-1-yl]benzoate

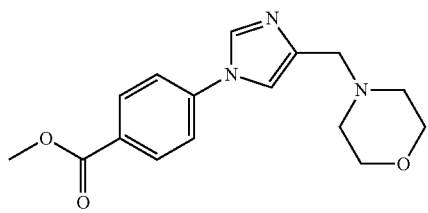 [SMILES: COC(=O)c1ccc(-n2cnc(CN3CCOCC3)c2)cc1]

To a solution of methyl 4-(4-formylimidazol-1-yl)benzoate (100.0 mg, 0.43 mmol) in DCE (4.50 mL) were sequentially added morpholine (46.0 µL, 0.52 mmol), NaBH(OAc)$_3$ (138.0 mg, 0.65 mmol) and the reaction mixture was then stirred for 2 days at rt. The mixture was diluted with 1.0 M NaOH (5.0 mL) and DCM (10.0 mL). The layers were separated, and the organic layer was washed with brine (10.0 mL), dried ($Na_2SO_4$), filtered and concentrated under reduced pressure. The material was purified by silica gel chromatography using a gradient of 0-10% MeOH in DCM as eluent to provide title compound (110 mg, 84%) as an oil. $^1$H NMR (500 MHz, $CDCl_3$) δ 8.15-8.21 (m, 2H), 7.92 (d, J=1.4 Hz, 1H), 7.45-7.51 (m, 2H), 7.29-7.30 (m, 1H), 3.97 (s, 3H), 3.77 (t, J=4.6 Hz, 4H), 3.60 (s, 2H), 2.61 (t, J=4.7 Hz, 4H). MS (ESI) [M+H]+ 302.1.

Step 3: [4-[4-(morpholinomethyl)imidazol-1-yl]phenyl]methanol

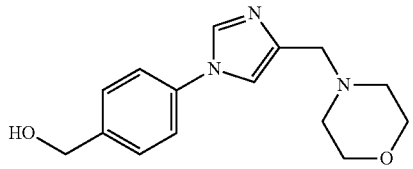 [SMILES: OCc1ccc(-n2cnc(CN3CCOCC3)c2)cc1]

To a solution of methyl 4-[4-(morpholinomethyl)imidazol-1-yl]benzoate (110.0 mg, 0.37 mmol) in a mixture of THF (5.0 mL) and EtOH (5.0 mL) was added $NaBH_4$ (69.0 mg, 1.83 mmol) portion wise and the reaction mixture was heated at reflux for 12 h. The mixture was cooled to rt and the volatiles were evaporated under reduced pressure. A saturated aqueous solution of ammonium chloride (20.0 mL) and ethyl acetate (20.0 mL) were added, the layers were separated, and the aqueous phase was extracted with ethyl acetate (2×20.0 mL). The combined organic extracts were washed with brine (30.0 mL), dried ($Na_2SO_4$), filtered and concentrated under reduced pressure. The material was purified by silica gel chromatography using a gradient of 0-10% MeOH in DCM as eluent to provide title compound (38.0 mg, 38%) as an oil. $^1$H NMR (500 MHz, $CDCl_3$) δ 7.78 (s, 1H), 7.44-7.51 (m, 2H), 7.34-7.41 (m, 2H), 7.21 (s, 1H), 4.75 (s, 2H), 3.67-3.81 (m, 5H), 3.58 (s, 2H), 2.51-2.69 (m, 4H). MS (ESI) [M+H]+ 274.1.

Step 4: 4-[[1-[4-(chloromethyl)phenyl]imidazol-4-yl]methyl]morpholine

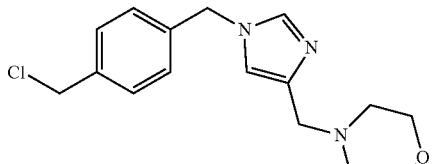

To a solution of [4-[4-(morpholinomethyl)imidazol-1-yl]phenyl]methanol (38.0 mg, 0.14 mmol) in DCM (5.0 mL) cooled to 0° C., was added thionyl chloride (50.0 µL, 0.70 mmol) dropwise at rt and the reaction mixture was stirred for 1 h. The volatiles were removed under reduced pressure, and then a saturated aqueous solution of $NaHCO_3$ (10.0 mL) and DCM (10.0 mL) were added. The layers were separated, and the aqueous phase was extracted with DCM (2×10.0 mL). The combined organic extracts were washed with brine (20.0 mL), dried (Na$_2$SO$_4$), filtered and concentrated under reduced pressure to provide title compound (40.0 mg, 98%) as a solid, which was used in the next step without further purification. MS (ESI) [M+H]$^+$ 292.1.

Step 5: 4-[[1-[4-[[7-(trifluoromethyl)-4-quinolyl]sulfanylmethyl]phenyl]imidazol-4-yl]methyl]morpholine

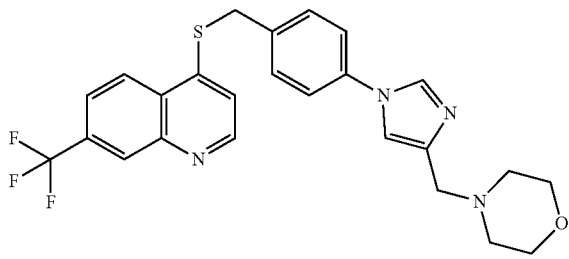 [SMILES: FC(F)(F)c1ccc2c(SCc3ccc(-n4cnc(CN5CCOCC5)c4)cc3)ccnc2c1]

To a solution of 7-(trifluoromethyl)quinoline-4-thiol (19.0 mg, 0.08 mmol) cooled to 0° C. was added NaH (60% in mineral oil, 3.0 mg, 0.08 mmol) and after stirring for 5 min, a solution of [4-[[1-[4-(chloromethyl)phenyl]imidazol-4-yl]methyl]morpholine (16.0 mg, 0.14 mmol) in THF (2.0 mL) was added dropwise. After the addition was completed, the reaction mixture was stirred at rt for 12 h. The volatiles were removed under reduced pressure, and then water (10.0 mL) and ethyl acetate (10.0 mL) were added. The layers were separated, and the aqueous phase was extracted with ethyl acetate (2×10.0 mL). The combined organic extracts were washed with brine (20.0 mL), dried (Na$_2$SO$_4$), filtered and concentrated under reduced pressure. The material was purified by silica gel chromatography using a gradient of 0-10% MeOH in DCM as eluent to provide title compound (11.0 mg, 40%) as a solid. $^1$H NMR (500 MHz, CD$_3$OD) δ 8.74 (d, J=4.9 Hz, 1H), 8.35 (d, J=8.8 Hz, 1H), 8.28 (s, 1H), 8.11 (s, 1H), 7.82 (dd, J=8.8, 1.9 Hz, 1H), 7.64-7.70 (m, 2H), 7.61 (d, J=4.9 Hz, 1H), 7.55 (dd, J=8.8, 2.2 Hz, 3H), 4.57 (s, 2H), 3.71 (t, J=4.7 Hz, 4H), 3.63 (s, 2H), 2.63 (t, J=4.7 Hz, 4H). MS (ESI) [M+H]$^+$ 485.0.

Example 9

Pharmacology
In Vitro Assays
1. Cell Viability Assay (MCF7)

In order to determine a compound's effect on cell viability, PrestoBlue assays were performed as previously described by Kuhn et al. (2013) with modifications. MCF-7 human breast cancer and IGR-1 human melanoma cell lines were seeded into 96-well plates 24 hours prior to addition of drug. Cells were treated with 0 to 200 µM (11 concentrations) of compound solubilized in DMSO, adjusting the final concentration of DMSO to 1% in the well. Three days after drug treatment, cell viability was measured by adding PrestoBlue (Life Technologies Ltd.; cat. No. A13262) reagent directly to wells containing media/drug to reach a final concentration of 10%. PrestoBlue is a modified molecule of the common Alamar Blue probe used to determine viability based on the ability of a cell to metabolize a nonfluorescent compound (resazurin) to a florescent molecule (resorufin). Following a 1 hour incubation period, total well fluorescence was measured using the microplate reader M1000 pro (Tecan) with excitation 560-5 nm and emission 590-5 nm. Data was analyzed using the GraphPad Prism software (GraphPad Software. Inc.), and IC$_{50}$ (dose leading to 50% cell death) was calculated from the dose-response curves. The percentage of living cells was then computed by comparison with control wells. Kuhn, Jonas et al., Assay and Drug Development Technologies, March 2013, Label-Free Cytotoxicity Screening Assay by Digital Holographic Microscopy.

2. Fluorescence Polarization Assay (Rac1 FP)

Direct binding of Rac1 compound inhibitors to Rac1 protein was performed using fluorescence polarization (FP). Briefly, Rac1 inhibitors were initially dissolved in DMSO and then serial drug dilutions in exchange buffer (20 mM Tris pH 7.5, 50 mM NaCl, 1 mM MgCl, 1 mM EDTA) were prepared in a flat black 96-well half-area plate (Greiner). Recombinant his-tagged Rac1 protein (Cytoskeleton Inc. Cat. # RC01) was added to the inhibitors at a final concentration of 125 nM along with 12.5 nM Bodipy-TR GTPγS (Life Technologies Inc. Cat. # G35780) in exchange buffer and incubated for 30 minutes at 37° C. in exchange buffer. After 30 minutes of incubation. FP was measured on the M1000 Pro (Tecan) fluorescent plate reader with 590 nm±5 nm excitation and 625 nm±5 nm emission spectra settings. Data were analyzed using the GraphPad Prism software (GraphPad Software, Inc.), and IC$_{50}$ (concentration leading to 50% polarization signal inhibition) was calculated from the concentration-response curves.

3. Rac Activation AlphaScreen Assay (Rac1 AS)

AlphaScreen® assays were performed in 96-well microplates in a final reaction volume of 60 µl. Recombinant His-Rac1, recombinant GST-PBD (PAK Binding Domain), donor and acceptor beads (PerkinElmer), and inhibitors were incubated in exchange buffer (20 mM Tris pH 7.5, 50 mM NaCl, 1 mM MgCl$_2$, 1 mM EDTA, 500 nM GTPγS (guanosine 5'-[γ-thio]triphosphate)) at 37° C. Readings were performed on a Tecan M1000 pro microplate reader after 1 hour. Data was analyzed using the GraphPad Prism software (GraphPad Software, Inc.), and IC$_{50}$ (dose leading to 50% disruption of complex) was calculated from the dose-response curves. The results are shown in Table 1.

Assay Results

TABLE 1

| Compound Designation | MCF7 IC$_{50}$ (uM) | Rac1 FP IC$_{50}$ (uM) | Rac1 AS IC$_{50}$(uM) |
| --- | --- | --- | --- |
| 0033131 | 6.7 | 0.36 | 6.5 |
| 0033043 | 7.8 | 100 | 9.6 |
| 0033042 | 9 | 2.35 | 7.2 |
| 0032956 | 10.66 | 1.41 | 8.2 |
| 0032939 | 19.5 | 1.27 | 23.1 |
| 0032938 | 37.8 | 2.02 | 28.2 |
| 0032897 | 11.6 | 2.79 | 35 |
| 0032896 | 13.8 | 4.76 | positive |
| 0032887 | 11.82 | 1.18 | 4.7 |
| 0032886 | 7.8 | 2.04 | 4.4 |
| 0032881 | 6.8 | 0.249 | 6 |
| 0032880 | 6.3 | 1 | 3.2 |
| 0032834 | 9.2 | 2.57 | positive |
| 0032833 | 7.8 | 4.32 | positive |
| 0032731 | 9.1 | 5.16 | 24.1 |
| 0032662 | 19.1 | 2.33 | 16.6 |
| 0032956 | 6.6 | 3.25 | 44.8 |
| 0032621 | 9.34 | 1.48 | positive |
| 0032371 | 11.3 | 3.73 | 62 |
| 0032253 | 4.38 | 3.42 | positive |
| 0031778 | 4.86 | 1.24 | positive |

TABLE 1-continued

| Compound Designation | MCF7 IC$_{50}$ (uM) | Rac1 FP IC$_{50}$ (uM) | Rac1 AS IC$_{50}$(uM) |
|---|---|---|---|
| 0033306 | 3.58 | 1.54 | 8.2 |
| 0033283 | 5.6 | 3.07 | 6.3 |
| 0033278 | 7.6 | 2.32 | 1.1 |
| 0033240 | 3.8 | 9.67 | 0.98 |
| 0033235 | 3.6 | 4.81 | 1.1 |
| 0033200 | 10.8 | 0.71 | 2.3 |
| 0033102 | 3.8 | 9.66 | 0.383 |

*Positive means that the signal generated was higher than the positive control

4. HUVEC Tube Formation Assay

The endothelial cell tube formation assay is an in vitro assay that is widely accepted to accurately reflect number of terminal stages of the angiogenic process such as attachment, migration and differentiation into tubular structures. In this model, endothelial cells are cultured on a monolayer of reconstituted basement membrane components (Matrigel) and form, in a few hours, capillary-like structure. Therefore, this system is a useful and powerful tool for rapidly screening anti-angiogenic agents by monitoring inhibition of endothelial cells morphogenesis on extracellular matrix.

HUVECs ($5 \times 10^3$) were seeded on top of Matrigel in a 24-well plate. The cells were treated either with DMSO or different concentrations of the Rac1 inhibitor 0032253 (5, 6.25, 10, 12.5 μM) for 8 h in triplicate. The plates were scanned by LICOR Odyssey Imaging system. The results are presented in FIG. 1. As seen in FIG. 1 the doses of 0032253 above 6.25 μM significantly reduce the ability of HUVECs to form tube like structures.

5. Cell Migration Assay

An essential characteristic of malignant cells is their ability to migrate, invade host tissues and to produce metastases. In order to evaluate the capacity of one compound to affect the ability of tumoral cells to migrate, migration assays were performed using HUVEC cells.

Figure 2:
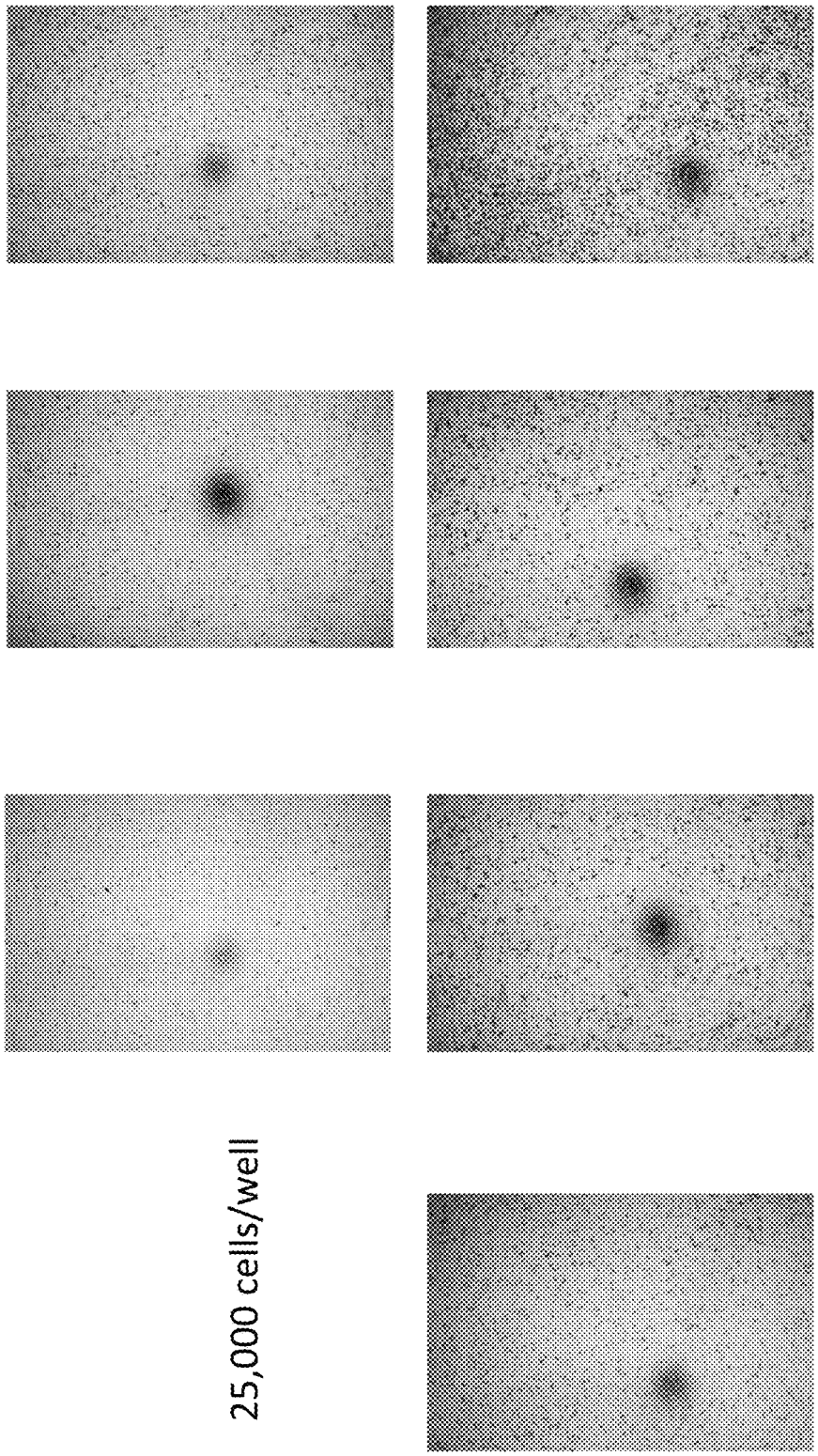
FIG. 2 shows the ability of different doses of the Rac1 inhibitor 0032253 to migrate through a Boyden Chamber.

HUVECs ($2.5 \times 10^4$) were seeded onto uncoated filters in a 24-well transwell Boyden chamber (8-mm pore size; Costar) and allowed to migrate in the presence and absence of different doses of the Rac1 inhibitor 0032253 (5, 6.25, 10, 12.5, 20, 25 μM). The cells that migrated to the underside of the filter were stained with crystal violet and counted under the bright field microscopy. The results are presented in FIG. 2. As seen in FIG. 2, 5 uM 0032253 impairs the ability of HUVECs to migrate through a Boyden Chamber.

Figure 3:
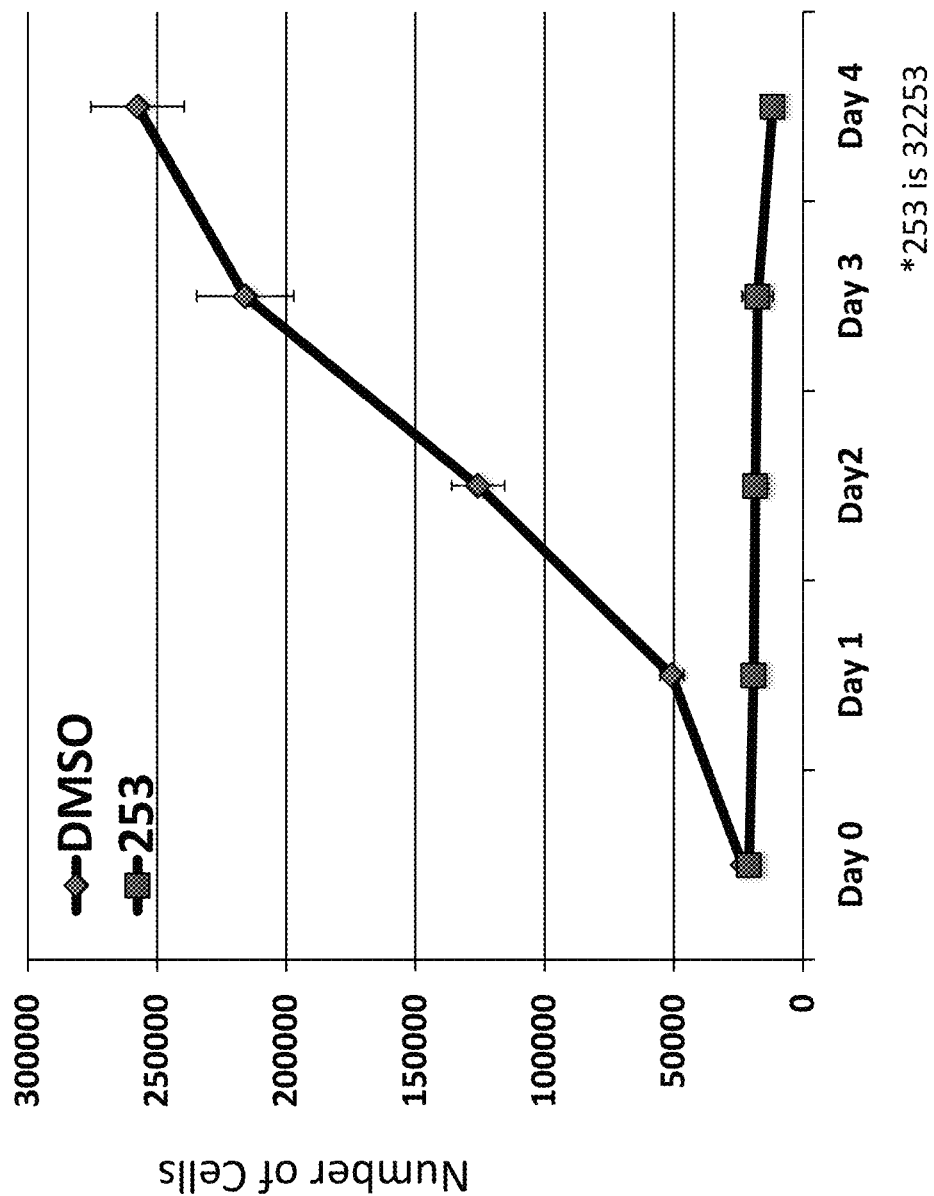
FIG. 3 shows the ability of 0032253 to inhibit the ability of HUVECs to proliferate.

6. Cellular Proliferation Assay 25,000 cells were seeded in 6-well plates. The next day, vehicle (DMSO) or 25 μM 0032253 was added to cells (Day 0). Cells were counted on days 0 through day 4 using a hemocytometer. The results are presented in FIG. 3. As seen in FIG. 3, 25 uM 0032253 completely inhibits the ability of HUVECs to proliferate.

7. Western Blot Analysis

Western blot analysis is used to identify specific proteins from a complex mixture of proteins extracted from cells. Equal amount of protein is run on the SDS-PAGE gel and after separating the protein mixture, it is transferred to a membrane. The transferred protein is then probed with a combination of antibodies: one antibody specific to the protein of interest (primary antibody) and another antibody specific to the host species of the primary antibody (secondary antibody). The secondary antibody is complexed with an enzyme, which when combined with an appropriate substrate, will produce a detectable signal.

Figure 4:
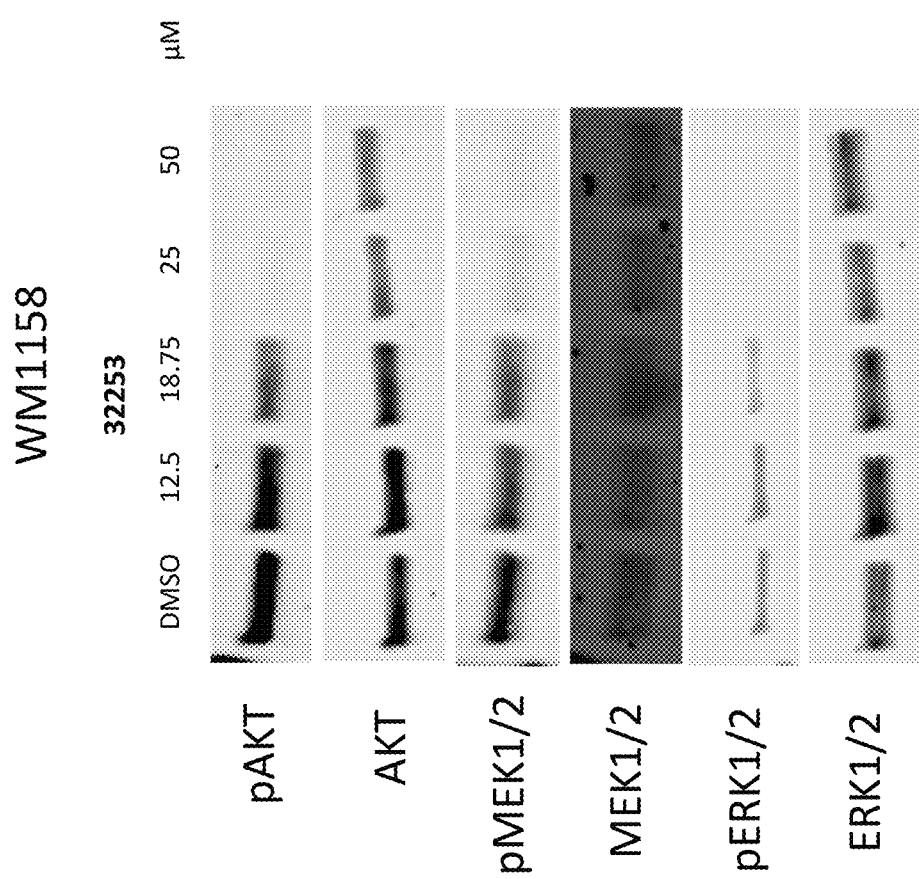
FIG. 4 is a Western blot analysis showing that following treatment with 0032253 the expression of phosphorylated AKT, MEK1/2, and ERK1/2 was reduced as compared to DMSO control.

WM1158 cells were treated with increasing concentrations of 0032253 for two hours. SDS-PAGE was conducted on cell lysates and Western Blot analysis was conducted on samples for total and phosphorylated AKT, MEK1/2, and ERK1/2. Following treatment with 0032253, the expression of phosphorylated AKT, MEK1/2 and ERK1/2 was reduced as compared to DMSO control as seen in FIG. 4. This suggests that Rac inhibitors target the key signaling components of the cells, which is required for cellular proliferation.

Kidney Damage Models

1. LPS Proteinuria Mouse Model

In the LPS proteinuria model LPS is used to induce kidney damage. Kidney damage is then measured by determining changes in the albumin-creatinine found in the urine. Kidney damage effects the clearance of albumin-creatinine which results in differences in the urine. The ratio of albumin to creatinine is utilized as a measure of proteinuria in kidney disease.

Rac1 inhibitors (50 μM) were injected into B6 mice 4 hours before and 4 hours after LPS (i.p) in 5% DMSO. Controls received the same amount of vehicle (5% DMSO/saline). Urine was collected at baseline and 24 hours after LPS injection and then analyzed for albumin and creatinine levels using the following albumin-creatinine assay. N=6 for each group. Urine from C57Bl6 mice were collected for baseline measurement. Baseline urine albumin excretion was measured as per the manufacturer's protocol using ELISA Albumin Kit (Bethyl Laboratories) and standardized to urine creatinine, before animals were administered an intraperitoneal injection with or without 200 μg of LPS (InvivoGen) in a total volume of 200 μl of sterile PBS.25.

Figure 5:
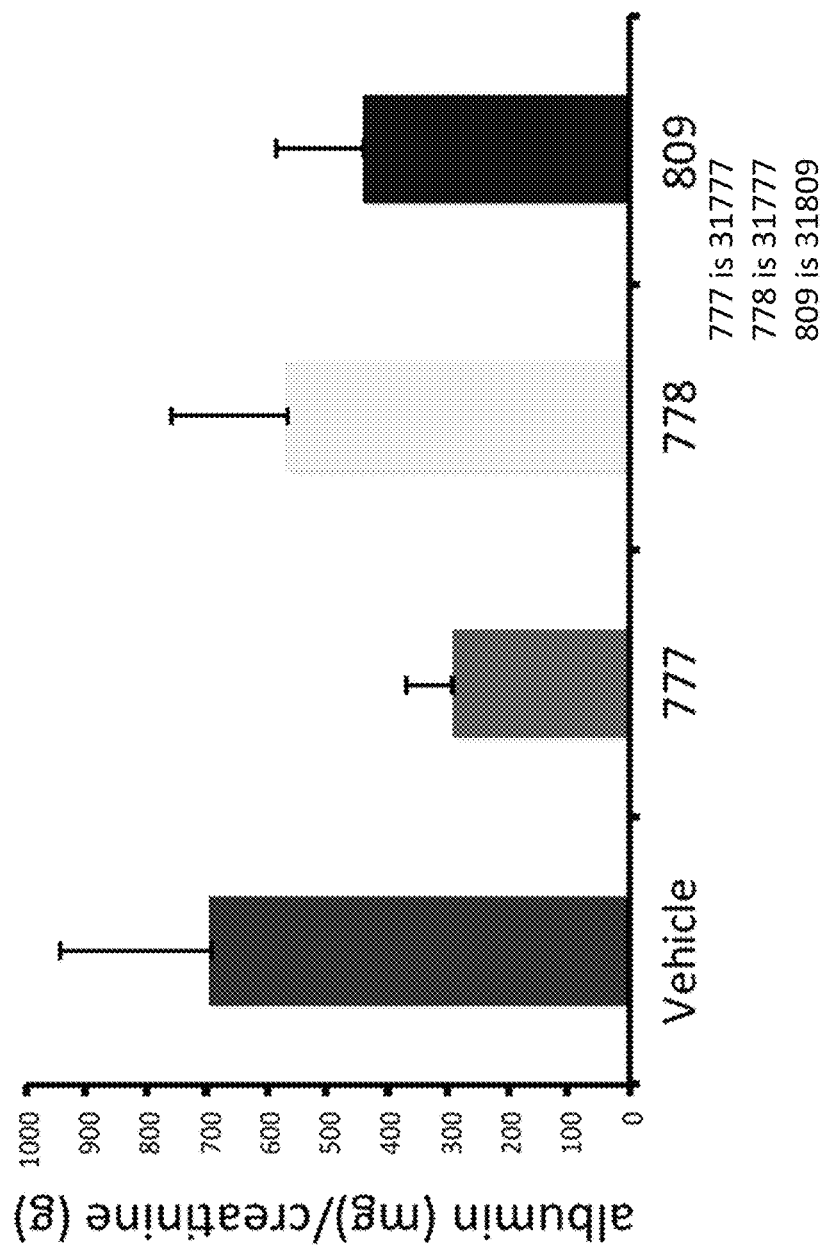
FIG. 5 shows the effect of different Rac1 inhibitors on LPS induced proteinuria.

The results are presented in FIG. 5.

2. Effect of Rac1 Inhibitors on Proteinuria in Podocyte Rac1 Transgenic Mice

The transgenic mouse model expresses constitutively active Rac1 in the kidney. Expression of constitutively active Rac1 results in kidney damage wherein the kidney damage in the Rac1 transgenic mouse is caused by Rac1.

Figure 6:
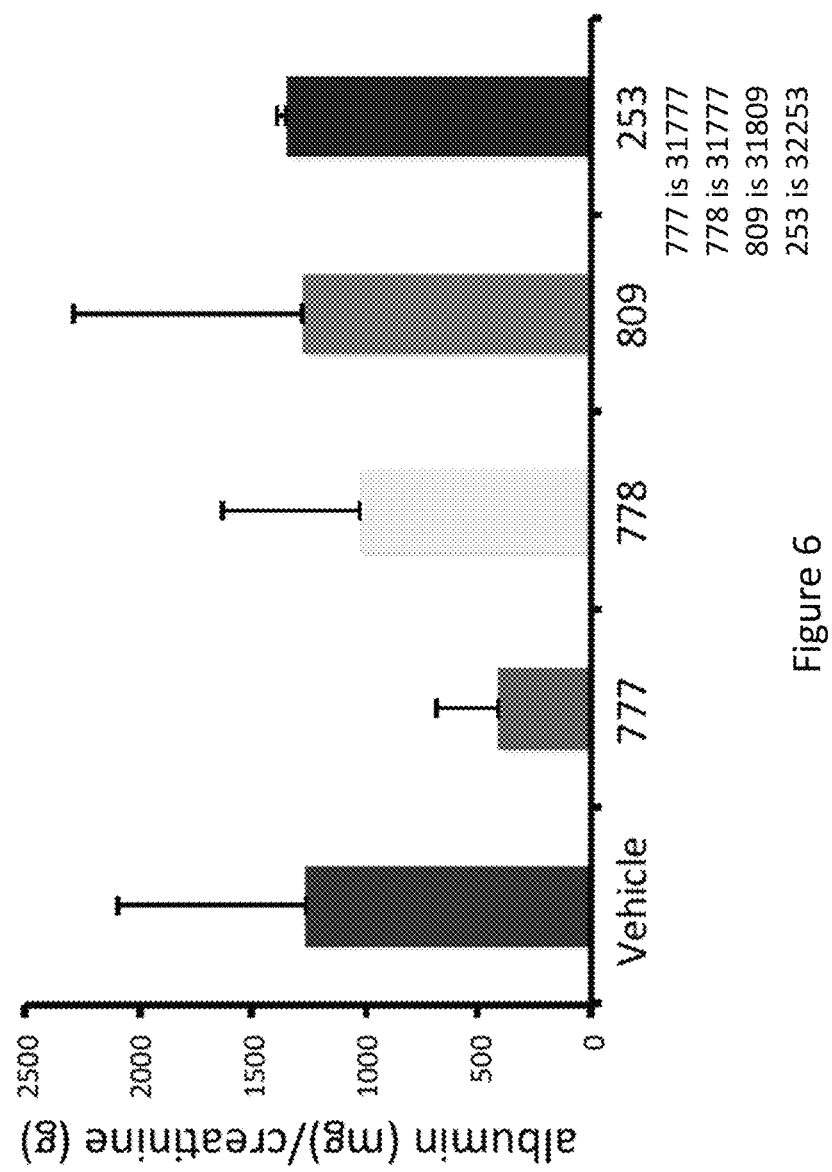
FIG. 6 shows the effect of different Rac1 inhibitors on proteinuria in podocyte Rac1 transgenic mice.

Rac1 inhibitors (50 μM, 60 μM for 0032253) were injected into Rac1 transgentic mice once a day for 4 days (i.p) (Rac1 transgenic mice were prepared using the method described in Haiyang, Yu. et al., Mol. Cell Biol., 33(23): 4755-64 (December 2013)). Controls received the same amount of vehicle (5% DMSO/saline). Urine was collected at baseline and 48 hours after the last injection, and then analyzed for albumin and creatinine levels using the same albumin-creatinine assay described above for the LPS proteinuria model. N=3 for each group. The results are presented in FIG. 6.

Administration of the Rac inhibitors attenuate the effect of kidney damage induced by either LPS or the expression of constitutively active Rac1.

The variously described embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Breast Cancer

1. Inhibition of Estrogen Receptor Target Gene Transcription

Figure 7:
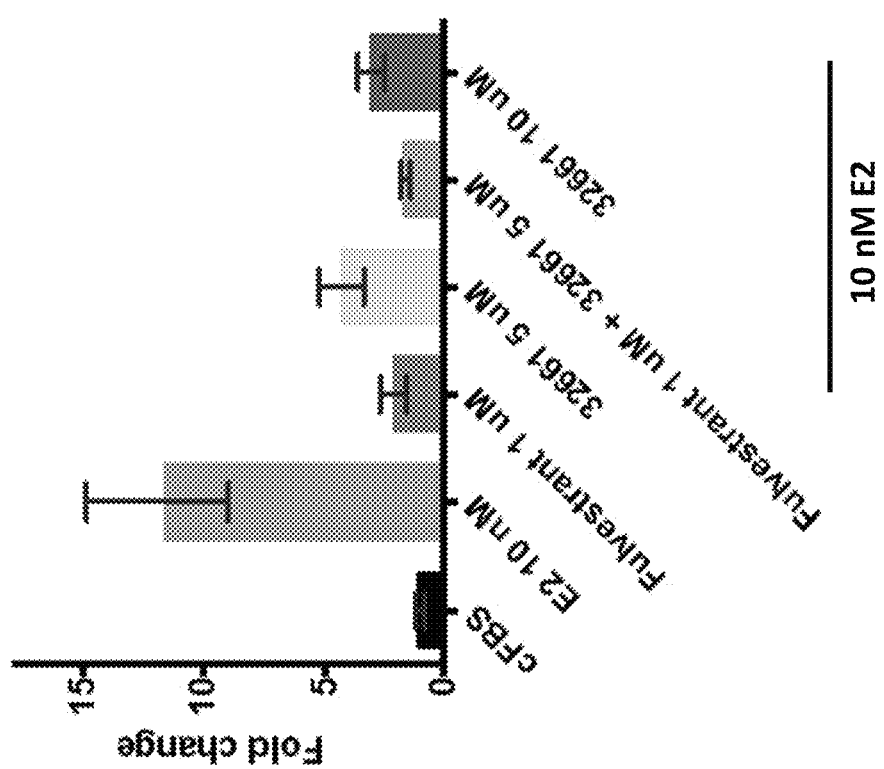
FIG. 7 shows the ability of fulvestrant and 0032661 to inhibit estrogen receptor target gene transcription.

MCF7 breast cancer cells grown in charcoal stripped FBS (5%) were treated for 4 hours with 10 nM estradiol (E2), 10 nM estradiol plus 1 uM fulvestrant, 10 nM estradiol plus 5 uM 0032661, 10 nM estradiol plus 10 uM 0032661, or 10 nM estradiol plus 1 uM fulvestrant plus 5 uM 0032661. After 4 hours, RNA was harvested and converted into cDNA. qPCR analysis for SDF was performed on all samples and normalized to expression of GAPDH. The data, shown in FIG. 7, is expressed as fold change relative to SDF expression of the cFBS sample. The data shows the potent induction of an estrogen receptor response gene (SDF). The data also shows that fulvesterant and 0032661 inhibit the estrogen receptor target gene transcription. The combination of fulvesterant plus 0032661 reduces SDF gene expression more than either single treatment alone.

2. Inhibition of Estrogen Receptor Target Gene Protein Expression

Figure 8:
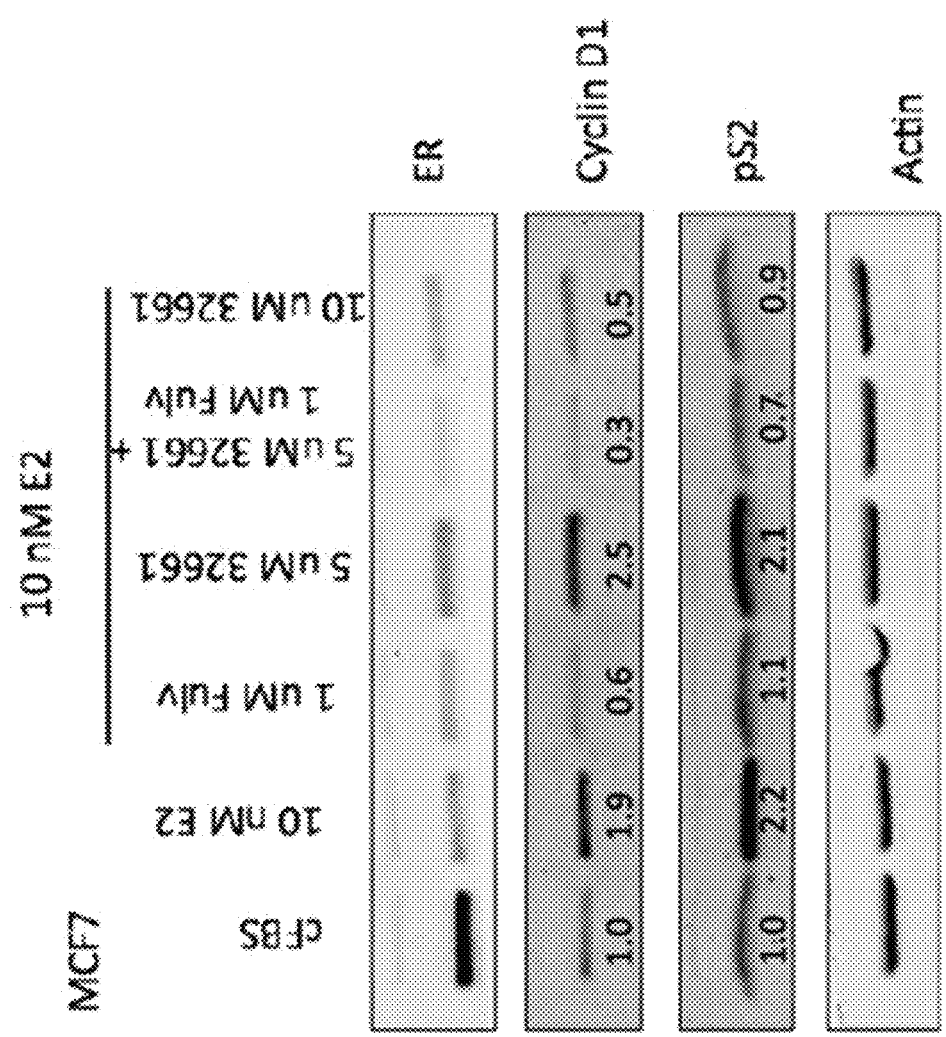
FIG. 8 shows the ability of fulvestrant and 0032661 to inhibit the increase in protein levels of estrogen receptor target genes.

MCF7 breast cancer cells grown in charcoal stripped FBS (5%) were treated for 18 hours with 10 nM estradiol (E2), 10 nM E2 plus 1 uM fulvestrant (fulv), 10 nM E2 plus 5 uM 0032661, 10 nM E2 plus 10 uM 0032661, or 10 nM E2 plus 1 uM fulv plus 5 uM 0032661. After 18 hours, protein was harvested. SDS-PAGE followed by immunoblotting of samples was performed using standard techniques. Protein lysates were immunoblotted for Estrogen Receptor (ER), Cyclin D1, pS2, and Actin. The data, presented in FIG. 8, shows the induction of the estrogen receptor response genes Cyclin D1 and pS2. FIG. 8 also shows that Faslodex® and 0032661 inhibit the increase in protein levels of estrogen receptor target genes. The combination of Faslodex® plus 0032661 reduces estrogen receptor target gene protein expression more than either single treatment alone.

3. Tumor Burden

Figure 9:
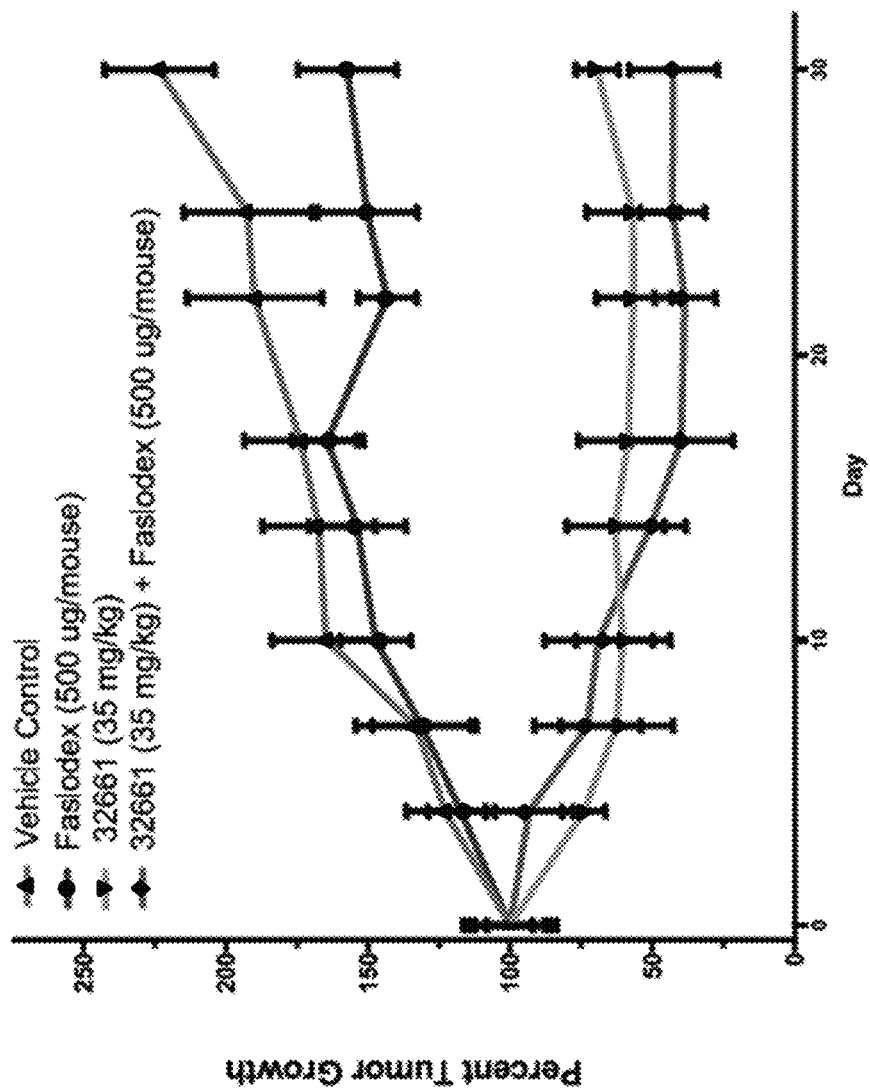
FIG. 9 shows the effect of Faslodex® and 0032661 on the growth of breast cancer tumors.

MCF7 breast cancer cells grown were innoculated into Nod/Scid-gamma null immunocomprimised mice. The resulting tumors were allowed to reach approximately 100 mm$^3$ in size and then mice were randomized into vehicle, Faslodex®, 0032661, or Faslodex® plus 0032661 treatment groups. Faslodex® treated mice were dosed with 500 ug Faslodex® once a week via intramuscular injection. 0032661 treated mice were dosed with 35 mg/kg 0032661 five days a week via intraparatoneal injection. Tumors were measured by calipers twice a week. The data, shown in FIG. 9, shows strong anti-tumoral effects of 0032661 treatment in vivo. Additionally, the combination of Faslodex® plus 0032661 reduces tumor burden more than either single treatment alone.

4. BT474 Four (4) Day Cell Viability Assay

Figure 10:
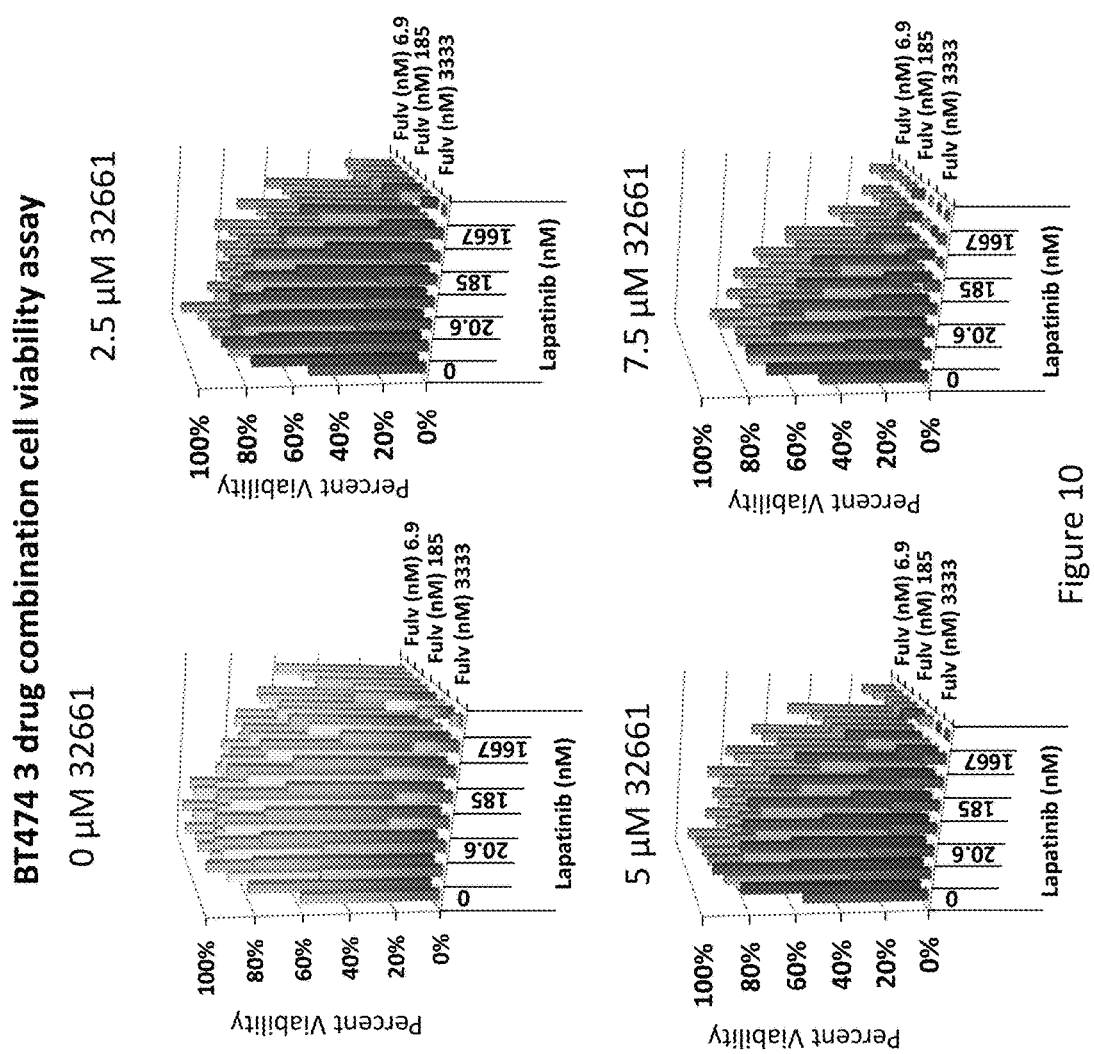
FIG. 10 shows that the addition of 0032661 enhanced the reduction of cellular viability of BT474 cells.

BT474 breast cancer cells that are Estrogen Receptor Positive and HER2+ were grown in 5% cFBS. 5,000 cells were seeded into each well of a 96-well plate and treated with escalating doses of lapatinib, fulvestrant, and 32661. After 4 days of drug treatment, cellular viability was analyzed by the PresoBlue cell viability assay. The results are shown in Tables 2-6 and FIG. 10. While the combinatorial inhibition of HER2 and the Estrogen Receptor reduced the cellular viability of BT474 breast cancer cells, the addition of 32661 further enhanced the reduction of cellular viability of the BT474 cells.

TABLE 2

0 µM 32661

| | | Lapatinib (nM) | | | | | | | |
|---|---|---|---|---|---|---|---|---|---|
| | | 0.0 | 6.9 | 20.6 | 61.7 | 185.2 | 555.6 | 1666.7 | 3333.0 |
| Fulvestrant (nM) | 3333.0 | 60% | 53% | 53% | 26% | 24% | 32% | 20% | 4% |
| | 1666.7 | 80% | 79% | 76% | 75% | 68% | 65% | 47% | 15% |
| | 555.6 | 87% | 90% | 90% | 88% | 82% | 74% | 58% | 26% |
| | 185.2 | 94% | 91% | 91% | 91% | 88% | 74% | 63% | 36% |
| | 61.7 | 91% | 89% | 89% | 90% | 88% | 77% | 66% | 34% |
| | 20.6 | 94% | 88% | 88% | 83% | 82% | 78% | 63% | 47% |
| | 6.9 | 94% | 96% | 96% | 87% | 85% | 79% | 69% | 51% |
| | 0.0 | 97% | 99% | 96% | 80% | 75% | 77% | 68% | 60% |

TABLE 3

2.5 µM 32661

| | | Lapatinib (nM) | | | | | | | |
|---|---|---|---|---|---|---|---|---|---|
| | | 0.0 | 6.9 | 20.6 | 61.7 | 185.2 | 555.6 | 1666.7 | 3333.0 |
| Fulvestrant (nM) | 3333.0 | 52% | 42% | 34% | 30% | 26% | 22% | 16% | 1% |
| | 1666.7 | 75% | 72% | 73% | 72% | 59% | 47% | 24% | 7% |
| | 555.6 | 83% | 78% | 80% | 79% | 75% | 62% | 48% | 14% |
| | 185.2 | 84% | 81% | 82% | 77% | 73% | 63% | 54% | 18% |
| | 61.7 | 87% | 78% | 78% | 78% | 73% | 63% | 53% | 21% |
| | 20.6 | 87% | 77% | 79% | 79% | 76% | 63% | 54% | 25% |
| | 6.9 | 90% | 83% | 80% | 80% | 78% | 66% | 55% | 25% |
| | 0.0 | 96% | 85% | 80% | 81% | 83% | 73% | 60% | 23% |

TABLE 4

5 µM 32661

| | | Lapatinib (nM) | | | | | | | |
|---|---|---|---|---|---|---|---|---|---|
| | | 0.0 | 6.9 | 20.6 | 61.7 | 185.2 | 555.6 | 1666.7 | 3333.0 |
| Fulvestrant (nM) | 3333.0 | 56% | 35% | 29% | 21% | 22% | 19% | 11% | 1% |
| | 1666.7 | 81% | 60% | 60% | 48% | 36% | 29% | 18% | 1% |
| | 555.6 | 86% | 79% | 74% | 72% | 56% | 48% | 29% | 6% |
| | 185.2 | 90% | 78% | 78% | 76% | 67% | 56% | 35% | 10% |
| | 61.7 | 90% | 80% | 78% | 76% | 67% | 60% | 39% | 11% |
| | 20.6 | 91% | 80% | 79% | 78% | 71% | 60% | 39% | 11% |
| | 6.9 | 93% | 83% | 82% | 82% | 77% | 65% | 42% | 14% |
| | 0.0 | 95% | 87% | 84% | 87% | 79% | 67% | 51% | 16% |

TABLE 5

7.5 µM 32661

| | | Lapatinib (nM) | | | | | | | |
|---|---|---|---|---|---|---|---|---|---|
| | | 0.0 | 6.9 | 20.6 | 61.7 | 185.2 | 555.6 | 1666.7 | 3333.0 |
| Fulvestrant (nM) | 3333.0 | 49% | 16% | 13% | 11% | 7% | 2% | 3% | 1% |
| | 1666.7 | 69% | 35% | 28% | 25% | 21% | 12% | 2% | 0% |
| | 555.6 | 76% | 59% | 52% | 45% | 38% | 19% | 3% | 1% |
| | 185.2 | 74% | 64% | 61% | 54% | 48% | 24% | 10% | 5% |
| | 61.7 | 76% | 66% | 61% | 58% | 52% | 24% | 12% | 4% |
| | 20.6 | 75% | 73% | 67% | 62% | 50% | 23% | 12% | 4% |
| | 6.9 | 81% | 72% | 71% | 64% | 52% | 27% | 12% | 9% |
| | 0.0 | 84% | 76% | 74% | 65% | 50% | 30% | 14% | 12% |

TABLE 6

10 µM 32661

| | | Lapatinib (nM) | | | | | | | |
|---|---|---|---|---|---|---|---|---|---|
| | | 0.0 | 6.9 | 20.6 | 61.7 | 185.2 | 555.6 | 1666.7 | 3333.0 |
| Fulvestrant (nM) | 3333.0 | 55% | 3% | 3% | 6% | 2% | 2% | 1% | 0% |
| | 1666.7 | 78% | 16% | 16% | 15% | 16% | 15% | 7% | 0% |
| | 555.6 | 81% | 31% | 29% | 29% | 24% | 23% | 18% | 1% |
| | 185.2 | 86% | 33% | 33% | 31% | 24% | 23% | 18% | 1% |
| | 61.7 | 86% | 37% | 35% | 33% | 27% | 23% | 20% | 2% |
| | 20.6 | 89% | 36% | 36% | 33% | 28% | 23% | 20% | 3% |
| | 6.9 | 90% | 38% | 35% | 33% | 27% | 24% | 20% | 3% |
| | 0.0 | 90% | 42% | 38% | 35% | 28% | 28% | 23% | 5% |

Prostate Cancer

1. Inhibition of Androgen Receptor Target Gene Transcription

Figure 11:
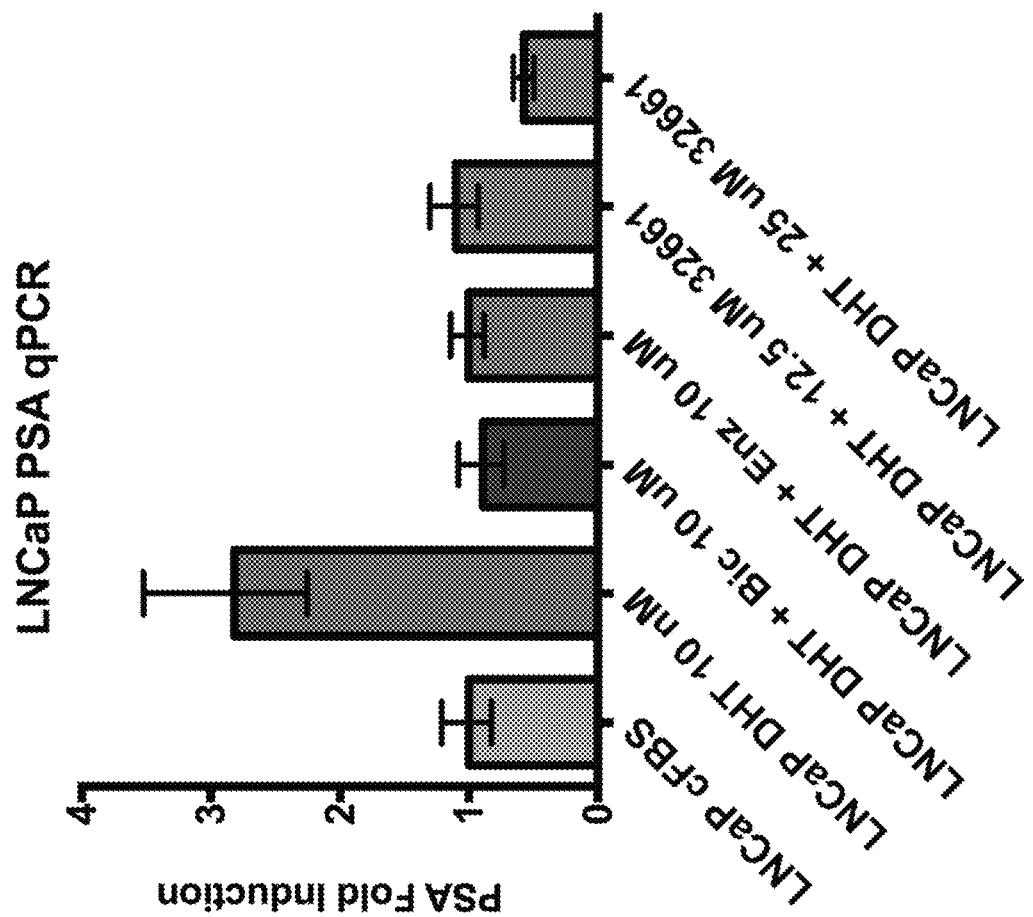
FIG. 11 shows the ability of bicalutamide, enzalutamide, and 0032661 to inhibit androgen receptor target gene transcription.

LNCaP prostate cancer cells grown in charcoal stripped FBS (5%) were treated for 4 hours with 10 nM di-hydroxytesterone (DHT), 10 nM DHT plus 10 uM bicalutamide (Bic), 10 nM DHT plus 10 uM enzalutamide (Enz), 10 nM DHT plus 12.5 uM 0032661 or 10 nM DHT plus 25 uM 0032661. After 4 hours, RNA was harvested and converted into cDNA. qPCR analysis for PSA was performed on all samples and normalized to expression of GAPDH. The data, shown in FIG. 11, is expressed as fold change relative to PSA expression of the cFBS sample. The data shows potent induction of an androgen receptor response gene (PSA) and that Bic, Enz, and 0032661 inhibit the androgen receptor target gene transcription.

2. Inhibition of Androgen Receptor Luciferase Expression

Figure 12:
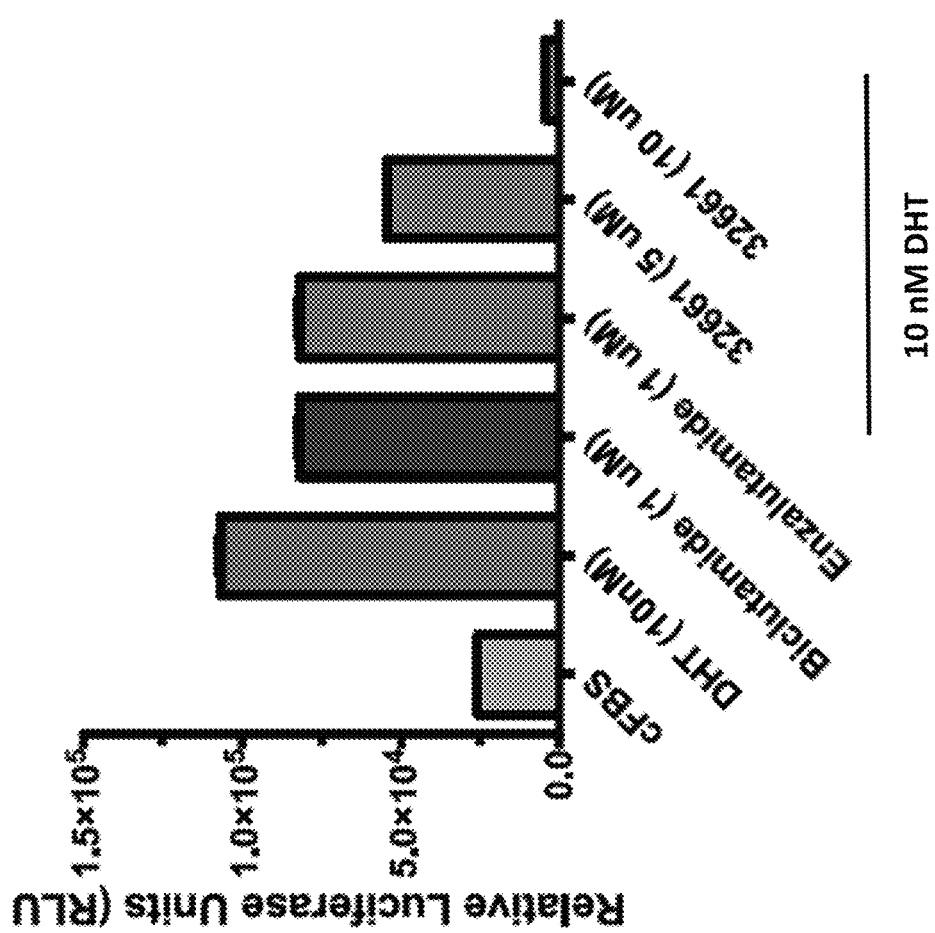
FIG. 12 shows the ability of bicalutamide, enzalutamide, and 0032661 to inhibit androgen receptor luciferase expression.

LNCaP prostate cancer cells expressing an Androgen Receptor (AR) luciferase reporter were grown in charcoal stripped FBS (5%) and were treated for 4 hours with 10 nM DHT, 10 nM DHT plus 1 uM bicalutamide, 10 nM DHT plus 1 uM enzalutamide, 10 nM DHT plus 5 uM 0032661, and 10 nM DHT plus 10 uM 0032661. After 4 hours, cell lysate was harvested. 50 µg protein lysates were used in a luciferase assay. The data, shown in FIG. 12, is expressed as relative luciferase units (RLU). The data shows potent induction of the androgen receptor luciferase reporter and that bicalutamide, enzalutamide, and 0032661 inhibit the androgen receptor luciferase expression.

3. Inhibition of Increased Protein Levels of PSA

Figure 13:
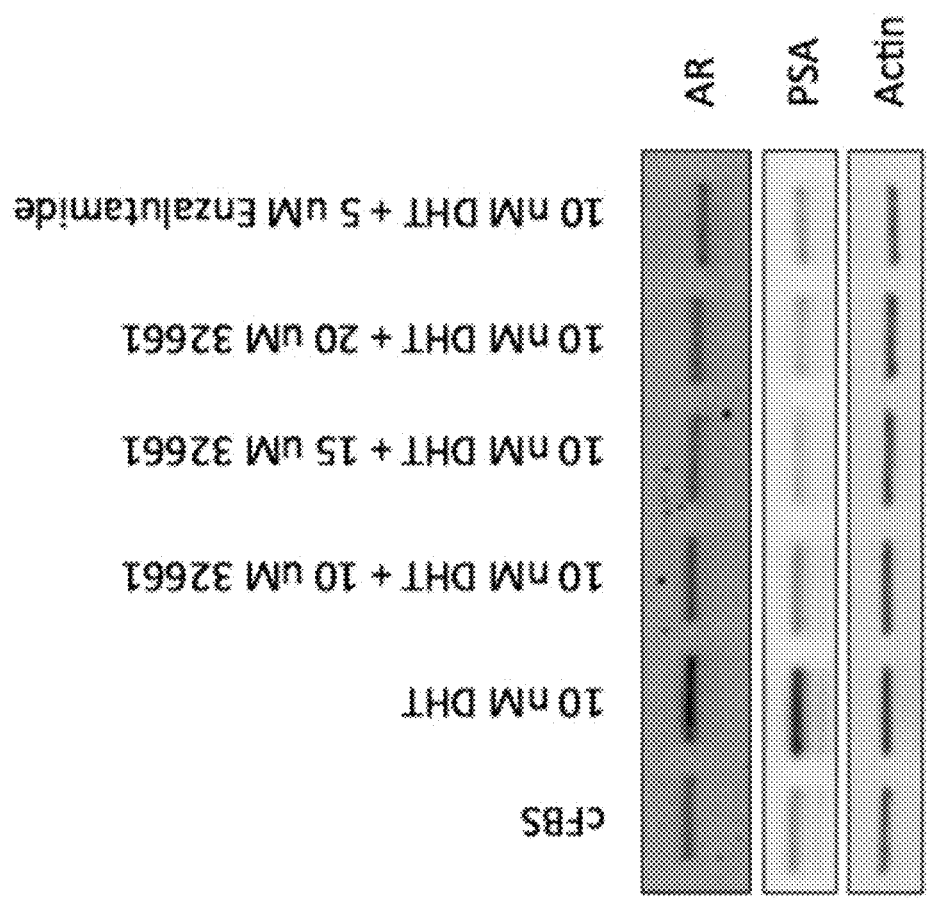
FIG. 13 shows the ability enzalutamide and 0032661 to inhibit the increase in protein levels of PSA.

LNCaP prostate cancer cells grown in charcoal stripped FBS (5%) were treated for 18 hours with 10 nM DHT, 10 nM DHT plus 5 uM enzalutamide, 10 nM DHT plus 10 uM 0032661, 10 nM DHT plus 15 uM 0032661, and 10 nM DHT plus 20 uM 0032661. After 18 hours protein was harvested. SDS-PAGE followed by immunoblotting of samples was performed using standard techniques. Protein lysates were immunoblotted for the Androgen Receptor (AR), PSA, and Actin. The data, as seen in FIG. 13, shows induction of PSA upon DHT treatment and that enzalutamide and 0032661 inhibit the increase in protein levels of PSA.

4. LNCaP ARE Luciferase Assay

Figure 14:
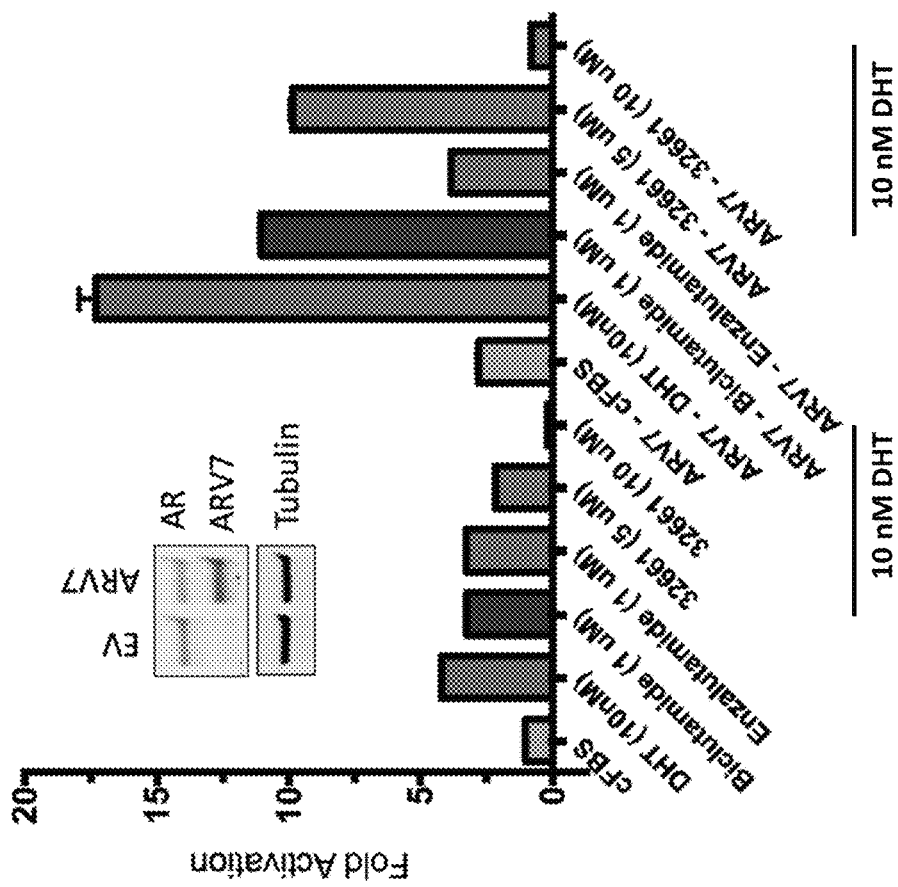
FIG. 14 shows the ability of bicalutamide, enzalutamide, and 0032661 to inhibit androgen receptor luciferase expression and the ability of 0032661 to inhibit androgen receptor luciferase expression of the ARV7 splice variant.

LNCaP prostate cancer cells as well as LNCaP cells that overexpress the oncogenic androgen receptor splice variant (designated ARV7) were engineered to express an Androgen Receptor (AR) luciferase reporter (SABiosciences). Both sets of cells were grown in charcoal stripped FBS (5%) and were treated for 4 hours with 10 nM DHT, 10 nM DHT plus 1 uM bicalutamide, 10 nM DHT plus 1 uM enzalutamide, 10 nM DHT plus 5 uM 0032661, or 10 nM DHT plus 10 uM 0032661. After 4 hours, cell lysate was harvested. 50 µg protein lysates were used in a luciferase assay. The data, as shown in FIG. 14, is expressed as fold activation relative to LNCaP cFBS controls. The data shows potent induction of the androgen receptor luciferase reporter while bicalutamide, enzalutamide, and 0032661 inhibit the androgen receptor luciferase expression. Additionally, 0032661 inhibited luciferase expression of the ARV7 splice variant.

What is claimed is:

1. A compound of formula I:

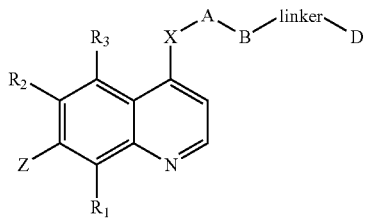

I or a pharmaceutically acceptable salt thereof, wherein

Z is selected from halogen and $C_{1-4}$ alkyl wherein said $C_{1-4}$ alkyl is optionally substituted with one or more halogen atoms;

$R_1$, $R_2$, and $R_3$ are independently selected from H and halogen;

X is —S—;

A is $C_{2-7}$ alkylene wherein one or more of the methylene groups is optionally replaced with O, N($R^b$), C(O), or phenylene;

B is selected from the group:

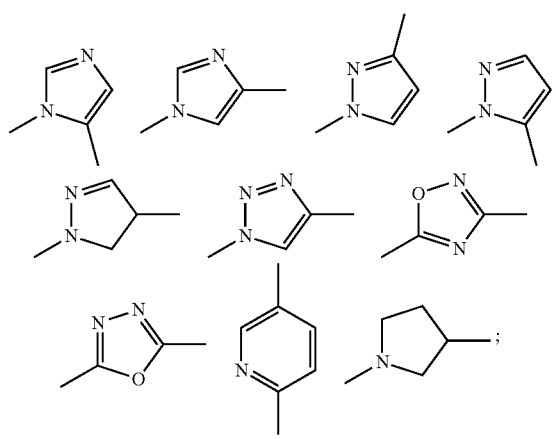

Linker is selected from a bond, —C(O)—, —CH$_2$—N(R$^c$)—, —CH$_2$—N(R$^d$)—C(O)—, and $C_{1-2}$ alkylene wherein said $C_{1-2}$ alkylene is optionally substituted with OH;

D is selected from:

(i) a 4-7 membered ring optionally containing 1 or 2 heteroatoms independently selected from N and O; wherein said ring optionally contains a C=O; and wherein said ring is optionally substituted with one or more groups selected from halogen, OH, $C_{1-4}$ alkoxy, $C_{1-4}$ alkyl optionally substituted with one or more halogen atoms, C(O)—R$^e$, phenyl optionally substituted with $C_{1-4}$ alkoxy, and a 5 or 6 membered ring containing 1 or 2 heteroatoms independently selected from N and O;

(ii) —N(R$^f$)(R$^g$); and (iii) —C(O)—O—$C_{1-4}$ alkyl;

$R^b$ is $C_{1-4}$ alkyl;

$R^c$ and Rd are independently selected from H and $C_{1-4}$ alkyl, $R^e$ is selected from $C_{1-4}$ alkyl and a 5- or 6-membered ring optionally containing 1 or 2 heteroatoms independently selected from N and O;

$R^f$ is selected from H, $C_{1-4}$ alkyl, C(O)—$C_{1-4}$ alkyl, and C(O)—O—$C_{1-4}$ alkyl; and $R^g$ is selected from $C_{1-4}$ alkyl, $C_{1-4}$ alkylene-O—$C_{1-4}$ alkyl.

2. A compound of claim 1 or a pharmaceutically acceptable salt thereof, wherein

Z is selected from Cl, F, CH$_3$, and CF$_3$;

$R_1$, $R_2$, and $R_3$ are independently selected from H and F;

A is selected from —(CH$_2$)$_m$—, —(CH$_2$)$_3$—O—(CH$_2$)$_3$—, —(CH$_2$)$_3$—O—(CH$_2$)$_2$—, —O—(CH$_2$)$_5$—, —(CH$_2$)$_5$—O—, —(CH$_2$)$_3$—N(CH$_3$)—(CH$_2$)$_2$—, —(CH$_2$)$_5$—C(O)—, and

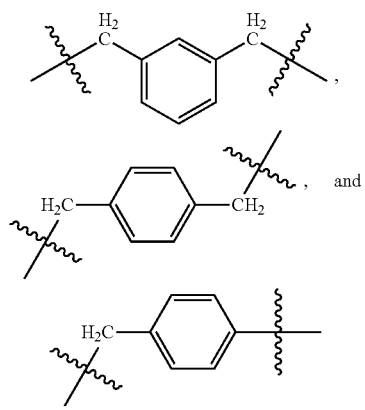

Linker is selected from a bond, —C(O)—, —CH$_2$—, —(CH$_2$)$_2$—, —CH(CH$_3$)—, —CH(OH)—, —CH$_2$—NH—, —CH$_2$—N(CH$_3$)—, —CH$_2$—N(CH$_3$)—C(O)—, and —CH$_2$—NH—C(O)—;

D is selected from:

(i) a 4-7 membered ring optionally containing 1 or 2 heteroatoms independently selected from N and O; wherein said ring optionally contains a C=O; and wherein said ring is optionally substituted with one or more groups selected from CH$_3$, F, OH, CF$_3$, O—CH$_3$, C(O)—R$^e$, phenyl, 4-methoxyphenyl, and piperazine;

(ii) —N(R$^f$)(R$^g$); and
(iii) —C(O)—O—C(CH$_3$)$_3$;

R$^e$ is selected from CH$_3$, CH(CH$_3$)$_2$, and tetrahydropyran;

R$^f$ is selected from H, CH$_3$, CH$_2$—CH$_3$, C(O)—CH$_3$, and C(O)—O—C(CH$_3$)$_3$;

Rg is selected from CH$_2$—CH$_2$—O—CH$_3$, CH(CH$_3$)—CH$_2$—O—CH$_3$, C(CH$_3$)$_2$—CH$_2$—O—CH$_3$, CH$_2$—C(CH$_3$)$_2$—O—CH$_3$, and CH$_2$—CH$_3$; and M is selected from 3, 4, 5, 6, and 7.

3. A compound of claim 1 where B is selected from the group:

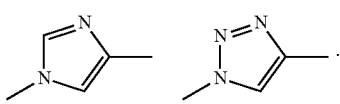

4. A compound of claim 2 where B is:

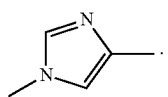

5. A compound of claim 2 where B is:

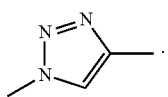

6. A compound of claim 1 wherein D is selected from the group:

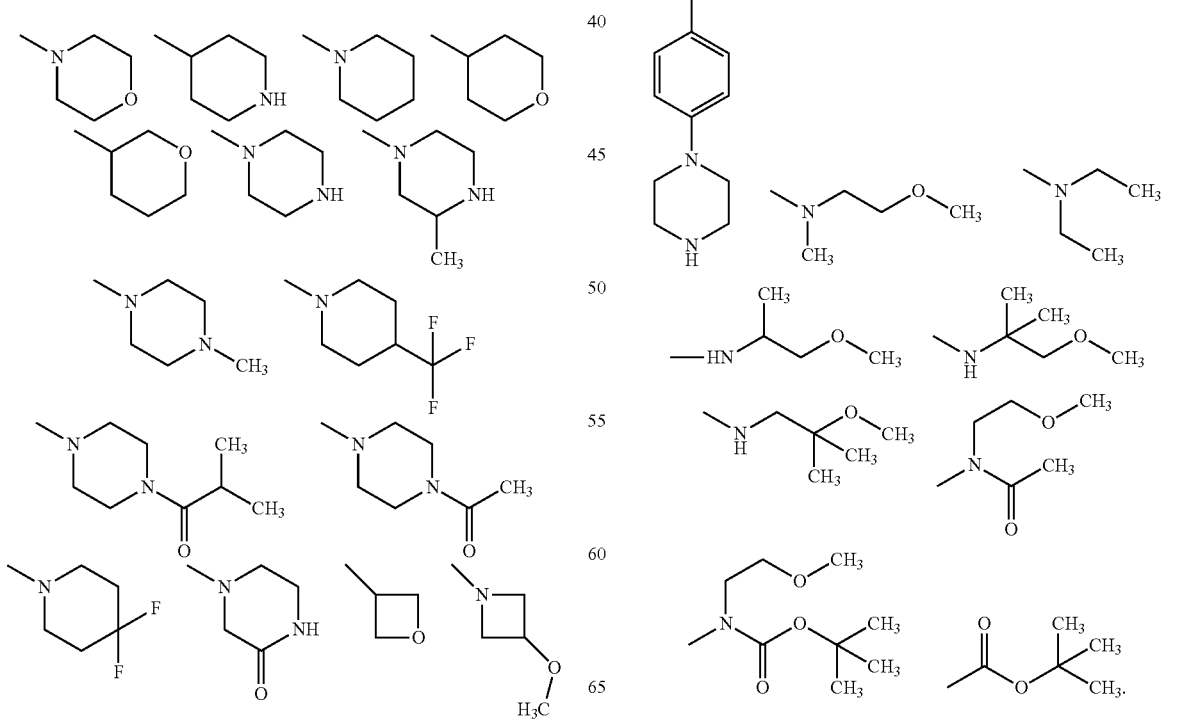

-continued

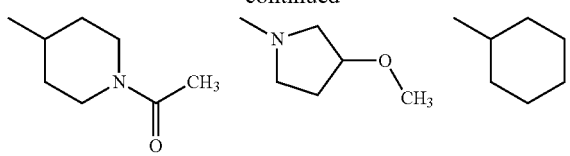

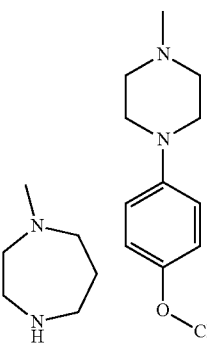

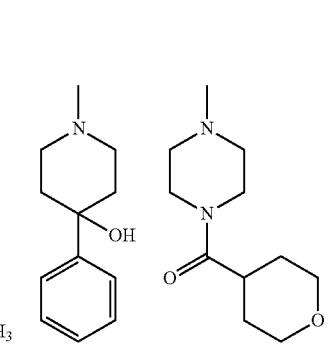

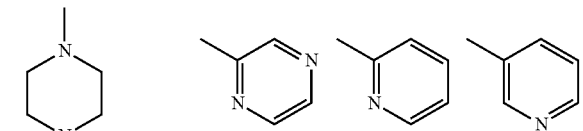

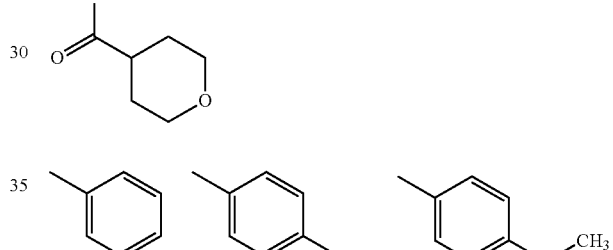

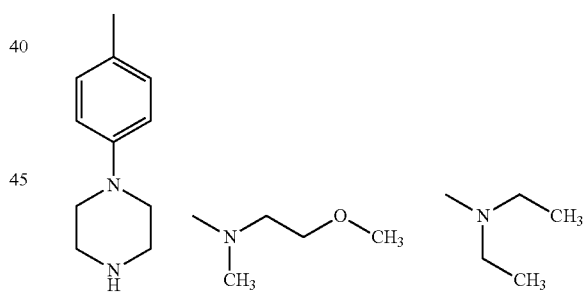

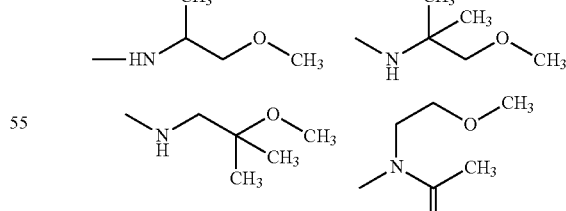

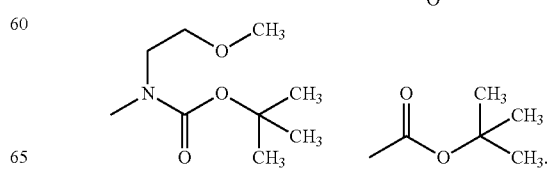

7. A compound of claim 1 where B is

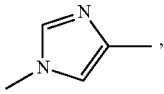

linker is —CH$_2$—, and D is

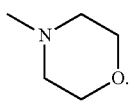

8. A compound of claim 1 where B is

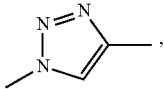

linker is —CH$_2$—, and D is

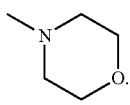

9. A compound of claim 1 selected from the following:
4-({1-[4-({[7-(trifluoromethyl)quinolin-4-yl]
  sulfanyl}methyl)phenyl]-1H-imidazol-4-yl}methyl)
  piperazin-2-one;
4-[({4-[4-(piperazin-1-ylmethyl)-1H-imidazol-1-yl]
  phenyl}methyl)sulfanyl]-7-(trifluoromethyl)quinoline;
4-[({4-[4-(morpholin-4-ylmethyl)-1H-imidazol-1-yl]
  phenyl}methyl)sulfanyl]-7-(trifluoromethyl)quinoline;
4-{[1-(6-{[7-(trifluoromethyl)quinolin-4-yl]
  sulfanyl}hexyl)-1H-1,2,3-triazol-4-yl]
  methyl}morpholin-3-one;
4-({6-[3-(morpholine-4-carbonyl)pyrrolidin-1-yl]
  hexyl}sulfanyl)-7-(trifluoromethyl)quinoline;
Tert-butyl 4-(6-{[7-(trifluoromethyl)quinolin-4-yl]
  sulfanyl}hexyl)piperazine-1-carboxylate;
1-[3-(morpholin-4-ylmethyl)pyrrolidin-1-yl]-6-{[7-(trifluoromethyl)quinolin-4-yl]sulfanyl}hexan-1-one;
4-({6-[4-(oxan-4-ylmethyl)-1H-1,2,3-triazol-1-yl]
  hexyl}sulfanyl)-7-(trifluoromethyl)quinoline;
4-[(6-{4-[(3-methylpiperazin-1-yl)methyl]-1H-1,2,3-triazol-1-yl}hexyl)sulfanyl]-7-(trifluoromethyl)quinoline;
4-methoxy-N-methyl-N-{[1-(6-{[7-(trifluoromethyl)quinolin-4-yl]sulfanyl}hexyl)-1H-imidazol-4-yl]
  methyl}aniline;
1-{4-[(1-{6-[(7-fluoroquinolin-4-yl)sulfanyl]hexyl}-1H-imidazol-4-yl)methyl]piperazin-1-yl}-2-methylpropan-1-one;
4-[(6-{4-[(4,4-difluoropiperidin-1-yl)methyl]-1H-imidazol-1-yl}hexyl)sulfanyl]-7-(trifluoromethyl)quinoline;
7-(trifluoromethyl)-4-{[6-(4-{[4-(trifluoromethyl)piperidin-1-yl]methyl}-1H-imidazol-1-yl)hexyl]
  sulfanyl}quinoline;
4-{[6-(4-phenyl-1H-imidazol-1-yl)hexyl]sulfanyl}-7-(trifluoromethyl)quinoline;
4-phenyl-1-{[1-(6-{[7-(trifluoromethyl)quinolin-4-yl]
  sulfanyl}hexyl)-1H-imidazol-4-yl]methyl}piperidin-4-ol;
4-(piperazin-1-yl)-N-{[1-(6-{[7-(trifluoromethyl)quinolin-4-yl]sulfanyl}hexyl)-1H-imidazol-4-yl]
  methyl}aniline;
7-fluoro-4-({6-[4-(morpholin-4-ylmethyl)-1H-imidazol-1-yl]hexyl}sulfanyl)quinoline;
4-[(6-{4-[1-(morpholin-4-yl)ethyl]-1H-imidazol-1-yl}hexyl)sulfanyl]-7-(trifluoromethyl)quinoline;
phenyl[1-(6-{[7-(trifluoromethyl)quinolin-4-yl]
  sulfanyl}hexyl)-1H-imidazol-4-yl]methanol;
N-[(1-{6-[(7-fluoroquinolin-4-yl)sulfanyl]hexyl}-1H-imidazol-4-yl)methyl]aniline;
4-[(1-{6-[(7-fluoroquinolin-4-yl)sulfanyl]hexyl}-1H-imidazol-4-yl)methyl]piperazin-2-one;
N-{[1-(6-{[7-(trifluoromethyl)quinolin-4-yl]
  sulfanyl}hexyl)-1H-1,2,3-triazol-4-yl]methyl}pyridin-3-amine;
4-({6-[4-(piperidin-1-ylmethyl)-1H-imidazol-1-yl]
  hexyl}sulfanyl)-7-(trifluoromethyl)quinoline;
4-({6-[4-(piperidin-4-ylmethyl)-1H-1,2,3-triazol-1-yl]
  hexyl}sulfanyl)-7-(trifluoromethyl)quinoline;
4-({6-[6-(morpholin-4-ylmethyl)pyridin-3-yl]
  hexyl}sulfanyl)-7-(trifluoromethyl)quinoline;
N-{[1-(6-{[7-(trifluoromethyl)quinolin-4-yl]
  sulfanyl}hexyl)-1H-1,2,3-triazol-4-yl]methyl}pyridin-2-amine;
N-methyl-N-{[1-(6-{[7-(trifluoromethyl)quinolin-4-yl]
  sulfanyl}hexyl)-1H-1,2,3-triazol-4-yl]
  methyl}pyrazine-2-carboxamide;
N-{[1-(6-{[7-(trifluoromethyl)quinolin-4-yl]
  sulfanyl}hexyl)-1H-1,2,3-triazol-4-yl]methyl}oxetan-3-amine;
N-{[1-(6-{[7-(trifluoromethyl)quinolin-4-yl]
  sulfanyl}hexyl)-1H-1,2,3-triazol-4-yl]methyl}oxan-3-amine;
(1-methoxypropan-2-yl)({[1-(6-{[7-(trifluoromethyl)quinolin-4-yl]sulfanyl}hexyl)-1H-1,2,3-triazol-4-yl]
  methyl})amine;
(1-methoxy-2-methylpropan-2-yl)({[1-(6-{[7-(trifluoromethyl)quinolin-4-yl]sulfanyl}hexyl)-1H-1,2,3-triazol-4-yl]methyl})amine;
4-[(6-{4-[(3-methoxyazetidin-1-yl)methyl]-1H-1,2,3-triazol-1-yl}hexyl)sulfanyl]-7-(trifluoromethyl)quinoline;
(2-methoxy-2-methylpropyl)({[1-(6-{[7-(trifluoromethyl)quinolin-4-yl]sulfanyl}hexyl)-1H-1,2,3-triazol-4-yl]methyl})amine;
4-{[6-(4-{[4-(4-methoxyphenyl)piperazin-1-yl]methyl}-1H-1,2,3-triazol-1-yl)hexyl]sulfanyl}-7-(trifluoromethyl)quinoline;
N-{[1-(6-{[7-(trifluoromethyl)quinolin-4-yl]
  sulfanyl}hexyl)-1H-1,2,3-triazol-4-yl]
  methyl}pyrazine-2-carboxamide;
4-[(6-{4-[(3-methoxypyrrolidin-1-yl)methyl]-1H-1,2,3-triazol-1-yl}hexyl)sulfanyl]-7-(trifluoromethyl)quinoline;
7,8-difluoro-4-({6-[4-(morpholin-4-ylmethyl)-1H-1,2,3-triazol-1-yl]hexyl}sulfanyl)quinoline; 5,7-difluoro-4-({6-[4-(morpholin-4-ylmethyl)-1H-1,2,3-triazol-1-yl]hexyl}sulfanyl)quinoline; 1-(4-{[1-(6-{[7-(trifluoromethyl)quinolin-4-yl]sulfanyl}hexyl)-1H-1,2,3-triazol-4-yl]methyl}piperazin-1-yl)ethan-1-one;
4-{[6-(4-{[4-(oxane-4-carbonyl)piperazin-1-yl]methyl}-1H-1,2,3-triazol-1-yl)hexyl]sulfanyl}-7-(trifluoromethyl)quinoline;

2-methyl-1-(4-{[1-(6-{[7-(trifluoromethyl)quinolin-4-yl]sulfanyl}hexyl)-1H-1,2,3-triazol-4-yl]methyl}piperazin-1-yl)propan-1-one;
1-(4-{[1-(6-{[7-(trifluoromethyl)quinolin-4-yl]sulfanyl}hexyl)-1H-1,2,3-triazol-4-yl]methyl}piperazin-1-yl)ethan-1-one;
N-{[1-(6-{[7-(trifluoromethyl)quinolin-4-yl]sulfanyl}hexyl)-1H-1,2,3-triazol-4-yl]methyl}pyridine-2-carboxamide;
4-({6-[4-(cyclohexylmethyl)-1H-1,2,3-triazol-1-yl]hexyl}sulfanyl)-7-(trifluoromethyl)quinoline;
N-{[1-(6-{[7-(trifluoromethyl)quinolin-4-yl]sulfanyl}hexyl)-1H-1,2,3-triazol-4-yl]methyl}oxane-4-carboxamide;
4-[(6-{4-[2-(morpholin-4-yl)ethyl]-1H-1,2,3-triazol-1-yl}hexyl)sulfanyl]-7-(trifluoromethyl)quinoline;
4-({6-[5-(morpholin-4-ylmethyl)-1H-pyrazol-1-yl]hexyl}sulfanyl)-7-(trifluoromethyl)quinoline;
4-({6-[3-(morpholin-4-ylmethyl)-1H-pyrazol-1-yl]hexyl}sulfanyl)-7-(trifluoromethyl)quinoline;
N-{[1-(6-{[7-(trifluoromethyl)quinolin-4-yl]sulfanyl}hexyl)-1H-1,2,3-triazol-4-yl]methyl}cyclohexane carboxamide;
N-{[1-(6-{[7-(trifluoromethyl)quinolin-4-yl]sulfanyl}hexyl)-1H-1,2,3-triazol-4-yl]methyl}benzamide;
N-methyl-N-{[1-(6-{[7-(trifluoromethyl)quinolin-4-yl]sulfanyl}hexyl)-1H-imidazol-4-yl]methyl}aniline;
N-{[1-(6-{[7-(trifluoromethyl)quinolin-4-yl]sulfanyl}hexyl)-1H-imidazol-4-yl]methyl}aniline;
4-methoxy-N-{[1-(6-{[7-(trifluoromethyl)quinolin-4-yl]sulfanyl}hexyl)-1H-imidazol-4-yl]methyl}aniline;
4-methyl-N-{[1-(6-{[7-(trifluoromethyl)quinolin-4-yl]sulfanyl}hexyl)-1H-imidazol-4-yl]methyl}aniline;
(2-methoxyethyl)(methyl){[1-(6-{[7-(trifluoromethyl)quinolin-4-yl]sulfanyl}hexyl)-1H-imidazol-4-yl]methyl}amine;
4-({6-[4-(1,4-diazepan-1-ylmethyl)-1H-1,2,3-triazol-1-yl]hexyl}sulfanyl)-7-(trifluoromethyl)quinoline;
4-({6-[4-(piperidin-1-ylmethyl)-1H-1,2,3-triazol-1-yl]hexyl}sulfanyl)-7-(trifluoromethyl)quinoline;
4-{[1-(6-{[7-(trifluoromethyl)quinolin-4-yl]sulfanyl}hexyl)-1H-1,2,3-triazol-4-yl]methyl}piperazin-2-one;
4-({6-[4-(morpholin-4-ylmethyl)-1H-pyrazol-1-yl]hexyl}sulfanyl)-7-(trifluoromethyl)quinoline;
diethyl({[1-(6-{[7-(trifluoromethyl)quinolin-4-yl]sulfanyl}hexyl)-1H-1,2,3-triazol-4-yl]methyl})amine;
4-({6-[3-(morpholin-4-ylmethyl)-1,2,4-oxadiazol-5-yl]hexyl}sulfanyl)-7-(trifluoromethyl)quinoline;
7-chloro-4-({6-[4-(morpholin-4-ylmethyl)-1H-1,2,3-triazol-1-yl]hexyl}sulfanyl)quinoline;
7-fluoro-4-({6-[4-(morpholin-4-ylmethyl)-1H-1,2,3-triazol-1-yl]hexyl}sulfanyl)quinoline;
4-({6-[4-(piperazin-1-ylmethyl)-1H-imidazol-1-yl]hexyl}sulfanyl)-7-(trifluoromethyl)quinoline;
(2-methoxyethyl)({[1-(6-{[7-(trifluoromethyl)quinolin-4-yl]sulfanyl}hexyl)-1H-imidazol-4-yl]methyl})amine;
4-({6-[5-(morpholin-4-ylmethyl)-1,3,4-oxadiazol-2-yl]hexyl}sulfanyl)-7-(trifluoromethyl)quinoline;
7-methyl-4-({6-[4-(morpholin-4-ylmethyl)-1H-1,2,3-triazol-1-yl]hexyl}sulfanyl)quinoline;
N-(2-methoxyethyl)-N-{[1-(6-{[7-(trifluoromethyl)quinolin-4-yl]sulfanyl}hexyl)-1H-1,2,3-triazol-4-yl]methyl}acetamide;
(2-methoxyethyl)(methyl){[1-(6-{[7-(trifluoromethyl)quinolin-4-yl]sulfanyl}hexyl)-1H-1,2,3-triazol-4-yl]methyl}amine;
4-[(6-{4-[(4-methylpiperazin-1-yl)methyl]-1H-1,2,3-triazol-1-yl}hexyl)sulfanyl]-7-(trifluoromethyl)quinoline;
4-({6-[4-(piperazin-1-ylmethyl)-1H-1,2,3-triazol-1-yl]hexyl}sulfanyl)-7-(trifluoromethyl)quinoline;
4-{[(3-{[4-(morpholin-4-ylmethyl)-1H-1,2,3-triazol-1-yl]methyl}phenyl)methyl]sulfanyl}-7-(trifluoromethyl)quinoline;
4-methyl-N-{[1-(6-{[7-(trifluoromethyl)quinolin-4-yl]sulfanyl}hexyl)-1H-1,2,3-triazol-4-yl]methyl}aniline;
4-methoxy-N-{[1-(6-{[7-(trifluoromethyl)quinolin-4-yl]sulfanyl}hexyl)-1H-1,2,3-triazol-4-yl]methyl}aniline;
N-{[1-(6-{[7-(trifluoromethyl)quinolin-4-yl]sulfanyl}hexyl)-1H-1,2,3-triazol-4-yl]methyl}aniline;
4-({6-[5-(morpholin-4-ylmethyl)-1H-imidazol-1-yl]hexyl}sulfanyl)-7-(trifluoromethyl)quinoline;
4-({6-[4-(morpholin-4-ylmethyl)-1H-imidazol-1-yl]hexyl}sulfanyl)-7-(trifluoromethyl)quinoline;
N-{6-[4-(morpholin-4-ylmethyl)-1H-1,2,3-triazol-1-yl]hexyl}-7-(trifluoromethyl)quinolin-4-amine;
(2-methoxyethyl)({[1-(6-{[7-(trifluoromethyl)quinolin-4-yl]sulfanyl}hexyl)-1H-1,2,3-triazol-4-yl]methyl})amine;
tert-butyl N-(2-methoxyethyl)-N-{[1-(6-{[7-(trifluoromethyl)quinolin-4-yl]sulfanyl}hexyl)-1H-1,2,3-triazol-4-yl]methyl}carbamate;
methyl({2-[4-(morpholin-4-ylmethyl)-1H-1,2,3-triazol-1-yl]ethyl})(3-{[7-(trifluoromethyl)quinolin-4-yl]sulfanyl}propyl)amine;
4-[(3-{3-[4-(morpholin-4-ylmethyl)-1H-1,2,3-triazol-1-yl]propoxy}propyl)sulfanyl]-7-(trifluoromethyl)quinoline;
4-[(3-{2-[4-(morpholin-4-ylmethyl)-1H-1,2,3-triazol-1-yl]ethoxy}propyl)sulfanyl]-7-(trifluoromethyl)quinoline;
4-({7-[4-(morpholin-4-ylmethyl)-1H-1,2,3-triazol-1-yl]heptyl}sulfanyl)-7-(trifluoromethyl)quinoline;
4-({6-[4-(morpholin-4-ylmethyl)-1H-1,2,3-triazol-1-yl]hexyl}sulfanyl)-7-(trifluoromethyl)quinoline;
4-({3-[4-(morpholin-4-ylmethyl)-1H-1,2,3-triazol-1-yl]propyl}sulfanyl)-7-(trifluoromethyl)quinoline;
4-({4-[4-(morpholin-4-ylmethyl)-1H-1,2,3-triazol-1-yl]butyl}sulfanyl)-7-(trifluoromethyl)quinoline;
4-({5-[4-(morpholin-4-ylmethyl)-1H-1,2,3-triazol-1-yl]pentyl}sulfanyl)-7-(trifluoromethyl)quinoline;
4-[(5-{[6-(morpholin-4-ylmethyl)pyridin-3-yl]oxy}pentyl)sulfanyl]-7-(trifluoromethyl)quinoline;
diethyl({5-[(5-{[7-(trifluoromethyl)quinolin-4-yl]sulfanyl}pentyl)oxy]pyridin-2-yl}methyl)amine; and
4-[[1-[[4-[[7-(trifluoromethyl)-4-quinolyl]sulfanylmethyl]phenyl]methyl]imidazol-4-yl]methyl]morpholine.

10. A compound of claim 1 wherein the compound is:

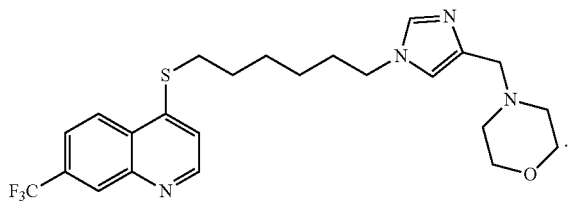 [SMILES: FC(F)(F)c1ccc2c(SCCCCCCn3cnc(CN4CCOCC4)c3)ccnc2c1]

11. A compound of claim 1 wherein the compound is:

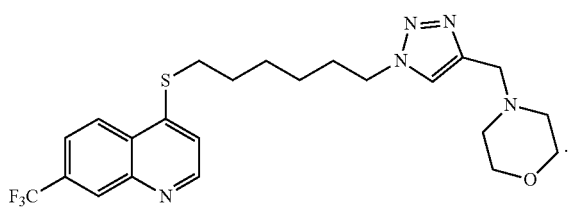 [SMILES: FC(F)(F)c1ccc2c(SCCCCCCn3cc(CN4CCOCC4)nn3)ccnc2c1]

12. A compound of claim 1 wherein the compound is:

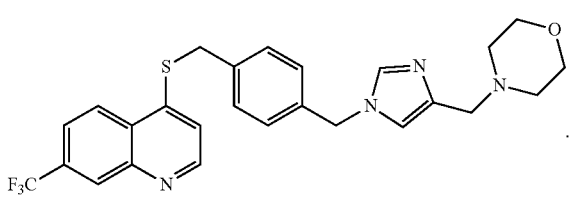 [SMILES: FC(F)(F)c1ccc2c(SCc3ccc(Cn4cnc(CN5CCOCC5)c4)cc3)ccnc2c1]

13. A compound of claim 1 wherein the compound is:

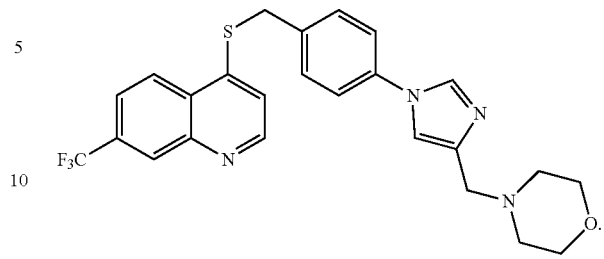

14. A pharmaceutical composition comprising a therapeutically effective amount of a compound of claim 1 and a pharmaceutically acceptable carrier.

15. A pharmaceutical composition comprising a therapeutically effective amount of a compound of claim 10 and a pharmaceutically acceptable carrier.

16. A pharmaceutical composition comprising a therapeutically effective amount of a compound of claim 11 and a pharmaceutically acceptable carrier.

17. A pharmaceutical composition comprising a therapeutically effective amount of a compound of claim 12 and a pharmaceutically acceptable carrier.

18. A pharmaceutical composition comprising a therapeutically effective amount of a compound of claim 13 and a pharmaceutically acceptable carrier.

\* \* \* \* \*